United States Patent
Fotouhi et al.

(12)

(10) Patent No.: US 6,803,384 B2
(45) Date of Patent: *Oct. 12, 2004

(54) DIAMINOPROPIONIC ACID DERIVATIVES

(75) Inventors: Nader Fotouhi, Chatham, NJ (US); Paul Gillespie, Westfield, NJ (US); Robert William Guthrie, Saddle Brook, NJ (US); Sherrie Lynn Pietranico-Cole, Nutley, NJ (US); Weiya Yun, Warren, NJ (US)

(73) Assignee: Hoffmann-La Roche Inc., Nutley, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 10/349,289

(22) Filed: Jan. 22, 2003

(65) Prior Publication Data

US 2004/0006236 A1 Jan. 8, 2004

Related U.S. Application Data

(62) Division of application No. 09/879,700, filed on Jun. 12, 2001, now abandoned, which is a division of application No. 09/407,534, filed on Sep. 29, 1999, now Pat. No. 6,331,640.

(60) Provisional application No. 60/104,120, filed on Oct. 13, 1998.

(51) Int. Cl.$^7$ ..................... A61K 31/166; A61K 31/33; C07C 235/52

(52) U.S. Cl. ..................... 514/563; 514/448; 514/471; 514/361; 514/378; 514/419; 514/315; 514/357; 546/245; 546/337; 548/127; 548/248; 548/503; 549/72; 549/487; 562/449

(58) Field of Search ................. 549/72, 487; 548/127, 548/248, 503; 546/245, 337; 562/449; 514/448, 471, 361, 378, 419, 315, 357, 563

(56) References Cited

U.S. PATENT DOCUMENTS

| 3,691,196 A | 9/1972 | Suter et al. |
| 4,005,188 A | 1/1977 | Tilly et al. |
| 4,014,986 A | 3/1977 | Tilly et al. |
| 4,607,123 A | 8/1986 | Schuster et al. |
| 5,288,854 A | 2/1994 | Diamond et al. |
| 5,464,855 A | 11/1995 | Capiris et al. |
| 5,489,598 A | 2/1996 | Connor et al. |
| 5,530,157 A | 6/1996 | Mewshaw et al. |
| 5,707,985 A | 1/1998 | McKenzie et al. |
| 5,708,141 A | 1/1998 | Moyle et al. |
| 6,331,640 B1 * | 12/2001 | Fotouhi et al. ............... 549/72 |

FOREIGN PATENT DOCUMENTS

| DE | 2524059 | 5/1975 |
| EP | 1958333 | 8/1970 |
| EP | 1488904 | 5/1974 |
| EP | 3407473 | 9/1985 |
| EP | 849 256 | 6/1998 |
| WO | WO 96/03155 | 2/1996 |
| WO | WO 96/38426 | 12/1996 |
| WO | WO 99/49856 | 10/1999 |

OTHER PUBLICATIONS

Suter, H. et al., (Eprova A.–G., Germany) Helv. Chim, Acta, 1971, vol. 54, pp. 2097–2107.
Dokl. Bulg. Akad. Nauk, 1991, 44(1) pp. 35–38.
Gilbert, B.A., et al., J. Am. Chem. Soc., 1995, vol. 117, pp. 8061–8066.
Skjoeldk, W. et al., J. Chromatogr., 1986, vol. 366, pp. 299–309.
Wegmann, H. et al., Chem. Ber., 1981, vol. 114, pp. 2580–2594.
Abstract corresponding to WO 96/03155, 1996.

* cited by examiner

Primary Examiner—Laura L. Stockton
(74) Attorney, Agent, or Firm—George W. Johnston; Dennis P. Tramaloni; Eileen M. Ebel

(57) ABSTRACT

A compound of formula Id

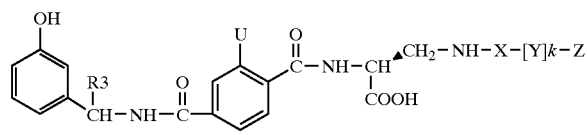

and pharmaceutically acceptable salts and esters thereof, wherein the substituent designations are as provided in the specification. Compounds of the invention are useful for treating reperfusion injury.

44 Claims, No Drawings

DIAMINOPROPIONIC ACID DERIVATIVES

This application is a divisional of application Ser. No. 09/879,700, filed Jun. 12, 2001, now abandoned, which is a divisional of application Ser. No. 09/407,534, filed Sep. 29, 1999, now U.S. Pat. No. 6,331,640, which claims priority under 35 U.S.C. §119(e) of provisional application Serial No. 60/104,120, filed Oct. 13, 1998.

BACKGROUND OF THE INVENTION

Inflammation is brought about when leukocytes migrate to the site of injury in tissue, for example, tissue injured as a result of acute myocardial infarction, cardiopulmonary bypass, or stroke. In myocardial infarction, interruption of blood flow to cardiac tissue causes damage due primarily to oxygen deprivation (ischemia). When blood flow is returned (reperfusion) further damage to the ischemic tissue can occur. This reperfusion injury is to a significant extent due to neutrophils which migrate from blood vessels into the damaged tissue by interacting with adhesion molecules on the surface of the blood vessels. The neutrophils mediate inflammation, tissue necrosis, and plugging of microvasculature. An effective approach for reducing reperfusion injury is to block the interaction between neutrophils and the adhesion molecules on the blood vessel walls.

One such adhesion molecule is intracellular adhesion molecule-1 (ICAM-1), a member of the immunoglobulin (Ig) supergene family, which is expressed on activated endothelial cells on the blood vessel wall, activated T cells, activated B cells and monocytes. ICAM-1 binds to receptors known as β2 integrins which are found on B and T lymphocytes, monocytes, and neutrophils. The binding of ICAM-1 expressed on endothelial cells to the β2 integrins Mac-1 (macrophage differentiation antigen also known as CD11b/CD18, CR3, and $\alpha_M\beta_2$) and/or LFA-1 (lymphocyte function-associated antigen-1, also known as CD11a/CD18 and $\alpha_L\beta_2$) expressed on neutrophils activated by inflammatory mediators such as platelet activating factor (PAF) and interleukin-8 (IL-8), mediates the firm adhesion that is required before extravasation of the neutrophils into sites of inflammation. Extravasated and activated neutrophils adhere to the tissue bed, causing tissue necrosis and microvasculatory plugging. In vitro studies have demonstrated that binding of neutrophils to activated cardiac myocytes is dependent on β2integrins (Entman et al. *J. Clin. Invest.* 1990, 85, 1497–1506).

Mac-1 also binds to fibrinogen, a plasma protein that mediates platelet aggregation in the presence of platelet activating factor. The platelets bind to damaged tissue resulting in the deposition of fibrinogen on the blood vessel wall. The Mac-1-fibrinogen interaction can therefore contribute to the adhesion of neutrophils and monocytes to endothelial cells. The murine antibody 7E3, directed against the integrin $\alpha_{IIb}\beta_3$, also binds to the integrins $\alpha_v\beta_3$and Mac-1, and it inhibits the interaction of neutrophils with immobilized fibrinogen (Plescia et al. *J. Biol. Chem.* 1998, 273, 20372–20377). The humanized Fab fragment of 7E3 is approved for the prevention of ischemic complications in patients undergoing cardiac percutaneous coronary intervention.

In humans, expression of the β2 integrin Mac-1 is upregulated during cardiopulmonary bypass (Gillinov et al. *Ann. Thorac. Surg.* 1993, 56, 847–853) and in the acute phase of myocardial infarction (Meisel et al. *J. Am. Coll. Card.* 1998, 31,120–125). Levels of soluble ICAM-1 are also elevated in acute myocardial infarction in humans (Kaikita et al. *Japanese Circ. Journal* 1997, 61, 741–748).

Reduction of the interaction between ICAM-1 and its receptors decreases neutrophil migration and resulting inflammation, consequently reduces reperfusion injury caused by inflammation following acute myocardial infarction. For example, ICAM-1-deficient mice show decreased neutrophil migration in response to chemical peritonitis (Sligh et al. *Proc. Natl. Acad. Sci. U.S.A.* 1993, 90, 8529–33) and are protected from reperfusion injury in models of stroke and renal failure (Soriano et al. *Ann. Neurol.* 1996, 39, 618–624; Kelly et al. *J Clin. Invest.* 1996, 97, 1056–63).

Antibody to ICAM-1 is protective in cat, dog, and rabbit models of cardiac reperfusion injury, and antibody to CD18 is protective in rat, rabbit, cat, dog, and various primate models of cardiac reperfusion injury (Ma et al. *Circulation* 1992, 86, 937–946; Lefer et al. *Am. J. Physiol.* 1996, 271, H2421–H2429; Zhao et al. *J. Leukocyte Biol.* 1997, 62, 292–300; Lefer et al. *Circulation* 1993, 88, 1779–1787). Biological molecules which block ICAM-1 activity, for example, antibodies to ICAM-1, CD11b and CD18, have also been shown to reduce inflammation damage in models of stroke (Zhang et al. *Stroke,* 1995, 26,1438–43; Chen et al. *Ann. Neurol.* 1994, 35, 458–63; Zhang et al. *Brain Res.* 1995, 698, 79–85; Bowes et al. *Exp. Neurol.* 1993, 119, 215–219). Antibody to CD11b is effective in attenuating neointimal growth in a rabbit model of restenosis (Rogers et al. *Proc. Natl. Acad. Sci. USA* 1998, 95, 10134–10137). Antibodies blocking ICAM-1 activity are the subject of International Patent Application Nos. 9302191, 9402175, 9404188, 9408620, 9412214, 9726912 and U.S. Pat. No. 5,695,760. Antisense oligonucleotides to murine ICAM-1 have been shown to attenuate reperfusion injury and renal failure in rats (Stepkowski et al. *J. Immunol.* 1994, 153, 5336–46; Haller et al. *Kidney Int.* 1996, 50, 473–480). Molecules of this type have been patented (U.S. Pat. Nos. 5,591,623 and 5,580,969).

However, compounds such as small molecule (i.e. low molecular weight) antagonists of the interaction between ICAM-1 and its ligands offer advantages over antibodies and antisense oligonucleotides for treating reperfusion injury because smaller molecules have increased tissue penetration, lack of immunogenicity, shorter half-lives, lower cost, and in general lower risks of serious adverse events. Therefore, compounds other than these biological molecules which block ICAM-1 activity are desirable as therapeutic agents for the treatment of acute inflammatory conditions such as ischemia-reperfusion injury. A number of patents and applications are directed to compounds which block ICAM-1 activity, e.g. U.S. Pat. Nos. 5,288,854, 5,530, 157, 5,489,598, 5,464,855, 5,708,141, 5,707,985, International Patent Application Nos. 9640641 and 9807423.

SUMMARY OF THE INVENTION

This invention is directed to compounds which are capable of blocking ICAM activity and are accordingly particularly useful in treatment of reperfusion injury following acute myocardial infarction. Such compounds are as follows:

Compounds of formula:

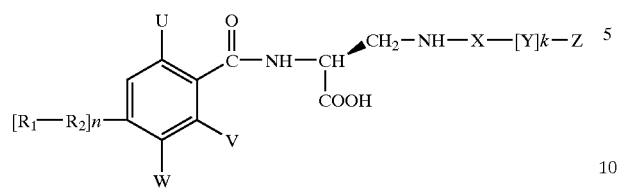

wherein R1 is a group of the formula

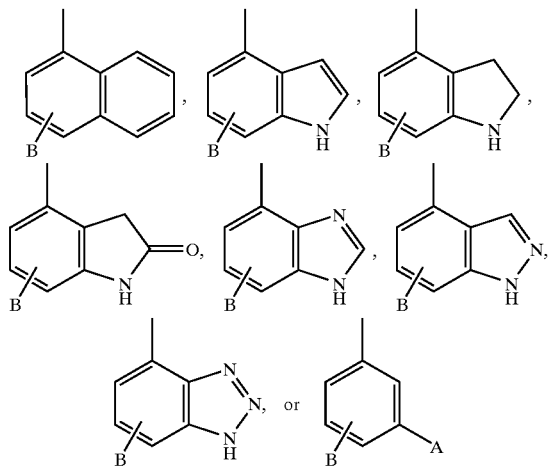

where A is hydrogen, hydroxy, amino, or halogen and B is amino, carboxy, hydrogen, hydroxy, cyano, trifluoromethyl, halogen, lower alkyl, or lower alkoxy;

$R_2$ is a group of the formula

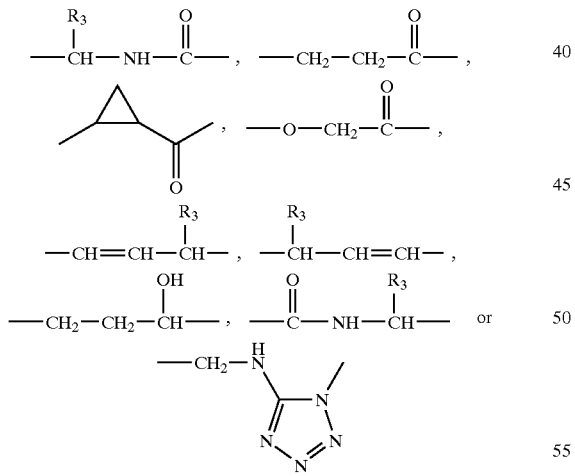

where $R_3$ is hydrogen, carboxy, or lower alkyl;
n is 0 or 1; U, V, and W are independently hydrogen, halogen, or lower alkyl provided U and V are not both hydrogen; X is carbonyl, phenyl-substituted loweralkylene, or sulfonyl; Y is lower alkylene which may be substituted by one or more of amino, substituted amino, loweralkyl, or cyclo lower alkyl, or Y is lower alkenylene or lower alkylenethio; k is 0 or 1; when k is 1: Z is hydrogen, lower alkylthio, —COOH, —CONH$_2$, or amino; or when k is 0 or 1 Z is: 1-adamantyl, diphenylmethyl, 3-[[(5-chloropyridin-2-yl)amino]carbonyl]pyrazin-2-yl, and may also in addition be hydroxy, phenylmethoxy, 2-chloro-4-[[[(3-hydroxyphenyl)methyl]amino]carbonyl]phenyl, [2,6-dichlorophenyl)methoxy]phenyl, or Z is one of the following:
cycloalkyl or aryl containing 0 to 3 heteroatoms which may be the same or different, or a fused ring system containing two or three rings which rings are independently cycloalkyl or aryl containing 0 to 3 heteroatoms which may be the same or different, any of which rings may be unsubstituted, or substituted with at least one of:
halogen, cyano, amino, substituted amino, aminosulfonyl, nitro, oxo, hydroxy, aryl, aryloxy, unsubstituted lower alkyl, halogen-substituted lower alkyl, lower alkoxy-substituted lower alkyl, lower alkoxy, lower alkanesulfonyl, lower alkylthio, acetyl, aminocarbonyl, hydrazino, carboxy, alkoxycarbonyl, acetoxy, or also in addition with amino lower alkyl and pharmaceutically acceptable salts and esters thereof,
compounds of the formula:

(a)

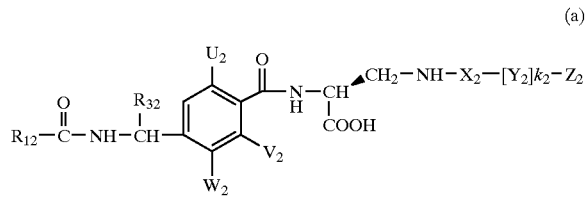

wherein $R_{12}$ is a group of the formula

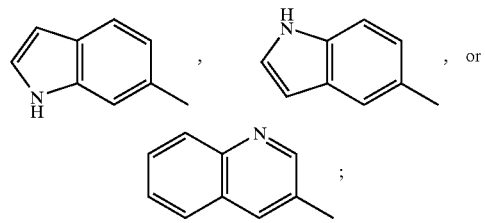

$R_{32}$ is hydrogen, carboxy, or lower alkyl; $U_2$, $V_2$, and $W_2$ are independently hydrogen, halogen, or is lower alkyl provided $U_2$ and $V_2$ are not both hydrogen; X is carbonyl, phenyl-substituted loweralkylene, or sulfonyl; $Y_2$ is lower alkenylene, lower alkylenethio, or is lower alkylene which may be substituted by amino, acetylamino, or cyclo-lower alkyl; $k_2$ is 0 or 1; when $k_2$ is 1, $Z_2$ is: hydrogen, lower alkylenethio,
—COOH, —CONH$_2$, or amino; or when $k_2$ is 0 or 1, Z is: 1-adamantyl, diphenylmethyl, 3-[[(5-chloropyridin-2-yl)amino]carbonyl]pyrazin-2-yl, or $Z_2$ is one of the following: cycloalkyl or aryl containing 0 to 3 heteroatoms which may be the same or different, or a fused ring system containing two or three rings which rings are independently cycloalkyl or aryl containing 0 to 3 heteroatoms which may be the same or different, any of which rings may be unsubstituted, or substituted with at least one of: halogen, cyano, amino, substituted amino, aminosulfonyl, nitro, oxo, hydroxy, aryl, aryloxy, lower alkyl unsubstituted halogen or substituted lower alkyl, lower alkoxy-substituted lower alkyl, slower alkoxy, carboxy, alkoxycarbonyl, or acetoxy; and pharmaceutically acceptable salts and esters thereof, compounds of the formula

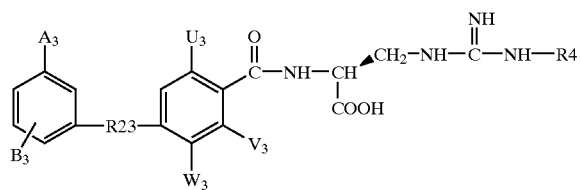

wherein $A_3$ is hydrogen, hydroxy, amino, or halogen and $B_3$ is amino, carboxy, hydrogen, hydroxy, cyano, trifluoromethyl, halogen, lower alkyl, or lower alkoxy;

$R_{23}$ is a group of the formula

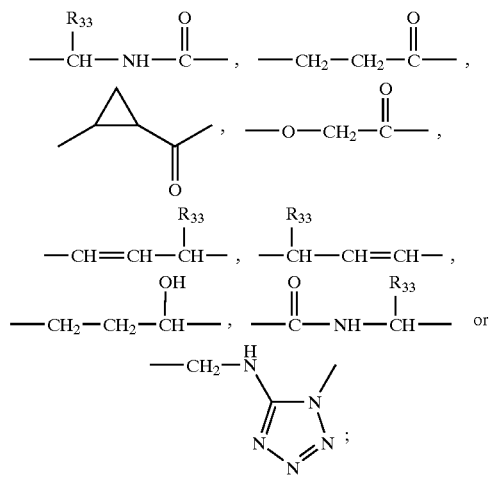

where $R_{33}$ is hydrogen, carboxy, or lower alkyl; $U_3$, $V_3$, and $W_3$ are independently hydrogen, halogen, or lower alkyl provided $U_3$ and $V_3$ are not both hydrogen; and R4 is hydrogen, lower alkyl, or aryl-lower-alkyl which can be unsubstituted or substituted with at least one of halogen, cyano, amino, substituted amino, aminosulfonyl, nitro, hydroxy, aryl, aryloxy, unsubstituted lower alkyl, halogen substituted lower alkyl, lower alkoxy-substituted lower alkyl, lower alkoxy, carboxy, alkoxycarbonyl, or acetoxy and pharmaceutically acceptable salts and esters thereof, and prodrug compounds of the formula

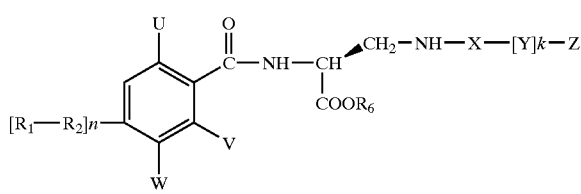

wherein $R_1$, $R_2$, n, U, V, W, X, Y, k, and Z are as in formula 1a; $R_6$ is lower alkyl or —CH$_2$CH$_2$—$R_7$ where $R_7$ is —N(CH$_3$)$_2$,

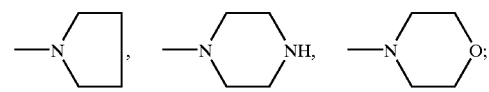

or

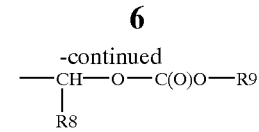

where R8 is hydrogen or methyl and $R_9$ is lower alkyl or lower cycloalkyl; and pharmaceutically acceptable salts and esters thereof.

This invention is also directed to pharmaceutical compositions and methods of treatment using the above compounds.

DETAILED DESCRIPTION OF THE INVENTION

This invention is directed to compounds of formula:

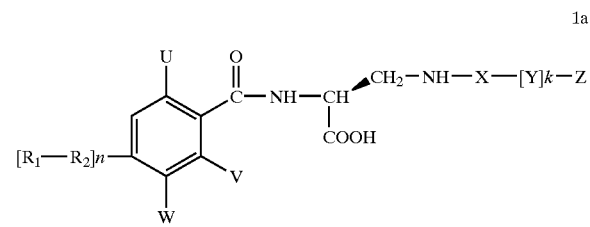

wherein $R_1$ is a group of the formula

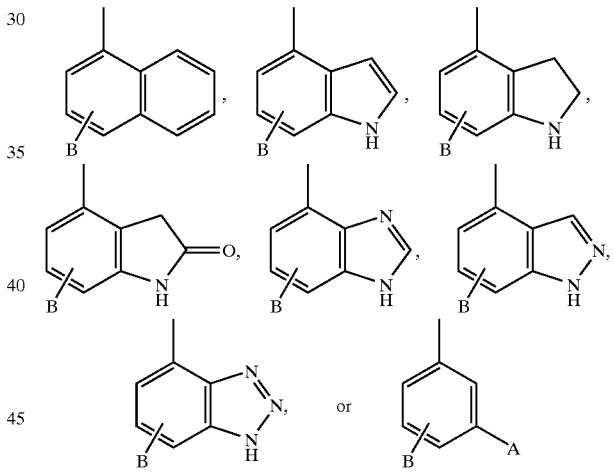

where A is hydrogen, hydroxy, amino, or halogen and B is amino, carboxy, hydrogen, hydroxy, cyano, trifluoromethyl, halogen, lower alkyl, or lower alkoxy;

$R_2$ is a group of the formula

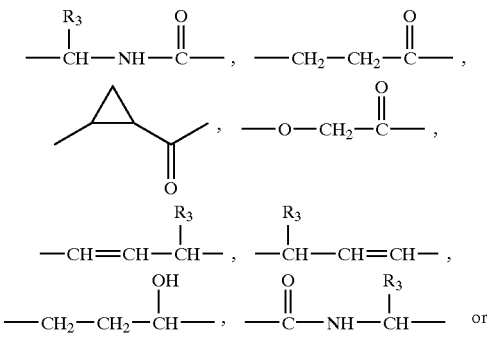

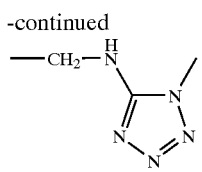

where R₃ is hydrogen, carboxy, or lower alkyl;

n is 0 or 1; U, V, and W are independently hydrogen, halogen, or lower alkyl provided U and V are not both hydrogen; X is carbonyl, phenyl-substituted loweralkylene, or sulfonyl; Y is lower alkylene which may be substituted by one or more of amino, substituted amino, loweralkyl, or cyclo lower alkyl, or Y is lower alkenylene or lower alkylenethio; k is 0 or 1; when k is 1: Z is hydrogen, lower alkylthio, —COOH, —CONH₂, amino, or when k is 0 or 1 Z is: 1-adamantyl, diphenylmethyl, 3-[[(5-chloropyridin-2-yl)amino]carbonyl]pyrazin-2-yl, and may also in addition be hydroxy, phenylmethoxy, 2-chloro-4-[[[(3-hydroxyphenyl)methyl]amino]carbonyl]phenyl,[2,6-dichlorophenyl)methoxy]phenyl, or Z is one of the following:

cycloalkyl or aryl containing 0 to 3 heteroatoms which may be the same or different, or a fused ring system containing two or three rings which rings are independently cycloalkyl or aryl containing 0 to 3 heteroatoms which may be the same or different, any of which rings may be unsubstituted, or substituted with at least one of:

halogen, cyano, amino, substituted amino, aminosulfonyl, nitro, oxo, hydroxy, aryl, aryloxy, unsubstituted lower alkyl, halogen-substituted lower alkyl, lower alkoxy-substituted lower alkyl, lower alkoxy, lower alkanesulfonyl, lower alkylthio, acetyl, aminocarbonyl, hydrazino, carboxy, alkoxycarbonyl, acetoxy, or also in addition with amino lower alkyl and pharmaceutically acceptable salts and esters thereof.

Also part of this invention is a compound of formula 1a or formula 1b or formula 1c or formula 1d or formula 1h or formula 1i or formula 3 where k is 1 and Z is hydrogen, lower alkylthio, —COOH, —CONH₂, amino, 1-adamantyl, diphenylmethyl, 3-[[(5-chloropyridin-2-yl)amino]carbonyl]pyrazin-2-yl, and may also in addition be hydroxy, phenylmethoxy, 2-chloro-4-[[[(3-hydroxyphenyl)methyl]amino]carbonyl]phenyl,[2,6-dichlorophenyl)methoxy]phenyl, or Z is one of the following:

cycloalkyl or aryl containing 0 to 3 heteroatoms which may be the same or different, or a fused ring system containing two or three rings which rings are independently cycloalkyl or aryl containing 0 to 3 heteroatoms which may be the same or different, any of which rings may be unsubstituted, or substituted with at least one of:

halogen, cyano, amino, substituted amino, aminosulfonyl, nitro, oxo, hydroxy, aryl, aryloxy, unsubstituted lower alkyl, halogen-substituted lower alkyl, lower alkoxy-substituted lower alkyl, lower alkoxy, lower alkanesulfonyl, lower alkylthio, acetyl, aminocarbonyl, hydrazino, carboxy, alkoxycarbonyl, acetoxy, or amino lower alkyl.

Another compound of this invention is a compound of formula 1a or formula 1b or formula 1c or formula 1d or formula 1h or formula 1i or formula 3 where k is 0 and Z is 1-adamantyl, diphenylmethyl, 3-[[(5-chloropyridin-2-yl) amino]carbonyl]pyrazin-2-yl, and may also in addition be hydroxy, phenylmethoxy, 2-chloro-4-[[[(3-hydroxyphenyl) methyl]amino]carbonyl]phenyl,[2,6-dichlorophenyl) methoxy]phenyl, or Z is one of the following:

cycloalkyl or aryl containing 0 to 3 heteroatoms which may be the same or different, or a fused ring system containing two or three rings which rings are independently cycloalkyl or aryl containing 0 to 3 heteroatoms which may be the same or different, any of which rings may be unsubstituted, or substituted with at least one of:

halogen, cyano, amino, substituted amino, aminosulfonyl, nitro, oxo, hydroxy, aryl, aryloxy, unsubstituted lower alkyl, halogen-substituted lower alkyl, lower alkoxy-substituted lower alkyl, lower alkoxy, lower alkanesulfonyl, lower alkylthio, acetyl, aminocarbonyl, hydrazino, carboxy, alkoxycarbonyl, acetoxy, or amino lower alkyl.

By halogen in general is meant bromine, chlorine, fluorine and iodine. In the case of U, V, and W, the preferred halogens are bromine, chlorine, and fluorine.

When W is hydrogen, then U and V are symmetric in that U and V are equivalent positions, and the labels U and V can be used interchangeably. Therefore for purposes of this application, a compound where W is hydrogen, and U is a first substituent while V is a second substituent, is effectively the equivalent compound if V is identified as the first substituent and U is identified as the second substituent. For example a compound where U is chlorine and V is hydrogen is equivalent to a compound where V is chlorine and U is hydrogen. Therefore description of one such compound also describes its equivalent. This does not mean in general that U and V must be the same. In any compound of this invention, U and V are independent of each other and accordingly may be the same or different. Thus in the context of this application, the phrase "when U is chlorine or bromine and V is hydrogen" describes a compound which is equivalent to the compound described by the phrase "when one of U or V is chlorine or bromine and the other is hydrogen." (all other groups being identical).

By lower alkyl is meant saturated hydrocarbon chains such as methyl, ethyl, propyl and the like. The length of the chains is preferably from 1 to 10 carbons and more preferably from 1 to 4 carbons, inclusive of any branching carbons as defined in this paragraph. A lower alkyl group of this invention may be branched, which means a lower alkyl group that contains a carbon which is bonded to at least three other carbons, such as isobutyl or 2-ethyl-4-methylpentyl. A lower alkyl substituent may also be unbranched, which means that it does not contain any carbons bonded to more than two other carbons. Examples of various lower alkyl groups are methyl, ethyl, n-propyl, isopropyl, n-butyl, sec.butyl, isobutyl, tert.butyl, n-pentyl, n-hexyl. Lower alkyl groups may be substituted with another group, preferably halogen, such asfluorine, or lower alkoxy as defined below. Examples of substituted lower alkyl groups include 2-hydroxyethyl, 2-methoxypropyl, 3-oxobutyl, cyanomethyl, trifluoromethyl, 2-nitropropyl, benzyl, including p-chlorobenzyl and p-methoxybenzyl, and 2-phenylethyl.

By lower alkoxy is meant a lower alkyl as defined above which may be branched or unbranched as also defined above and which is bonded by an oxygen to another group (i.e. alkyl ethers). Examples are methoxy, ethoxy, n-propoxy, isopropoxy, n-butoxy, tert-butoxy and the like. Such groups may be substituted, preferably by halogen or lower alkyl as defined above.

By lower alkylene is meant a hydrocarbon chain which links together two other groups, i.e. is bonded to another group at either end, for example methylene, ethylene, butylene and the like. Such a substituent is preferably from 1 to 10 carbons and more preferably from 1 to 5 carbons. Such groups may be substituted, preferably with an amino, acetylamino (a lower alkylcarbonyl group bonded via a nitrogen atom), or cyclo loweralkyl group. By the latter is meant a saturated hydrocarbon ring, preferably with a total of 3 to 10 methylenes (inclusive of the attachment carbons), more preferably 3 to 6. Examples are cyclopropyl, cyclobutyl, cyclohexyl.

By lower alkenylene is meant a hydrocarbon chain containing one double bond and which links together two other groups, i.e. is bonded to another group at either end. Such a substituent is preferably from 1 to 10 carbons and more preferably from 2 to 6 carbons inclusive of branching carbons, and may be branched or unbranched as defined above with regard to alkyl groups. Examples are —CH=CH—, —CH=CH—CH$_2$—CH$_2$—CH$_2$—, —CH$_2$—CH$_2$—CH=CH—CH$_2$—.

By lower alkylthio is meant a lower alkyl group bonded through a divalent sulfur atom, for example, a methylmercapto or an isopropylmercapto group. By lower alkylenethio is meant such a group which is bonded at each end.

By cycloalkyl containing 0 to 3 heteroatoms which may be the same or different is meant a nonaromatic ring with 3–10, preferably 3–6 ring atoms. For purposes of this application cycloalkyl includes heterocycloalkyl. Thus as defined above such a ring may be made up of only hydrocarbon residues (i.e. methylene groups), or may include one or more heteroatoms, preferably nitrogen, sulfur, or oxygen singly or in any combination, in place of one or more methylenes. Such a ring may contain one double bond. Such rings may be unsubstituted or may be substituted with at least one of various possible substituents. By "at least one of" is meant that the ring may be substituted by one of the possible substituents, or by more than one of the same substituent, or by any combination of the various possible substituents. Preferably substitution is on a carbon and not on a heteroatom. Examples of such rings are cyclohexyl, ethylcyclopentyl, piperidinyl, pyrrolidinyl, morpholinyl and the like. When specific rings such as cyclohexyl and the like are referred to, unless otherwise indicated these rings are unsubstituted. Thus cyclohexyl means "unsubstituted cyclohexyl", while substituted cyclohexyl means cyclohexyl with one or more substituents.

By aryl containing 0 to 3 heteroatoms which may be the same or different is meant an aromatic ring with 5–6 ring atoms. For purposes of this definition, aryl includes heteroaryl. Thus as defined above such a ring may be made up only of carbon, or may include one or more heteroatoms, preferably nitrogen, sulfur, or oxygen singly or in any combination, in place of one or more of the carbons. Such rings may be unsubstituted or substituted as described above for cycloalkyls. Examples of such rings are phenyl, thiophene, methylthiophene, pyridine, m- or o-nitrophenyl, p-tolyl, m- or p-methoxyphenyl, 3,4-dimethoxyphenyl, p-chlorophenyl, p-cyanophenyl, 3-methylthienyl, 2-methyl-5-nitrophenyl, 2,6-dichlorophenyl, perfluorophenyl and the like. When specific rings such as phenyl, thiophene, pyridine, and the like are referred to, unless otherwise indicated these rings are unsubstituted. Thus "thiophene" means unsubstituted thiophene while substituted thiophene means thiophene with one or more substituents.

By aryl-loweralkyl is meant an aryl ring with a lower alkyl substituent, which is attached through the substituent to another group. By aryl-substituted lower alkylene is meant a lower alkylene group as defined above with an aryl substituent. In this context aryl means an aromatic ring with five or six ring atoms, preferably all are carbon atoms and the ring is preferably not otherwise substituted. By phenyl-loweralkyl is meant a phenyl ring with a lower alkyl substituent, which is attached through the substituent to another group. Examples are benzyl (phenylmethyl), phenylethyl, and the like. By phenyl-substituted lower alkylene is meant a lower alkylene group as defined above with a phenyl substituent.

By fused ring system containing two or three rings which are independently cycloalkyl or aryl as defined above is meant two or three fused rings, in any combination of aromatic and nonaromatic which may be unsubstituted, or substituted with halogen, cyano, amino, substituted amino, aminosulfonyl, nitro, oxo, hydroxy, aryl, aryloxy, unsubstituted lower alkyl, halogen-substituted lower alkyl, lower alkoxy-substituted lower alkyl, lower alkoxy, lower alkanesulfonyl, lower alkylthio, acetyl, aminocarbonyl, hydrazino, carboxy, alkoxycarbonyl, or acetoxy as defined above. Examples of such rings are naphthalene, indole, indoline, benzimidazole, oxindole, benzotriazole, and the like.

By amino lower alkyl is meant an amino group which is substituted by a lower alkyl group, which is bonded to another group by a carbon of the lower alkyl group. This is distinct from substituted amino, which is bonded to another group by the nitrogen.

By substituted amino is meant an amino group which is mono- or di-substituted with another group, preferably a lower alkyl (e.g., methyl) or a lower acyl group (e.g., acetyl).

By lower acyl is meant a group derived from a lower alkyl carboxylic acid or an aryl carboxylic acid. Examples are acetyl, propionyl, butyryl, pivaloyl, benzoyl, and the like.

By lower alkylamino is meant an amino group which is substituted by a lower alkyl group. Examples are methylamino, ethylamino, and the like.

By aryloxy is meant an aryl group which is bonded via an oxygen atom to another group. An example is phenoxy.

By lower alkanesulfonyl is meant an alkyl group attached to a sulfonyl group, which is attached to another group, such as methylsulfonyl and the like.

By lower alkoxycarbonyl is meant a lower alkoxy group bonded via a carbonyl group to another group. Examples of lower alkoxycarbonyl groups are methoxycarbonyl, ethoxycarbonyl, t-butoxycarbonyl and the like.

By "substituted with at least one of" followed by a list of several possible substituents is meant substitution by one or more of one type of substituent or by a combination of more than one type of substituent. For example substituted by at least one of halogen, methyl, or hydroxy includes substitution by two bromines, or one chlorine, one bromine, and one iodine, or one chlorine and one methyl, or a fluorine, a methyl, and a hydroxy, or two hydroxys, or two methyls and a hydroxy, or one methyl, or one bromine, and so on. The selection of available substituents in any such claim is limited to the specific substituents listed in that claim. Thus a claim directed to a group substituted by at least one of methyl or hydroxy would not include groups substituted, for example, with a methyl and a bromine or a methyl, a hydroxy, and a nitro. Also, substitutions are understood to be only on those atoms which are covalently able to accept substituents. For example, substitution would not occur on the N of a pyridine or at a position of fusion between two aromatic rings.

Pharmaceutically acceptable salts and esters are well known in the art and can be made by conventional methods taking into account the chemical nature of the compound. Examples of pharmaceutically acceptable salts for acidic compounds are alkali metal or alkaline earth metals such as sodium, potassium, calcium, magnesium, basic amines or basic amino acids, ammonium or alkyl ammonium salts. Particularly desirable salts for compounds of this invention are sodium salts. The sodium salt of any compound of this invention is easily obtained from the acid by treatment with sodium hydroxide. Examples of such sodium salts are 3-benzoylamino-N-[2-chloro-4-[[[(3-hydroxyphenyl)methyl]amino]carbonyl]benzoyl]-L-alanine, sodium salt and N-[2-chloro-4-[[[(3-hydroxyphenyl)methyl]amino]carbonyl]benzoyl]-3-(thiophene-2-carbonyl)amino-L-alanine, sodium salt. For basic compounds, examples are salts of inorganic or organic acids such as hydrochloric, hydrobromic, sulfuric, nitric, phosphoric, citric, formic, fumaric, maleic, acetic, succinic, tartaric, methanesulfonic, and p-toluenesulfonic. Examples of pharmaceutically acceptable esters include unbranched lower alkyl esters such as methyl, ethyl, n-propyl and the like.

This invention includes the following compounds:

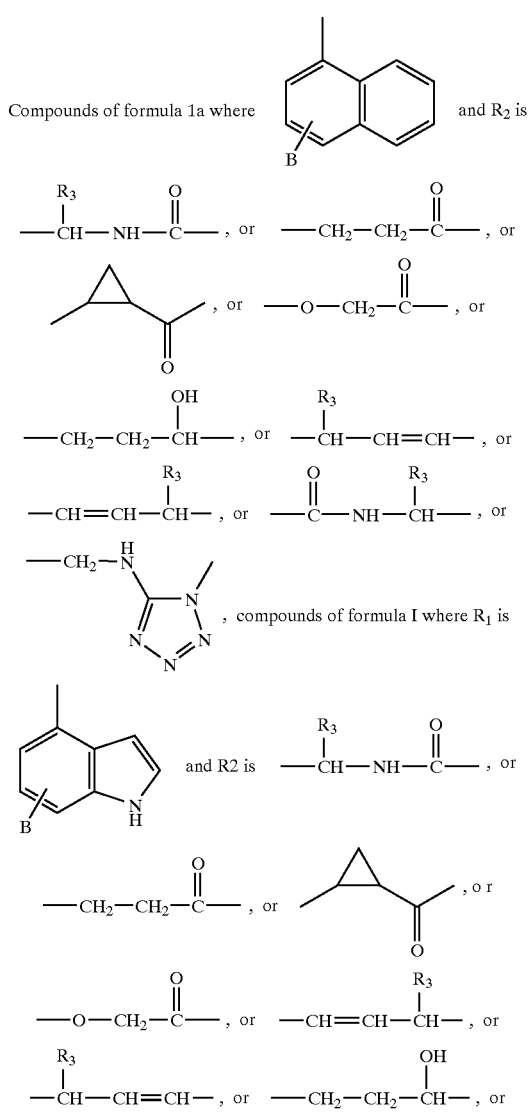

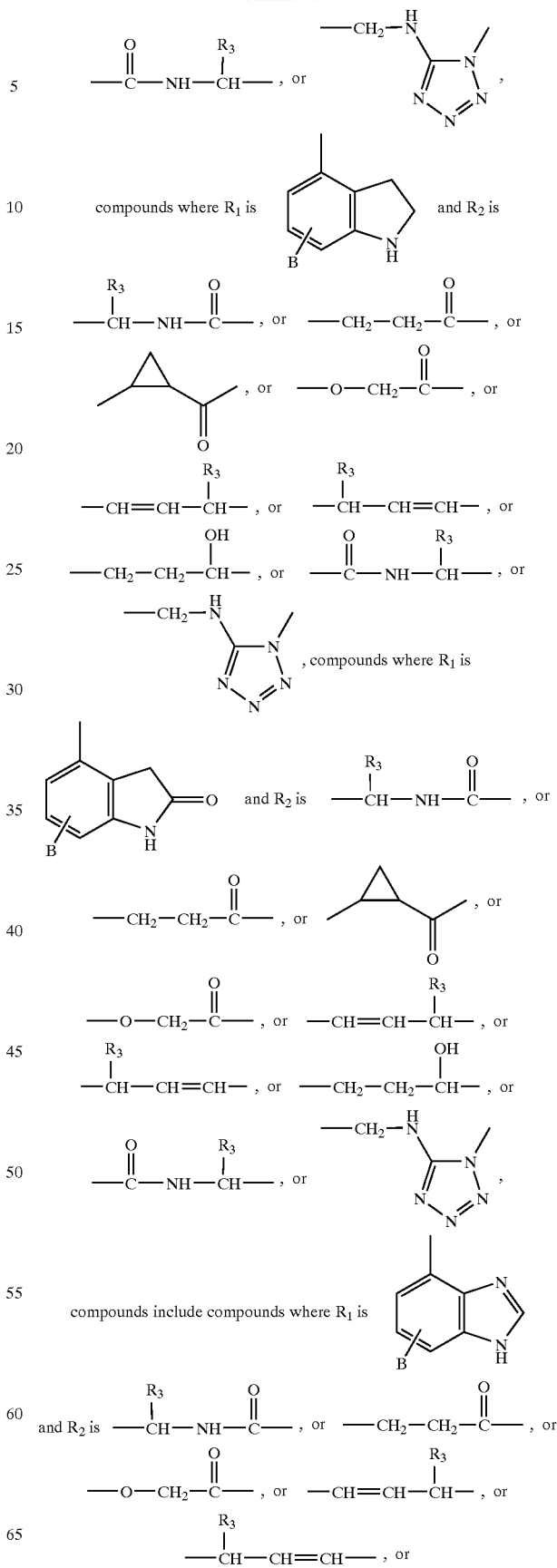

-continued

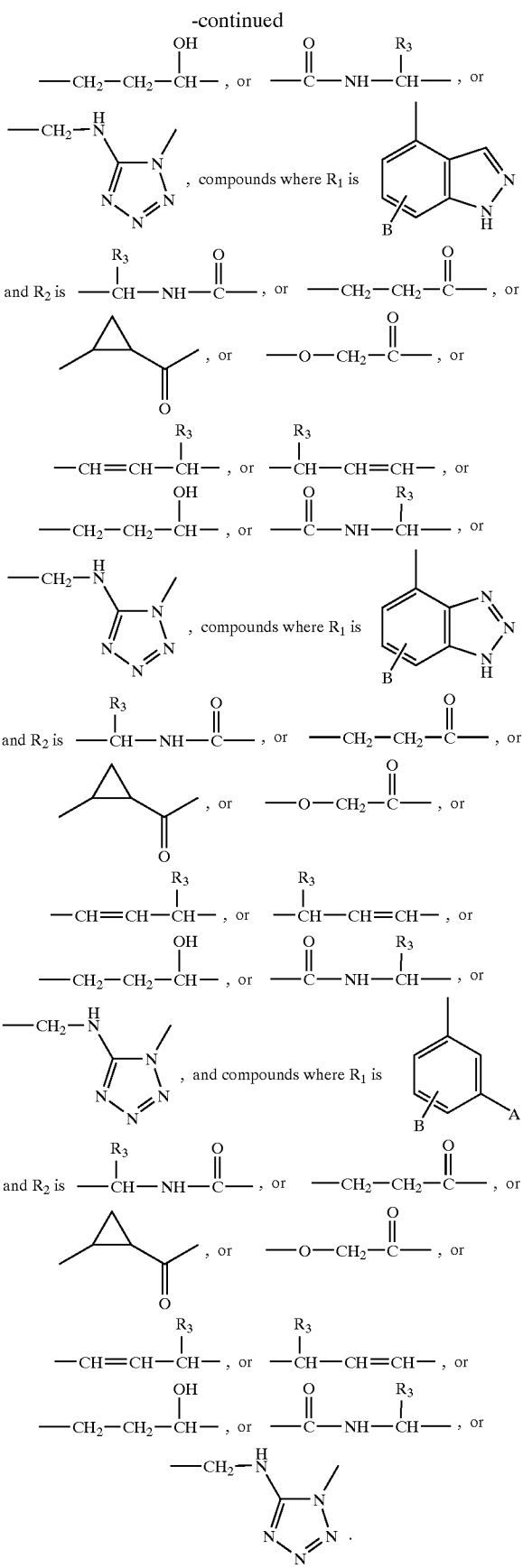

A preferred compound of formula 1a has formula 1d:

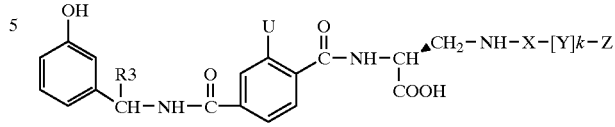

wherein U is chlorine, bromine, fluorine, or methyl and $R_3$, X, :Y, K, and Z are as in formula 1a. Such a compound is 3-(11-aminoundecanoyl)amino-N-[2-chloro-4-[[[(3-hydroxyphenyl)methyl]amino]carbonyl]benzoyl]-L-alanine.

Also preferred is such a compound where X is carbonyl and k is 0. More preferred is such a compound where $R_3$ is hydrogen; k is 0 or Y is methylene; X is carbonyl; and Z is thiophene or phenyl which may be unsubstituted or substituted by at least one of lower alkyl, lower alkoxy, hydroxy, halogen, carboxy, nitro, aminosulfonyl, cyano, or lower alkoxy carbonyl. The latter compound is particularly preferred when the thiophene or phenyl are substituted by at least one of methyl, methoxy, hydroxy, chlorine, bromine, fluorine, or nitro, especially when k is 0. Also preferred is a compound where R1 is a group of formula

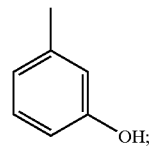

$R_2$ is a group of formula

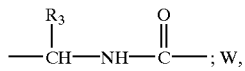

$R_3$ is hydrogen, one of U or V is chlorine and the other is hydrogen; and X is carbonyl. In a more preferred such compound, k is 0.

An especially preferred such compound has formula

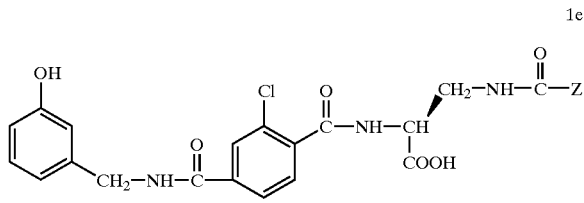

where Z is 1-adamantyl, diphenylmethyl, 3-[[(5-chloropyridin-2-yl)amino]carbonyl]pyrazin-2-yl, 2-chloro-4-[[[(3-hydroxyphenyl)methyl]amino]carbonyl]phenyl, [(2,6-dichlorophenyl)methoxy]phenyl, or Z is a ring or ring system which may be unsubstituted or substituted. Specifically, Z may be cycloalkyl or aryl containing 0 to 3 heteroatoms which may be the same or different, or a fused ring system containing two or three rings which rings are independently cycloalkyl or aryl containing 0 to 3 heteroatoms which may be the same or different. Any of these rings may be unsubstituted. If substituted, these rings may be substituted with at least one of:

halogen, cyano, amino, substituted amino, aminosulfonyl, nitro, oxo, hydroxy, aryl, aryloxy, unsubstituted lower alkyl, halogen-substituted lower alkyl, lower alkoxy-substituted lower alkyl, lower alkoxy, lower alkanesulfonyl, lower alkylthio, acetyl, aminocarbonyl, hydrazino, carboxy, lower alkoxycarbonyl, acetoxy, or aminomethyl.

Examples of such especially preferred compounds are

N-[2-chloro-4-[[[(3-hydroxyphenyl)methyl]amino]carbonyl]benzoyl]-3-(diphenylacetyl)amino-L-alanine;
3-(1-adamantylcarbonyl)amino-N-[2-chloro-4-[[[(3-hydroxyphenyl)methyl]amino]carbonyl]benzoyl]-L-alanine;
N-[2-chloro-4-[[[(3-hydroxyphenyl)methyl]amino]carbonyl]benzoyl]-3-[(2S)-5-oxotetrahydrofuran-2-carbonyl]amino-L-alanine;
N-[2-chloro-4-[[[(3-hydroxyphenyl)methyl]amino]carbonyl]benzoyl]-3-(1,4-dioxa-8-thiaspiro[4.5]decane-6-carbonyl)amino-L-alanine;
N-[2-chloro-4-[[[(3-hydroxyphenyl)methyl]amino]carbonyl]benzoyl]-3-(2-phenoxybenzoyl)amino-L-alanine;
N-[2-chloro-4-[[[(3-hydroxyphenyl)methyl]amino]carbonyl]benzoyl]-3-(furan-2-carbonyl)amino-L-alanine;
N-[2-chloro-4-[[[(3-hydroxyphenyl)methyl]amino]carbonyl]benzoyl]-3-(5-nitrofuran-2-carbonyl)amino-L-alanine;
N-[2-chloro-4-[[[(3-hydroxyphenyl)methyl]amino]carbonyl]benzoyl]-3-(5-bromofuran-2-carbonyl)amino-L-alanine;
N-[2-chloro-4-[[[(3-hydroxyphenyl)methyl]amino]carbonyl]benzoyl]-3-[(3,5-dimethylisoxazol-4-yl)carbonyl]amino-L-alanine;
N-[2-chloro-4-[[[(3-hydroxyphenyl)methyl]amino]carbonyl]benzoyl]-3-(piperidine-4-carbonyl)amino-L-alanine;
N-[2-chloro-4-[[[(3-hydroxyphenyl)methyl]amino]carbonyl]benzoyl]-3-(L-prolyl)amino-L-alanine;
N-[2-chloro-4-[[[(3-hydroxyphenyl)methyl]amino]carbonyl]benzoyl]-3-( 1,2,3-thiadiazol-4-carbonyl)amino-L-alanine;
N-[2-chloro-4-[[[(3-hydroxyphenyl)methyl]amino]carbonyl]benzoyl]-3-(4-methyl-1,2,3-thiadiazol-5-carbonyl)amino-L-alanine;
N-[2-chloro-4-[[[(3-hydroxyphenyl)methyl]amino]carbonyl]benzoyl]-3-(isoxazole-5-carbonyl)amino-L-alanine;
N-[2-chloro-4-[[[(3-hydroxyphenyl)methyl]amino]carbonyl]benzoyl]-3-(4-chloro-2-nitrobenzoyl)amino-L-alanine;
N-[2-chloro-4-[[[(3-hydroxyphenyl)methyl]amino]carbonyl]benzoyl]-3-(2,4-dimethylthiazole-5-carbonyl)amino-L-alanine.
N-[2-chloro-4-[[[(3-hydroxyphenyl)methyl]amino]carbonyl]benzoyl]-3-[[2-chloro-4-[[[(3-hydroxyphenyl)methyl]amino]carbonyl]benzoyl]amino]-L-alanine;
N-[2-chloro-4-[[[(3-hydroxyphenyl)methyl]amino]carbonyl]benzoyl]-3-[[[(3S)-2,3,4,9-tetrahydro-1H-pyrido[3,4-b]indol-3-yl]carbonyl]amino]-L-alanine.

Examples of such especially preferred compounds where Z is cycloalkyl are:

N-[2-chloro-4-[[[(3-hydroxyphenyl)methyl]amino]carbonyl]benzoyl]-3-(cyclopropylcarbonyl)amino-L-alanine;
N-[2-chloro-4-[[[(3-hydroxyphenyl)methyl]amino]carbonyl]benzoyl]-3-[(2,2-dichloro-1-methylcyclopropyl)carbonyl]amino-L-alanine;
N-[2-chloro-4-[[[(3-hydroxyphenyl)methyl]amino]carbonyl]benzoyl]-3-[(1-phenylcyclopropyl)carbonyl]amino-L-alanine;
N-[2-chloro-4-[[[(3-hydroxyphenyl)methyl]amino]carbonyl]benzoyl]-3-(cyclobutylcarbonyl)amino-L-alanine;
N-[2-chloro-4-[[[(3-hydroxyphenyl)methyl]amino]carbonyl]benzoyl]-3-(cyclopentylcarbonyl)amino-L-alanine;
N-[2-chloro-4-[[[(3-hydroxyphenyl)methyl]amino]carbonyl]benzoyl]-3-[1-(2-methoxyethyl)cyclopentylcarbonyl]amino-L-alanine;
N-[2-chloro-4-[[[(3-hydroxyphenyl)methyl]amino]carbonyl]benzoyl]-3-[(1-phenylcyclopentyl)carbonyl]amino-L-alanine;
N-[2-chloro-4-[[[(3-hydroxyphenyl)methyl]amino]carbonyl]benzoyl]-3-(cyclohexylcarbonyl)amino-L-alanine;
N-[2-chloro-4-[[[(3-hydroxyphenyl)methyl]amino]carbonyl]benzoyl]-3-(1-methylcyclohexylcarbonyl)amino-L-alanine;
N-[2-chloro-4-[[[(3-hydroxyphenyl)methyl]amino]carbonyl]benzoyl]-3-[1-aminocyclopentyl)carbonyl]amino-L-alanine;
N-[2-chloro-4-[[[(3-hydroxyphenyl)methyl]amino]carbonyl]benzoyl]-3-[cis-4-aminocyclohexyl)carbonyl]amino-L-alanine;
N-[2-chloro-4-[[[(3-hydroxyphenyl)methyl]amino]carbonyl]benzoyl]-3-[trans-6-amino-3-cyclohexene-1-carbonyl]amino-L-alanine;
3-[[trans-4-(aminomethyl)cyclohexyl]carbonyl]amino-N-[2-chloro-4-[[[(3-hydroxyphenyl)methyl]amino]carbonyl]benzoyl]-L-alanine;
3-[(1-aminocyclohexyl)carbonyl]amino-N-[2-chloro-4-[[[(3-hydroxyphenyl)methyl]amino]carbonyl]benzoyl]-L-alanine;
3-[(3-aminocyclohexyl)carbonyl]amino-N-[2-chloro-4-[[[(3-hydroxyphenyl)methyl]amino]carbonyl]benzoyl]-L-alanine.

Another preferred compound of this invention is a compound of formula 1e wherein Z is thiophene, or Z is phenyl, or Z is thiophene substituted with at least one of halogen or methyl, or Z is phenyl substituted with at least one of halogen, hydroxy, cyano, lower alkyl, lower alkoxy, amino, substituted amino, aminocarbonyl, nitro, aminosulfonyl, acetoxy, or substituted lower alkyl, or Z is a five- or six-membered ring with 0 to 3 heteroatoms selected from O, N, and S which may be the same or different, which ring may be unsubstituted or substituted with hydroxy, or Z is a fused ring system containing at least one benzene ring and containing one or two other rings which are independently 5 or 6-membered cycloalkyl or aryl with 0 to 3 heteroatoms selected from O, N, and S which may be the same or different, any of which may be unsubstituted or substituted with at least one of lower alkoxy, halogen, oxo, or hydroxy.

Examples of such preferred compounds are:

3-(3-amino-5-nitrobenzoyl)amino-N-[2-chloro-4-[[[(3-hydroxyphenyl)methyl]amino]carbonyl]benzoyl]-L-alanine;
3-(3-bromo-5-nitrobenzoyl)amino-N-[2-chloro-4-[[[(3-hydroxyphenyl)methyl]amino]carbonyl]benzoyl]-L-alanine;
N-[2-chloro-4-[[[(3-hydroxyphenyl)methyl]amino]carbonyl]benzoyl]-3-(3-nitro-5-trifluoromethylbenzoyl)amino-L-alanine;

N-[2-chloro-4-[[[(3-hydroxyphenyl)methyl]amino]carbonyl]benzoyl]-3-(3-methyl-5-nitrobenzoyl)amino-L-alanine;
N-[2-chloro-4-[[[(3-hydroxyphenyl)methyl]amino]carbonyl]benzoyl]-3-(3-methyl-4-nitrobenzoyl)amino-L-alanine;
3-(4-amino-3-methylbenzoyl)amino-N-[2-chloro-4-[[[(3-hydroxyphenyl)methyl]amino]carbonyl]benzoyl]-L-alanine;
3-(4-bromo-3-methylbenzoyl)amino-N-[2-chloro-4-[[[(3-hydroxyphenyl)methyl]amino]carbonyl]benzoyl]-L-alanine;
N-[2-chloro-4-[[[(3-hydroxyphenyl)methyl]amino]carbonyl]benzoyl]-3-(3-methoxy-4-nitrobenzoyl)amino-L-alanine;
N-[2-chloro-4-[[[(3-hydroxyphenyl)methyl]amino]carbonyl]benzoyl]-3-(3-hydroxy-4-methoxybenzoyl)amino-L-alanine;
N-[2-chloro-4-[[[(3-hydroxyphenyl)methyl]amino]carbonyl]benzoyl]-3-(2-methyl-3-nitrobenzoyl)amino-L-alanine;
3-(1H-benzotriazole-5-carbonyl)amino-N-[2-chloro-4-[[[(3-hydroxyphenyl)methyl]amino]carbonyl]benzoyl]-L-alanine;
3-(3-aminocarbonylbenzoyl)amino-N-[2-chloro-4-[[[(3-hydroxyphenyl)methyl]amino]carbonyl]benzoyl]-L-alanine;
N-[2-chloro-4-[[[(3-hydroxyphenyl)methyl]amino]carbonyl]benzoyl]-3-(furan-3-carbonyl)amino-L-alanine;;
N-[2-chloro-4-[[[(3-hydroxyphenyl)methyl]amino]carbonyl]benzoyl]-3-(3-fluoro-5-trifluoromethylbenzoyl)amino-L-alanine;
N-[2-chloro-4-[[[(3-hydroxyphenyl)methyl]amino]carbonyl]benzoyl]-3-[(4R)-thiazolidine-4-carbonyl]amino-L-alanine;
N-[2-chloro-4-[[[(3-hydroxyphenyl)methyl]amino]carbonyl]benzoyl]-3-[(4R)-4-hydroxy-L-prolyl]amino-L-alanine;
N-[2-chloro-4-[[[(3-hydroxyphenyl)methyl]amino]carbonyl]benzoyl]-3-[2,3-dihydro-1H-indole-2-carbonyl]amino-L-alanine.

In the above described compound of formula 1e (e.g. the compounds defined two paragraphs above where Z is thiophene, phenyl, a five or six membered ring, etc.), it is especially preferred that Z is thiophene, (i.e. unsubstituted thiophene as defined above) or thiophene substituted with at least one of halogen or methyl (as defined above this usage means one halogen or one methyl or two or more halogen or two or more methyl or any combination of halogen and methyl. Examples of such compounds are:

N-[2-chloro-4-[[[(3-hydroxyphenyl)methyl]amino]carbonyl]benzoyl]-3-(thiophene-2-carbonyl)amino-L-alanine;
3-(3-bromothiophene-2-carbonyl)amino-N-[2-chloro-4-[[[(3-hydroxyphenyl)methyl]amino]carbonyl]benzoyl]-L-alanine;
3-(5-bromothiophene-2-carbonyl)amino-N-[2-chloro-4-[[[(3-hydroxyphenyl)methyl]amino]carbonyl]benzoyl]-L-alanine;
N-[2-chloro-4-[[[(3-hydroxyphenyl)methyl]amino]carbonyl]benzoyl]-3-[(3-chlorothiophene-2-carbonyl)]amino-L-alanine;
N-[2-chloro-4-[[[(3-hydroxyphenyl)methyl]amino]carbonyl]benzoyl]-3-[(5-chlorothiophene-2-carbonyl)]amino-L-alanine;
N-[2-chloro-4-[[[(3-hyroxyphenyl)methyl]amino]carbonyl]benzoyl]-3-[(4,5-dibromothiophene-2-carbonyl)]amino-L-alanine;
N-[2-chloro-4-[[[(3-hydroxyphenyl)methyl]amino]carbonyl]benzoyl]-3-[(3-methylthiophene-2-carbonyl)]amino-L-alanine;
N-[2-chloro-4-[[[(3-hydroxyphenyl)methyl]amino]carbonyl]benzoyl]-3-[(5-methylthiophene-2-carbonyl)]amino-L-alanine;
N-[2-chloro-4-[[[(3-hydroxyphenyl)methyl]amino]carbonyl]benzoyl]-3-[(thiophene-3-carbonyl)]amino-L-alanine).

In the above-described compounds of formula 1e, Z may be a five- or six-membered ring with one to three nitrogens, i.e. a heterocycle with one to three nitrogens included among the ring atoms (for example N-[2-chloro-4-[[[(3-hydroxyphenyl)methyl]amino]carbonyl]benzoyl]-3-(pyrrole-2-carbonyl)amino-L-alanine;
N-[2-chloro-4-[[[(3-hydroxyphenyl)methyl]amino]carbonyl]benzoyl]-3-[(5-nitropyrazole-3-carbonyl)]amino-L-alanine;
N-[2-chloro-4-[[[(3-hydroxyphenyl)methyl]amino]carbonyl]benzoyl]-3-[(pyridine-2-carbonyl)]amino-L-alanine;
N-[2-chloro-4-[[[(3-hydroxyphenyl)methyl]amino]carbonyl]benzoyl]-3-[(6-methylpyridine-2-carbonyl)]amino-L-alanine;
N-[2-chloro-4-[[[(3-hydroxyphenyl)methyl]amino]carbonyl]benzoyl]-3-[5-(3,4-dibromobutyl)pyridine-2-carbonyl]amino-L-alanine;
N-[2-chloro-4-[[[(3-hydroxyphenyl)methyl]amino]carbonyl]benzoyl]-3-[(pyridine-3-carbonyl)]amino-L-alanine;
N-[2-chloro-4-[[[(3-hydroxyphenyl)methyl]amino]carbonyl]benzoyl]-3-[(2-chloropyridine-3-carbonyl)]amino-L-alanine;
N-[2-chloro-4-[[[(3-hydroxyphenyl)methyl]amino]carbonyl]benzoyl]-3-[(6-chloropyridine-3-carbonyl)]amino-L-alanine;
N-[2-chloro-4-[[[(3-hydroxyphenyl)methyl]amino]carbonyl]benzoyl]-3-[(2,6-dimethoxypyridine-3-carbonyl)]amino-L-alanine;
N-[2-chloro-4-[[[(3-hydroxyphenyl)methyl]amino]carbonyl]benzoyl]-3-[(2-hydroxypyridine-3-carbonyl)]amino-L-alanine;
N-[2-chloro-4-[[[(3-hydroxyphenyl) methyl]amino]carbonyl]benzoyl]-3-[(pyrazine-2-carbonyl)]amino-L-alanine;
N-[2-chloro-4-[[[(3-hydroxyphenyl)methyl]amino]carbonyl]benzoyl]-3-[3-[[(5-chloro-2-pyridinyl)amino]carbonyl]pyrazine-2-carbonyl]amino-L-alanine;
N-[2-chloro-4-[[[(3-hydroxyphenyl)methyl]amino]carbonyl]benzoyl]-3-[(2,4-dihydroxypyrimidine-5-carbonyl)]amino-L-alanine;
N-[2-chloro-4-[[[(3-hydroxyphenyl)methyl]amino]carbonyl]benzoyl]-3-[(2,4-dihydroxypyrimidine-6-carbonyl)]amino-L-alanine).

In the above-described compounds of formula 1e, Z may be phenyl (i.e. unsubstituted phenyl as defined above) or phenyl substituted with at least one of hydroxy, cyano, lower alkyl or substituted lower alkyl (for example 3-benzoylamino-N-[2-chloro-4-[[[(3-hydroxyphenyl)methyl]amino]carbonyl]benzoyl]-L-alanine;

N-[2-chloro-4-[[[(3-hydroxyphenyl)methyl]amino]
carbonyl]benzoyl]-3-(3-cyanobenzoyl)amino-L-alanine;
N-[2-chloro-4-[[[(3-hydroxyphenyl)methyl]amino]
carbonyl]benzoyl]-3-(3-hydroxybenzoyl)amino-L-
alanine;
N-[2-chloro-4-[[[(3-hydroxyphenyl)methyl]amino]
carbonyl]benzoyl]-3-(2-methylbenzoyl)amino-L-alanine;
N-[2-chloro-4-[[[(3-hydroxyphenyl)methyl]amino]
carbonyl]benzoyl]-3-(3-methylbenzoyl)amino-L-alanine;
N-[2-chloro-4-[[[(3-hydroxyphenyl)methyl]amino]
carbonyl]benzoyl]-3-(4-methylbenzoyl)amino-L-alanine;
N-[2-chloro-4-[[[(3-hydroxyphenyl)methyl]amino]
carbonyl]benzoyl]-3-[3-(trifluoromethyl)benzoyl]amino-
L-alanine);
N-[2-chloro-4-[[[(3-hydroxyphenyl)methyl]amino]
carbonyl]benzoyl]-3-(3,5-dimethylbenzoyl)amino-L-
alanine;
N-[2-chloro-4-[[[(3-hydroxyphenyl)methyl]amino]
carbonyl]benzoyl]-3-(3,4-dimethylbenzoyl)amino-L-
alanine;
N-[2-chloro-4-[[[(3-hydroxyphenyl)methyl]amino]
carbonyl]benzoyl]-3-(3-hydroxy-4-methylbenzoyl)
amino-L-alanine;
N-[2-chloro-4-[[[(3-hydroxyphenyl)methyl]amino]
carbonyl]benzoyl]-3-(2-hydroxy-4-methylbenzoyl)
amino-L-alanine.

In the above-described compounds of formula 1e, Z may be phenyl substituted with at least one hydroxy. Examples of such especially preferred compounds are N-[2-chloro-4-[[[(3-hydroxyphenyl)methyl]amino]
carbonyl]benzoyl]-3-(3-hydroxybenzoyl)amino-L-
alanine;
N-[2-chloro-4-[[[(3-hydroxyphenyl)methyl]amino]
carbonyl]benzoyl]-3-(3,5-dihydroxybenzoyl)amino-L-
alanine.

Z may be phenyl substituted with at least one of lower alkoxy, lower alkoxycarbonyl, —O—C(O)—CH$_3$, or —C(O)—O—CH$_3$ (for example N-[2-chloro-4-[[[(3-hydroxyphenyl)methyl]amino]
carbonyl]benzoyl]-3-(3-methoxybenzoyl)amino-L-
alanine;
3-(2-acetoxybenzoyl)amino-N-[2-chloro-4-[[[(3-
hydroxyphenyl)methyl]amino]carbonyl]benzoyl]-L-
alanine;
N-[2-chloro-4-[[[(3-hydroxyphenyl)methyl]amino]
carbonyl]benzoyl]-3-(4-ethoxybenzoyl)amino-L-alanine;
N-[2-chloro-4-[[[(3-hydroxyphenyl)methyl]amino]
carbonyl]benzoyl]-3-(2-methoxybenzoyl)amino-L-
alanine;
N-[2-chloro-4-[[[(3-hydroxyphenyl)methyl]amino]
carbonyl]benzoyl]-3-(4-methoxybenzoyl)amino-L-
alanine;
N-[2-chloro-4-[[[(3-hydroxyphenyl)methyl]amino]
carbonyl]benzoyl]-3-[3-(methoxycarbonyl)benzoyl]
amino-L-alanine;
N-[2-chloro-4-[[[(3-hydroxyphenyl)methyl]amino]
carbonyl]benzoyl]-3-(4-pentyloxybenzoyl)amino-L-
alanine;
N-[2-chloro-4-[[[(3-hydroxyphenyl)methyl]amino]
carbonyl]benzoyl]-3-(3,4,5-trimethoxybenzoyl)amino-L-
alanine;
N-[2-chloro-4-[[[(3-hydroxyphenyl)-methyl]amino]
carbonyl]benzoyl]-3-(3,5-dimethoxybenzoyl)amino-L-
alanine;
N-[2-chloro-4-[[[(3-hydroxyphenyl)methyl]amino]
carbonyl]benzoyl]-3-(3,4-dimethoxybenzoyl)amino-L-
alanine).

In the above-described compounds of formula 1e, Z may be phenyl substituted with at least one halogen (for example 3-(2-bromobenzoyl)amino-N-[2-chloro-4-[[[(3-
hydroxyphenyl)methyl]amino]-carbonyl]benzoyl]-L-
alanine;
3-(3-bromobenzoyl)amino-N-[2-chloro-4-[[[(3-
hydroxyphenyl)methyl]amino]carbonyl]benzoyl]-L-
alanine;
3-(2-chlorobenzoyl)amino-N-[2-chloro-4-[[[(3-
hydroxyphenyl)methyl]amino]carbonyl]benzoyl]-L-
alanine;
3-(3-chlorobenzoyl)amino-N-[2-chloro-4-[[[(3-
hydroxyphenyl)methyl]amino]carbonyl]benzoyl]-L-
alanine;
3-(4-chlorobenzoyl)amino-N-[2-chloro-4-[[[(3-
hydroxyphenyl)methyl]amino]carbonyl]benzoyl]-L-
alanine;
N-[2-chloro-4-[[[(3-hydroxyphenyl)methyl]amino]
carbonyl]benzoyl]-3-(3-fluorobenzoyl)amino-L-alanine;
N-[2-chloro-4-[[[(3-hydroxyphenyl)methyl]amino]
carbonyl]benzoyl]-3-(3-iodobenzoyl)amino-L-alanine;
N-[2-chloro-4-[[[(3-hydroxyphenyl)methyl]amino]
carbonyl]benzoyl]-3-(3,5-difluorobenzoyl)amino-L-
alanine;
3-(3-chloro-5-fluorobenzoyl)amino-N-[2-chloro-4-[[[(3-
hydroxyphenyl)methyl]amino]carbonyl]benzoyl]-L-
alanine;
N-[2-chloro-4-[[[(3-hydroxyphenyl)methyl]amino]
carbonyl]benzoyl]-3-(3,5-dichlorobenzoyl)amino-L-
alanine;
N-[2-chloro-4-[[[(3-hydroxyphenyl)methyl]amino]
carbonyl]benzoyl]-3-(3,5-dibromobenzoyl)amino-L-
alanine);
N-[2-chloro-4-[[[(3-hydroxyphenyl)methyl]amino]
carbonyl]benzoyl]-3-(2,4,5-trifluorobenzoyl)amino-L-
alanine).

Or in the above-described compounds of formula 1e, Z may be phenyl substituted with at least one of amino, substituted amino, nitro, or aminosulfonyl (for example 3-(3-aminobenzoyl)amino-N-[2-chloro-4-[[[(3-
hydroxyphenyl)methyl]amino]carbonyl]-benzoyl]-L-
alanine;
3-(4-aminosulfonylbenzoyl)amino-N-[2-chloro-4-[[[(3-
hydroxyphenyl)methyl]amino]carbonyl]benzoyl]-L-
alanine;
N-[2-chloro-4-[[[(3-hydroxyphenyl)methyl]amino]
carbonyl]benzoyl]-3-(3-dimethylaminobenzoyl)amino-L-
alanine;
N-[2-chloro-4-[[[(3-hydroxyphenyl)methyl]amino]
carbonyl]benzoyl]-3-(4-dimethylaminobenzoyl)amino-L-
alanine;
N-[2-chloro-4-[[[(3-hydroxyphenyl)methyl]-amino]
carbonyl]benzoyl]-3-(3,5-dinitrobenzoyl)amino-L-
alanine;
N-[2-chloro-4-[[[(3-hydroxyphenyl)methyl]amino]
carbonyl]benzoyl]-3-(2-nitrobenzoyl)amino-L-alanine;
N-[2-chloro-4-[[[(3-hydroxyphenyl)methyl]amino]
carbonyl]benzoyl]-3-(3-nitrobenzoyl)amino-L-alanine;
N-[2-chloro-4-[[[(3-hydroxyphenyl)methyl]amino]
carbonyl]benzoyl]-3-(4-nitrobenzoyl)amino-L-alanine), in the above-described compounds of formula 1e Z may be a fused ring system containing at least one benzene ring and containing one or two other rings which are independently 5 or 6-membered cycloalkyl or aryl with 0 to 2 heteroatoms selected from O, N, and S which may be the same or different, any of which may be unsubstituted or substituted with at least one of lower alkoxy, halogen, oxo, or hydroxy (for example N-[2-chloro-4-[[[(3-hydroxyphenyl)methyl]amino] carbonyl]benzoyl]-3-[(1,2,3,4-tetrahydronaphthalene-2-carbonyl)]amino-L-alanine;

N-[2-chloro-4-[[[(3-hydroxyphenyl)methyl]amino] carbonyl]benzoyl]-3-[(DL-7-methoxy-1,2,3,4,4αβ,9,10,10αβ-octahydro-2β-phenanthrenecarbonyl)]amino-L-alanine;

3-(6-bromo-2-oxo-1,2,3,4-tetrahydroquinoline-4-carbonyl)amino-N-[2-chloro-4-[[[(3-hydroxyphenyl)methyl]amino]carbonyl]benzoyl]-L-alanine;

N-[2-chloro-4-[[[(3-hydroxyphenyl)methyl]amino]carbonyl]benzoyl]-3-(benzofuran-2-carbonyl)amino-L-alanine;

N-[2-chloro-4-[[[(3-hydroxyphenyl)methyl]amino]carbonyl]benzoyl]-3-(benzothiophene-2-carbonyl)amino-L-alanine;

N-[2-chloro-4-[[[(3-hydroxyphenyl)methyl]amino]carbonyl]benzoyl]-3-(benzimidazole-5-carbonyl)amino-L-alanine;

N-[2-chloro-4-[[[(3-hydroxyphenyl)methyl]amino]carbonyl]benzoyl]-3-(benzothiazole-6-carbonyl)amino-L-alanine;

N-[2-chloro-4-[[[(3-hydroxyphenyl)methyl]amino]carbonyl]benzoyl]-3-(naphthalene-1-carbonyl)amino-L-alanine;

N-[2-chloro-4-[[[(3-hydroxyphenyl)methyl]amino]carbonyl]benzoyl]-3-(naphthalene-2-carbonyl)amino-L-alanine;

N-[2-chloro-4-[[[(3-hydroxyphenyl)methyl]amino]carbonyl]benzoyl]-3-(isoquinoline-1-carbonyl)amino-L-alanine;

N-[2-chloro-4-[[[(3-hydroxyphenyl)methyl]amino]carbonyl]benzoyl]-3-(quinoline-2-carbonyl)amino-L-alanine;

N-[2-chloro-4-[[[(3-hydroxyphenyl)methyl]amino]carbonyl]benzoyl]-3-(4-methoxyquinoline-2-carbonyl)amino-L-alanine;

N-[2-chloro-4-[[[(3-hydroxyphenyl)methyl]amino]carbonyl]benzoyl]-3-(quinoline-3-carbonyl)amino-L-alanine;

N-[2-chloro-4-[[[(3-hydroxyphenyl)methyl]amino]carbonyl]benzoyl]-3-[(quinoline-4-carbonyl)]amino-L-alanine;

N-[2-chloro-4-[[[(3-hydroxyphenyl)methyl]amino]carbonyl]benzoyl]-3-[(cinnoline-4-carbonyl)]amino-L-alanine;

N-[2-chloro-4-[[[(3-hydroxyphenyl)methyl]amino]carbonyl]benzoyl]-3-(2-hydroxyquinoxaline-3-carbonyl)amino-L-alanine;

N-[2-chloro-4-[[[(3-hydroxyphenyl)methyl]amino]carbonyl]benzoyl]-3-(4-oxo-4H-1-benzopyran-2-carbonyl)amino-L-alanine;

N-[2-chloro-4-[[[(3-hydroxyphenyl)methyl]amino]carbonyl]benzoyl]-3-(2-oxo-2H-1-benzopyran-3-carbonyl)amino-L-alanine;

3-(anthracene-9-carbonyl)amino-N-[2-chloro-4-[[[(3-hydroxyphenyl)methyl]amino]carbonyl]benzoyl]-L-alanine;

N-[2-chloro-4-[[[(3-hydroxyphenyl)methyl]amino]carbonyl]benzoyl]-3-(1,2,3,4-tetrahydroacridine-9-carbonyl)amino-L-alanine;

N-[2-chloro-4-[[[(3-hydroxyphenyl)methyl]amino]carbonyl]benzoyl]-3-(2-methoxy-11-oxo-11H-pyrido[2,1]quinazoline-8-carbonyl)amino-L-alanine;

N-[2-chloro-4-[[[(3-hydroxyphenyl)methyl]amino]carbonyl]benzoyl]-3-(9-oxo-9H-thioxanthene-3-carbonyl)amino-L-alanine.

Another preferred compound of this invention is a compound of formula 1d which has formula

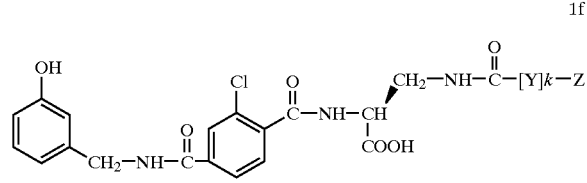

1f where Y is lower alkylene which may be substituted with one or more of amino, substituted amino, loweralkyl, or cyclo lower alkyl, or Y is lower alkenylene or lower alkylenethio; k is 1; Z is hydrogen, lower alkylthio, —COOH, —CONH2, amino, 1-adamantyl, diphenylmethyl, 3-[[(5-chloropyridin-2-yl)amino]carbonyl]pyrazin-2-yl, 2-chloro-4-[[[(3-hydroxyphenyl)methyl]amino]carbonyl]phenyl, [(2,6-dichlorophenyl)methoxy]phenyl, phenylmethoxy, hydroxy or Z is one of the following: cycloalkyl or aryl containing 0 to 3 heteroatoms which may be the same or different, or a fused ring system containing two or three rings which rings are independently cycloalkyl or aryl containing 0 to 3 heteroatoms which may be the same or different, any of which rings may be unsubstituted, or substituted with at least one of: halogen, cyano, amino, substituted amino, aminosulfonyl, nitro, oxo, hydroxy, aryl, aryloxy, unsubstituted lower alkyl, halogen-substituted lower alkyl, lower alkoxy-substituted lower alkyl.

In a compound of formula 1f, Y may be methylene. (In other words, the compound of formula 1a where $R_1$ is a group of formula

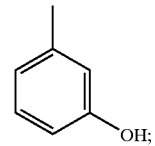

$R_2$ is a group of formula

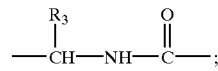

W and $R_3$ are hydrogen, one of U or V is chlorine and the other is hydrogen; and X is carbonyl and Y is methylene.

Examples of such compounds are:

3-acetylamino-N-[2-chloro-4-[[[(3-hydroxyphenyl)methyl]amino]carbonyl]benzoyl]-L-alanine;

N-[2-chloro-4-[[[(3-hydroxyphenyl)methyl]amino]carbonyl]benzoyl]-3-(cyclopentylacetyl)amino-L-alanine;

N-[2-chloro-4-[[[(3-hydroxyphenyl)methyl]amino]carbonyl]benzoyl]-3-(cyclohexylacetyl)amino-L-alanine;

N-[2-chloro-4-[[[(3-hydroxyphenyl)methyl]amino]carbonyl]benzoyl]-3-(phenylacetyl)amino-L-alanine;
N-[2-chloro-4-[[[(3-hydroxyphenyl)methyl]amino]carbonyl]benzoyl]-3-(4-methoxyphenylacetyl)amino-L-alanine;
N-[2-chloro-4-[[[(3-hydroxyphenyl)methyl]amino]carbonyl]benzoyl]-3-(4-nitrophenylacetyl)amino-L-alanine;
N-[2-chloro-4-[[[(3-hydroxyphenyl)methyl]amino]carbonyl]benzoyl]-3-(3-trifluoromethylphenylacetyl)amino-L-alanine;
N-[2-chloro-4-[[[(3-hydroxyphenyl)methyl]amino]carbonyl]benzoyl]-3-(3,5-dinitrophenylacetyl)amino-L-alanine;
N-[2-chloro-4-[[[(3-hydroxyphenyl)methyl]amino]carbonyl]benzoyl]-3-(2-thienylacetyl)amino-L-alanine;
N-[2-chloro-4-[[[(3-hydroxyphenyl)methyl]amino]carbonyl]benzoyl]-3-(3-pyridylacetyl)amino-L-alanine;
N-[2-chloro-4-[[[(3-hydroxyphenyl)methyl]amino]carbonyl]benzoyl]-3-(2-naphthylacetyl)amino-L-alanine;
N-[2-chloro-4-[[[(3-hydroxyphenyl)methyl]amino]carbonyl]benzoyl]-3-(9H-fluoren-9-ylacetyl)amino-L-alanine;
3-[[(2S)-2-carboxy-2-[2-chloro-4-[(3-hydroxyphenyl)methyl]amino]carbonyl]benzoylamino]ethylaminocarbonyl]methyl]benzothiazol-3-ium salt);
N-[2-chloro-4-[[[(3-hydroxyphenyl)methyl]amino]carbonyl]benzoyl]-3-[3-amino-2-oxo-1(2H)-pyridineacetyl]amino-L-alanine;
3-(3-aminohexahydro-2-oxo-1H-azepine-1-acetyl)amino-N-[2-chloro-4-[[[(3-hydroxyphenyl)methyl]amino]carbonyl]benzoyl]-L-alanine;
3-(4-amino-1,3,4,5-tetrahydro-3-oxo-2H-2-benzazepine-2-acetyl)amino-N-[2-chloro-4-[[[(3-hydroxyphenyl)methyl]amino]carbonyl]benzoyl]-L-alanine.

Also part of this invention are compounds where Y is CH₂CH₂CH₂— in a compound of formula 1f, examples of which are 3-(4-aminobutanoyl)amino-N-[2-chloro-4-[[[(3-hydroxyphenyl)methyl]amino]carbonyl]benzoyl]-L-alanine; and N-[2-chloro-4-[[[(3-hydroxyphenyl)methyl]amino]carbonyl]benzoyl]-3-(4-carboxy-1-oxobutyl)amino-L-alanine).

This invention includes compounds of formula 1f where Y is —CH₂CH₂ or —C(CH₃)₂CH₂—, or —CH(CH₃)CH₂—, or —CH₂CH(CH₃)CH₂—, or —CH₂CH(CH₃)—, or

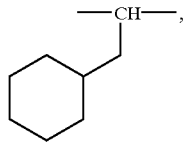

for example

N-[2-chloro-4-[[[(3-hydroxyphenyl)methyl]amino]carbonyl]benzoyl]-3-(3-phenylpropanoyl)amino-L-alanine;
N-[2-chloro-4-[[[(3-hydroxyphenyl)methyl]amino]carbonyl]benzoyl]-3-[(3,5-dimethylisoxazol-4-yl)propanoyl]amino-L-alanine;
N-[2-chloro-4-[[[(3-hydroxyphenyl)methyl]amino]carbonyl]benzoyl]-3-[3-(piperidin-1-yl)propanoyl]amino-L-alanine;
N-[2-chloro-4-[[[(3-hydroxyphenyl)methyl]amino]carbonyl]benzoyl]-3-[(3RS)-3-phenylbutanoyl]-L-alanine;
N-[2-chloro-4-[[[(3-hydroxyphenyl)methyl]amino]carbonyl]benzoyl]-3-[3-cyclohexyl-(2S)-2-(1-pyrrolyl)propanoyl)]amino-L-alanine;
N-[2-chloro-4-[[[(3-hydroxyphenyl)methyl]amino]carbonyl]benzoyl]-3-(trimethylacetyl)amino-L-alanine;
N-[2-chloro-4-[[[(3-hydroxyphenyl)methyl]amino]carbonyl]benzoyl]-3-(2-methylpropanoyl)amino-L-alanine;
N-[2-chloro-4-[[[(3-hydroxyphenyl)methyl]amino]carbonyl]benzoyl]-3-(3-methylbutanoyl)amino-L-alanine).

Also part of this invention are compounds of formula 1f where Y is —CH=CH—, —CH=CH—CH₂—, or —CH₂S— (for example N-[2-chloro-4-[[[(3-hydroxyphenyl)methyl]amino]carbonyl]benzoyl]-3-(4-pyridylthioacetyl)amino-L-alanine;

N-[2-chloro-4-[[[(3-hydroxyphenyl)methyl]amino]carbonyl]benzoyl]-3-[(pyrimidin-2-ylthio)acetyl]amino-L-alanine;
3-(but-2-enoyl)amino-N-[2-chloro-4-[[[(3-hydroxyphenyl)methyl]amino]carbonyl]benzoyl]-L-alanine;
N-[2-chloro-4-[[[(3-hydroxyphenyl)methyl]amino]carbonyl]benzoyl]-3-[3-(4-methoxyphenyl)prop-2-enoyl]amino-L-alanine;
N-[2-chloro-4-[[[(3-hydroxyphenyl)methyl]amino]carbonyl]benzoyl]-3-[3-(pyridin-3-yl)prop-2-enoyl]amino-L-alanine;
N-[2-chloro-4-[[[(3-hydroxyphenyl)methyl]amino]carbonyl]benzoyl]-3-[3-(2-thienyl)prop-2-enoyl]amino-L-alanine).

Also included are compounds of formula 1f where Y is lower alkylene substituted by an amino group. In this latter compound, Y may be

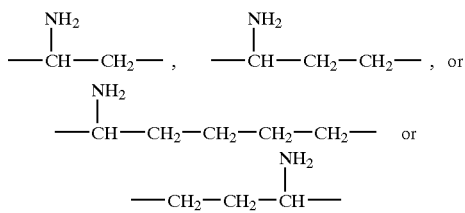

(for example

N-[2-chloro-4-[[[(3-hydroxyphenyl)methyl]amino]carbonyl]benzoyl]-3-(L-methionyl)amino-L-alanine;
N-[2-chloro-4-[[[(3-hydroxyphenyl)methyl]amino]carbonyl]benzoyl]-3-(L-lysyl)amino-L-alanine;
N-[2-chloro-4-[[[(3-hydroxyphenyl)methyl]amino]carbonyl]benzoyl]-3-(L-phenylalanyl)amino-L-alanine;
N-[2-chloro-4-[[[(3-hydroxyphenyl)methyl]amino]carbonyl]benzoyl]-3-(L-asparaginyl)amino-L-alanine;
N-[2-chloro-4-[[[(3-hydroxyphenyl)methyl]amino]carbonyl]benzoyl]-3-(L-tryptophyl)amino-L-alanine); or
N-[2-chloro-4-[[[(3-hydroxyphenyl)methyl]amino]carbonyl]benzoyl]-3-(L-γ-glutamyl)amino-L-alanine).

In this regard, compounds of formula 1f where Y is lower alkylene substituted by amino, lower alkyl, lower alkylamino, or trifluoromethyl are also part of this invention. Examples of such compounds are the above compounds, and also the compounds following:

N-[2-chloro-4-[[[(3-hydroxyphenyl)methyl]amino] carbonyl]benzoyl]-3-(N-methyl-L-alanyl)amino-L-alanine;
N-[2-chloro-4-[[[(3-hydroxyphenyl)methyl]amino] carbonyl]benzoyl]-3-(N-methylglycyl)amino-L-alanine;
N-[2-chloro-4-[[[(3-hydroxyphenyl)methyl]amino] carbonyl]benzoyl]-3-(L-leucyl)amino-L-alanine;
3-(2-amino-2-methylpropanoyl)amino-N-[2-chloro-4-[[[(3-hydroxyphenyl)methyl]amino]carbonyl]benzoyl]-L-alanine;
3-(3-amino-4,4,4-trifluorobutanoyl)amino-N-[2-chloro-4-[[[(3-hydroxyphenyl)methyl]amino]carbonyl]benzoyl]-L-alanine;
3-(3-amino-2-methylpropanoyl)amino-N-[2-chloro-4-[[[(3-hydroxyphenyl)methyl]amino]carbonyl]benzoyl]-L-alanine;
N-[2-chloro-4-[[[(3-hydroxyphenyl)methyl]amino] carbonyl]benzoyl]-3-[4-(2,6-dichlorophenyl)methoxy-L-phenylalanyl]amino-L-alanine;
N-[2-chloro-4-[[[(3-hydroxyphenyl)methyl]amino] carbonyl]benzoyl]-3-(L-seryl)amino-L-alanine;
N-[2-chloro-4-[[[(3-hydroxyphenyl)methyl]amino] carbonyl]benzoyl]-3-[O-(phenylmethyl)-L-seryl]amino-L-alanine;
N-[2-chloro-4-[[[(3-hydroxyphenyl)methyl]amino] carbonyl]benzoyl]-3-(L-phenylglycyl)amino-L-alanine;
N-[2-chloro-4-[[[(3-hydroxyphenyl)methyl]amino] carbonyl]benzoyl]-3-(4-nitro-L-phenylalanyl)amino-L-alanine;
N-[2-chloro-4-[[[(3-hydroxyphenyl)methyl]amino] carbonyl]benzoyl]-3-(4-fluoro-D,L-phenylalanyl)amino-L-alanine;
N-[2-chloro-4-[[[(3-hydroxyphenyl)methyl]amino] carbonyl]benzoyl]-3-(D-tyrosyl)amino-L-alanine;
3-(D-aspartyl)amino-N-[2-chloro-4-[[[(3-hydroxyphenyl)methyl]amino]carbonyl]benzoyl]-L-alanine;
N-[2-chloro-4-[[[(3-hydroxyphenyl)methyl]amino] carbonyl]benzoyl]-3-(D-tryptophyl)amino-L-alanine;
N-[2-chloro-4-[[[(3-hydroxyphenyl)methyl]amino] carbonyl]benzoyl]-3-(L-alanyl)amino-L-alanine;
N-[2-chloro-4-[[[(3-hydroxyphenyl)methyl]amino] carbonyl]benzoyl]-3-(D-alanyl)amino-L-alanine.

Also part of this invention is a compound of formula 1a where $R_1$ is a group of formula

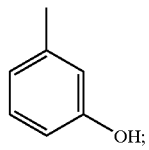

$R_2$ is a group of formula

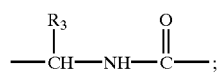

W is hydrogen and one of U or V is chlorine, fluorine, bromine, or methyl while the other is hydrogen, X is carbonyl; Y is —CH=CH— or k is 0; and Z is thiophene or phenyl, or thiophene or phenyl substituted by one or more of lower alkyl, lower alkoxy, hydroxy, halogen, carboxy, nitro, aminosulfonyl, cyano, or lower alkoxy carbonyl. Preferably such a compound is a compound of formula 1d where X is carbonyl, k is 0, and Z is thiophene or phenyl, or thiophene or phenyl substituted by one or more of lower alkyl, lower alkoxy, hydroxy, halogen, carboxy, nitro, aminosulfonyl, cyano, or lower alkoxy carbonyl (differing from the above compound in that preferably Y is absent). In either case, it is preferred that Z is thiophene or phenyl, or thiophene or phenyl substituted by methyl, methoxy, chlorine, bromine, fluorine, hydroxy, or nitro. Examples are N-[2-chloro-4-[[[(3-hydroxyphenyl)methyl]amino]carbonyl]benzoyl]-3-(4-methoxythiophene-3-carbonyl)amino-L-alanine; and N-[2-chloro-4-[[[(3-hydroxyphenyl)methyl]amino] carbonyl]benzoyl]-3-(5-chloro-4-methoxythiophene-3-carbonyl)amino-L-alanine).

Also part of this invention is a compound of formula 1a wherein $R_1$ is a group of formula

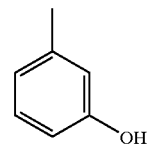

or R1 is a group of the formula

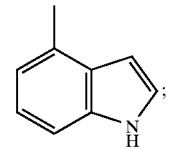

$R_2$ is a group of the formula

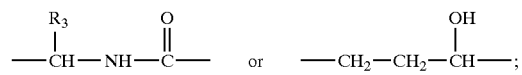

W is hydrogen and one of U or V is chlorine or bromine while the other is hydrogen or one of U or V is methyl and the other is chlorine or bromine; X is carbonyl; Y is lower alkylene substituted with cycloalkyl (preferably cyclohexyl), lower alkylthio, unbranched lower alkyl or alkenyl or k is 0; and Z is thiophene, furan, cyclopentyl, cyclohexyl, piperidine, pyridine, naphthalene, benzothiophene, benzothiazole, 1,4-dioxa-8-thiaspiro[4,5] decyl, or phenyl, or phenyl substituted by one or more of lower alkoxy, lower alkyl, chlorine, bromine, fluorine, hydroxy, nitro, cyano, amino, substituted amino, methyl, aminosulfonyl, trifluoromethyl, alkoxycarbonyl, or carboxy.

Another compound of this invention is a compound of formula 1a wherein U, V, and W are independently chlorine, bromine, or fluorine.

Yet another compound of this invention is a compound of formula 1a wherein Z is thiophene, furan, thiazole, cyclopentyl, cyclohexyl, piperidine, pyridine, naphthalene, benzothiophene, benzothiazole, 1,4-dioxa-8-thiaspiro[4,5] decyl or phenyl, or phenyl which may be substituted by one or more of lower alkoxy, lower alkyl, chlorine, bromine, fluorine, hydroxy, nitro, cyano, amino, substituted amino, aminosulfonyl, trifluoromethyl, or carboxy.

A compound of this invention is a compound of formula 1a wherein $R_1$ is a group of the formula

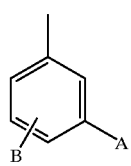

and A is hydroxy, hydrogen, or amino and B is hydrogen or hydroxy or $R_1$ is a group of the formula

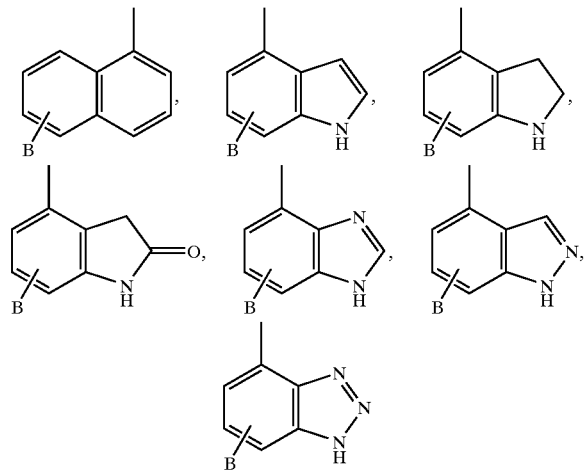

and B is hydrogen or hydroxy; $R_2$ is a group of the formula

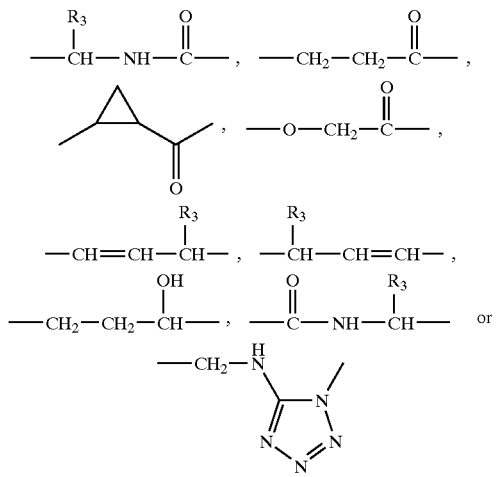  or

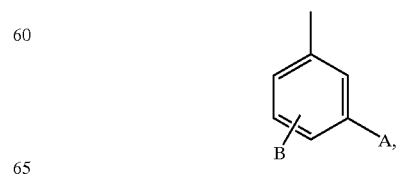

W is hydrogen and at least one of U and V is methyl or halogen; X is carbonyl, sulfonyl or phenyl-substituted lower alkylene; k is 0 or Y is lower alkylene; and Z is hydrogen, phenyl, thiophene, furan, pyrrole, pyrazole, imidazole, thiazole, or isoxazole. As explained above, these specific rings are unsubstituted unless otherwise indicated. Z may also be a six-membered aromatic ring with one to three nitrogens, which may be substituted or unsubstituted. Any of these rings (phenyl, thiophene, furan, pyrrole, pyrazole, imidazole, thiazole, isoxazole, or six-membered aromatic ring with one to three nitrogens) may be unsubstituted, or substituted with at least one of halogen, hydroxy, lower alkoxy, nitro, amino, substituted amino, cyano, carboxy, trifluoromethyl, lower alkyl, aminosulfonyl, or lower alkoxycarbonyl (for example N-[2-chloro-4-[[[(3-hydroxyphenyl)methyl]amino]carbonyl]benzoyl]-3-(phenylsulfonyl)amino-L-alanine; N-[2-fluoro-4-[[[(3-hydroxyphenyl)methyl]amino]carbonyl]benzoyl]-3-(thiophene-2-carbonyl)amino-L-alanine; N-[2-chloro-4-[[[(3-hydroxyphenyl)methyl]amino]carbonyl]benzoyl]-3-(phenylmethyl)amino-L-alanine;3-(3-carboxybenzoyl)amino-N-[2-chloro-4-[[(3-hydroxyphenyl)methyl]amino]carbonyl]benzoyl]-L-alanine; N-[4-[[[(3-aminophenyl)methylamino]carbonyl]-2-bromobenzoyl]-3-(thiophene-2-carbonyl)amino-L-alanine; 3-(benzoylamino)-N-[2-chloro-4-[[(3,5-dihydroxybenzoyl)amino]methyl]benzoyl]-L-alanine; 3-(benzoylamino)-N-[2-chloro-4-[[(2-hydroxybenzoyl)amino]methyl]benzoyl]-L-alanine; 3-(benzoylamino)-N-[2-chloro-4-[[(3-hydroxybenzoyl)amino]methyl]benzoyl]-L-alanine; N-[4-[[(3-aminobenzoyl)amino]methyl]-2-chlorobenzoyl]-3-(benzoyl)amino-L-alanine; N-[2-bromo-4-[[[(3-hydroxyphenyl)methyl]amino]carbonyl]benzoyl]-3-(thiophene-2-carbonyl)amino-L-alanine); N-[2-chloro-4-[[[(3,5-dihydroxyphenyl)methyl]amino]carbonyl]benzoyl]-3-[thiophene-2-carbonyl]amino-L-alanine.

Thus, the compound is as depicted in formula 1a except that A, when present, is hydroxy, hydrogen, or amino and B is hydrogen or hydroxy; W is hydrogen and at least one of U and V are methyl or halogen, k is 0 or Y is lower alkylene; and Z is hydrogen, phenyl, thiophene, furan, pyrrole, pyrazole, imidazole, thiazole, or isoxazole or a six-membered aromatic ring with one to three nitrogens any of which may be unsubstituted or substituted with at least one of halogen, hydroxy, lower alkoxy, nitro, amino, substituted amino, cyano, carboxy, trifluoromethyl, lower alkyl, aminosulfonyl, lower alkoxycarbonyl, or in addition substituted amino. In a more preferred compound, one of U or V is chlorine or bromine and the other is hydrogen and X is carbonyl and Y is methylene or k is 0 and Z is thiophene or phenyl, or thiophene or phenyl substituted by at least one of lower alkyl, lower alkoxy, hydroxy, halogen, carboxy, nitro, aminosulfonyl, cyano, or lower alkoxy carbonyl. In any such preferred compound, $R_1$ may be a group of the formula The above compound is preferred when X is carbonyl (for example N-[2-chloro-4-[5-[(3-hydroxy)phenylmethylamino]tetrazol-1-yl]benzoyl]-3-(thiophene-2-carbonyl)amino-L-alanine; N-[2-chloro-4-[1-oxo-3-(3-hydroxyphenyl)propyl]benzoyl]-3-(thiophene-2-carbonyl)amino-L-alanine; N-[2-chloro-4-[1-hydroxy-3-(3-hydroxyphenyl)propyl]benzoyl]-3-(thiophene-2-carbonyl)amino-L-alanine; N-[2-chloro-4-(1-oxo-3-phenylpropyl)benzoyl]-3-(thiophene-2-carbonyl)amino-L-alanine).

Also preferred is the above compound when X is carbonyl and $R_1$ is a group of the formula and preferably a group of the formula

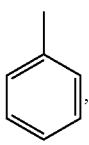

e.g. where A and B are hydrogen, especially when W is hydrogen and one of U or V is chlorine or bromine and the other is hydrogen (or V is hydrogen when U is chlorine or bromine, which as defined earlier is the equivalent compound), and particularly when k is 0 or when Y is methylene.

Even more preferred is the compound where k is 0 when Z is phenyl or thiophene, or phenyl or thiophene substituted by at least one of lower alkyl, lower alkoxy, hydroxy, halogen, carboxy, nitro, aminosulfonyl, cyano, or lower alkoxy carbonyl. When Z is phenyl or thiophene as described above, in a preferred compound $R_2$ is a group of the formula

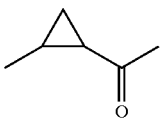

(for example N-[2-chloro-4-[(2-phenyl-trans-cyclopropyl)carbonyl]benzoyl]-3-(thiophene-2-carbonyl)amino-L-alanine). In another such preferred compound $R_2$ is a group of the formula

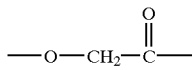

(for example N-[2-chloro-4-(phenoxyacetyl)benzoyl]-3-(thiophene-2-carbonyl)amino-L-alanine). In yet another such preferred compound, $R_2$ is a group of the formula

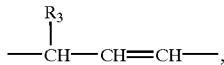

especially where $R_3$ is hydrogen (for example N-[2-chloro-4-(3-phenyl-1-propenyl)benzoyl]-3-(thiophene-2-carbonyl)amino-L-alanine).

A compound of this invention is a compound of formula 1a wherein $R_1$ is a group of the formula

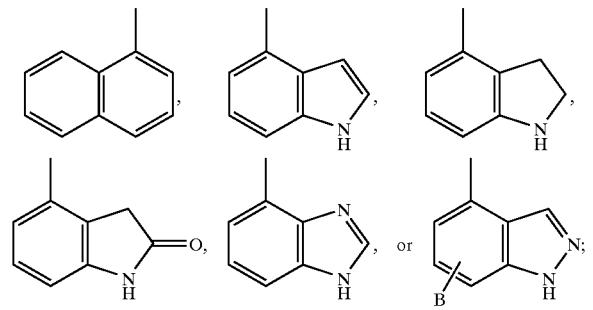

$R_2$ is a group of the formula

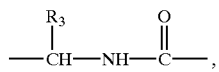

W is hydrogen and at least one of U and V are chlorine, bromine, or methyl; X is carbonyl, sulfonyl or phenyl-substituted lower alkylene; k is 0 or Y is butylene; and Z is hydrogen, phenyl, thiophene, or thiazole or phenyl, thiophene, or thiazole substituted with at least one of methyl or acetylamino.

This compound can also be described as a compound of claim 1 having formula

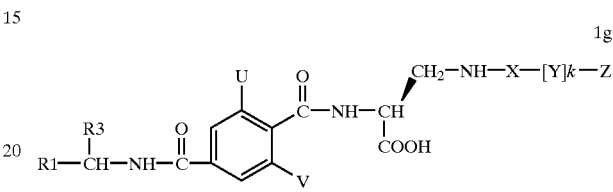

wherein $R_1$ is a group of the formula

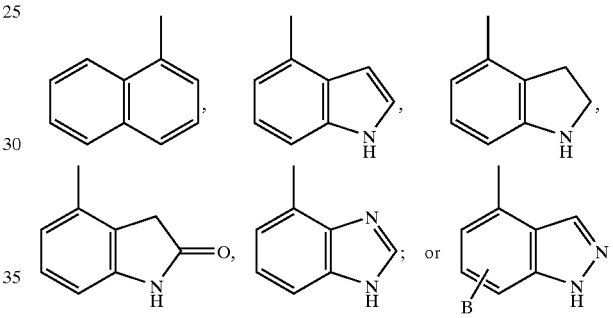

at least one of U and V are chlorine, bromine, or methyl; k is 0 or Y is butylene; X is carbonyl, phenyl-substituted lower alkylene, or sulfonyl; and Z is hydrogen, phenyl, thiazole, or thiophene, or Z is phenyl, thiazole, or thiophene substituted with at least one of methyl or acetylamino.

Part of this invention are the following compounds of formula 1 g where $R_3$ is hydrogen (for example 3-(benzoylamino)-N-[2-chloro-4-[[(2,3-dihydro-2-oxo-1H-indol-4-ylmethyl)amino]carbonyl]benzoyl]-L-alanine;
3-(benzoylamino)-N-[2-chloro-4-[[(1H-indol-4-ylmethyl)amino]carbonyl]benzoyl]-L-alanine;
N-[2-chloro-4-[[(1H-benzimidazol-4-ylmethyl)amino]carbonyl]benzoyl]-3-(thiophene-2-carbonyl)amino-L-alanine;
N-[2-chloro-4-[[(1H-indol-4-ylmethyl)amino]carbonyl]benzoyl]-3-(thiophene-2-carbonyl)amino-L-alanine;
N-[2-chloro-4-[[(2,3-dihydro-1H-indol-4-ylmethyl)amino]carbonyl]benzoyl]-3-(thiophene-2-carbonyl)amino-L-alanine;
N-[2-bromo-4-[[(1H-indol-4-ylmethyl)amino]carbonyl]benzoyl]-3-(thiophene-2-carbonyl)amino-L-alanine;
N-[2-chloro-4-[[(1H-indol-4-ylmethyl)amino]carbonyl]benzoyl]-3-(thiophene-3-carbonyl)amino-L-alanine;
N-[2-chloro-4-[[(1H-indol-4-ylmethyl)amino]carbonyl]benzoyl]-3-[(5-methylthiophene-2-carbonyl)]amino-L-alanine), and
N-[2-chloro-4-[[[(1H-indazol-4-yl)methyl]amino]carbonyl]benzoyl]-3-(thiophene-2-carbonyl)amino-L-alanine
or where $R_3$ is methyl (for example 3-(1-butanesulfonyl)amino-N-[2-chloro-4-[[[(1R)-1-(1-naphthalenyl)ethyl]amino]carbonyl]benzoyl]-L-alanine;

3-[(2-acetamido-4-methylthiazol-5-yl)sulfonyl]amino-N-[2-chloro-4-[[[(1R)-1-(1-naphthalenyl)ethyl]amino]carbonyl]benzoyl]-L-alanine;

N-[2,6-dimethyl-4-[[[(1R)-1-(1-naphthalenyl)ethyl]amino]carbonyl]benzoyl]-3-(thiophene-2-carbonyl)amino-L-alanine;

N-[2-bromo-4-[[[(1R)-1-(1-naphthalenyl)ethyl]amino]carbonyl]benzoyl]-3-(thiophene-2-carbonyl)amino-L-alanine), and N-[2,6-dichloro-4-[[[(1R)-1-(1-naphthalenyl)ethyl]amino]carbonyl]benzoyl]-3-[(thiophene-2-carbonyl)amino]-L-alanine;

N-[2-methyl-4-[[[(1R)-1-(1-naphthalenyl)ethyl]amino]carbonyl]benzoyl]-3-[(thiophene-2-carbonyl)amino]-L-alanine;

3-(benzoylamino)-N-[2-methyl-4-[[[(1R)-1-(1-naphthalenyl)ethyl]amino]carbonyl]benzoyl]-L-alanine;

3-(benzoylamino)-N-[2,6-dichloro-4-[[[(1R)-1-(1-naphthalenyl)ethyl]amino]carbonyl]benzoyl]-L-alanine.

The last four compounds are particularly preferred.

Another compound of this invention is a compound of formula 1a wherein $R_1$ is a group of the formula

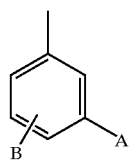

and A is hydroxy or amino and B is hydrogen; $R_2$ is a group of the formula

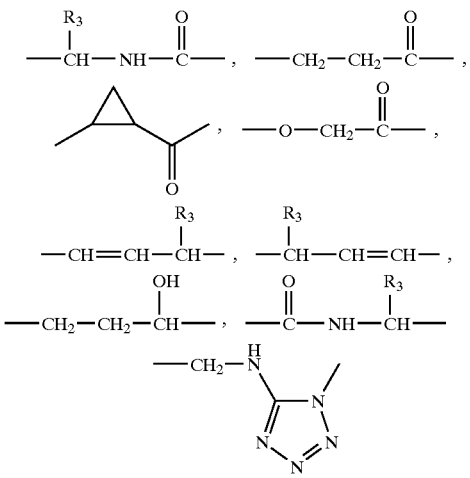

W is hydrogen and at least one of U and V are methyl or halogen; X is carbonyl, sulfonyl or phenyl-substituted lower alkylene; k is 0 or Y is lower alkylene; and Z is hydrogen, phenyl, thiophene, furan, pyrrole, pyrazole, imidazole, thiazole, or isoxazole or a six-membered aromatic ring with one to three nitrogens any of which may be unsubstituted or substituted with at least one of halogen, hydroxy, lower alkoxy, nitro, amino, cyano, carboxy, trifluoromethyl, lower alkyl, aminosulfonyl, or lower alkoxycarbonyl. In any such compound $R_1$ may be a group of the formula

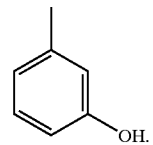

Another compound of this invention which is preferred is a compound of formula 1a wherein $R_1$ is a group of the formula

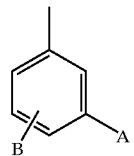

and A is hydroxy or amino and B is hydrogen; $R_2$ is a group of the formula

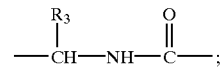

W is hydrogen and at least one of U and V is methyl or halogen; X is carbonyl; k is 0 or Y is methylene; and Z is thiophene or phenyl, or thiophene or phenyl substituted by at least one of methyl, methoxy, hydroxy, chlorine, bromine, fluorine, or nitro. In a preferred such compound $R_3$ is hydrogen and k is 0, and this compound is even more preferred when Z is thiophene or thiophene substituted with at least one of methyl, methoxy, hydroxy, chlorine, bromine, fluorine, or nitro. In another preferred compound one of U or V is chlorine or bromine and the other is hydrogen. In any such preferred compound $R_1$ may be a group of the formula

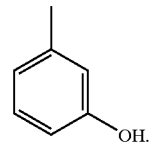

Also part of this invention is a compound of formula 1a wherein $R_1$ is a group of the formula

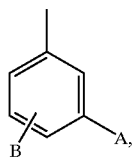

A is amino or hydroxy and B is hydrogen; $R_2$ is a group of formula

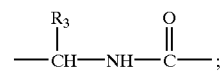

any or all of U, V, and W are hydrogen, halogen or methyl provided U and V are not both hydrogen; X is carbonyl or sulfonyl; and k is 0 or Y is methylene. In one preferred such compound, one of U or V is chlorine or bromine and the other is hydrogen. In another preferred such compound the halogen is bromine, chlorine, or fluorine (preferably chlorine or bromine), in particular where Z is phenyl, thiophene, furan, pyrrole, pyrazole, imidazole, thiazole, or isoxazole or a six-membered aromatic ring with one to three nitrogens any of which may be unsubstituted or substituted with at least one of: halogen, hydroxy, lower alkoxy, nitro, amino, cyano, carboxy, trifluoromethyl, lower alkyl, aminosulfonyl, or lower alkoxycarbonyl, and especially where Z is substituted by at least one of lower alkyl, lower alkoxy, hydroxy, halogen, carboxy, nitro, aminosulfonyl, cyano, or lower alkoxy carbonyl, for example at least one of methyl, methoxy, hydroxy, chlorine, bromine, fluorine, or nitro.

In another preferred such compound, $R_3$ is hydrogen; one of U or V is halogen (especially bromine, chlorine, or fluorine) and the other is hydrogen; X is sulfonyl; and k is 0. In a preferred compound W is hydrogen and one of U or V is chlorine or bromine and the other is hydrogen; X is carbonyl; Y is methylene or k is 0; Z is thiophene or phenyl or thiophene or phenyl substituted by at least one of methyl, methoxy, hydroxy, chlorine, bromine, fluorine, or nitro.

In yet another preferred compound where the halogen is bromine, chlorine, or fluorine, W is hydrogen and U and V are halogen or methyl (independently of each other, e.g. any combination of any halogen and methyl such as two chlorines, or a bromine and a methyl, and so forth). In a preferred such compound, X is carbonyl. Z may in addition be thiophene or phenyl, or thiophene or phenyl which may be substituted by at least one of lower alkyl, lower alkoxy, hydroxy, halogen, carboxy, nitro, aminosulfonyl, cyano, or lower alkoxy carbonyl.

In another preferred compound Z is thiophene or phenyl, or thiophene or phenyl which may be substituted by at least one of lower alkyl, lower alkoxy, hydroxy, halogen, carboxy, nitro, aminosulfonyl, cyano, or lower alkoxy carbonyl. Preferably Z is thiophene. In an especially preferred such compound, W is hydrogen, U and V are halogen or methyl, X is carbonyl, and Z is thiophene In any such preferred compound $R_1$ may be a group of the formula

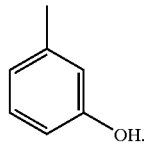

In particular, this invention includes compounds of claim 1 having the formula

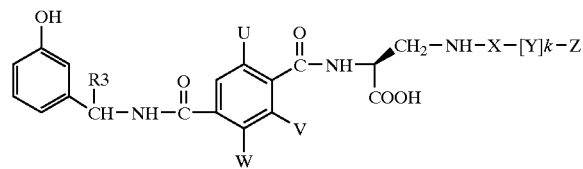

Ih where any or all of U, V, and W are halogen, hydrogen, or methyl, provided U and V are not both hydrogen; X is carbonyl or sulfonyl; k is 0 or Y is methylene, $R_3$ is hydrogen or lower alkyl; and when Y is methylene, Z is: hydrogen, lower alkylthio, —COOH, —CONH2, or amino, or when k is 0 or Y is methylene, Z is: 1-adamantyl, diphenylmethyl, 3-[[(5-chloropyridin-2-yl)amino]carbonyl] pyrazin-2-yl, or Z is one of the following: cycloalkyl or aryl containing 0 to 3 heteroatoms which may be the same or different, or a fused ring system containing two or three rings which rings are independently cycloalkyl or aryl containing 0 to 3 heteroatoms which may be the same or different, any of which cycloalkyl, aryl, or fused rings may be unsubstituted, or substituted with at least one of: halogen, cyano, amino, substituted amino, aminosulfonyl, nitro, oxo, hydroxy, aryl, aryloxy, unsubstituted lower alkyl, halogen-substituted lower alkyl, lower alkoxy-substituted lower alkyl, lower alkoxy, lower alkanesulfonyl, lower alkylthio, acetyl, aminocarbonyl, hydrazino, carboxy, lower alkoxycarbonyl, or acetoxy.

As stated above, also part of this invention is a compound of formula 1h where Y is methylene and Z is hydrogen, lower alkylthio, —COOH, —CONH$_2$, amino, 1-adamantyl, diphenylmethyl, 3-[[(5-chloropyridin-2-yl)amino]carbonyl] pyrazin-2-yl, and may also in addition be hydroxy, phenylmethoxy, 2-chloro-4-[[[(3-hydroxyphenyl)methyl] amino]carbonyl]phenyl, [2,6-dichlorophenyl)methoxy] phenyl, or Z is one of the following:

cycloalkyl or aryl containing 0 to 3 heteroatoms which may be the same or different, or a fused ring system containing two or three rings which rings are independently cycloalkyl or aryl containing 0 to 3 heteroatoms which may be the same or different, any of which rings may be unsubstituted, or substituted with at least one of:

halogen, cyano, amino, substituted amino, aminosulfonyl, nitro, oxo, hydroxy, aryl, aryloxy, unsubstituted lower alkyl, halogen-substituted lower alkyl, lower alkoxy-substituted lower alkyl, lower alkoxy, lower alkanesulfonyl, lower alkylthio, acetyl, aminocarbonyl, hydrazino, carboxy, alkoxycarbonyl, acetoxy, or amino lower alkyl.

As stated above, another compound of this invention is a compound of formula 1 h where k is 0 and Z is 1-adamantyl, diphenylmethyl, 3-[[(5-chloropyridin-2-yl)amino]carbonyl] pyrazin-2-yl, and may also in addition be hydroxy, phenylmethoxy, 2-chloro-4-[[[(3-hydroxyphenyl)methyl] amino]carbonyl]phenyl,[2,6-dichlorophenyl)methoxy] phenyl, or Z is one of the following:

cycloalkyl or aryl containing 0 to 3 heteroatoms which may be the same or different, or a fused ring system containing two or three rings which rings are independently cycloalkyl or aryl containing 0 to 3 heteroatoms which may be the same or different, any of which rings may be unsubstituted, or substituted with at least one of:

halogen, cyano, amino, substituted amino, aminosulfonyl, nitro, oxo, hydroxy, aryl, aryloxy, unsubstituted lower alkyl, halogen-substituted lower alkyl, lower alkoxy-substituted lower alkyl, lower alkoxy, lower alkanesulfonyl, lower alkylthio, acetyl, aminocarbonyl, hydrazino, carboxy, alkoxycarbonyl, acetoxy, or amino lower alkyl.

This invention includes compounds of formula 1h where $R_3$ is hydrogen, one of U or V is halogen and the other is hydrogen (or equivalently U is halogen and V is hydrogen), X is sulfonyl, and k is 0, especially where W is hydrogen.

Preferred is a compound having formula 1h where W is hydrogen and Z is hydrogen or Z is one of the following: cycloalkyl or aryl containing 0 to 3 heteroatoms which may be the same or different, or a fused ring system containing two or three rings which rings are independently cycloalkyl or aryl containing 0 to 3 heteroatoms which may be the same or different, any of which cycloalkyl, aryl, or fused rings may be unsubstituted, or substituted with at least one of: halogen, cyano, amino, substituted amino, aminosulfonyl, nitro, oxo, hydroxy, aryl, aryloxy, unsubstituted lower alkyl, halogen-substituted lower alkyl, lower alkoxy-substituted lower alkyl, lower alkoxy, lower alkanesulfonyl, lower alkylthio, acetyl, aminocarbonyl, hydrazino, carboxy, lower alkoxycarbonyl, or acetoxy. In particularly preferred compounds U is methyl and V is hydrogen. Examples of such compounds are N-[4-[[[(3-hydroxyphenyl)methyl]amino]carbonyl]-2-methyl-benzoyl]-3-[(thiophene-2-carbonyl)amino]-L-alanine, 3-(benzoylamino)-N-[4-[[[(3-hydroxyphenyl)methyl]amino]carbonyl]-2-methyl-benzoyl]-L-alanine.

Also preferred is the above compound where U and V are independently bromine, chlorine, fluorine or methyl, especially where Z is phenyl, thiophene, furan, pyrrole, pyrazole, imidazole, thiazole, or isoxazole or a six-membered aromatic ring with one to three nitrogens any of which may be unsubstituted or substituted with at least one of: halogen, hydroxy, lower alkoxy, nitro, amino, cyano, carboxy, trifluoromethyl, lower alkyl, aminosulfonyl, or lower alkoxycarbonyl. This compound is preferred when Z is substituted by at least one of methyl, methoxy, hydroxy, chlorine, bromine, fluorine, or nitro. This compound is also preferred where Z is thiophene or phenyl, or thiophene or phenyl substituted by at least one of methyl, halogen, methoxy, or hydroxy.

The above compound where U and V are independently bromine, chlorine, fluorine or methyl is also preferred where X is carbonyl. The compound where X is carbonyl is particularly preferred where Z is thiophene or phenyl, or thiophene or phenyl substituted by at least one of lower alkyl, lower alkoxy, hydroxy, halogen, carboxy, nitro, aminosulfonyl, cyano, or lower alkoxy carbonyl. This latter compound is preferred where U and V are independently chlorine or methyl, and especially where Z is substituted thiophene. Examples of such compounds include:

3-[(3-bromothiophene-2-carbonyl)amino]-N-[2,6-dichloro-4-[[[(3-hydroxyphenyl)methyl]amino]carbonyl]benzoyl]-L-alanine;

3-[(5-bromothiophene-2-carbonyl)amino]-N-[2,6-dichloro-4-[[[(3-hydroxyphenyl)methyl]amino]carbonyl]benzoyl]-L-alanine;

3-[(3-chlorothiophene-2-carbonyl)amino]-N-[2,6-dichloro-4-[[[(3-hydroxyphenyl)methyl]amino]carbonyl]benzoyl]-L-alanine;

3-[(4,5-dibromothiophene-2-carbonyl)amino]-N-[2,6-dichloro-4-[[[(3-hydroxyphenyl)methyl]amino]carbonyl]benzoyl]-L-alanine;

N-[2,6-dichloro-4-[[[(3-hydroxyphenyl)methyl]amino]carbonyl]benzoyl]-3-[(3-methylthiophene-2-carbonyl)amino]-L-alanine;

N-[2,6-dichloro-4-[[[(3-hydroxyphenyl)methyl]amino]carbonyl]benzoyl]-5-[(3-methylthiophene-2-carbonyl)amino]-L-alanine.

The latter compound is also preferred where Z is substituted phenyl. Examples of such compounds include:

3-(3,5-difluorobenzoylamino)-N-[2,6-dimethyl-4-[[[(3-hydroxyphenyl)methyl]amino-carbonyl]benzoyl]-L-alanine;

N-[2-chloro-4-[[[(3-hydroxyphenyl)methyl]amino]carbonyl]-6-methylbenzoyl]-3-[(3,5-difluorobenzoyl)amino]-L-alanine;

3-[(3-chlorobenzoyl)amino]-N-[2,6-dichloro-4-[[[(3-hydroxyphenyl)methyl]amino]carbonyl]benzoyl]-L-alanine;

N-[2,6-dichloro-4-[[[(3-hydroxyphenyl)methyl]amino]carbonyl]benzoyl]-3-[(3-fluorobenzoyl)amino]-L-alanine;

N-[2,6-dichloro-4-[[[(3-hydroxyphenyl)methyl]amino]carbonyl]benzoyl]-3-[(3-hydroxybenzoyl)amino]-L-alanine;

N-[2,6-dichloro-4-[[[(3-hydroxyphenyl)methyl]amino]carbonyl]benzoyl]-3-[(3-hydroxy-4-methoxybenzoyl)amino]-L-alanine;

N-[2,6-dichloro-4-[[[(3-hydroxyphenyl)methyl]amino]carbonyl]benzoyl]-3-[(3-methylbenzoyl)amino]-L-alanine;

N-[2-chloro-4-[[[(3-hydroxyphenyl)methyl]amino]carbonyl]-6-methylbenzoyl]-3-(3,5-dihydroxybenzoylamino)-L-alanine;

N-[2,6-dichloro-4-[[[(3-hydroxyphenyl)methyl]amino]carbonyl]benzoyl]-3-[(3,5-difluorobenzoyl)amino]-L-alanine;

N-[2,6-dichloro-4-[[[(3-hydroxyphenyl)methyl]amino]carbonyl]benzoyl]-3-(3,5-dihydroxybenzoylamino)-L-alanine;

N-[2,6-dichloro-4-[[[(3-hydroxyphenyl)methyl]amino]carbonyl]benzoyl]-3-[(3-hydroxybenzoyl)amino]-L-alanine.

The last four of these compounds are particularly preferred.

In the above compound where U and V are independently bromine, chlorine, fluorine or methyl, X is carbonyl, and Z is thiophene or phenyl, or thiophene or phenyl substituted by at least one of lower alkyl, lower alkoxy, hydroxy, halogen, carboxy, nitro, aminosulfonyl, cyano, or lower alkoxy carbonyl, it is preferred that Z is thiophene, especially where U and V are independently chlorine or methyl. Examples of such compounds are N-[2,6-dimethyl-4-[[[(3-hydroxyphenyl)methyl]amino]carbonyl]benzoyl]-3-(thiophene-2-carbonyl)amino-L-alanine and N-[2,6-dimethyl-4-[[[(3-hydroxyphenyl)methyl]amino]carbonyl]benzoyl]-3-(thiophene-3-carbonyl)amino-L-alanine), both of which are particularly preferred compounds. Also preferred are compounds where U is chlorine and V is chlorine or methyl, for example N-[2-chloro-4-[[[(3-hydroxyphenyl)methyl]amino]carbonyl]-6-methylbenzoyl]-3-[(thiophene-2-carbonyl)amino]-L-alanine;

N-[2,6-dichloro-4-[[[(3-hydroxyphenyl)methyl]amino]carbonyl]benzoyl]-3-[(thiophene-2-carbonyl)amino]-L-alanine;

N-[2,6-dichloro-4-[[[(3-hydroxyphenyl)methyl]amino]carbonyl]benzoyl]-3-[(thiophene-3-carbonyl)amino]-L-alanine;

N-[2-chloro-4-[[[(3-hydroxyphenyl)methyl]amino]carbonyl]-6-methylbenzoyl]-3-[(thiophene-3-carbonyl)amino]-L-alanine. These compounds are also particularly preferred.

In a preferred compound of formula 1a, $R_1$ is a group of the formula

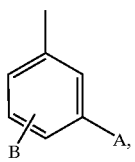

A is amino or hydroxy and B is hydrogen; $R_2$ is a group of formula

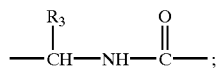

$R_3$ is hydrogen or methyl; one of U or V is chlorine, bromine, or fluorine and the other is hydrogen, and W is hydrogen, X is carbonyl; k is 0 or Y is methylene, and Z is phenyl, thiophene, furan, pyrrole, pyrazole, imidazole, thiazole, or isoxazole or a six-membered aromatic ring with one to three nitrogens any of which may be unsubstituted or substituted with at least one of: halogen, hydroxy, lower alkoxy, nitro, amino, cyano, carboxy, trifluoromethyl, lower alkyl, aminosulfonyl, or lower alkoxycarbonyl, especially at least one of lower alkyl, lower alkoxy, hydroxy, halogen, carboxy, nitro, aminosulfonyl, cyano, or lower alkoxy carbonyl, in particular at least one of methyl, methoxy, hydroxy, chlorine, bromine, fluorine, or nitro. In a preferred such compound, Z is thiophene or phenyl, or thiophene or phenyl substituted with least one of methyl, halogen, or hydroxy. In any such preferred compound $R_1$ may be a group of the formula

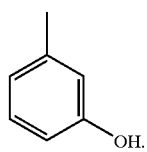

In another preferred compound of formula 1a, $R_1$ is a group of the formula

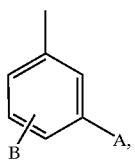

A is amino or hydroxy and B is hydrogen; $R_2$ is a group of formula

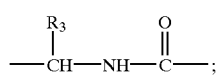

$R_3$ is hydrogen; one of U or V is chlorine, bromine, or methyl and the other is hydrogen, and W is hydrogen, X is carbonyl; k is 0 or Y is methylene, and Z is phenyl, thiophene, furan, pyrrole, pyrazole, imidazole, thiazole, or isoxazole or a six-membered aromatic ring with one to three nitrogens any of which may be unsubstituted or substituted with at least one of: halogen, hydroxy, lower alkoxy, nitro, amino, cyano, carboxy, trifluoromethyl, lower alkyl, aminosulfonyl, or lower alkoxycarbonyl. In any such preferred compound $R_1$ may be a group of the formula

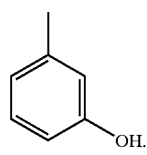

In yet another preferred compound of formula 1a, $R_1$ is a group of the formula

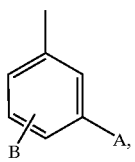

A is amino or hydroxy and B is hydrogen; $R_2$ is a group of formula

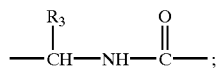

$R_3$ is hydrogen or methyl; one of U or V is chlorine, bromine, or methyl and the other is hydrogen, and W is hydrogen, X is carbonyl; k is 0 or Y is methylene, and Z is phenyl, or Z is phenyl substituted with at least one of halogen, hydroxy, methoxy, nitro, amino, cyano, carboxy, or trifluoromethyl, or Z is thiophene, or Z is thiophene substituted with at least one of halogen, methyl, methoxy, or nitro, or Z is selected from the group of furan, pyrrole, pyrazole, imidazole, thiazole, or isoxazole (which are unsubstituted as defined above for phenyl, thiophene, et al.), or Z is selected from the group of furan, pyrrole, pyrazole, imidazole, thiazole, or isoxazole substituted with at least one of halogen, methyl, methoxy, or nitro, or Z is pyridine, which may be substituted with at least one of methyl, methoxy, halogen, or hydroxy, or Z is a six-membered aromatic ring with two nitrogens, which may be substituted with at least one of methyl, methoxy, halogen, or hydroxy, or Z is a six-membered aromatic ring with three nitrogens, which may be substituted with at least one of methyl, methoxy, halogen, or hydroxy. Such a compound where Z may be any of the above-mentioned groups is also part of this invention. In any such preferred compound $R_1$ may be a group of the formula

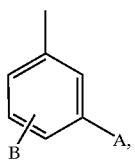

Another compound of this invention is a compound of formula 1a wherein $R_1$ is a group of the formula

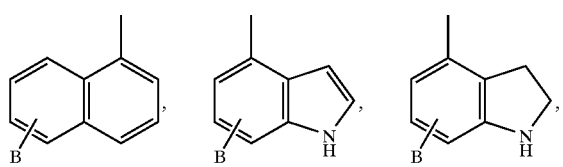

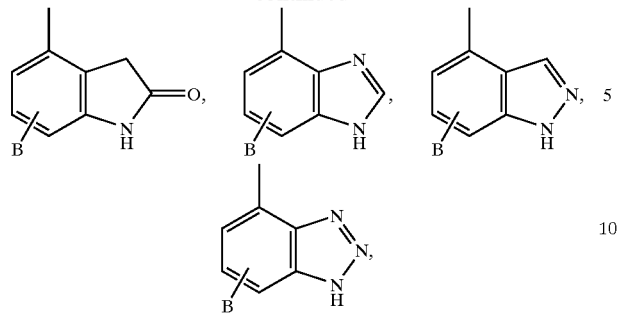

where R₂ is a group of the formula

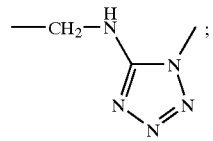

W is hydrogen and one of U and V is fluorine, chlorine or bromine and the other is hydrogen; X is sulfonyl or carbonyl; k is 0 or Y is lower alkylene; and Z is hydrogen, phenyl, thiophene, furan, pyrrole, pyrazole, imidazole, thiazole, or isoxazole or a six-membered aromatic ring with one to three nitrogens any of which may be unsubstituted or substituted with at least one of halogen, hydroxy, lower alkoxy, nitro, amino, cyano, carboxy, trifluoromethyl, lower alkyl, aminosulfonyl, NHC(O)CH₃, or lower alkoxycarbonyl. In a preferred such compound, Z is substituted by at least one of lower alkyl, lower alkoxy, hydroxy, halogen, carboxy, nitro, aminosulfonyl, cyano, or lower alkoxy carbonyl, specifically by at least one of methyl, methoxy, hydroxy, chlorine, bromine, fluorine, or nitro.

In another preferred compound of the preceding paragraph, X is carbonyl. In another, X is sulfonyl. In the latter compound, preferably R₁ is a group of the formula

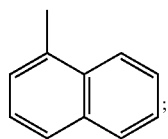

R₃ is methyl; Y is butylene or k is 0; and Z is hydrogen or thiazole substituted with —NHC(O)CH₃.

Another compound of this invention is a compound of formula 1a where R₁ is a group of formula

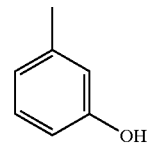

and R₂ is

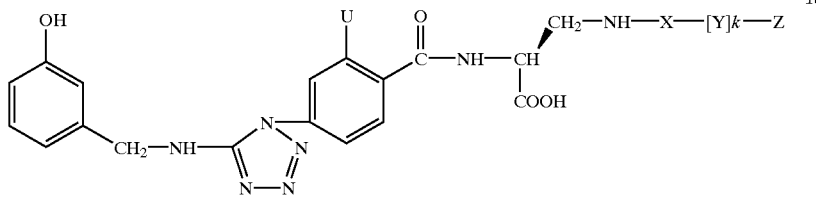

U and W are hydrogen and V is chlorine or bromine (this includes the equivalent compound where U is chlorine or bromine and V and W are hydrogen). This is a compound of formula wherein U is chlorine or bromine; X is carbonyl, phenyl-substituted loweralkylene, or sulfonyl; Y is lower alkylene which may be substituted by one or more of amino, lower alkyl, substituted amino, or cyclo-lower alkyl or Y is lower alkenylene or lower alkylenethio, and k is 0 or 1; when k is 1, Z is: hydrogen, lower alkylthio, —COOH, —CONH₂, or amino, or when k is 0 or 1, Z is: 1-adamantyl, diphenylmethyl, 3-[[(5-chloropyridin-2-yl)amino]carbonyl]pyrazin-2-yl, or Z is one of the following: cycloalkyl or aryl containing 0 to 3 heteroatoms which may be the same or different, or a fused ring system containing two or three rings which rings are independently cycloalkyl or aryl containing 0 to 3 heteroatoms which may be the same or different, any of which rings may be unsubstituted, or substituted with at least one of: halogen, cyano, amino, substituted amino, aminosulfonyl, nitro, oxo, hydroxy, aryl, aryloxy, lower alkyl which may be unsubstituted or substituted with halogen or lower alkoxy, lower alkoxy, lower alkanesulfonyl, lower alkylthio, acetyl, aminocarbonyl, hydrazino, carboxy, lower alkoxycarbonyl, or acetoxy. Preferred is such a compound where X is carbonyl, k is 0; and Z is thiophene.

Yet another compound of this invention is a compound of formula 1a wherein R₁ is a group of formula $R_2$ is

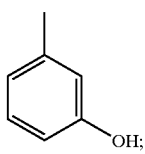

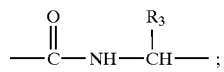

$R_3$, U and W are hydrogen and V is chlorine or bromine. (This includes the equivalent compound where U is chlorine or bromine and V and W are hydrogen.) In a preferred such compound, X is carbonyl, k is 0; and Z is thiophene or phenyl, especially thiophene. This is a compound of formula 1c

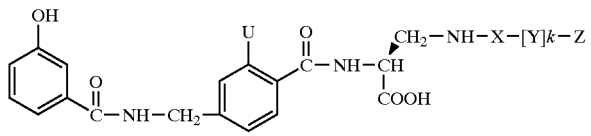

where U is chlorine or bromine; X is carbonyl, phenyl-substituted loweralkylene, or sulfonyl; Y is lower alkylene which may be substituted by one or more of amino, substituted amino, lower alkyl, or cyclo-lower alkyl, or Y is lower alkenylene or lower alkylenethio, and k is 0 or 1; when k is 1, Z is: hydrogen, lower alkylthio, —COOH, —CONH$_2$, or amino, or when k is 0 or 1, Z is: 1-adamantyl, diphenylmethyl, 3-[[(5-chloropyridin-2-yl)amino]carbonyl]pyrazin-2-yl, or Z is one of the following: cycloalkyl or aryl containing 0 to 3 heteroatoms which may be the same or different, or a fused ring system containing two or three rings which rings are independently cycloalkyl or aryl containing 0 to 3 heteroatoms which rings may be the same or different, any of which may be unsubstituted, or substituted with at least one of: halogen, cyano, amino, substituted amino, aminosulfonyl, nitro, oxo, hydroxy, aryl, aryloxy, unsubstituted lower alkyl, halogen-substituted lower alkyl, lower alkoxy-substituted lower alkyl, lower alkoxy, lower alkanesulfonyl, lower alkylthio, acetyl, aminocarbonyl, hydrazino, carboxy, lower alkoxycarbonyl, or acetoxy. Preferred is such a compound where X is carbonyl, k is 0; and Z is thiophene.

Compounds of this invention include compounds of formula 1a where n is 0, e.g. a compound having the formula 1i

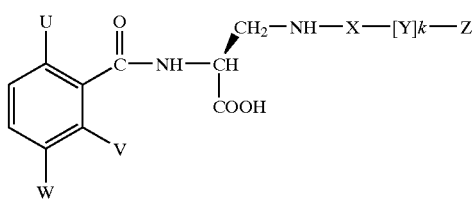

wherein

U, V, and W are independently hydrogen, halogen, or lower alkyl provided U and V are not both hydrogen;

X is carbonyl, phenyl-substituted loweralkylene, or sulfonyl; Y is lower alkylene which may be substituted by one or more of amino, substituted amino, lower alkyl, or cyclo-lower alkyl, or Y is lower alkenylene or, lower alkylenethio, and k is 0 or 1; when k is 1, Z is: hydrogen, lower alkylthio, —COOH, —CONH2, or amino, or when k is 0 or 1, Z is: 1-adamantyl, diphenylmethyl, 3-[[(5-chloropyridin-2-yl)amino]carbonyl]pyrazin-2-yl, or Z is one of the following: cycloalkyl or aryl containing 0 to 3 heteroatoms which may be the same or different, or a fused ring system containing two or three rings which rings are independently cycloalkyl or aryl containing 0 to 3 heteroatoms which rings may be the same or different, any of which may be unsubstituted, or substituted with at least one of: halogen, cyano, amino, substituted amino, aminosulfonyl, nitro, oxo, hydroxy, aryl, aryloxy, unsubstituted lower alkyl, halogen-substituted lower alkyl, lower alkoxy-substituted lower alkyl, lower alkoxy, lower alkanesulfonyl, lower alkylthio, acetyl, aminocarbonyl, hydrazino, carboxy, lower alkoxycarbonyl, or acetoxy.

In preferred compounds, U is chlorine, V is chlorine or fluorine, and W is hydrogen; and X is carbonyl, particularly where Y is methylene, —CH$_2$CH$_2$—, —CH=CH—, or —CH$_2$CH(CH$_3$)— (for example N-(2,6-dichlorobenzoyl)-3-[3-(2-thienyl)prop-2-enoyl]amino-L-alanine; N-(2,6-dichlorobenzoyl)-3-(phenylacetyl)amino-L-alanine;

N-(2,6-dichlorobenzoyl)-3-[(4-nitrophenylacetyl)]amino-L-alanine;

N-(2,6-dichlorobenzoyl)-3-[(3-RS)-3-phenylbutanoyl]amino-L-alanine;

N-(2-chloro-6-fluorobenzoyl)-3-[(3RS)-3-phenylbutanoyl]amino-L-alanine) or k is 0 (for example N-(2,6-dichlorobenzoyl)-3-[(2S)-5-oxotetrahydrofuran-2-carbonyl]amino-L-alanine;

N-(2-chloro-6-fluorobenzoyl)-3-[(2S)-5-oxotetrahydrofuran-2-carbonyl]amino-L-alanine;

3-(6-bromo-2-oxo-1,2,3,4-tetrahydroquinoline-4-carbonyl)amino-N-(2,6-dichlorobenzoyl)-L-alanine;

3-(benzoylamino)-N-(2,6-dichlorobenzoyl)-L-alanine;

3-(benzoylamino)-N-(2-chloro-6-fluorobenzoyl)-L-alanine;

N-(2,6-dichlorobenzoyl)-3-[(3-methoxybenzoyl)]amino-L-alanine;

N-(2-chloro-6-fluorobenzoyl)-3-[(3-methoxybenzoyl)]amino-L-alanine;

N-(2,6-dichlorobenzoyl)-3-[(5-bromothiophene-2-carbonyl)]amino-L-alanine;

N-(2-chloro-6-fluorobenzoyl)-3-[(5-bromothiophene-2-carbonyl)]amino-L-alanine;

N-(2,6-dichlorobenzoyl)-3-[(indole-5-carbonyl)]amino-L-alanine;

N-(2,6-dichlorobenzoyl)-3-[(6-methylpyridine-2-carbonyl)]amino-L-alanine;

3-(1H-benzotriazole-5-carbonyl)amino-N-(2-chloro-6-fluorobenzoyl)-L-alanine).

In the latter compound, Z is preferably lower cycloalkyl (for example

N-(2,6-dichlorobenzoyl)-3-(cyclopropylcarbonyl)amino-L-alanine;

N-(2-chloro-6-fluorobenzoyl)-3-(cyclopropylcarbonyl)amino-L-alanine;

N-(2,6-dichlorobenzoyl)-3-(cyclobutylcarbonyl)amino-L-alanine;

N-(2,6-dichlorobenzoyl)-3-(cyclopentylcarbonyl)amino-L-alanine;

N-(2-chloro-6-fluorobenzoyl)-3-(cyclopentylcarbonyl) amino-L-alanine;
N-(2,6-dichlorobenzoyl)-3-(cyclohexylcarbonyl)amino-L-alanine;
N-(2-chloro-6-fluorobenzoyl)-3-(cyclohexylcarbonyl) amino-L-alanine), or Z is phenyl, or phenyl substituted with at least one of methyl, hydroxy, alkoxy, or halogen.

Also part of this invention are compounds of formula 1a where n is 0, W is hydrogen, chlorine, bromine or fluorine and at least one of U and V are methyl, chlorine, bromine or fluorine; X is carbonyl or sulfonyl; k is 0 or Y is methylene; Z is phenyl, thiophene, furan, pyrrole, pyrazole, imidazole, thiazole, or isoxazole or a six-membered aromatic ring with one to three nitrogens any of which may be unsubstituted or substituted with at least one of halogen, hydroxy, lower alkoxy, nitro, amino, cyano, carboxy, trifluoromethyl, lower alkyl, aminosulfonyl, NHC(O)CH$_3$, or lower alkoxycarbonyl, preferably where Z is substituted by at least one of lower alkyl, lower alkoxy, hydroxy, halogen, carboxy, nitro, aminosulfonyl, cyano, or lower alkoxy carbonyl, especially where Z is substituted by at least one of methyl, methoxy, hydroxy, chlorine, bromine, fluorine, or nitro.

Preferred compounds are those having the formula

1j

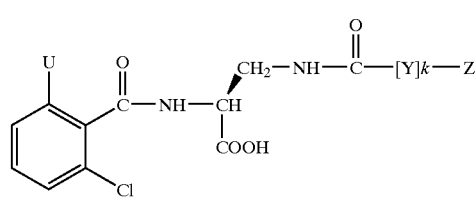

where U is fluorine or chlorine; Y is methylene or k is 0; Z is one of the following: cycloalkyl or aryl containing 0 to 3 heteroatoms which may be the same or different, or a fused ring system containing two or three rings which rings are independently cycloalkyl or aryl containing 0 to 3 heteroatoms which may be the same or different, any of which rings may be unsubstituted, or substituted with at least one of: halogen, cyano, amino, substituted amino, aminosulfonyl, nitro, oxo, hydroxy, aryl, aryloxy, unsubstituted lower alkyl, halogen-substituted lower alkyl, lower alkoxy-substituted lower alkyl, lower alkoxy, lower alkanesulfonyl, lower alkylthio, acetyl, aminocarbonyl, hydrazino, carboxy, lower alkoxycarbonyl, or acetoxy.

Another compound of this invention is a compound of formula 1a having the formula 1k

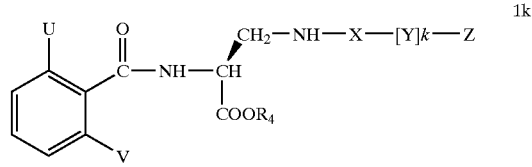

where U, V, R4, X, Y, k, and Z are as in formula 1a.

In a preferred such compound X is carbonyl, Y is lower alkylene or lower alkenylene or k is 0; and Z is 3-6 membered cycloalkyl; aryl or heteroaryl, which may be substituted with lower alkyl, lower alkoxy, halogen, or nitro; heterocycloalkyl substituted with oxo; indole; indazole, benzimidazole; benzotriazole; or dihydroquinolone substituted with halogen. In another preferred compound of formula 1a, U and V are independently halogen or methyl.

In another preferred compound of formula 1a V is bromine, chlorine or fluorine, especially bromine or chlorine. In yet another preferred compound of formula 1a one of U or V is halogen or methyl and the other is hydrogen. In another preferred compound U and V are independently halogen or methyl (e.g. U is halogen and V is methyl, or U and V are both methyl, or U and V are both halogen) especially where the halogen is chlorine, fluorine, or bromine.

In another compound of formula 1a, especially where U and V are independently halogen or methyl, X is carbonyl or sulfonyl; k is 0 or Y is methylene; and Z is phenyl, thiophene, furan, pyrrole, pyrazole, imidazole, thiazole, or isoxazole or a six-membered aromatic ring with one to three nitrogens any of which may be unsubstituted or substituted with at least one of halogen, hydroxy, lower alkoxy, nitro, amino, cyano, carboxy, trifluoromethyl, lower alkyl, aminosulfonyl, NHC(O)CH$_3$, or lower alkoxycarbonyl, especially where Z is substituted by at least one of lower alkyl, lower alkoxy, hydroxy, halogen, carboxy, nitro, aminosulfonyl, cyano, or lower alkoxy carbonyl, in particular where Z is substituted by at least one of methyl, methoxy, hydroxy, chlorine, bromine, fluorine, or nitro.

The compound described in the previous paragraph is also preferred when Z is phenyl, or when Z is phenyl substituted with at least one of halogen, hydroxy, methoxy, nitro, amino, cyano, carboxy, or trifluoromethyl, or when Z is thiophene, or when Z is thiophene substituted with at least one of halogen, methoxy, methyl, or nitro, or when Z is selected from the group of furan, pyrrole, pyrazole, imidazole, thiazole, or isoxazole, or when Z is selected from the group of furan, pyrrole, pyrazole, imidazole, thiazole, or isoxazole substituted with at least one of halogen, methyl, or nitro, or when Z is pyridine, especially when the pyridine is substituted with at least one of methyl, methoxy, halogen, or hydroxy, or when Z is a six-membered aromatic ring with two nitrogens, especially when the six-membered aromatic ring with two nitrogens is substituted with at least one of methyl, methoxy, halogen, or hydroxy, or when Z is a six-membered aromatic ring with three nitrogens, especially when the six-membered aromatic ring with three nitrogens is substituted with at least one of methyl, methoxy, halogen, or hydroxy.

Also part of this invention are compounds of formula (a)

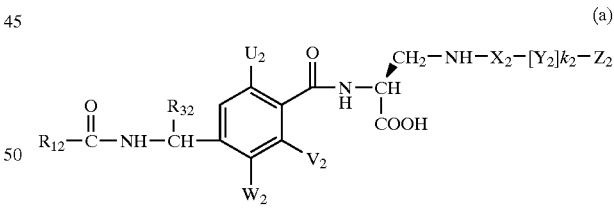

wherein R$_{12}$ is a group of the formula

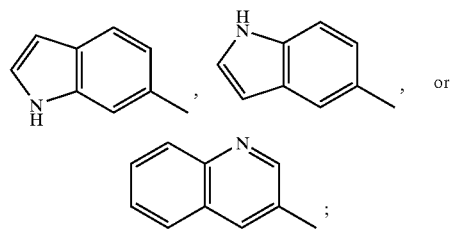

R$_{32}$ is hydrogen, carboxy, or lower alkyl; U$_2$, V$_2$, and W$_2$ are independently hydrogen, halogen, or lower alkyl provided $U_2$ and $V_2$ are not both hydrogen; X is carbonyl, phenyl-substituted loweralkylene, or sulfonyl; $Y_2$ is lower alkenylene, lower alkylenethio, or Y is lower alkylene which may be substituted by amino, substituted amino, lower alkyl, or cyclo-lower alkyl, and $k_2$ is 0 or 1; when $k_2$ is 1, $Z_2$ is: hydrogen, lower alkylthio, —COOH, —$CONH_2$, or amino, or when $k_2$ is 0 or 1, Z is: 1-adamantyl, diphenylmethyl, 3-[[(5-chloropyridin-2-yl)amino]carbonyl]pyrazin-2-yl, or $Z_2$ is one of the following:

cycloalkyl or aryl containing 0 to 3 heteroatoms which may be the same or different, or a fused ring system containing two or three rings which rings are independently cycloalkyl or aryl containing 0 to 3 heteroatoms which may be the same or different, any of which rings may be unsubstituted, or substituted with at least one of:

halogen, cyano, amino, substituted amino, aminosulfonyl, nitro, oxo, hydroxy, aryl, aryloxy, unsubstituted lower alkyl, halogen-substituted lower alkyl, lower alkoxy-substituted lower alkyl, lower alkoxy, carboxy, alkoxycarbonyl, or acetoxy; and pharmaceutically acceptable salts and esters thereof, Examples of such compounds are 3-(benzoylamino)-N-[2-chloro-4-[[(quinoline-3-carbonyl)amino]methyl]benzoyl]-L-alanine; 3-(benzoylamino)-N-[2-chloro-4-[[(1H-indole-6-carbonyl)amino]methyl]benzoyl]-L-alanine and 3-(benzoylamino)-N-[2-chloro-4-[[(1H-indole-5-carbonyl)amino]methyl]benzoyl]-L-alanine.

Compounds of formula 2 are part of this invention.

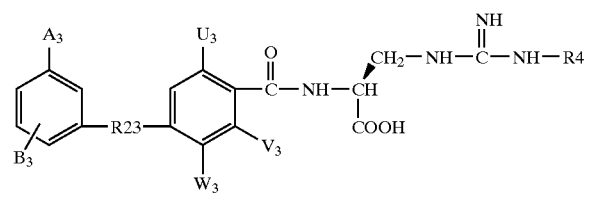

2 wherein $A_3$ is hydrogen, hydroxy, amino, or halogen and $B_3$ is amino, carboxy, hydrogen, hydroxy, cyano, trifluoromethyl, halogen, lower alkyl, or lower alkoxy;

$R_{23}$ is a group of the formula

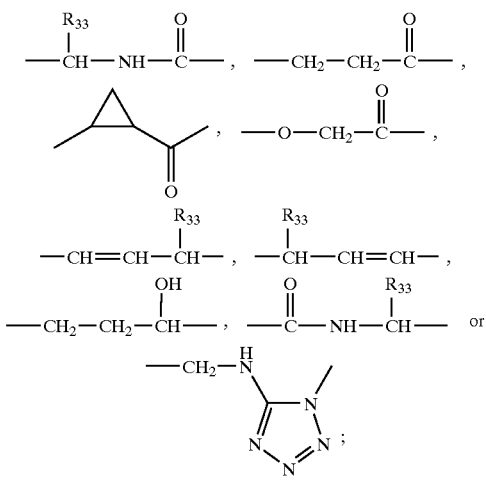

where $R_{33}$ is hydrogen, carboxy, or lower alkyl; $U_3$, $V_3$, and $W_3$ are independently hydrogen, halogen, or-lower alkyl provided $U_3$ and $V_3$ are not both hydrogen; $R_4$ is hydrogen, lower alkyl, or aryl-lower-alkyl which can be unsubstituted or substituted with at least one of halogen, cyano, amino, substituted amino, aminosulfonyl, nitro, hydroxy, aryl, aryloxy, lower alkyl which may be unsubstituted or substituted with halogen or lower alkoxy, lower alkoxy, carboxy, lower alkoxycarbonyl, or acetoxy; and pharmaceutically acceptable salts and esters thereof. An example of such a compound is N-[2-chloro-4-[[[(3-hydroxyphenyl)methyl]amino]carbonyl]benzoyl]-3-[(aminoiminomethyl)]amino-L-alanine.

Also part of this invention are compounds of formula 3, which are prodrugs. By prodrug is meant a metabolic precursor of a drug which when administered to a patient breaks down into the drug and acceptable by-products. In the prodrug of this invention, the $R_4$ hydrogen is replaced by other groups, which come off when administered to leave a hydrogen and reconstitute the resulting carboxy group. Any individual compound of this invention may be obtained as a prodrug described below.

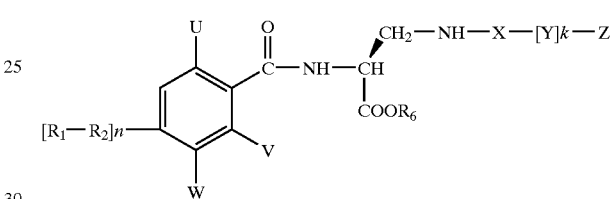

3 wherein $R_1$, $R_2$, n, U, V, W, X, Y, k, and Z are as in formula 1a, e.g. $R_1$ is a group of the formula

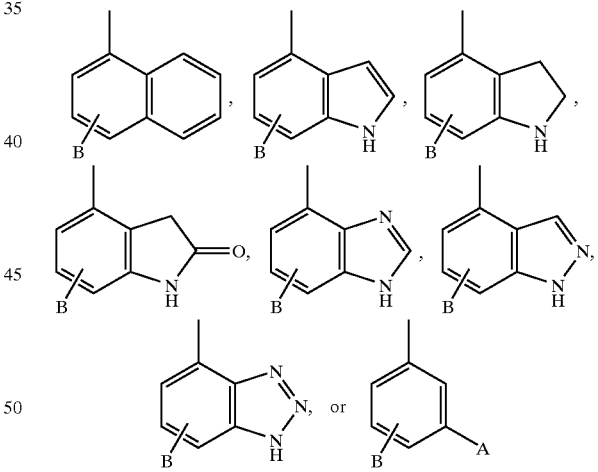

where A is hydrogen, hydroxy, amino, or halogen and B is amino, carboxy, hydrogen, hydroxy, cyano, trifluoromethyl, halogen, lower alkyl, or lower alkoxy; $R_2$ is a group of the formula

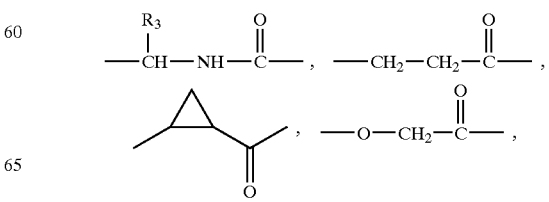

-continued

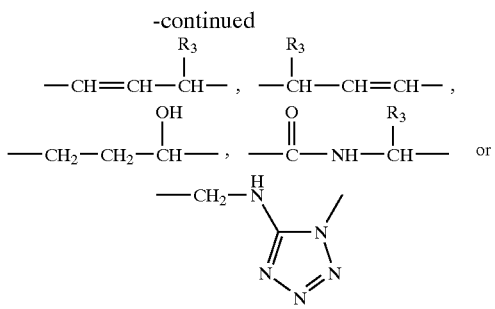

where $R_3$ is hydrogen, carboxy, or lower alkyl; n is 0 or 1; U, V, and W are independently hydrogen, halogen, or lower alkyl provided U and V are not both hydrogen; $R_6$ is lower alkyl (preferably unbranched) or —$CH_2CH_2$—$R_7$ where $R_7$ is

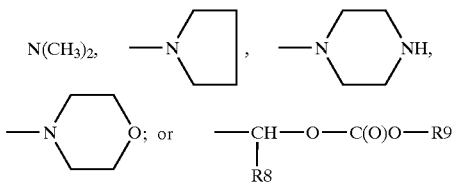

where $R_8$ is hydrogen or methyl and $R_9$ is lower-alkyl or lower cycloalkyl; X is carbonyl, phenyl-substituted loweralkylene, or sulfonyl; Y is lower alkylene which may be substituted by one or more of amino, substituted amino, loweralkyl, or cyclo lower alkyl, or Y is lower alkenylene or lower alkylenethio; k is 0 or 1; when k is 1, Z is: hydrogen, lower alkylthio, amino, —COOH, or —$CONH_2$, or when k is 0 or 1, Z is: 1-adamantyl, diphenylmethyl, 3-[[(5-chloropyridin-2-yl)amino]carbonyl]pyrazin-2-yl, or in addition hydroxy, phenylmethoxy, 2-chloro-4-[[[(3-hydroxyphenyl)methyl]amino]carbonyl]phenyl, [(2,6-dichlorophenyl)methoxy]phenyl or Z is one of the following: cycloalkyl or aryl containing 0 to 3 heteroatoms which may be the same or different, or a fused ring system containing two or three rings which rings are independently cycloalkyl or aryl containing 0 to 3 heteroatoms which may be the same or different, any of which rings may be unsubstituted, or substituted with at least one of halogen, cyano, amino, substituted amino, aminosulfonyl, nitro, oxo, hydroxy, aryl, aryloxy, unsubstituted lower alkyl, halogen-substituted lower alkyl, lower alkoxy-substituted lower alkyl, lower alkoxy, carboxy, alkoxycarbonyl, or acetoxy; and pharmaceutically acceptable salts and esters thereof.

In a preferred such compound $R_6$ is unbranched lower alkyl, in particular ethyl. In another preferred such compound, $R_6$ is $CH_2CH_2$—$R_7$. In the latter compound it is preferred that $R_7$ is —$N(CH_3)_2$, or

In another such compound $R_6$ is

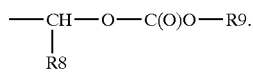

In this compound it is preferred that $R_8$ is hydrogen or methyl and $R_9$ is ethyl or cyclohexyl.

The compounds of this invention and their pharmaceutically acceptable salts inhibit the binding of the beta-2 integrins LFA-1 and Mac-1, expressed on activated lymphocytes, monocytes and neutrophils, to the immunoglobulin ICAM-1 which is expressed on activated endothelial cells, epithelial cells, synovial cells, myocytes, glial cells and neurons as well as on lymphocytes and antigen presenting cells. The compounds in this invention can therefore be used in the treatment of disorders that involve the binding of beta-2 integrins LFA-1 and Mac-1 with ICAM-1. Examples of such disorders include but are not limited to rheumatoid arthritis, psoriasis, multiple sclerosis, Crohn's disease, ulcerative colitis, artherosclerosis, restenosis, pancreatitis, transplant rejection, delayed graft function and diseases of ischemia reperfusion injury, including acute myocardial infarction and stroke. The compounds of the invention are preferably used in the treatment of ischemia reperfusion injury. The inflammatory response in reperfusion injury requires the binding and extravasation of the neutrophils to activated endothelium which is mediated by the interaction of LFA-1 with ICAM-1. The binding of Mac-1 with ICAM-1 activates the neutrophils to release inflammatory cytokines e.g. IL-1, IL-6, IL-8, TNF-alpha and endothelial cells to release chemotactic factors e.g. platelet activating factor. The result of this interaction is the generation of superoxide and free hydroxyl radicals which cause tissue destruction. Any compound of Formula 1a which has the pharmaceutical activity described is part of this invention. In vitro assays for determining the desired pharmaceutical activity are provided below in the Examples for the compounds of this invention. Another indicator of pharmaceutical activity is the ability to inhibit a biological activity associated with LFA-1, such as T lymphocyte proliferation in a mixed lymphocyte reaction or Mac-1 adhesion to fibrinogen. Competitive binding assays, for example with ICAM-1 for Mac-1, also indicate pharmaceutical activity. In vivo assays for pharmaceutical activity are also provided. Compounds of this invention inhibit induced paw and ear swelling in mice. Activities within the ranges exemplified in the Examples are indicative of desired pharmaceutical activity.

Accordingly part of this invention is pharmaceutical compositions which comprise a compound of formula 1a or any other compound of this invention, and a pharmaceutically acceptable carrier. One such composition comprises a compound of formula 1a wherein $R_1$ is a group of formula

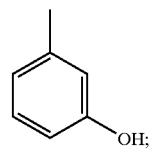

$R_2$ is a group of formula

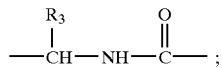

W is hydrogen and one of U or V is chlorine, fluorine, bromine, or methyl while the other is hydrogen; $R_3$ and $R_4$ are hydrogen; X is carbonyl; k is 0 or Y is methylene, and Z is thiophene or phenyl, or thiophene or phenyl substituted by at least one of lower alkyl, lower alkoxy, hydroxy, halogen, carboxy, nitro, aminosulfonyl, cyano, or lower alkoxy carbonyl. Another composition comprises a similar compound of formula 1a however $R_3$ is as in formula 1a and U and V are (independently) halogen or methyl, and Z is thiophene.

Preferred compositions include compounds having formula

1e

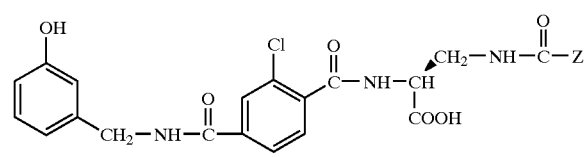

where Z is a five- or six-membered ring with one to three nitrogens, and compounds having formula 1h

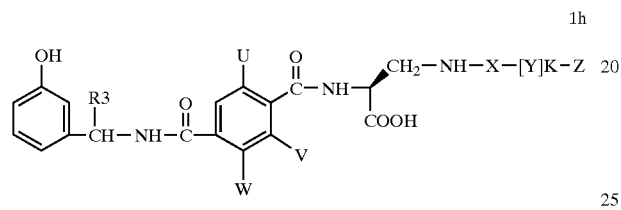

where U and V are independently bromine, chlorine, fluorine or methyl and W is hydrogen, X is carbonyl; k is 0 or Y is methylene, $R_3$ is hydrogen, carboxy, or lower alkyl; and Z is thiophene or phenyl, or thiophene or phenyl substituted by at least one of lower alkyl, lower alkoxy, hydroxy, halogen, carboxy, nitro, aminosulfonyl, cyano, or lower alkoxy carbonyl.

Compositions which include particularly preferred individual compounds of this invention, are also preferred.

The pharmaceutical compositions can be made up in any conventional form, including a solid form for oral administration such as tablets, capsules, pills, powders, granules, and the like. The pharmaceutical compositions may be sterilized and/or may contain adjuvants such as preservatives, stabilizers, wetting agents, emulsifiers, salts for varying the osmotic pressure, and/or buffers. Another active compound may be added.

Typical preparations for administration by injection would be sterile aqueous solutions of the compounds of this invention including water/buffered solutions. Injection is by any conventional mode, e.g. intravenous, intramuscular, subcutaneous, or intraperitoneal. Pharmaceutically acceptable carriers or vehicles may include fluid such as water, nutrient and electrolyte replenishers, sugars such as sucrose, glucose, invert sugar. Preservatives and other additives may also be present such as antibiotics and antioxidants. Adjuvants which may be present include alcohol, polyols, glycerol, vegetable oil. Pharmaceutically acceptable excipients typically used in such preparations may be added to control such properties as pH, viscosity, sterility, stability, and dissolution rate.

Typical preparations for oral administration contain compounds of this invention in association with a compatible pharmaceutically acceptable carrier material. Any conventional pharmaceutically acceptable carrier material can be utilized. Any conventional oral dosage form such as tablets, capsules, pills, powders, granules, and the like may be used. The pharmaceutically acceptable carrier can be an organic or inorganic inert carrier material suitable for oral administration. Suitable carriers include water, gelatin, gum arabic, lactose, starch, magnesium stearate, talc, vegetable oils, polyalkylene-glycols, petroleum jelly, water, vegetable oils, fats, liquid and semisolid polyols and the like. Furthermore, the pharmaceutical composition may contain other pharmaceutically active agents. Additional additives such as flavoring agents, preservatives, stabilizers, antioxidants, emulsifying agents, masking agents, buffers and the like may be added in accordance with accepted practices of pharmaceutical compounding. Administration by suppository is also possible. Carriers for this purpose include oils, waxes, fats, polyols.

Also part of this invention is a method of attenuating tissue damage resulting from reperfusion following acute myocardial infarction which comprises administering an amount of a compound of formula 1a or any compound of this invention effective to reduce inflammation in tissue affected by acute myocardial infarction, for example a compound of Formula 1a wherein $R_1$ is a group of formula

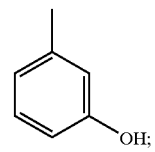

$R_2$ is a group of formula

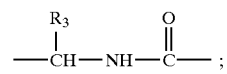

W is hydrogen and one of U or V is chlorine, fluorine, bromine, or methyl while the other is hydrogen; $R_3$ and $R_4$ are hydrogen; X is carbonyl; k is 0 or Y is methylene, and Z is thiophene or phenyl, or thiophene or phenyl substituted by at least one of lower alkyl, lower alkoxy, hydroxy, halogen, carboxy, nitro, aminosulfonyl, cyano, or lower alkoxy carbonyl. Another composition for use in attenuating tissue damage comprises a similar compound of formula 1a however $R_3$ is as in formula 1a and U and V are (independently) halogen or methyl, and Z is thiophene.

Preferred compositions for use in a method of attenuating tissue damage resulting from reperfusion following acute myocardial infarction include compounds having formula 1e

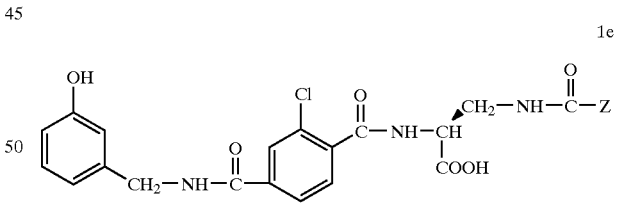

where Z is a five- or six-membered ring with one to three nitrogens, and compounds having formula 1h

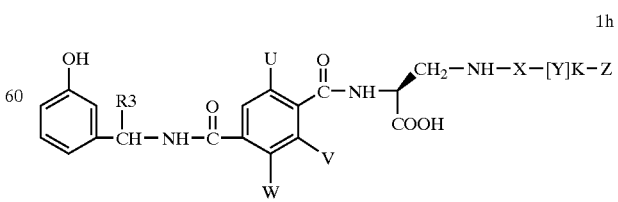

where U and V are independently bromine, chlorine, fluorine or methyl and W is hydrogen, X is carbonyl; k is 0 or Y is methylene, $R_3$ is hydrogen, carboxy, or lower alkyl; and Z is thiophene or phenyl, or thiophene or phenyl substituted by at least one of lower alkyl, lower alkoxy, hydroxy, halogen, carboxy, nitro, aminosulfonyl, cyano, or lower alkoxy carbonyl.

Compositions which include particularly preferred individual compounds of this invention, are also preferred.

The compounds of the invention can be administered orally, rectally, or parentally, e.g., intravenously, intramuscularly, by infusion, subcutaneously, intrathecally or transdermally; or sublingually, or as opthalmalogical preparations, or as an aerosol for the treatment of pulmonary inflammation. Capsules, tablets, suspensions or solutions for oral administration, suppositories, injection solutions, eye drops, salves or spray solutions are examples of administration forms.

The compounds of the invention are preferably administered parenterally, for example by intravenous bolus injection or infusion (although other routes such as oral, subcutaneous, intramuscular, topical, or rectal are also contemplated). Thus a preferred carrier is saline, although other pharmaceutically acceptable carriers such as those described above may be used. The dosages in which the compounds of the invention are administered in effective amounts depend on the nature of the specific active ingredient, the age and the requirements of the patient and the mode of administration. The dosage for any given person may be determined by a skilled person based on the information provided here. Dosages may be determined by any conventional means, however in the methods of this invention, it is preferred that the amount of compound is from about 1.0 to about 100 mg/kg/day. The compound may be administered by a skilled person to create a preselected circulatory concentration, preferably a plasma level of about 5.0 mg/ml of plasma in a patient to whom the compound is administered. Such plasma levels may be determined by conventional methods. Dosages of about 1.0 to about 100 mg/kg body weight per day are preferred, with dosages of about 1 to about 25 mg/kg per day being particularly preferred, and dosages of about 1.0 to about 10 mg/kg body weight per day being especially preferred. Dosages are preferably administered by intravenous infusion, but may alternately be provided in equal doses, for example about 4 to about 15 times daily. Higher doses may be administered if necessary.

Thus, it is preferred to administer compositions including compounds having formula

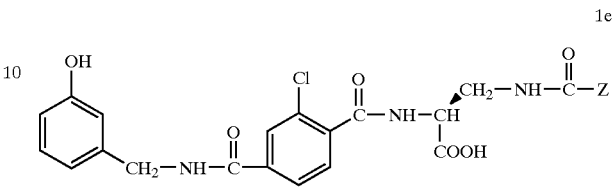

1e where Z is a five- or six-membered ring with one to three nitrogens, and compounds having formula

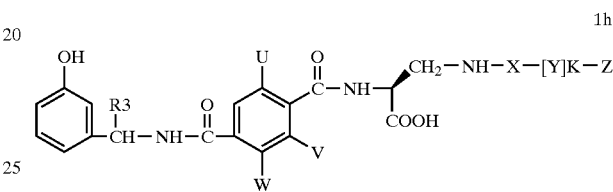

1h where U and V are independently bromine, chlorine, fluorine or methyl and W is hydrogen, X is carbonyl; k is 0 or Y is methylene, $R_3$ is hydrogen, carboxy, or lower alkyl; and Z is thiophene or phenyl, or thiophene or phenyl substituted by at least one of lower alkyl, lower alkoxy, hydroxy, halogen, carboxy, nitro, aminosulfonyl, cyano, or lower alkoxy carbonyl, and compositions which include particularly preferred individual compounds of this invention, in the dosage ranges and/or to attain the plasma levels described above.

The compounds of this invention can be prepared by a skilled practitioner with the information provided below. The following Examples are illustrative and are not intended to limit the invention in any way.

General Route to DAPA Compounds

Synthesis of compounds of structure I
(R4 = optionally substituted alkyl)

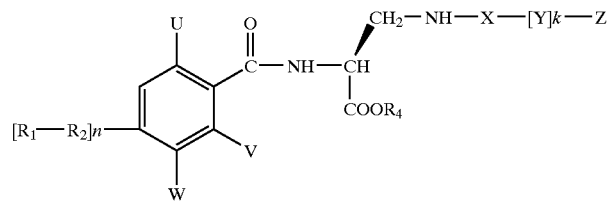 

Structure I
R4 = optionally substituted alkyl

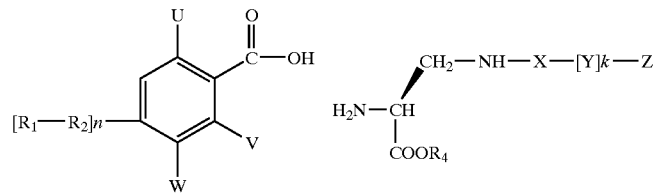 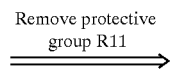

Structure 7        Structure 6

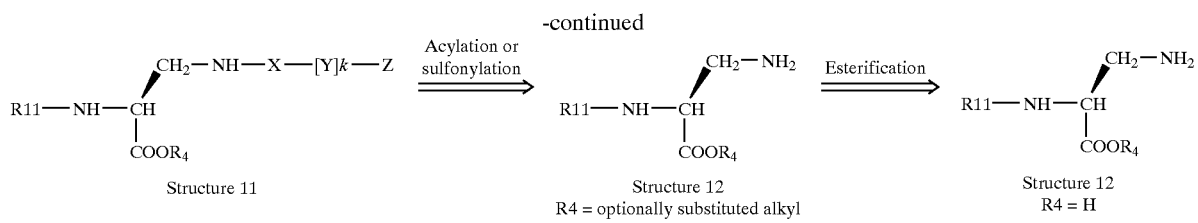

Compounds of structure 12 are generally known compounds, or analogues of known compounds, or can be prepared in a similar manner to the known compounds, or as described in the Examples, or in analogy thereto.

(Note: there are two ways to make compounds of structure I (R4 = opt. sub. alkyl). The other route is on the previuos page.)

Synthesis of compounds of structure 7

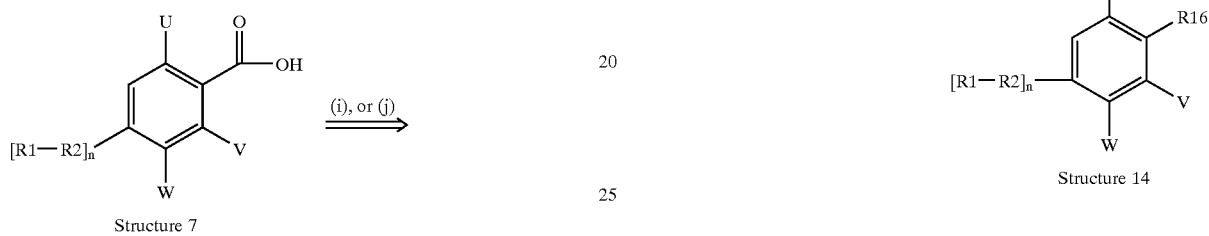

Synthesis of compounds of structure 13

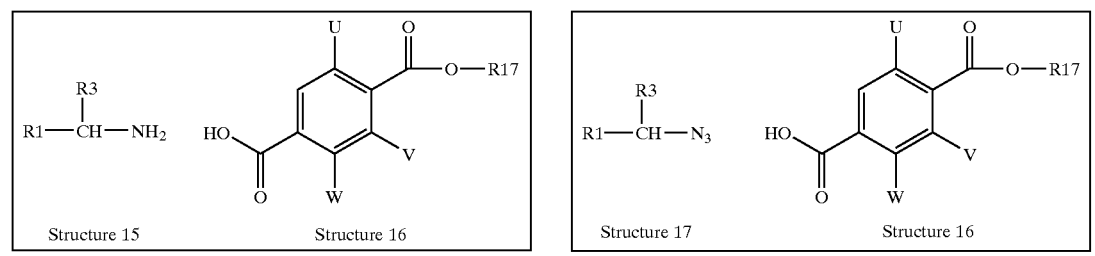

-continued

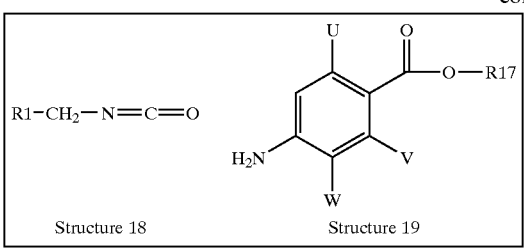

Structure 18  Structure 19

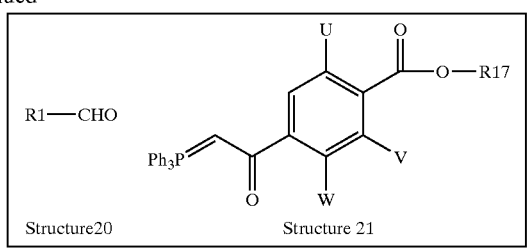

Structure 20  Structure 21

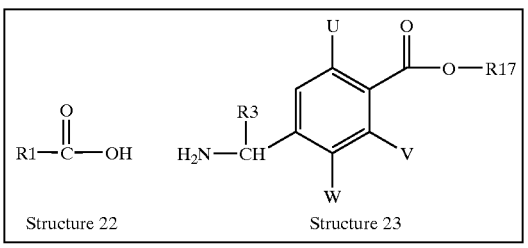

Structure 22  Structure 23

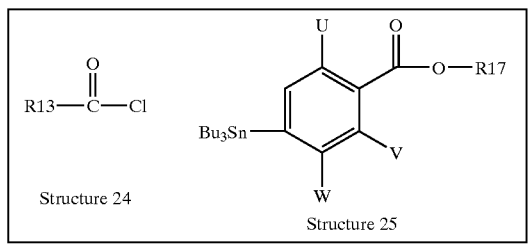

Structure 24  Structure 25

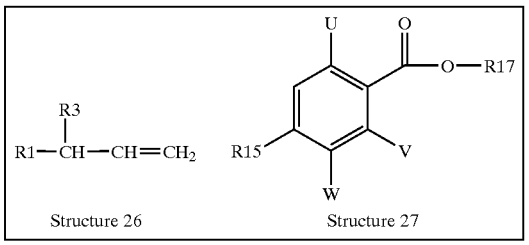

Structure 26  Structure 27

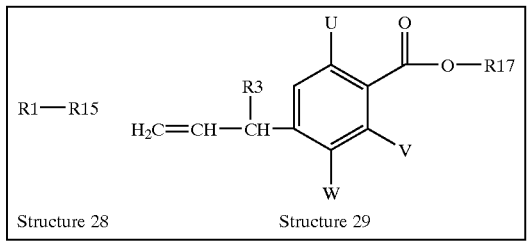

Structure 28  Structure 29

The starting materials of structure 15, 19, 20, 22, 24 and 28 are generally known compounds. Insofar as they are not known compounds or analogues of known compounds, they can be prepared in a similar manner to the known compounds or as described in the Examples hereinafter or in analogy thereto (Note: eight ways are shown to make different compounds of structure 13)

Synthesis of compounds of structure 16

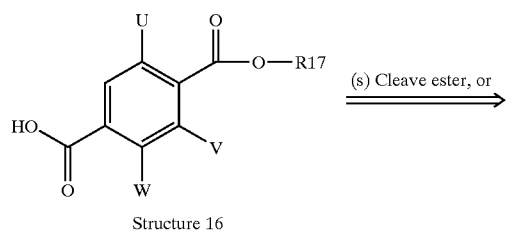

Structure 16

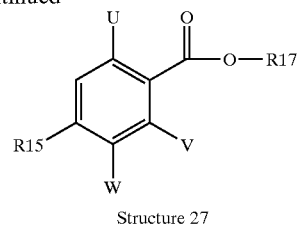

Structure 27

Some compounds of structure 30 are known compounds. Others can be prepared according to the following Scheme.

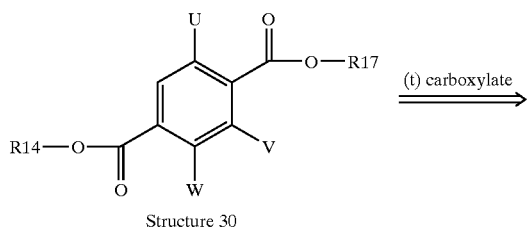

Structure 30

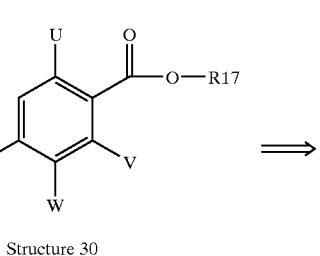

Structure 30

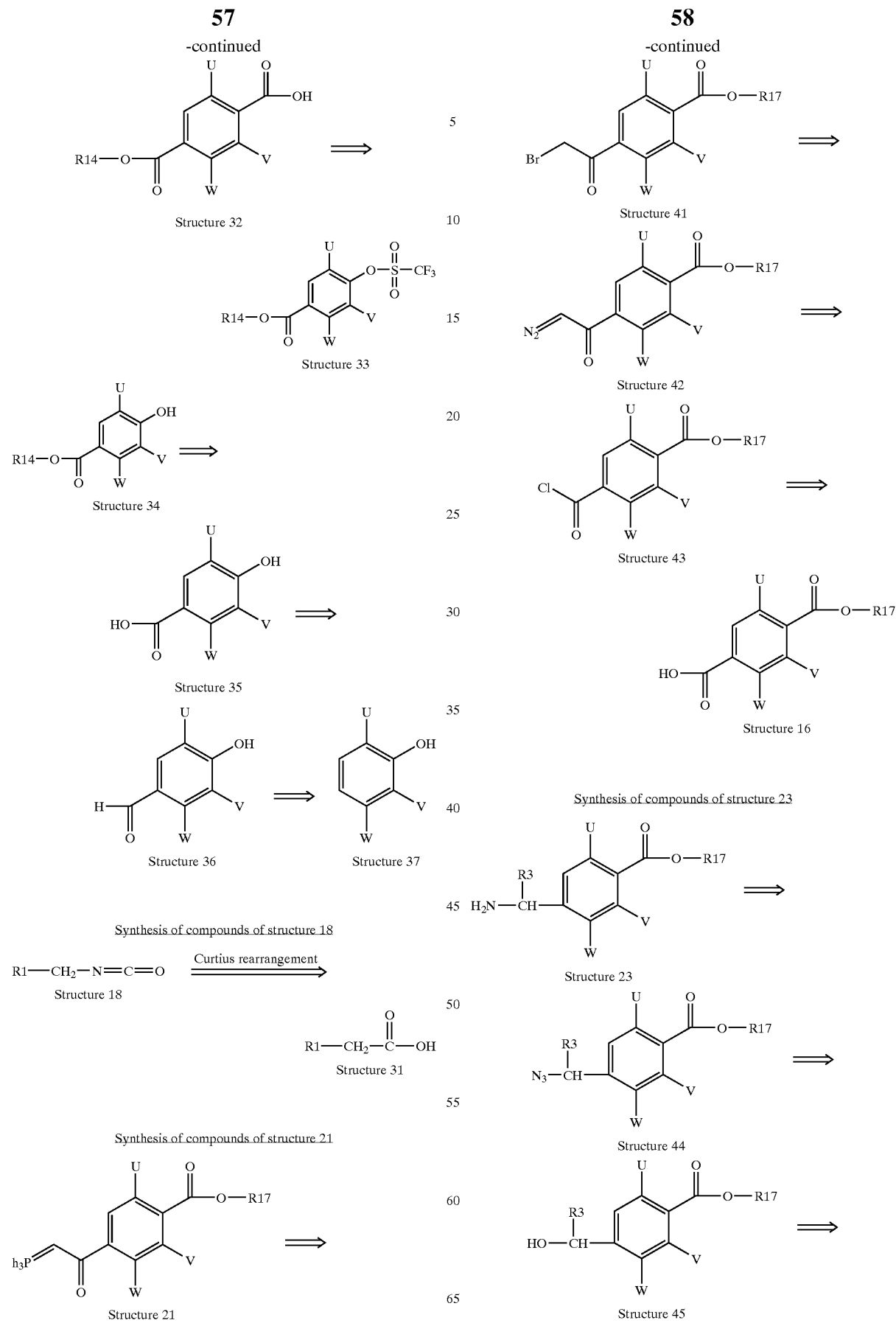

-continued

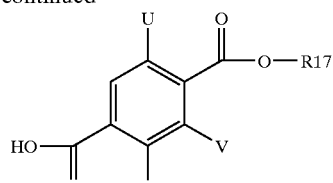

Structure 16

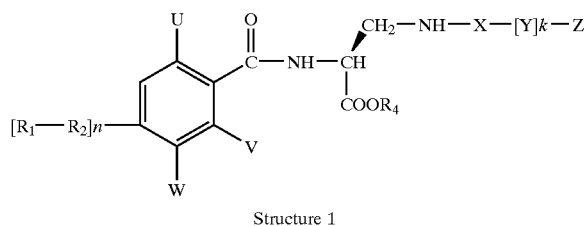

Structure 1

The compounds of the present invention can be prepared by any conventional means. For example, compounds of structure 1 can be manufactured by (a) for the preparation of a compound of structure 1 in which $R_4$ is hydrogen from a compound of structure 1 in which $R_4$ is an optionally substituted alkyl group that can be cleaved under acidic conditions, such as tert-butyl or aralkyl (for example Wang resin) and the like, by treatment with a strong acid, or (b) for the preparation of a compound of structure 1 in which $R_4$ is hydrogen from a compound of structure 1 in which $R_4$ is a lower alkyl or aralkyl group, unbranched on the carbon next to oxygen, for example, the methyl, ethyl, n-propyl, n-butyl, benzyl groups, and the like, by treatment with alkali metal hydroxide solution, or (c) for the preparation of a compound of structure 1 in which $R_4$ is hydrogen from a compound of structure 1 in which $R_4$ represents a moiety that can be removed hydrogenolytically, such as benzyl, and in which the rest of the molecule is stable to hydrogenolysis, by catalytic hydrogenation, and/or (d) if desired, separating a mixture of diastereoisomers into the optically pure diastereomers, and/or (e) if desired, converting a compound of structure 1 which bears a basic nitrogen into a pharmaceutically acceptable acid addition salt, and/or (f) if desired, converting a compound of structure 1 in which $R_4$ is hydrogen into a pharmaceutically acceptable alkali metal salt.

The cleavage of an acid-labile ester moiety in accordance with procedure (a) can be carried out in accordance with methods that are known per se. For example, the ester may be treated with a strong inorganic acid, for example a hydrohalic acid such as hydrogen chloride or hydrogen bromide, or a strong organic acid, for example a halogenated alkane carboxylic acid such as trifluoroacetic acid and the like. The reaction is conveniently carried out in the presence of an inert organic solvent (such as dichloromethane) and at a temperature between about 0 degrees and about room temperature, preferably at about room temperature.

The cleavage of an alkali-labile ester moiety in accordance with procedure (b) can be carried out according to known procedures. For example, the ester may be treated with an alkali metal hydroxide, for example lithium hyroxide, in a suitable inert solvent system, for example a mixture of methanol, tetrahydrofuran and water. The reaction is carried out at a temperature between about 0 degrees and about room temperature.

The cleavage of a hydrogenolytically labile ester moiety by catalytic hydrogenation in accordance with procedure (c) can be carried out in a known manner. The reaction may be carried out by hydrogenation in the presence of a noble metal catalyst such as palladium-on-carbon in the presence of an inert solvent (for example, an alcohol such as ethanol) at about room temperature and under atmospheric pressure.

The optional separation in accordance with procedure (d) can be carried out according to known methods such as column chromatography, thin-layer chromatography, high pressure liquid chromatography etc.

The optional conversion of a compound of structure 1 into a pharmaceutically acceptable acid addition salt in accordance with procedure (e) can be effected by conventional means. For example, the compound can be treated with an inorganic acid, for example hydrochloric acid, hydrobromic acid, sulfuric acid, nitric acid, phosphoric acid etc., or with an appropriate organic acid such as acetic acid, trifluoroacetic acid, citric acid, tartaric acid, methanesulfonic acid, p-toluenesulfonic acid, or the like.

The optional conversion of a compound of structure 1 into a pharmaceutically acceptable alkali metal salt in accordance with procedure (f) can be effected by conventional means. For example, the compound can be treated with an inorganic base such as lithium hydroxide, sodium hydroxide, potassium hydroxide, or the like.

The compounds of structure 1 in which $R_4$ represents an optionally substituted alkyl moiety can be prepared by means which are well known to one of ordinary skill in the field. For example, they can be prepared by Structure 5

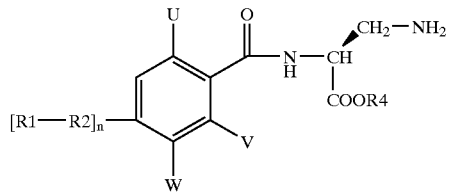

Structure 6

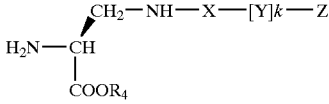

Structure 7

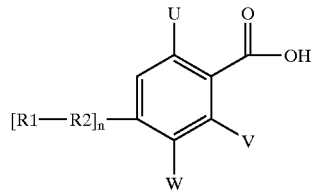

(g) treatment of a compound of structure 5 with an agent yielding a carboxamide or sulfonamide, or (h) coupling a compound of structure 6 with a compound of structure 7.

The acylation or sulfonylation of compounds of structure 5 in accordance with procedure (g) can be effected using procedures that are known per se. For example, compounds of structure 1 in which X represents a sulfonyl group can be prepared by reaction of compounds of structure 5 with a sulfonyl chloride in the presence of an appropriate base for example pyridine which can also be used as solvent. The reaction may also be performed by using a tertiary amine as the base, in the presence of an inert solvent such as tetrahydrofuran or dichloromethane; or in aqueous solution using an alkali metal hydroxide such as sodium hydroxide as the base. The reaction is conveniently carried out at a temperature of between about room temperature and about 80 degrees, preferably at about room temperature. Compounds of structure 1 in which X represents a carbonyl group can be prepared by reaction of compounds of structure 5 with carboxylic acids in the presence of a coupling agent, many examples of which are well known per se in peptide chemistry, and in the optional presence of a substance that increases the rate of the reaction, such as 1-hydroxybenzotriazole or 1-hydroxy-7-azabenzotriazole; or by reaction of compounds of structure 5 with reactive derivatives of carboxylic acids such as the corresponding acid halides (for example, the acid chlorides), acid anhydrides, mixed anhydrides, activated esters etc. The reaction is conveniently carried out by treating the compound of structure 5 with a carboxylic acid in the presence of a carbodiimide reagent such as diisopropyl carbodiimide and 1-hydroxy-7-azabenzotriazole in an inert solvent such as N,N-dimethylformamide or N-methylpyrrolidinone at a temperature between about 0 degrees and about room temperature, preferably at about,room temperature.

The carboxylic acids and reactive derivatives thereof used for the acylation of compounds of structure 5 and compounds of structure 12, and the sulfonyl chlorides used for the sulfonylation of compounds of structure 5 and compounds of structure 12, are generally known compounds. Insofar as they are not known compounds or analogues of known compounds, they can be prepared in a similar manner to the known compounds or as described in the Examples hereinafter or in analogy thereto. Examples of reactions that can be used for the preparation of such acids are: saponification of known carboxylate esters, alkylation of known carboxylate esters followed by carboxylation, conversion of the amino group of an α-amino acid to pyrrole, protection of known amino acids with the (9H-fluoren-9-ylmethoxy) carbonyl group, oxidation of known aldehydes, and haloform reaction of known methylketones.

The coupling of compounds of structure 6 with compounds of structure 7 in accordance with procedure (h) can be achieved using methods well known to one of ordinary skill in the art. For example, the transformation can be carried out by reaction of carboxylic acids of structure 7 or of appropriate derivatives thereof such as activated esters, with amines of structure 6 or their corresponding acid addition salts (e.g., the hydrochloride salts) in the presence, if necessary, of a coupling agent, many examples of which are well known per se in peptide chemistry. The reaction is conveniently carried out by treating the carboxylic acid of structure 7 with the hydrochloride of the amine of structure 6 in the presence of an appropriate base, such as diisopropylethylamine, a coupling agent such as O-(benzotriazol-1-yl)-1,1,3,3-tetramethyluronium hexafluorophosphate, and in the optional additional presence of a substance that increases the rate of the reaction, such as 1-hydroxybenzotriazole or 1-hydroxy-7-azabenzotriazole, in an inert solvent, such as a chlorinated hydrocarbon (e.g., dichloromethane) or N,N-dimethylformamide or N-methylpyrrolidinone, at a temperature between about 0 degrees and about room temperature, preferably at about room temperature.

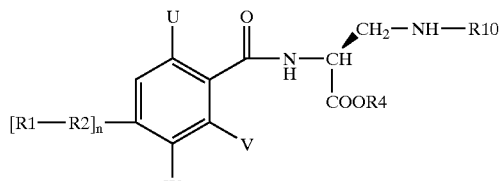

Structure 8

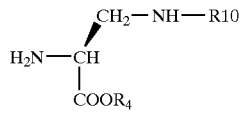

Structure 9

The compounds of structure 5 can be prepared by methods that are well known in the field, such as by removal of the protective group $R_{10}$ from a compound of structure 8, in which $R_{10}$ represents one of a number of amine protective groups commonly used in the field of peptide chemistry, for example a carbamate such as tert-butoxycarbonyl, allyloxycarbonyl, benzyloxycarbonyl, 9H-fluoren-9-ylmethoxycarbonyl or the like, using the appropriate conditions that are conventionally used for the removal of such a protective group. For example, compounds of structure 5 may be prepared from compounds of structure 8 in which $R_{10}$ represents the allyloxycarbonyl group by treatment with a source of palladium(0), for example bis (triphenylphosphine)palladium(II) chloride, and a reducing agent, for example, tri-n-butyltin hydride. The reaction is conveniently carried out in an inert solvent such as a halogenated hydrocarbon (e.g., dichloromethane) at about room temperature.

The compounds of structure 8 may be prepared by conventional means by coupling a carboxylic acid of structure 7, or an activated derivative thereof such as an activated ester (e.g., the N-hydroxysuccinimide ester), with an amine of structure 9, or a salt thereof. This coupling can be carried out in a manner analogous to that described earlier in connection with the coupling of carboxylic acids of structure 7 with amines of structure 6 or salts thereof.

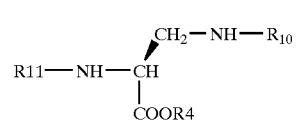

Structure 10

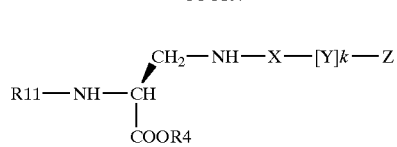

Structure 11

The compounds of structure 9 may be prepared from compounds of structure 10 in which $R_{10}$ and $R_{11}$ each represent one of a number of amine protective groups commonly used in the field of peptide chemistry, for example a carbamate such as tert-butoxycarbonyl, allyloxycarbonyl, benzyloxycarbonyl, 9H-fluoren-9-ylmethoxycarbonyl or the like, provided that the protective group represented by $R_{11}$ is not the same as the protective group represented by $R_{10}$, by procedures well known to one of ordinary skill in the art. For example, in the case of a compound of structure 10 in which $R_{11}$ represents a tert-butoxycarbonyl group and $R_{10}$ represents an allyloxycarbonyl group, the compound of structure 9 may conveniently be obtained by treatment with a strong acid, for example a halogenated alkane carboxylic acid such as trifluoroacetic acid. The reaction may be carried out in an inert organic solvent (such as dichloromethane) at a temperature between about 0 degrees and about room temperature, preferably at about room temperature.

The compounds of structure 10 in which $R_4$ represents an optionally substituted alkyl group, for example, lower alkyl (e.g., methyl or ethyl), aralkyl (e.g., benzyl), or a resin commonly used in solid-phase synthesis (e.g., Wang resin), can be made by any conventional methods. For example, they may conveniently be made from the corresponding carboxylic acid of structure 10 in which $R_4$ represents hydrogen by any esterification reaction, many of which are well known to one of ordinary skill in the art. For example, compounds of structure 10 in which $R_4$ represents methyl can be prepared from compounds of structure 10 in which $R_4$ represents hydrogen by treatment with an ethereal solution of diazomethane. The reaction is conveniently carried out in an inert solvent such as an ether (e.g., diethyl ether or tetrahydrofuran) or an alcohol (e.g., methanol), at a temperature of between about 0 degrees and about room temperature, preferably at about 0 degrees.

The starting materials of structure 10 in which $R_4$ represents hydrogen are generally known compounds. Insofar as they are not known compounds or analogues of known compounds, they can be prepared in a similar manner to the known compounds or as described in the Examples hereinafter or in analogy thereto.

The compounds of structure 6 may be prepared by methods that are well known in the field of peptide chemistry for the removal of amino protective groups from compounds of structure 11, in which $R_{11}$ represents one of a number of amine protective groups commonly used in the field of peptide chemistry, for example a carbamate such as tert-butoxycarbonyl, allyloxycarbonyl, benzyloxycarbonyl, 9H-fluoren-9-ylmethoxycarbonyl or the like. For example, in the case of a compound of structure 11 in which $R_{11}$ is a tert-butoxycarbonyl group, the compound of structure 6 may be conveniently obtained in a manner analogous to that described earlier in connection with the removal of a tert-butoxycarbonyl group from a compound of structure 10 in which $R_{11}$ represents a tert-butoxycarbonyl group.

The compound of structure 11 in which $R_4$ represents an alkyl group, an aralkyl group, or a resin such as is commonly used in solid-phase synthesis (e.g., Wang resin), is prepared from a compound of structure 11, in which $R_4$ represents hydrogen and X represents carbonyl, by any conventional methods. For example, the compound of structure 11 in which $R_4$ represents hydrogen and X represents carbonyl can be converted to a compound of structure 11 in which $R_4$ represents methyl and X represents carbonyl by treatment with an ethereal solution of diazomethane. The reaction is conveniently carried out under conditions analogous to those described above for the preparation of compounds of structure 10 in which $R_4$ represent methyl.

Structure 12

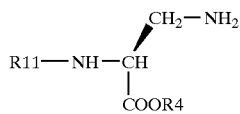

Structure 13

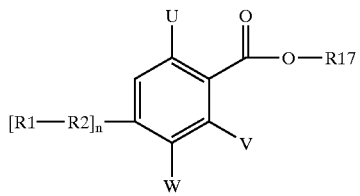

The compounds of structure 11, in which $R_4$ represents hydrogen, may be conveniently prepared by acylation or sulfonylation of compounds of structure 12, in which $R_4$ represents hydrogen, by conventional methods. For example, in the case where $R_4$ represents hydrogen and X represents sulfonyl, the compound of structure 11 may be conveniently prepared by treating a compound of structure 12 in which $R_4$ represents hydrogen with a sulfonyl chloride in the presence of an appropriate base, such as pyridine or a tertiary amine (e.g., diisopropylethylamine) in the optional presence of an inert solvent such as tetrahydrofuran. The reaction can be conveniently be carried out at a temperature between about 0 degrees and about room temperature, preferably at about room temperature. As a further example, in the case where R4 represents hydrogen and X represents carbonyl, the compound of structure 11 may be obtained by treating a compound of structure 12, in which $R_4$ represents hydrogen, with reactive derivatives of carboxylic acids such as the corresponding acid halides (for example, the acid chlorides), acid anhydrides, mixed anhydrides, activated esters etc. The reaction is conveniently carried out in a mixture of water and an ether such as dioxane, at a temperature between about 0 degrees and about room temperature, preferably at about room temperature.

The starting materials of structure 12 in which $R_4$ represents hydrogen and $R_{11}$ represents one of a number of amine protective groups commonly used in the field of peptide chemistry, are generally known compounds. Insofar as they are not known compounds or analogues of known compounds, they can be prepared in a similar manner to the known compounds or as described in the Examples hereinafter or in analogy thereto.

The starting materials of structure 7 in which n represents zero are generally known compounds. Insofar as they are not known compounds or analogues of known compounds, they can be prepared in a similar manner to the known compounds.

The compounds of structure 7 in which n represents 1 are prepared by methods that are well known in the field of organic chemistry. For example, they can be prepared by:
  (i) by the removal of carboxylic acid protective groups from compounds of structure 13, in which $R_{17}$ represents for example an unbranched lower alkyl group (e.g., methyl or ethyl), an aralkyl group, or a tert-butyl group or the like.
  (j) by carboxylation of compounds of structure 14, where $R_{16}$ represents a group that can be carboxylated under noble metal catalysis, and where the rest of the molecule is stable to such treatment.

For the deprotection of ester protective groups in accordance with procedure (i), any conventional means can be used. For example, in the case where $R_{17}$ represents an unbranched lower alkyl group (e.g., methyl), the reaction may be carried out by treating the compound of structure 13 with an alkali methyl hydroxide, such as potassium hydroxide, sodium hydroxide or lithium hydroxide, preferably lithium hydroxide, in an appropriate solvent, such as a mixture of tetrahydrofuran, methanol and water. The reaction is conveniently carried out at a temperature between about 0 degrees and about room temperature, preferably at about room temperature.

For the carboxylation of compounds of structure 14 where $R_{16}$ represents a group that can be carboxylated under noble metal catalysis, in accordance with procedure (j), a variety of procedures can be used. For example, the reaction can be carried out by reacting the compound of structure 14 with water under carbon monoxide gas at a pressure between about 14 pounds per square inch and about 50 pounds per square inch, preferably at about 40 pounds per square inch, in the presence of a base, for example a tertiary amine, such as triethylamine, in an inert solvent, such as N,N-dimethylformamide, dimethylsulfoxide, acetonitrile, or the like. The reaction can be carried out at a temperature between about 40 degrees and about 100 degrees, preferably at about 80 degrees. Compounds of structure 14 can be made by routes similar to those described below for the preparation of compounds of structure 13.

The compounds of structure 13, in which $R_{17}$ represents for example an unbranched lower alkyl group (e.g., methyl or ethyl), an aralkyl group, or a tert-butyl group or the like, may be prepared by any conventional means. For example, they may be prepared by

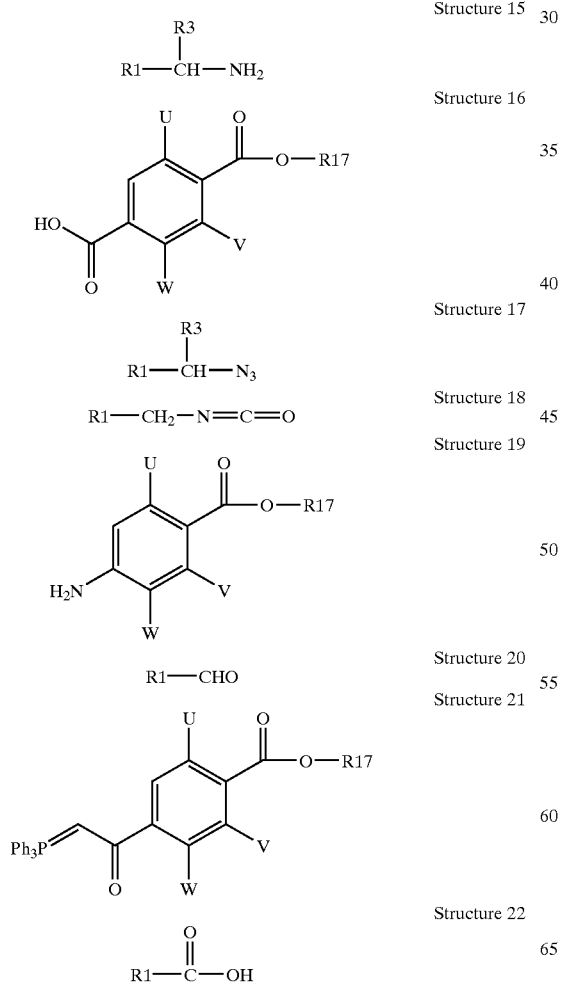

Structure 15

Structure 16

Structure 17

Structure 18

Structure 19

Structure 20

Structure 21

Structure 22

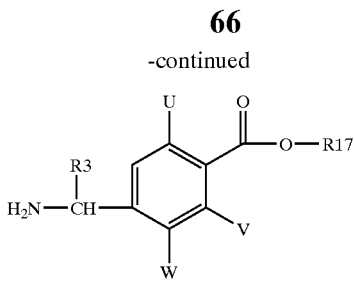

Structure 23

Structure 24

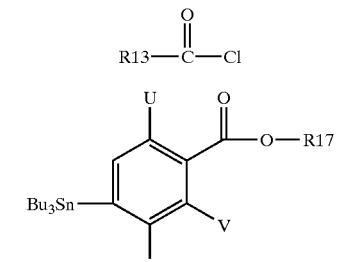

Structure 25

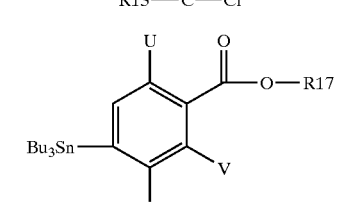

Structure 26

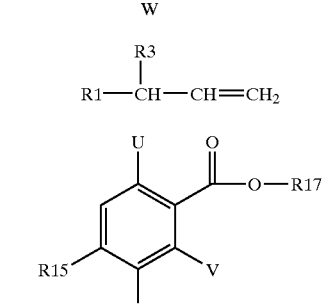

Structure 27

Structure 28

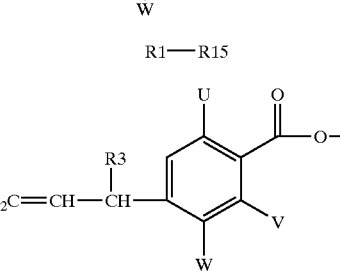

Structure 29

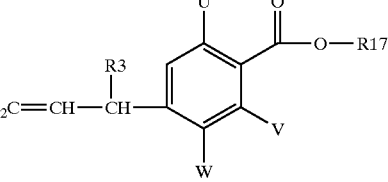

(k) for the preparation of a compound of structure 13 in which $R_2$ represents

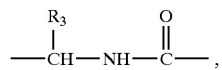

by reacting a compound of structure 15 or a salt thereof with a compound of structure 16 or a reactive derivative thereof, or (l) for the preparation of a compound of structure 13 in which $R_2$ represents

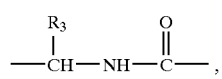

by reacting a compound of structure 17 with a reactive derivative of a compound of structure 16 under reducing conditions, or (m) for the preparation of a compound of structure 13 in which $R_2$ represents

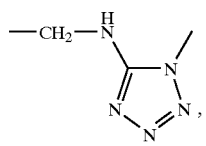

by reacting an isocyanate of structure 18 with an aniline of structure 19, and converting the resulting urea into an aminotetrazole, or (n) for the preparation of a compound of structure 13 in which $R_2$ represents

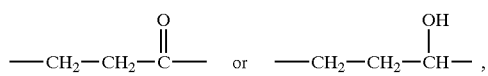

by treating an aldehyde of structure 20 with a phosphorane of structure 21, and reducing the resulting chalcone, or (o) for the preparation of a compound of structure 13 in which $R_2$ represents

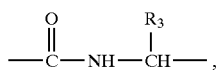

by reacting a compound of structure 22 or a reactive derivative thereof with a compound of structure 23 or a salt thereof.

(p) for the preparation of a compound of structure 13 in which $R_2$ represents

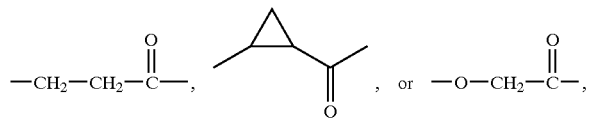

by reacting a compound of structure 24, in which $R_{13}$ and carbonyl taken together represent $R_1$–$R_2$—, with a compound of structure 25.

(q) for the preparation of a compound of structure 13 in which $R_2$ represents

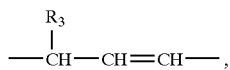

by reacting a compound of structure 26 with a compound of structure 27, in which $R_{15}$ represents a group that can be substituted under conditions of the Heck reaction.

(r) for the preparation of a compound of structure 13 in which $R_2$ represents

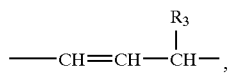

by reacting a compound of structure 28 with a compound of structure 29, in which $R_{15}$ represents a group that can be substituted under conditions of the Heck reaction.

The acylation of compounds of structure 15 to give compounds of structure 13, in which $R_2$ represents

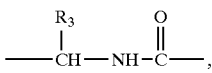

in accordance with procedure (k) can be effected in a manner analogous to that described earlier in connection with the coupling of a compound of structure 6 with a compound of structure 7.

The coupling of compounds of structure 17 with reactive derivatives of compounds of structure 16 in accordance with procedure (I) can be carried out under conditions that are known per se. Examples of reactive derivatives of compounds of structure 16 that can be used in the reaction are acid anhydrides, mixed anhydrides, and activated esters (e.g., the N-hydroxysuccinimidyl ester), preferably activated esters. The reaction can be conveniently carried out using palladium-on-carbon as the reduction catalyst in the presence of hydrogen at a pressure between about 14 pounds per square inch and about 50 pounds per square inch, preferably about 14 pounds per square inch. The reaction may be conducted in the presence of an inert solvent such as ethyl acetate, or an aromatic hydrocarbon (e.g., benzene), or an alcohol (e.g., methanol), or in a mixture of such solvents. The reaction may be conveniently carried out at a temperature about room temperature.

The coupling of isocyanates of structure 18 with anilines of structure 19 to give ureas, in accordance with procedure (m), may be carried out by methods known per se. For example, the reaction may be carried out by reacting the isocyanate of structure 18 with the aniline of structure 19 in the presence of a suitable base, such as a tertiary amine (e.g., diisopropylethylamine), in an inert solvent such as an aromatic hydrocarbon (e.g., benzene). The reaction can be carried out conveniently at a temperature between about 80 degrees and about 110 degrees, preferably at about 80 degrees. The resulting urea can be converted to the aminotetrazole using any conventional means for effecting such a transformation, such as by treatment with trimethylsilylazide under dehydrating conditions. For example, the reaction can be conveniently carried out by treating the urea with trimethylsilylazide, diethylazodicarboxylate, and triphenylphosphine in an inert solvent, such as tetrahydrofuran, at a temperature between about 0 degrees and about room temperature, preferably at about room temperature.

The coupling of aldehydes of structure 20 with phosphoranes of structure 21 to give chalcones, in accordance with procedure (n), may be carried out by methods that are well known in the field of organic chemistry. For example, the phosphorane may be treated with the aldehyde in an inert solvent such as an aromatic hydrocarbon (e.g., benzene) at a temperature between about 80 degrees and about 110 degrees, preferably at about 80 degrees. The resulting chalcone can be reduced by catalytic hydrogenation to give a compound of structure 13, in which $R_2$ represents

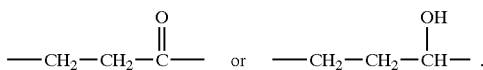

The reaction may be carried out by hydrogenation in the presence of a noble metal catalyst such as palladium-on-carbon in the presence of an inert solvent (for example, ethyl acetate or an alcohol such as ethanol) at about room temperature and under 1 atmosphere of hydrogen.

The coupling of a carboxylic acid of structure 22, or a reactive derivative thereof, such as the acid halide (e.g., acid chloride), acid anhydride, mixed anhydride, or activated ester, with an amine of structure 23 or salt thereof, in accordance with procedure (o), can be effected using one of a variety of conditions that are well known in the field of peptide chemistry. For example, the reaction can be carried out in a manner analogous to that described earlier in connection with the coupling of a compound of structure 6 with a compound of structure 7.

The coupling of a compound of structure 24 with a compound of structure 25 in accordance with procedure (p) can be carried out under conditions that are well known to organic chemists. For example, the reaction can be carried out in the presence of a palladium catalyst such as tetrakis (triphenylphosphine)palladium(0), dichlorobis (triphenylphosphine)palladium(II), tris (dibenzylideneacetone)dipalladium(0), or trans-benzyl (chloro)bis(triphenylphosphine)palladium(II), preferably tris(dibenzylideneacetone)dipalladium(0), and in the optional additional presence of bases such as potassium carbonate, diisopropylethylamine and/or triethylamine, in an inert solvent, such as an aromatic hydrocarbon (e.g., benzene or toluene), dichloroethane, or an ether such as dioxane or tetrahydrofuran, preferably tetrahydrofuran, at a temperature between about room temperature and about 100 degrees, preferably at about room temperature.

The coupling of a compound of structure 26 with a compound of structure 27, in which $R_{15}$ represents a group that can be substituted under conditions of the Heck reaction, in accordance with procedure (q) can be carried out by procedures that are known to one of average skill in the art. For example, the reaction can be carried out by treating the compound of structure 26 with the compound of structure 27 in the presence of a source of palladium(0) such as palladium(II) acetate, in the optional presence of a phosphine such as tributylphosphine, triphenylphosphine or tri-ortho-tolylphosphine, preferably triphenylphosphine, in the optional presence of tetrabutylammonium chloride, in the presence of a base which may be organic (e.g., triethylamine) or inorganic (e.g, potassium carbonate, sodium hydrogen carbonate, thallium(I) acetate or silver acetate), in an inert solvent (e.g., N,N-dimethylformamide or N,N-dimethylacetamide) at a temperature between about room temperature and about 110 degrees, preferably at about 100 degrees.

The coupling of a compound of structure 28 with a compound of structure 29, in which $R_{15}$ represents a group that can be substituted under conditions of the Heck reaction, in accordance with procedure (r) can be carried out by procedures that are well known. For example, the reaction can be carried out in a manner analogous to that described in connection with the coupling of a compound of structure 26 with a compound of structure 27.

The starting materials of structure 15, 19, 20, 22, 24, and 28 are generally known compounds. Insofar as they are not known compounds or analogues of known compounds, they can be prepared in a similar manner to the known compounds or as described in the Examples hereinafter or in analogy thereto.

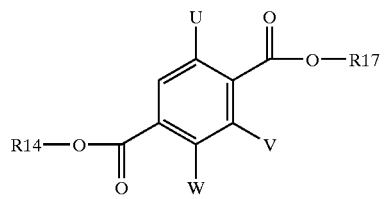

Structure 30

The compounds of structure 16 can be made by any conventional means. For example, they may be prepared by:
(s) hydrolyzing a compound of structure 30 in which $R_{17}$ and $R_{14}$ separately represent an unbranched lower alkyl group (e.g., methyl or ethyl), an aralkyl group, or a tert-butyl group or the like, or
(t) carboxylating a compound of structure 27, in which $R_{15}$ is a group that can be substituted under noble metal catalysis, such as iodide, bromide, or trifluoromethanesulfonate.

The hydrolysis of compounds of structure 30 in accordance with procedure (s) can be effected by any conventional means. For example, in the case of a compound of structure 30 in which $R_{14}$ is a group that can be cleaved by basic hydrolysis, the reaction can be conveniently effected by treating the compound with one equivalent of an alkali metal hydroxide, such as potassium hydroxide, sodium hydroxide, or lithium hydroxide, preferably lithium hydroxide, in a suitable solvent, such as a mixture of tetrahydrofuran, methanol, and water. The reaction can be carried out at a temperature between about 0 degrees and about room temperature, preferably at about room temperature.

The carboxylation of compounds of structure 27, in which $R_{15}$ is a group that can be substituted under noble metal catalysis, such as iodide, bromide, or trifluoromethanesulfonate, in accordance with procedure (t) can be carried out using conventional methods. For example, the reaction can be carried out by reacting the compound of structure 27 with water under carbon monoxide gas at a pressure between about 14 pounds per square inch and about 50 pounds per square inch, preferably at about 40 pounds per square inch, in the presence of a base, for example a tertiary amine, such as triethylamine, in an inert solvent, such as N,N-dimethylformamide, dimethylsulfoxide, acetonitrile, or the like. The reaction can be carried out at a temperature between about 40 degrees and about 100 degrees, preferably at about 80 degrees.

Compounds of structure 17 may be prepared by any conventional means. For example, in the case where $R_3$ is hydrogen, they may be prepared from compounds of structure 38 by substitution of the bromine. The reaction may be carried out by treating a compound of structure 38 with an alkali metal azide salt, preferably sodium azide, in the optional additional presence of an agent that will increase the rate of the reaction, such as potassium iodide. The reaction may be carried out in the presence of an inert solvent such as acetone or N,N-dimethylformamide at a temperature of between about room temperature and about 60 degrees, preferably at about 60 degrees. In the case where $R_3$ is a lower alkyl group, compounds of structure 17 may be prepared by reaction of an alcohol of structure 39 with a reagent such as diphenylphoshoryl azide. The reaction is conveniently carried out in the presence of a base such as 1,8-diazabicyclo[5.4.0]undec-7-ene and an inert solvent such as tetrahydrofuran at a temperature around room temperature.

Structure 31

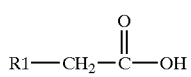

Compounds of structure 18 can be prepared by reactions that are known per se. For example, they can be prepared by Curtius rearrangement of compounds of structure 31. The reaction can be conveniently carried out by treating the compound of structure 31 with a reagent such as diphenylphosphoryl azide and a base such as a tertiary amine (e.g., diisopropylethylamine) in an inert solvent such as an aromatic hydrocarbon (e.g., benzene). The reaction can be carried out conveniently at a temperature around 70 degrees.

Compounds of structure 21 can be prepared by a variety of methods well known in the field of organic chemistry. For example, they can be prepared by deprotonation of the corresponding phosphonium salts by treatment with a base, for example sodium carbonate, in an inert solvent, such as a mixture of an aromatic hydrocarbon (e.g., benzene) and water. The reaction can conveniently be carried out at about room temperature. The phosphonium salts can be prepared by any conventional means. For example, they can be prepared by a substitution reaction of compounds of structure 41. The reaction may conveniently be carried out by treating a compound of structure 41 with triphenylphosphine in the optional presence of a catalytic amount of pyridine in an inert solvent such as acetonitrile. The reaction can be run at a temperature between about room temperature and about 80 degrees, preferably at about room temperature.

Compounds of structure 23 may be made by methods that are known per se in the field of organic chemistry. For example, they may be made by the reduction of azides of structure 44 by one of a variety of methods including catalytic hydrogenation using a noble metal catalyst, treatment with triphenylphosphine and water, or treatment with sodium borohydride. For example, in the case where the compound of structure 23 is prepared by catalytic hydrogenation, a noble metal catalyst such as palladium-on-carbon may be used, and the reaction may be carried out in the presence of an inert solvent (for example, an alcohol such as ethanol) at about room temperature and under 1 atmosphere of hydrogen.

Compounds of structure 25 can be made by procedures that are well known. For example, they can be prepared by coupling a compound of structure 27 where $R_{15}$ represents iodide, bromide, or trifluoromethansulfonate, with hexabutyldistannane in the presence of a noble metal catalyst such as tetrakis(triphenylphosphine)palladium(0), allylpalladium (II) chloride dimer, or dichlorobis(triphenylphosphine) palladium(II), in a solvent such as an aromatic hydrocarbon (e.g, toluene), an ether (e.g., tetrahydrofuran, dioxane, or dimethoxyethane) or an amine (e.g., triethylamine). The reaction is conveniently carried out at a temperature between about 60 degrees and about 100 degrees, preferably at about 80 degrees.

Compounds of structure 26 are either known compounds or they can be prepared by methods that are known per se. For example, they can be prepared by the reaction of allylstannanes with compounds of structure 28 under palladium catalysis. This reaction can be conveniently carried out by treatment of the compound of structure 28 with the allylstannane in the presence of a catalysts such as tetrakis (triphenylphosphine)palladium(0), dichlorobis (triphenylphosphine)palladium(II), tris (dibenzylideneacetone)dipalladium(0), or trans-benzyl (chloro)bis(triphenylphosphine)palladium(II), preferably tetrakis(triphenylphosphine)palladium(0), in the optional additional presence of lithium chloride, in an inert solvent such as an aromatic hydrocarbon (for example benzene) or a polar aprotic solvent such as N-methylformamide or N-methylpyrrolidinone, at a temperature between about room temperature and about 150 degrees, conveniently at around 100 degrees Compounds of structure 27 can be made by reactions that are well known in the field of organic chemistry. They can be made by (u) for the preparation of compounds of structure 27, in which $R_{17}$ represents a lower alkyl group (e.g., methyl or ethyl), an aralkyl group, or a tert-butyl group or the like, esterifying a carboxylic acid of structure 27, in which $R_{17}$ represents hydrogen, or (v) for the preparation of compounds of structure 27 in which $R_{17}$ represents a lower alkyl group (e.g., methyl or ethyl), an aralkyl group, or a tert-butyl group or the like, and $R_{15}$ represents iodide, diazotizing an aniline of structure 19 in which $R_{17}$ represents a lower alkyl group (e.g., methyl or ethyl), an aralkyl group, or a tert-butyl group or the like, and treating the resulting diazonium salt with iodide, or (w) for the preparation of compounds of structure 27 in which $R_{17}$ represents a lower alkyl group (e.g., methyl or ethyl), an aralkyl group, or a tert-butyl group or the like, and $R_{15}$ represents trifluoromethanesulfonate, reacting a phenol of structure 27, in which $R_{17}$ represents a lower alkyl group (e.g., methyl or ethyl), an aralkyl group, or a tert-butyl group or the like, and $R_{15}$ represents hydroxyl, with a reactive derivative of trifluoromethanesulfonic acid.

Carboxylic acids of structure 27 in which $R_{17}$ represents hydrogen can be converted to the corresponding esters, for example those in which $R_{17}$ represents a lower alkyl group (e.g., methyl or ethyl), an aralkyl group, or a tert-butyl group or the like, in accordance with procedure (u), using one of a number of procedures that are familiar to one of ordinary skill in the art. For example, a compound of structure 27 in which $R_{17}$ represents methyl can be prepared by reacting a carboxylic acid of structure 27 in which $R_{17}$ represents hydrogen with an ethereal solution of diazomethane. The reaction is conveniently carried out in an inert solvent such as an ether (e.g., diethyl ether or tetrahydrofuran) or an alcohol (e.g., methanol), at a temperature of between about 0 degrees and about room temperature, preferably at about 0 degrees.

Anilines of structure 19, in which $R_{17}$ represents a lower alkyl group (e.g., methyl or ethyl), an aralkyl group, or a tert-butyl group or the like, can be converted to the corresponding aryl iodides of structure 27, in which $R_{17}$ represents a lower alkyl group (e.g., methyl or ethyl), an aralkyl group, or a tert-butyl group or the like, and $R_{15}$ represents iodide, in accordance with procedure (v), by reactions that are well known per se. For example, the transformation can be effected by converting the aniline of structure 19, in which $R_{17}$ represents a lower alkyl group (e.g., methyl or ethyl), an aralkyl group, or a tert-butyl group or the like, to the corresponding diazonium salt by treatment with an aqueous solution of sodium nitrite. The reaction is convenient carried out in an aqueous acid solution, such as aqueous hydrochloric acid, at a temperature of between about −10 degrees and about 10 degrees, preferably at about 0 degrees. The resulting diazonium salt solution can then be converted to the iodide in a manner that is well known in the field. For example, it may be treated with an aqueous solution of potassium iodide. The reaction is conveniently carried out at a temperature of between 0 degrees and about room temperature, preferably at about 0 degrees.

Phenols of structure 27, in which $R_{17}$ represents a lower alkyl group (e.g., methyl or ethyl), an aralkyl group, or a tert-butyl group or the like, and $R_{15}$ represents hydroxyl, can be converted to the corresponding trifluoromethanesulfonates of structure 27, in which $R_{17}$ represents a lower alkyl group (e.g., methyl or ethyl), an aralkyl group, or a tert-butyl group or the like, and $R_{15}$ represents trifluoromethanesulfonate, in accordance with procedure (w), by any conventional means. For example, the transformation can be effected by reacting the phenol of structure 27, in which $R_{17}$ represents a lower alkyl group (e.g., methyl or ethyl), an aralkyl group, or a tert-butyl group or the like, and $R_{15}$ represents hydroxy, in a manner analogous to that described earlier in connection with the preparation of compounds of structure 33 from compounds of structure 34.

Compounds of structure 27, in which $R_{17}$ represents a lower alkyl group (e.g., methyl or ethyl), an aralkyl group, or a tert-butyl group or the like, and $R_{15}$ represents amino or hydroxyl, can be prepared by any conventional means. For example, compounds of structure 27, in which $R_{17}$ represents methyl, and $R_{15}$ represents amino or hydroxyl, can be conveniently prepared by treating the carboxylic acid of structure 27, in which $R_{17}$ represents hydrogen, and $R_{15}$ represents amino or hydroxyl, with a solution of methanol containing a strong inorganic acid, for example sulfuric acid or a hydrohalic acid such as hydrogen chloride. The reaction is conveniently carried out at a temperature between about room temperature and about 65 degrees, preferably at about room temperature.

Carboxylic acids of structure 27, in which $R_{17}$ represents hydrogen, and $R_{15}$ represents bromine, amino or hydroxy are generally known compounds. Insofar as they are not known compounds or analogues of known compounds, they can be prepared in a similar manner to the known compounds or as described in the Examples hereinafter or in analogy thereto.

Compounds of structure 29 can be conveniently prepared from compounds of structure 27 by methods that are known in the field of organic synthesis. For example, the reaction can be carried out in a manner analogous to that described in connection with the coupling of a compound of structure 28 with an allylstannane to give a compound of structure 26.

Compounds of structure 30 are generally known compounds, or if they are not known compounds, they can be prepared by any conventional means. For example, compounds of structure 30 can be prepared by esterification of compounds of structure 32. This reaction can be effected by methods that are well known to one of ordinary skill in the field. For example, a compound of structure 30, in which $R_{17}$ represents methyl, can be prepared from a compound of structure 32 by reaction with an ethereal solution of diazomethane. The reaction is conveniently carried out in an inert solvent such as an ether (e.g., diethyl ether or tetrahydrofuran) or an alcohol (e.g., methanol), at a temperature of between about 0 degrees and about room temperature, preferably at about 0 degrees.

Compounds of structure 30 in which U and V both represent chlorine can be prepared from compounds of structure 47 by reactions that are well known. For example, in the case where U and V both represent chlorine, and W represents hydrogen, compounds of structure 30 can be prepared by reaction of compounds of structure 47 with a diazotizing reagent, preferably an alkyl nitrite, most preferably isoamyl nitrite, in a suitable solvent which can also act as a hydrogen donor, for example N,N-dimethylformamide or preferably tetrahydrofuran, at a suitable temperature, for example at about 65 degrees. Compounds of structure 30 in which U and V both represent chlorine and W represents halogen can be prepared from compounds of structure 47 by reactions that are well-known, for example by Sandmeyer reactions or Schiemann reactions. Compounds of structure 30 in which U and V both represent chlorine and W represents lower alkyl can be prepared from compounds of structure 30 in which U and V both represent chlorine and W represents iodine by reaction with an organotin reagent under palladium catalysis. For example, compounds of structure 30 in which U and V both represent chlorine and W represents methyl can be made from compounds of structure 30 in which U and V both represent chlorine and W represents iodine by reaction with tetramethyltin in the presence of tetrakis(triphenylphosphine)palladium(0), and in the optional presence of lithium chloride, in a suitable solvent such as a polar aprotic solvent such as N,N-dimethylformamide or N-methylpyrrolidinone at a suitable temperature such as at about 100 degrees.

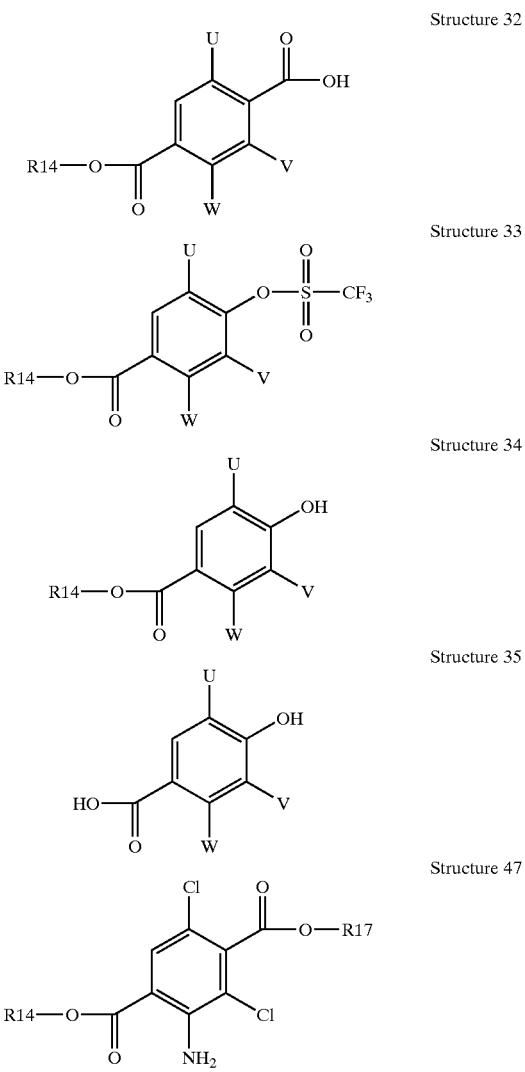

Structure 32

Structure 33

Structure 34

Structure 35

Structure 47

Compounds of structure 32 can be prepared by reactions that are well known. For example, they can be made from the trifluoromethanesulfonate derivatives of structure 33 by reaction with carbon monoxide and water under noble metal catalysis. This reaction can be carried out in a manner analogous to that described earlier in connection with the carboxylation of compounds of structure 27.

Compounds of structure 33 can be prepared by reactions that are known per se. For example, they can be prepared by reacting compounds of structure 34 with a reactive derivative of trifluoromethanesulfonic acid, such as trifluoromethanesulfonic anhydride or N-phenyltrifluoromethanesulfonimide, preferably trifluoromethanesulfonic anhydride, in the presence of a base, such as a tertiary amine (e.g., diisopropylethylamine), in an inert solvent, such as halogenated hydrocarbon (e.g., dichloromethane). The reaction can be conveniently carried out between about −78 degrees and about room temperature, preferably at about −40 degrees.

Compounds of structure 34 can be prepared by any conventional means. For example, they can be prepared by esterifying compounds of structure 35 by a number of different reactions, such as those conventionally used to prepare esters of carboxylic acids, preferably by reactions that permit the esterification of the carboxylic acid in the presence of the phenolic hydroxyl group. For example, the compounds of structure 34, in which $R_{14}$ represents methyl, can be prepared by treatment of compounds of structure 35 with a solution of methanol containing a strong inorganic acid, for example sulfuric acid or a hydrohalic acid such as hydrogen chloride. The reaction is conveniently carried out at a temperature between about room temperature and about 65 degrees, preferably at about room temperature.

Structure 36

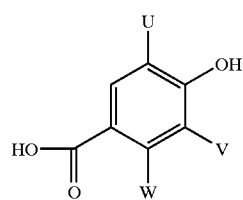

Structure 37

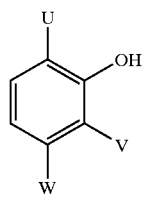

Compounds of structure 35 can be prepared by a variety of methods that are known in the field of organic chemistry. For example, they may be prepared by oxidation of compounds of structure 36. This oxidation can be carried out conveniently by treating the compound of structure 36 with an oxidizing agent such as sodium chlorite, in the optional presence of a scavenger of chlorine dioxide such as sulfamic acid. The reaction is conveniently carried out in an inert solvent system such as a mixture of water and tert-butanol, at a temperature between about 0 degrees and about 50 degrees, preferably at about room temperature.

Compounds of structure 36 can be prepared by any conventional means. For example, they can be prepared from compounds of structure 37 by a variety of procedures, such as by treatment of the compound of structure 37 with hexamethylenetetramine under acidic conditions, for example by carrying out the reaction in an acidic solvent such as trifluoroacetic acid. The reaction is conveniently carried out at about 70 degrees.

Structure 38

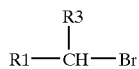

Structure 39

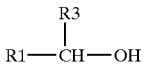

Structure 40

Compounds of structure 38 can be made by any conventional means. For example, in the case where $R_3$ represents hydrogen, they may be made by bromination of compounds of structure 40 where $R_1$ may contain appropriate protective groups that will be apparent to one of ordinary skill in the art of organic synthesis. The bromination may be carried out by treatment of a compound of structure 40 with a brominating agent such as N-bromo-succinimide, 1,3-dibromo-5,5-dimethylhydantoin, or bromine, preferably N-bromosuccinimide. The reaction may be carried out in the presence of an agent that will increase the rate of the reaction such as azodiisobutyronitrile or benzoyl peroxide, and/or under irradiation from a light source such as a low pressure mercury lamp. The reaction may be carried out in the presence of an inert solvent such as carbon tetrachloride, at a suitable temperature such as about 76 degrees.

Compounds of structure 40 are generally known compounds. Insofar as they are not known compounds or analogues of known compounds, they can be prepared in a similar manner to the known compounds or as described in the Examples hereinafter or in analogy thereto.

Structure 41

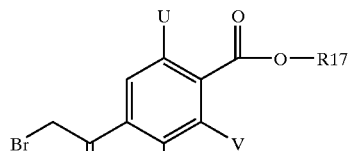

Structure 42

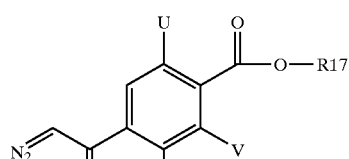

Structure 43

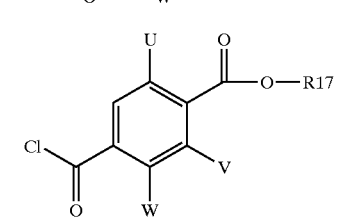

Compounds of structure 41 can be made by any conventional means. For example, such compounds can be made by reacting a diazoketone of structure 42 with hydrogen bromide. The reaction can be conveniently carried out by bubbling hydrogen bromide gas into a suspension of the compound of structure 42 in an inert solvent such as diethyl ether. The reaction may be carried out at a temperature between about 0 degrees and about room temperature, preferably at about room temperature.

Compounds of structure 42 can be made by any conventional means. For example, they can be made by treating compounds of structure 43 with diazomethane. The reaction is conveniently carried out in the presence of a base, such as a tertiary amine (e.g., triethylamine) in an inert solvent such as ether at a temperature of between –10 degrees and about room temperature, preferably at about 0 degrees.

Compounds of structure 43 can be made a variety of methods familiar to one of ordinary skill in the art. For example, they can be made by reaction of a compound of structure 16 with a reagent that is commonly used for the conversion of carboxylic acids to acid chlorides such as thionyl chloride or oxalyl chloride in the presence or absence of an inert solvent such as an aromatic hydrocarbon (e.g., benzene) or dichloromethane. In the case where thionyl chloride is used, the reaction can be carried out at a temperature of about 80 degrees.

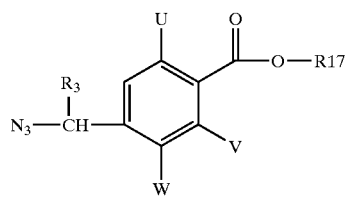

Structure 44

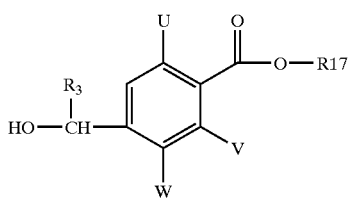

Structure 45

Compounds of structure 44 can be made by a variety of means. For example, they may be made by substitution of the hydroxyl group in compounds of structure 45 by azide. This can be accomplished conveniently by reaction of the compound of structure 44 with a reagent such as diphenylphosphoryl azide. The reaction is conveniently carried out in the presence of a base such as 1,8-diazabicyclo[5.4.0]undec-7-ene and an inert solvent such as tetrahydrofuran at a temperature around room temperature.

Compounds of structure 45 can be made by a variety of means. For example, in the case where $R_3$ represents hydrogen, they may be made by reduction of compounds of structure 16 by treatment with a reducing agent that will effect the reduction of the carboxylic acid while leaving the carboxylate ester intact. An example of such a reagent is borane methyl sulfide complex. The reaction may be conveniently carried out in the presence of an inert solvent such as tetrahydrofuran at a temperature of between about room temperature and about 65 degrees, preferably at about 65 degrees.

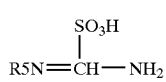

Structure 46

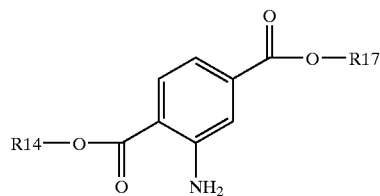

Structure 48

Compounds of structure 47 can be made by any conventional means. For example, compounds of structure 47 can be made by chlorination of compounds of structure 48, for example by treatment with a chlorinating agent such as N-chlorosuccinimide in a polar solvent such as acetonitrile at a suitable temperature, such as at around 65 degrees. Compounds of structure 48 are generally known compounds, or can be prepared in a similar manner to the known compounds.

Compounds of structure (a) can be prepared by procedures analogous to those described above for synthesis of compounds of structure 1 in which $R_2$ represents $$-\overset{O}{\underset{\|}{C}}-NH-\overset{R_3}{\underset{|}{CH}}-.$$

Compounds of structure 2 can be prepared by any conventional means. For example, they can be prepared by the reaction of compounds of structure 5 wherein $R_1$ represents

[structure with A and B substituents on ring]

with compounds of structure 46. The reaction is conveniently carried out in an inert solvent such as methanol or acetonitrile at a temperature between about room temperature and about 80 degrees, preferably at about room temperature. Compounds of structure 46 are known compounds, or can be prepared in a similar manner to the known compounds, for example, by using the procedure of Maryanoff, C. A. et al. *J. Org. Chem.* 1986, 51, 1882–1884.

Compounds of structure 3 can be prepared by a variety of procedures. For example, they can be prepared from compounds of structure 1 where $R_4$ represents hydrogen by reaction with an alkylating reagent of structure $R_6$–$R_{16}$ where $R_{16}$ represents iodine, bromine or chlorine. The reaction is conveniently carried out in the presence of a base, such as potassium carbonate, in the optional presence of a catalyst such as potassium iodide, in an inert solvent such as N,N-dimethylformamide at a temperature between about room temperature and about 80 degrees, preferably at about 60 degrees. Compounds of structure $R_6$–$R_{16}$ are generally known compounds, or can be prepared in a similar manner to the known compounds.

The in vitro inhibition of the interaction of ICAM-1 with LFA-1 and with Mac-1 by compounds of the present invention can be demonstrated by means of the following tests:

(a) LFA-1/ICAM-1 screening test: LFA-1/ICAM-1 antagonist activity, defined as the ability of compounds of the invention to block LFA-1 binding to immobilized ICAM-1, was quantitated using a solid-phase ELISA.

Typically, fusion protein consisting of the entire extracellular domain of human ICAM-1 and the Fc domain of human IgG (5dICAM-Ig) was coated onto 96-well microtiter plates (0.15 µg in 100 µL PBS) overnight at 4° C. The plates were then blocked with 150 µL of 1% BSA/1 mM MnCl$_2$/0.14 M NaCl/20 mM HEPES, pH 7.2 for 1 h at 37° C. and washed 3 times (150 µL each) with Wash Buffer (50 mM Tris, pH 7.4/100 mM NaCl/1 mM MnCl$_2$/0.05% Tween 20). Stock solutions (100 µM in 100% DMSO) of test compounds were diluted 50 fold with 150 µL of Binding Buffer (0.05% BSA/0.05% Tween 20/1 mM MnCl$_2$/0.14 M NaCl/20 mM HEPES, pH 7.2) plus 10% DMSO. A series of 1:4 dilutions were performed to achieve a concentration range of 0.12 nM–2 µM. Fifty µL per well of each dilution was added to the ICAM-1 coated plates, followed by 50 µL per well of membrane-bound LFA-1 (280 ng/mL in Binding Buffer) derived from transfected 293 cells. The plates were shaken vigorously for 1 min (room temperature) and gently for 2 h (37° C.). After incubation, the plates were washed 3 times (150 µL each) with Wash Buffer. Mouse anti-human integrin β2 monoclonal antibody was added (100 µL/well, 1 µg/mL in Binding Buffer) and allowed to incubate for 1 h (37° C.) with gentle agitation. The plates were then washed 3 times with Wash Buffer. HRP-conjugated goat anti-mouse IgG (100 µL/well, 1:1500 dilution in Binding Buffer) was added to each well, followed by incubation for 1 h (37° C.), and concluded by three washes (150 µL each) with Wash Buffer. TMB solution (100 µL per well) was added for color development (10 min). The reaction was stopped by the addition of 100 µL of 1 M H$_3$PO$_4$ to each well. The plates were then read at 450 nm. The inhibitory activities of test compounds were determined by the IC$_{50}$s.

(b) Mac-1/ICAM-1 screening test: Mac-1/ICAM-1 antagonist activity, defined as the ability to compete with ICAM-1 binding to immobilized Mac-1, was quantitated by a solid-phase ELISA.

Membrane-bound Mac-1 derived from transfected 293 cells was coated onto 96-well microtiter plates (50 µL/well, 3 µg/mL Mac-1 in 20 mM Hepes, pH 7.2/0.14 M NaCl/1 mM MnCl$_2$) overnight at 4° C. The plates were blocked with 100 µL/well of 0.5% BSA in 20 mM Hepes, pH 7.2/0.14 M NaCl/1 mM MnCl$_2$ at 37° C. for 1 h and washed 3 times (120 µL each) with Binding Buffer (20 mM Hepes, pH 7.2/0.14 M NaCl/1 mM MnCl$_2$/0.05% Tween 20). Test compounds were dissolved in 100% DMSO and diluted 1:50 in Binding Buffer plus 10% DMSO. A series of 1:4 dilutions were performed for each compound (concentration range, 0.12 nM–20 µM). Each dilution (25 µL/well) was added to the plates, followed by 25 µL/well of 5 dICAM-Ig (40 µg/mL in Binding Buffer). The plates were shaken vigorously for 1 min (room temperature), followed by gentle agitation for 2 h (37° C.), and washed with Binding Buffer (3 times, 120 µL each). HRP-conjugated goat anti-human IgG(Fc-specific) antibody (0.125 µg/mL in Binding Buffer plus 0.05% BSA) was added to each well (50 µL/well), followed by incubation for 1 h at 37° C. The plates were then washed 3 times with Binding Buffer (120 µL each). TMB solution (100 µL/well) was added to each well for color development for 10 min. The reaction was stopped with 1 M H$_3$PO$_4$ (100 µL/well) and the plates were read at 450 nm. The inhibitory activities of test compounds were determined by the IC$_{50}$s.

The results obtained in the foregoing tests using representative compounds of structure 1 as the test compound are compiled in the following Table.

| Compound | LFA-1/ICAM IC$_{50}$ (nM) | Mac-1/ICAM IC$_{50}$ (nM) |
| --- | --- | --- |
| A | 1.2 | 43.4 |
| B | 0.9 | 31.2 |
| C | 6.4 | 101.3 |
| D | 0.5 | 6.4 |
| E | 15.2 | 520.8 |
| F | 6.4 | 81.7 |
| G | 1.3 | 22.4 |
| H | 1.4 | 43.4 |
| I | 2.6 | 75.5 |
| J | 11.9 | 1413 |

Compound A: N-[2-chloro-4-[[[(3-hydroxyphenyl)methyl]amino]carbonyl]benzoyl]-3-(3-methoxybenzoyl)amino-L-alanine Compound B: 3-benzoylamino-N-[2-chloro-4-[[[(3-hydroxyphenyl)methyl]amino]carbonyl]benzoyl]-L-alanine Compound C: N-[2-chloro-4-[[[(3-hydroxyphenyl)methyl]amino]carbonyl]benzoyl]-3-(5-nitropyrazole-3-carbonyl)amino-L-alanine Compound D: N-[2-chloro-4-[[[(3-hydroxyphenyl)methyl]amino]carbonyl]benzoyl]-3-(thiophene-2-carbonyl)amino-L-alanine Compound E: N-[2-chloro-4-[[[(3-hydroxyphenyl)methyl]amino]carbonyl]benzoyl]-3-(4-methoxyquinoline-2-carbonyl)amino-L-alanine Compound F: 3-(5-bromothiophene-2-carbonyl)amino-N-(2,6-dichlorobenzoyl)-L-alanine Compound G: N-[2-chloro-4-[[(1H-indol-4-ylmethyl)amino]carbonyl]benzoyl]-3-(thiophene-2-carbonyl)amino-L-alanine Compound H: N-[2-chloro-4-[1-oxo-3-(3-hydroxyphenyl)propyl]benzoyl]-3-(thiophene-2-carbonyl)amino-L-alanine Compound I: N-[2-chloro-4-[5-[[(3-hydroxyphenyl)methyl]amino]tetrazol-1-yl]benzoyl]-3-(thiophene-2-carbonyl)amino-L-alanine Compound J: 3-(phenylmethyl)amino-N-[2-chloro-4-[[(1H-indol-4-ylmethyl)amino]carbonyl]benzoyl]-L-alanine.

General Electron impact (EI, 70 ev) and fast atom bombardment (FAB) mass spectra were taken on VG Autospec or VG 70E-HF mass spectrometers. Reversed phase high pressure liquid chromatography (RP-HPLC) was carried out using a Waters Delta Prep 3000 with a Waters 484 detector, employing a 2.0×5 cm YMC ODS-A C-18 column and using a linear gradient of acetonitrile:water (each containing 0.1% TFA), or a Rainin Dynamax HPLC system employing a 41.4 mm×250 mm Dynamax 60A reverse phase C18 preparative column using a using a linear gradient of acetonitrile:water (each containing 0.075–0.1% TFA).

Definitions

Alloc is allyloxycarbonyl,
BSA is bovine serum albumin,
DCC is dicyclohexylcarbodiimide,
DCU is N,N'-dicyclohexylurea,
DICI is diisopropylcarbodiimide,
DMF is N,N-dimethylformamide,
DMSO is dimethylsulfoxide,
ELISA is enzyme-linked immunosorbent assay,
Fc is the crystallizable fragment of an antibody,
Fmoc is (9H-fluoren-9-ylmethoxy)carbonyl,
HATU is O-(7-azabenzotriazol-1-yl)-1,1,3,3-tetramethyluronium hexafluorophosphate, HEPES is 4-(2-hydroxyethyl)piperazine-1-ethanesulfonic acid,
HOAT is 1-hydroxy-7-azabenzotriazole,
HBTU is O-(benzotriazol-1-yl)-1,1,3,3-tetramethyluronium hexafluorophosphate,
HOBT is hydroxybenzotriazole,
HPLC is high-pressure liquid chromatography,
HRP is horseradish peroxidase,
ICAM-1 is intercellular adhesion molecule-1,
IgG is immunoglobulin G,
IMDM is Iscove's Modified Dulbecco's Medium,
LFA-1 is lymphocyte function-associated antigen-1 (CD11a/CD18; αLβ2),
LSM is Lymphocyte Separation Medium,
Mac-1 is macrophage differentiation antigen associated with type three complement receptor (CD11b/CD18; αMβ2),
PBS is phosphate-buffered saline,
PVP is polyvinylpyrrolidone
TBS is tris(hydroxymethyl)aminomethane hydrochloride-Buffered Saline,
TMB is 3,3',5,5' tetramethylbenzidine

EXAMPLES

Example 1

Preparation of 2-chloro-1,4-benzenedicarboxylic acid, 1-methyl ester

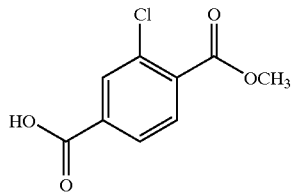

To a 2 L round-bottom flask, equipped with a mechanical stirrer, was charged 2-chloro-1,4-benzenedicarboxylic acid, dimethyl ester (25.15 g, 0.11 mol), methanol (300 mL) and tetrahydrofuran (300 mL). Over 10 min, a solution of lithium hydroxide monohydrate (4.62 g, 0.11 mol) in deionized water (200 mL) was added. After the reaction had proceeded at ambient temperature overnight, the solution was concentrated in vacuo to about 150 mL and then diluted with of deionized water (200 mL). The precipitated solid was filtered off, and washed with deionized water (2×20 mL) to give the starting 2-chloro-1,4-benzenedicarboxylic acid, dimethyl ester (1.8 g) as shiny platelets. The combined filtrates were stirred while 1 N hydrochloric acid (112 mL, 0.112 mol) was added. The resulting solid was filtered off, washed with deionized water (2×50 mL) and air dried. The solid was dissolved in methanol (300 mL) and warmed to about 45° C., then to the stirred solution deionized water was added to just before the cloud point. The solution was left at room temperature overnight. The resulting colorless solid was filtered off, washed in turn with a cold mixture of methanol-deionized water (1:2; 30 mL) and cold deionized water (30 mL). The solid was recrystallized once more from methanol-deionized water as described above and dried, to give 2-chloro-1,4-benzenedicarboxylic acid, 1-methyl ester (13.1 g, 55.5%) as colorless needles.

Example 2

Preparation of 2-bromo-1,4-benzenedicarboxylic acid, 1-methyl ester

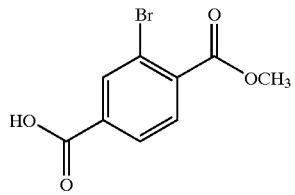

Potassium hydroxide (2.87 g, 51 mmol) was added to a solution of 2-bromo-1,4-benzenedicarboxylic acid, dimethyl ester (14 g, 51 mmol) in methanol (50 mL) at 25° C. The reaction mixture was stirred at 25° C. for 24 h, and then at 50° C. for 3 h. The solvent was concentrated under reduced pressure and the residue was diluted with water (100 mL) and extracted with ethyl acetate (2×200 mL). The water layer was acidified to pH 2 with 2 M HCl and extracted with ethyl acetate (2×200 mL). The combined organic layers were washed with brine (100 mL), dried (MgSO4), filtered, and concentrated. The resulting solid was boiled in toluene (100 mL) and the insolubles were filtered. The filtrate was concentrated and the resulting solid was flash chromatographed (silica, 50% ethyl acetate in petroleum ether with 1% acetic acid) to give 2-bromo-1,4-benzenedicarboxylic acid, 1-methyl ester (3.28 g, 24%) as a white solid.

Example 3

Preparation of 2-methylbenzene-1,4-dicarboxylic acid 1-methyl ester

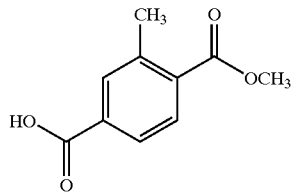

A. 4-Bromo-2-methylbenzoic acid, methyl ester

A mixture of 4-bromo-2-methylbenzoic acid (14.77 g, 68.7 mmol) and sulfuric acid (5 mL) in methanol (200 mL) was heated at reflux for 3 h. The solvent was evaporated and dichloromethane (200 mL) was added. The solution was washed with water, 1 M NaOH, and brine (200 mL each), dried (MgSO$_4$), filtered and evaporated to give 4-bromo-2-methylbenzoic acid, methyl ester (12.21 g, 78%) as a colorless liquid.

B. 2-Methylbenzene-1,4-dicarboxylic acid 1-methyl ester

A mixture of 4-bromo-2-methylbenzoic acid, methyl ester (22.59 g, 98.6 mmol), triethylamine (32.00 g, 316.2 mmol), palladium(II) acetate (0.56 g, 2.5 mmol), bis(diphenylphosphino)propane (1.04 g, 2.5 mmol) and water (32 mL, 1776.3 mmol) in acetonitrile (80 mL) was pressurized to 40 psi with carbon monoxide and the pressure was released. After six such cycles, the bottle was pressurized again and the contents were stirred at 83° C. for 3 h. The reaction mixture was cooled to room temperature and depressurized. Ethyl acetate (200 mL) was added. The solution was filtered and then extracted with water (2×300 mL). The combined aqueous layers were acidified with 12 M HCl to pH 0. The resulting mixture was extracted with ethyl acetate (2×300 mL). The combined organic layers were dried (MgSO₄), filtered and evaporated to give 2-methylbenzene-1,4-dicarboxylic acid 1-methyl ester (16.57 g, 87%) as a white solid, mp 134–136° C.

Example 4

Preparation of 2,6-dichlorobenzene-1,4-dicarboxylic acid, 1-methyl ester

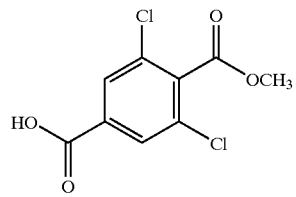

N-Chlorosuccinimide (60.00 g, 449.3 mmol) was added carefully to a solution of 2-aminoterephthalic acid dimethyl ester (50.00 g, 239 mmol) at ~60° C. and the solution was then heated to 80° C. for 6 h. The reaction mixture was allowed to stand at room temperature for 4 days and then the solvent was evaporated. Ether (500 mL) was added and the mixture was washed with 1 M NaOH (200 mL). The aqueous layer was extracted with ether (100 mL) and the combined ether layers were dried (MgSO₄), filtered and evaporated to give a red oil. This was extracted with boiling hexanes (4×300 mL) and the hexane was evaporated to give a red oil (67.77 g). Tetrahydrofuran (300 mL) was added, followed by isoamyl nitrite (70 g, 597.5 mmol) (CAUTION: this reaction is exothermic and the isoamyl nitrite should be added cautiously) and the solution was heated at reflux for 2 h. The reaction mixture was allowed to stand at room temperature for 2 days, then the solvent was evaporated (using aspirator pressure at first, then 0.5 mm Hg). The residue was chromatographed (3% ethyl acetate/hexanes) to give a pale yellow liquid (27.56 g). Tetrahydrofuran (100 mL) was added, followed by a solution of sodium hydroxide (4.20 g, 105 mmol) in water (100 mL). The solution was stirred at room temperature for 2 days and then the solvent was evaporated. Water (80 mL) was added and the mixture was swirled at ~50° C. for 10 min to give a clear yellow-orange solution. 1 M HCl (120 mL) was added with swirling and the mixture was swirled for another 15 min. The solid was filtered off and recrystallized twice from methanol/water to give 2,6-dichlorobenzene-1,4-dicarboxylic acid, 1-methyl ester (18.85 g, 32%) as a white solid.

Example 5

Preparation of 1-[[3-chloro-4-(methoxycarbonyl)benzoyl]oxy]-2,5-pyrrolidinedione

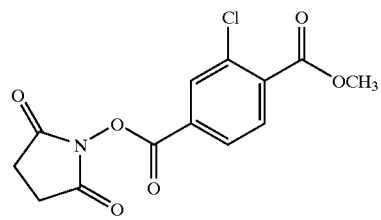

A 3-neck 1 L round-bottom flask equipped with a magnetic stirrer, ice cooling bath, thermometer and an argon inlet tube was set up and charged with 2-chloro-1,4-benzenedicarboxylic acid, 1-methyl ester (Example 1; 21.5 g, 0.1 mol) in tetrahydrofuran (250 mL). The solution was cooled to 10° C. under argon and was treated in succession with N-hydroxysuccinimide (12.66 g, 0.11 mol) and 1,3-dicyclohexylcarbodiimide (21.66 g, 0.105 mol). These reagents were washed in with additional tetrahydrofuran (100 mL). A precipitate started to form immediately. The cooling bath was removed and the reaction mixture was stirred at ambient temperature overnight, and then diluted with diethyl ether (400 mL) and stirred for another 30 min. The precipitate was collected by filtration, and the filter cake was washed with diethyl ether (3×50 mL). The dried solids (DCU) weighed 22.2 g (>99% of theory). The combined filtrates were diluted with hexane (100 mL) then were transferred to a 2 L separatory funnel and were washed in turn with cold saturated sodium bicarbonate solution (150 mL) and brine (150 mL). Each aqueous layer was back-extracted in turn with diethyl ether (200 mL), then the combined organic extracts were dried (MgSO₄), and evaporated to give crude 1-[[3-chloro-4-(methoxycarbonyl)benzoyl]oxy]-2,5-pyrrolidinedione (~35 g) as a colorless solid. This material was used directly in the next step without purification.

Also prepared by this procedure was:

| Example | Structure | Starting Material | Yield |
|---|---|---|---|
| 6 | 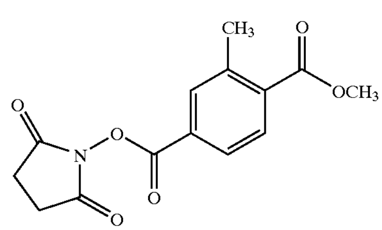 | Example 3 | 99%<br>mp 99–101° C. |

Example 7

Preparation of (3-hydroxyphenyl)methylamine hydrochloride salt

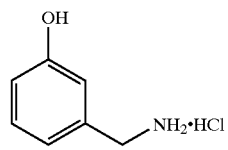

Methanol (100 mL) and 10% palladium on carbon (2 g) were charged to a 250 mL Parr bottle followed by 3-cyanophenol (19.0 g, 0.1595 mol) and concentrated HCl (16.66 mL, 0.2 mol). The mixture was hydrogenated at room temperature and 50 psi until the uptake of hydrogen stopped (about 10 h). The reaction was filtered through a bed of Celite and the filter cake was washed with methanol (3×25 mL). The combined filtrates were evaporated under reduced pressure. Remaining volatiles were removed by evaporating the residue twice from 50 mL portions of absolute ethanol. The crude amine hydrochloride, essentially free of residual HCl, was dissolved with warming in a minimum amount of absolute ethanol (~80 mL) and the stirred solution was diluted with anhydrous diethyl ether (500 mL). The mixture was stirred in an ice bath for 1 h then the colorless crystalline product was filtered off, washed with anhydrous diethyl ether (3×50 mL) and dried in vacuo to furnish (3-hydroxyphenyl)methylamine hydrochloride salt (20.6 g, 80.9%), mp 146–148° C.

Example 8

Preparation of 3-[[(1,1-dimethylethyl)dimethylsilyl]oxy]benzenemethanamine

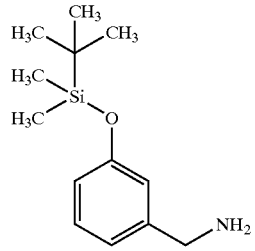

A. 3-[[(1,1-dimethylethyl)dimethylsilyl]oxy]benzonitrile

To a solution of 3-cyanophenol (5 g, 42 mmol) and imidazole (6.3 g, 92 mmol) in N,N-dimethylformamide (85 mL) at 0° C. was added tert-butyldimethylsilylchloride (7.6 g, 50 mmol). After 10 min, the reaction was warmed to room temperature and stirred for 24 h. The solvent was removed under vacuum. The residual oil was diluted with water (100 mL) and extracted with ether (300 mL). The ether layer was back-extracted with water (3×100 mL) and brine (100 mL), dried (MgSO$_4$) and filtered. Concentration and flash chromatography (silica, 50% ethyl acetate in petroleum ether) afforded 3-[[(1,1-dimethylethyl)dimethylsilyl]oxy]benzonitrile (9 g, 92%) as an oil.

B. 3-[[(1,1-dimethylethyl)dimethylsilyl]oxy]benzenemethanamine

Under an atmosphere of nitrogen, 10% palladium on carbon (250 mg) was added to a solution of 3-[[(1,1-dimethylethyl)dimethylsilyl]oxy]benzonitrile (1 g, 4.3 mmol) in methanol (25 mL) at 25° C. The reaction mixture was hydrogenated at 50 psi in a Parr shaker for 3 h. The reaction mixture was then filtered through Celite and the filter cake was washed well with methanol (50 mL). The solvents were concentrated under reduced pressure and the residue was dried under vacuum for 1 h to give 3-[[(1,1-dimethylethyl)dimethylsilyl]oxy]-benzenemethanamine (950 mg, 95%) as an oil.

Example 9

Preparation of 2,3-dihydro-2-oxo-1H-indole-4-methanamine hydrochloride

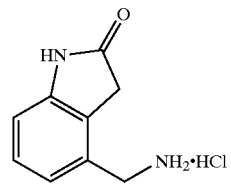

A. 4-Cyano-3,3-dibromo-1,3-dihydro-1H-indol-2-one 1H-indole-4-carbonitrile (prepared according to Clark, Robin D.; Repke, David B. *J. Heterocycl. Chem.* 1985, 22,121–5; 3.26 g, 22.9 mmol) was dissolved in a 3:1 mixture of tBuOH/H$_2$O (100 mL). Pyridinium perbromide (25.6 g, 80.1 mmol) was then added to the stirring mixture in portions over 30 min. The mixture was stirred for 1 h and then the mixture was made neutral by the addition of sat. aq. NaHCO$_3$. The mixture was stirred for an additional 2 h and the product was filtered off. A further portion of pyridinium perbromide (7.3 g, 22.9 mmol) was added to the filtrate, the resulting mixture was stirred overnight, and a further quantity of the product was filtered off. The filtrate was concentrated and the black residue was partially dissolved in CHCl$_3$. It was filtered through a plug of silica gel which was flushed several times with warm chloroform. The solids collected from the filtrations were combined and purified in the same manner. 4-Cyano-3,3-dibromo-1,3-dihydro-1H-indol-2-one was obtained as a light brown solid (5.20 g, 72%).

B. 4-Cyano-1,3-dihydro-1H-indol-2-one

4-Cyano-3,3-dibromo-1,3-dihydro-1H-indol-2-one (2.5 g, 7.9 mmol) was suspended in AcOH (50 mL). The mixture was heated to 80° C. and zinc dust (5.20 g, 79 mmol) was added in portions over 15 min. The solution was stirred for 20 min, then it was filtered hot. The filtrate was concentrated to give a light yellow solid. Water was added and the mixture was filtered and washed with water to give 4-cyano-1,3-dihydro-2H-indol-2-one (1.12 g, 90%).

C. 2,3-Dihydro-2-oxo-1H-indole-4-methanamine hydrochloride

Palladium on carbon (10%; 0.10 g) and concentrated HCl (a few drops) were added to a solution of 4-cyano-1,3-dihydro-1H-indol-2-one (0.10 g, 0.63 mmol) in methanol (10 mL). The mixture was hydrogenated for 36 h at 65 psi and then filtered. The filtrate was concentrated to give 2,3-dihydro-2-oxo-1H-indole-4-methanamine hydrochloride (0.120 g, 95%).

Example 10

Preparation of 1H-indole-4-methanamine

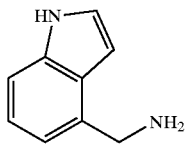

Lithium aluminum hydride (3.80 g, 100.0 mmol) was added in 0.5 g portions over 30 min to a solution of 1H-indole-4-carbonitrile (prepared according to Clark, Robin D.; Repke, David B. *J. Heterocycl. Chem.* 1985, 22, 121–5; 7.50 g, 52.8 mmol) in tetrahydrofuran (250 mL). The mixture was heated at reflux for 30 min. A solution of 1 M sodium hydroxide was added to quench excess lithium aluminum hydride. The mixture was filtered and the filter cake was washed with water. The filtrate was first made acidic with 1 N HCl and then made basic again by the addition of saturated aqueous $NaHCO_3$. The water layer was then extracted with nBuOH. Evaporation of nBuOH, and drying under vacuum gave 1H-indole-4-methanamine (6.24 g, 80%) as a beige solid.

Example 11

Preparation of 1H-indole-4-methanamine hydrochloride

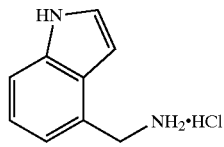

A. 1H-Indole-4-carboxylic acid, methyl ester

N,N-Dimethylaminopyridine (7.6 mg, 0.06 mmol) was added to a mixture of 1H-indole-4-carboxylic acid (100 mg, 0.62 mmol), 1-(3-dimethylaminopropyl)-3-ethylcarbodiimide hydrochloride (131 mg, 0.68 mmol), and methanol (1 mL, 24.7 mmol) in dichloromethane (2 mL). The mixture was allowed to stir at room temperature overnight, then the solvent was evaporated and ethyl acetate (20 mL) was added. The solution was washed with 1 M HCl (2×15 mL), saturated sodium hydrogen carbonate (15 mL) and brine (10 mL), dried ($MgSO_4$), filtered and evaporated to give 1H-indole-4-carboxylic acid, methyl ester (85.4 mg, 79%) as a pale yellow solid.

B. 1H-indole-4-methanol

Diisobutylaluminum hydride (1 M in toluene; 1.3 mL, 1.3 mmol) was added to a solution of 1H-indole-4-carboxylic acid, methyl ester (85 mg, 0.49 mmol) in ether (1.6 mL) at −70° C. The solution was allowed to stir at −70° C. for 1 h, then at room temperature for 1 h. Ethyl acetate (20 mL) was added, and the solution was stirred with an aqueous solution of potassium sodium tartrate (30% w/v; 20 mL) for 30 min. The layers were separated and the aqueous layer was extracted with ethyl acetate. The combined organic layers were dried ($MgSO_4$), filtered, evaporated, and dried under high vacuum to give 1H-indole-4-methanol (73.2 mg, quantitative yield) which was used in the next step without further purification.

C. 4-(azidomethyl)-1H-indole

To a solution of 1H-indole-4-methanol (71 mg, 0.48 mmol) in tetrahydrofuran (1 mL) at 0° C. was added diphenylphosphoryl azide (156 µL, 0.72 mmol) followed by 1,8-diaza[5.4.0]undec-7-ene (87.4 µL, 0.58 mmol). The cooling bath was removed and the solution was allowed to stir for 5 h. The solvent was evaporated and ethyl acetate was added. The solution was washed with 1 M HCl and brine, dried ($MgSO_4$), filtered, concentrated and chromatographed (12% ethyl acetate/hexanes) to give 4-(azidomethyl)-1H-indole (1.496 g, 88%) as an oil.

D. 1H-indole-4-methanamine hydrochloride

To a solution of 4-(azidomethyl)-1H-indole (628 mg, 3.65 mmol) in tetrahydrofuran (10 mL) at 25° C. was added triphenylphosphine (1.05 g, 3.65 mmol) and the reaction was stirred for 24 h. Water (1.0 mL) was added and the reaction was stirred at 25° C. for 24 h. The solvent was evaporated under reduced pressure and the residue was diluted with ethyl acetate (20 mL) and washed with 0.5 M HCl (8 mL). The acid layer was freeze dried to give 1H-indole-4-methanamine hydrochloride (510 mg, 77%) as an off-white solid.

Example 12

Preparation of 4-aminomethyl-1-(tetrahydro-2H-pyran-2-yl)-1H-indazole

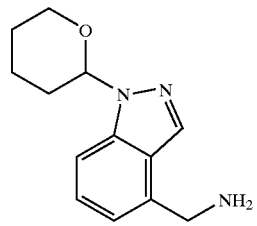

A. 1-Acetyl-1H-indazole-4-methanol, acetate ester

Acetic anhydride (1.68 mL, 17.8 mmol) was added to a suspension of 3-amino-2-methylbenzyl alcohol (0.82 g, 5.98 mmol) in chloroform (25 mL). Potassium acetate was added and the resulting mixture was stirred at room temperature for 3 h, under reflux for 2 h, and then at room temperature overnight. Amyl nitrite (1.82 mL, 13.7 mmol) and 18-crown-6 (79 mg, 0.3 mmol) were added and the pale yellow cloudy mixture was heated at reflux overnight, then allowed to cool to room temperature and stir for 5 h. The reaction mixture was poured into acetic anhydride (5 mL) and stirred at room temperature overnight. Dichloromethane (20 mL) was added and the solution was washed with sodium hydrogen carbonate solution, water, and brine (10 mL each), dried ($Na_2SO_4$), filtered, concentrated, and chromatographed (10–40% ethyl acetate/petroleum ether) to give 1-acetyl-1H-indazole-4-methanol, acetate ester (1.19 g, 86%) as a pale yellow solid.

B. 1H-Indazole-4-methanol hydrobromide salt

A solution of 1-acetyl-1H-indazole-4-methanol, acetate ester (0.5 g, 2.15 mmol) and 48% HBr in water (2.5 mL) was stirred overnight at room temperature. The solid was filtered off, washed with 48% HBr and dried under high vacuum to give 61 mg of tan solid. This procedure was repeated to give 39.8 mg of light tan solid. The mother liquors from both reactions were combined, concentrated, and held under high vacuum overnight to give 1H-indazole-4-methanol hydrobromide salt (0.918 g) as a pale orange solid. Overall yield: 1.019 g (103%).

C. 4-Bromomethyl-1H-indazole hydrobromide salt

A mixture of 1H-indazole-4-methanol hydrobromide salt (0.60 g, 2.6 mmol) and 48% HBr in water (6 mL) was heated in an 80° C. oil-bath for 4.75 h, then the heating was stopped and the reaction mixture was allowed to stir for 15 min. The solid was filtered off, washed with cold water and dried under high vacuum overnight to give 5-bromomethyl-1H-indazole hydrobromide salt (0.609 g, 80%) as a tan solid.

D. 4-Bromomethyl-1-(tetrahydro-2H-pyran-2-yl)-1H-indazole

A solution of 5-bromomethyl-1H-indazole hydrobromide salt (194 mg, 0.665 mmol) and 3,4-dihydro-2H-pyran (0.118 mL, 1.29 mmol) in tetrahydrofuran (4.7 mL) was heated at reflux for 2 h and then stirred overnight at room temperature. Dichloromethane (12 mL) was added and the solution was washed with aqueous sodium hydrogen carbonate, water, and brine (10 mL each), dried (MgSO$_4$), concentrated, and chromatographed (5–60% ethyl acetate/petroleum ether) to give 4-bromomethyl-1-(tetrahydro-2H-pyran-2-yl)-1H-indazole (153 mg, 78%) as an off-white solid.

E. 4-Azidomethyl-1-(tetrahydro-2H-pyran-2-yl)-1H-indazole

A mixture of 4-bromomethyl-1-(tetrahydro-2H-pyran-2-yl)-1H-indazole (150 mg, 0.508 mmol) and sodium azide (132 mg, 2.0 mmol) in N,N-dimethylformamide (1.5 mL) was heated in a 90° C.-oil-bath for 30 min, then allowed to cool, and poured into water (5 mL). The mixture was extracted with ether (2×10 mL), dried (MgSO$_4$), filtered, evaporated, and dried under high vacuum overnight to give 4-azidomethyl-1-(tetrahydro-2H-pyran-2-yl)-1H-indazole (124 mg, 95%) as a yellow oil.

F. 4-Aminomethyl-1-(tetrahydro-2H-pyran-2-yl)-1H-indazole

A solution of lithium aluminum hydride in tetrahydrofuran (1.0 M; 0.51 mL, 0.51 mmol) was added dropwise over 12 min to a cooled (0° C.) solution of 4-azidomethyl-1-(tetrahydro-2H-pyran-2-yl)-1H-indazole (130 mg, 0.505 mmol) in dry tetrahydrofuran (1.5 mL). The solution was stirred at ~0° C. for 1 h and then quenched with 1 M sodium hydroxide (75 µL) over approx. 1 min. The cooling bath was removed and the mixture was stirred for 1 h. The mixture was diluted with ethyl acetate (3 mL), dried (Na$_2$SO$_4$), filtered through Celite (which was washed with ethyl acetate), and concentrated to give 4-aminomethyl-1-(tetrahydro-2H-pyran-2-yl)-1H-indazole (106 mg, 91%) as a yellow solid.

Example 13

Preparation of 4-(azidomethyl)benzimidazole-1-carboxylic acid, 1,1-dimethylethyl ester

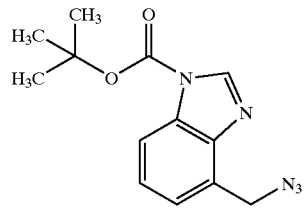

A. 4-Methylbenzimidazole

A solution of 3-methyl-1,2-diaminobenzene (5.00 g, 40.9 mmol) in formic acid (25 mL) was heated at 105° C. for 2 h. The reaction mixture was allowed to cool and then concentrated ammonium hydroxide (50 mL) was added dropwise. The mixture was extracted with dichloromethane (2×100 mL). The extracts were washed with brine, dried (Na$_2$SO$_4$), treated with charcoal, filtered, and evaporated to dryness. The residue was triturated with cold ether, filtered, and washed with cold ether, ether/hexane (1:1), and hexane to give 4-methylbenzimidazole (3.85 g, 71%) as a yellow solid.

B. 4-Methylbenzimidazole-1-carboxylic acid, 1,1-dimethylethyl ester

A solution of 4-methylbenzimidazole (810 mg, 6.1 mmol), N,N-dimethylaminopyridine (75 mg, 0.6 mmol) and di-tert-butyl dicarbonate (1.54 g, 7.1 mmol) in acetonitrile (20 mL) was stirred at room temperature for 15 min. The solvent was evaporated and the residue was chromatographed (10% ethyl acetate/hexanes) to give 4-methylbenzimidazole-1-carboxylic acid, 1,1-dimethylethyl ester (1.35 g, 95%).

C. 4-(Bromomethyl)benzimidazole-1-carboxylic acid, 1,1-dimethylethyl ester

A mixture of 4-methylbenzimidazole-1-carboxylic acid, 1,1-dimethylethyl ester (6.50 g, 28.0 mmol) and N-bromosuccinimide (5.50 g, 30.9 mmol) in carbon tetrachloride (75 mmol) was stirred and irradiated with a 250 W flood lamp for 1 h. The reaction mixture was allowed to cool and the solid was filtered off and discarded. The filtrate was evaporated and purified by HPLC (20% ethyl acetate/hexanes) to give 4-(bromomethyl)benzimidazole-1-carboxylic acid, 1,1-dimethylethyl ester (3.69 g, 42%).

D. 4-(Azidomethyl)benzimidazole-1-carboxylic acid, 1,1-dimethylethyl ester

A mixture of 4-(bromomethyl)benzimidazole-1-carboxylic acid, 1,1-dimethylethyl ester (1.08 g, 3.5 mmol), sodium azide (240 mg, 3.7 mmol), and sodium iodide (5 mg) in acetone (10 mL) was heated at reflux for 66 h. The solvent was evaporated and dichloromethane was added. The solution was washed with dilute aqueous sodium hydrogen carbonate, dried (Na$_2$SO$_4$), filtered and evaporated to give 4-(azidomethyl)benzimidazole-1-carboxylic acid, 1,1-dimethylethyl ester (800 mg, 84%).

Example 14

Preparation of 2-bromo-4-[[[(3-hydroxyphenyl)methyl]amino]carbonyl]benzoic acid, methyl ester

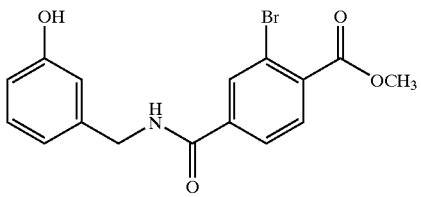

Diisopropylethylamine (8.4 mL, 48.2 mmol) was added dropwise to a cooled (~0° C.) solution of 2-bromo-1,4-benzenedicarboxylic acid, 1-methyl ester (Example 2; 5.00 g, 19.3 mmol), HBTU (7.31 g, 19.3 mmol), 3-hydroxybenzylamine HCl salt (Example 7; 3.37 g, 21.2 mmol), and HOBT (2.6 g, 19.2 mmol) in N,N-dimethylformamide (50 mL). The solution was allowed to stir at ~0° C. for 1 h, then at room temperature for 4 h, and it was then concentrated to remove most of the N,N-dimethylformamide. The residue was partitioned between ethyl acetate and 1 M HCl (200 mL each). The ethyl acetate layer was washed with 1 M HCl (2×100 mL) and the combined aqueous layers were extracted with ethyl acetate (50 mL). The combined ethyl acetate layers were washed with saturated sodium hydrogen carbonate solution (2×100 mL), and brine, then dried (MgSO$_4$), filtered, evaporated and recrystallized from hot ethyl acetate (~60 mL) and hexanes (15 mL) to give 2-bromo-4-[[[(3-hydroxyphenyl)methyl]amino]carbonyl]benzoic acid, methyl ester (5.15 g, 73%) as white crystals.

Example 15

Preparation of 2-bromo-4-[[[(1H-indol-4-yl)methyl]amino]carbonyl]benzoic acid, methyl ester

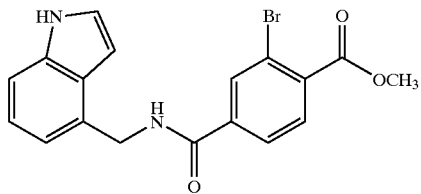

Diisopropylethylamine (2.3 mL, 13.2 mmol) was added dropwise to a solution of 2-bromo-1,4-benzenedicarboxylic acid, 1-methyl ester (Example 2; 861 mg, 3.32 mmol), HBTU (1.39 g, 3.65 mmol), 1H-indole-4-methanamine hydrochloride salt (Example 11; 528 mg, 3.98 mmol), and HOBT (493 mg, 3.65 mmol) in N,N-dimethylformamide (6.5 mL) at 0° C. The solution warmed to room temperature and stirred for 24 h. The solvent was concentrated under vacuum to remove most of the N,N-dimethylformamide. The residue was diluted with ethyl acetate (50 mL) and washed with 1 M HCl (10 mL), water (10 mL), saturated aqueous NaHCO3 (10 mL) and brine (10 mL). The organic layer was dried (MgSO$_4$), filtered, evaporated and flash chromatographed (silica, 25–35% ethyl acetate/petroleum ether) to give 2-bromo-4-[[[(1H-indol-4-yl)methyl]amino]carbonyl]benzoic acid, methyl ester (900 mg, 70%) as an off-white solid.

The following were also prepared by this route, with the modifications indicated:

| Example | Structure | Starting Materials | Yield |
|---|---|---|---|
| 16[a,b,c] | 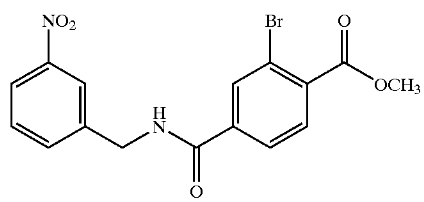 | Example 2 and 3-nitrobenzylamine | 82% |
| 17[b,c] | 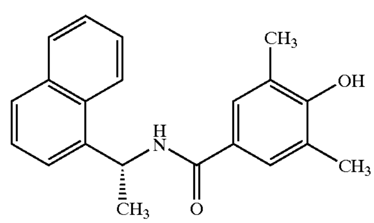 | 3,5-dimethyl-4-hydroxybenzoic acid and (R)-(+)-1-(1-naphthyl)-ethylamine | 56% |
| 18[b,e] | 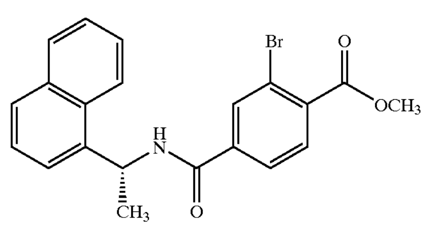 | Example 2 and (R)-(+)-1-(1-naphthyl)-ethylamine | 89% |

[a]Reaction time: 6 h.
[b]The product was a white solid.
[c]The eluent used for chromatography was 30–35% ethyl acetate/petroleum ether
[d]The eluent used for chromatography was 25% ethyl acetate/petroleum ether
[e]The eluent used for chromatography was 20% ethyl acetate/petroleum ether

Example 19

Preparation of 2-chloro-4-[1-oxo-3-(3-hydroxyphenyl)propyl]benzoic acid, methyl ester and 2-chloro-4-[1-hydroxy-3-(3-hydroxyphenyl)propyl]benzoic acid, methyl ester

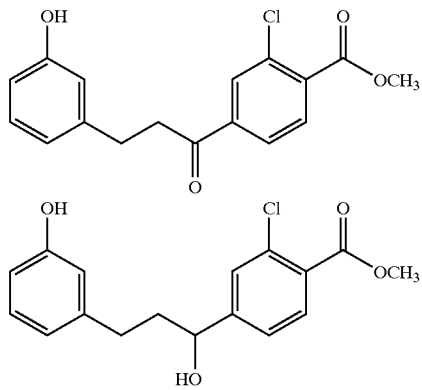

A. 2-Chloro-4-(diazoacetyl)benzoic acid, methyl ester

Oxalyl chloride (0.25 mL, 2.9 mmol) was added to a cooled (~10° C.) slurry of 2-chlorobenzene-1,4-dicarboxylic acid 1-methyl ester (Example 1; 430 mg, 2.0 mmol) in benzene (15 mL). A drop of N,N-dimethylformamide was added and the solution was stirred at room temperature for 3 h. The solvent was evaporated and the residue was evaporated from toluene (2×25 mL) to give the acid chloride as a colorless waxy solid. Ether (20 mL) was added, followed by excess ethereal diazomethane. The reaction mixture was left overnight at room temperature, then it was concentrated. Addition of hexanes, followed by filtration, gave 2-chloro-4-(diazoacetyl)benzoic acid, methyl ester (410 mg, 86%) as bright yellow crystals.

B. 4-(Bromoacetyl)-2-chlorobenzoic acid, methyl ester

Hydrogen bromide gas was bubbled through a suspension of 2-chloro-4-(diazoacetyl)benzoic acid, methyl ester (400 mg, 1.7 mmol) in ether (30 mL) for 10 min. The solvent was evaporated and the residue was triturated with ether/hexane and filtered to give 4-(bromoacetyl)-2-chlorobenzoic acid, methyl ester (385 mg, 79%) as a colorless solid.

C. [2-Oxo-2-[2-chloro-4-(methoxycarbonyl)phenyl]ethyl]triphenylphosphonium bromide A mixture of 4-(bromoacetyl)-2-chlorobenzoic acid, methyl ester (372 mg, 1.3 mmol), triphenylphosphine (336 mg, 1.3 mmol) and pyridine (1 drop) in acetonitrile (5 mL) was stirred at room temperature for 3 h. The solvent was evaporated and the residue was triturated with tetrahydrofuran. Ether was added, then the mixture was filtered and the residue was washed with ether to give [2-oxo-2-[2-chloro-4-(methoxycarbonyl)phenyl]ethyl]triphenylphosphonium bromide (641 mg, 90%) as a colorless solid.

D. 2-Chloro-4-[1-oxo-3-(3-hydroxyphenyl)-2-propenyl]benzoic acid, methyl ester

Sodium carbonate (215 mg, 2.0 mmol) was added to [2-oxo-2-[2-chloro-4-(methoxycarbonyl)phenyl]ethyl]triphenylphosphonium bromide (620 mg, 1.1 mmol), benzene (5 mL) and water (5 mL) in a separatory funnel. The mixture was shaken until the solids dissolved (about 10 min). The aqueous layer was separated and extracted with benzene. The organic layers were washed with brine, combined, dried (MgSO₄) and concentrated to dryness. Benzene (4 mL) was added, followed by 3-hydroxybenzaldehyde (137 mg, 1.1 mmol), and the solution was heated at reflux for 35 h. The solution was allowed to cool, hexane (3 mL) was added, and the solid was filtered off, washed with benzene/hexane, and then hexane to give 2-chloro-4-[1-oxo-3-(3-hydroxyphenyl)-2-propenyl]benzoic acid, methyl ester (260 mg, 73%) as a yellow solid.

E. 2-Chloro-4-[1-oxo-3-(3-hydroxyphenyl)propyl]benzoic acid, methyl ester and 2-chloro-4-[1-hydroxy-3-(3-hydroxyphenyl)propyl]benzoic acid, methyl ester A mixture of 2-chloro-4-[1-oxo-3-(3-hydroxyphenyl)-2-propenyl]benzoic acid, methyl ester (250 mg, 0.8 mmol) and 10% palladium-on-charcoal (25 mg) in ethyl acetate (5 mL) was hydrogenated at atmospheric pressure for 90 min. The reaction mixture was filtered through Celite and the filter cake was washed with ethyl acetate. The solvent was evaporated and the residue chromatographed (20–50% ethyl acetate/hexanes) to give 2-chloro-4-[1-oxo-3-(3-hydroxyphenyl)propyl]benzoic acid, methyl ester (160 mg, 64%) and 2-chloro-4-[1-hydroxy-3-(3-hydroxyphenyl)propyl]benzoic acid, methyl ester (65 mg, 26%). The alcohol was obtained as a racemic mixture and was not resolved.

Example 20

Preparation of 2-bromo-4-[[[3-[[(1,1-dimethylethoxy)carbonyl]aminophenyl]methyl]amino]carbonyl]benzoic acid, methyl ester

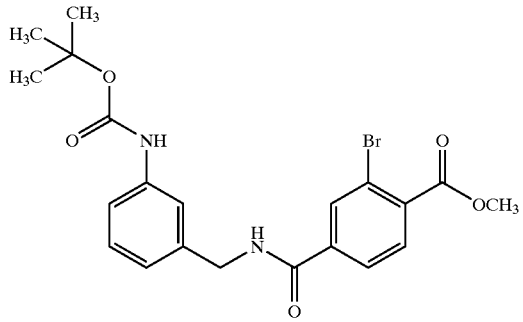

A. 4-[[[(3-aminophenyl)methyl]amino]carbonyl]-2-bromobenzoic acid, methyl ester

Iron powder (135 mg, 2.4 mmol) was added to a suspension of 2-bromo-4-[[[(3-nitrophenyl)methyl]amino]carbonyl]benzoic acid, methyl ester (Example 16; 125 mg, 3.18 mmol) in water (530 µL) and acetic acid (111 µL) at 25° C. The reaction was heated to reflux for 30 min and then cooled to 25° C. The suspension was diluted with water (20 mL), stirred for 15 min, and filtered through Celite. The filter cake was washed well with water (100 mL). The filtrate was extracted with ethyl acetate (50 mL) followed by ethyl acetate containing 2% methanol (50 mL). The organic layers were combined, dried (MgSO₄), filtered, and concentrated. The residue was diluted with 10% methanol in dichloromethane and stirred with Celite. After 1 h, the suspension was filtered and washed well with 10% methanol in dichloromethane. Concentration of the filtrate afforded 4-[[[(3-aminophenyl)methyl]amino]carbonyl]-2-bromobenzoic acid, methyl ester (100 mg, 87%) as an off-white solid.

B. 2-Bromo-4-[[[3-[[(1,1-dimethylethoxy)carbonyl]aminophenyl]-methyl]amino]carbonyl]benzoic acid, methyl ester To a solution of 4-[[[(3-aminophenyl)methyl]amino]carbonyl]-2-bromobenzoic acid, methyl ester (420 mg, 1.16 mmol) in 1,4-dioxane (6.5 mL) at 25° C. was added a solution of sodium carbonate (135 mg, 1.3 mmol) in water (2.1 mL) followed by di-tert-butyl dicarbonate (304 mg, 1.39 mmol). After stirring 24 h, the reaction mixture was diluted with water (200 mL) and washed with dichloromethane (300 mL). The organic layer was separated and washed with 10% acetic acid in water (100 mL), water (50 mL), and brine (50 mL). The organic layer was dried (MgSO$_4$), filtered, evaporated and flash chromatographed (silica, 25–35% ethyl acetate in petroleum ether) to give 2-bromo-4-[[[3-[[(1,1-dimethylethoxy)carbonyl]aminophenyl]methyl]-amino]carbonyl]benzoic acid, methyl ester (499 mg, 93%) as a white foam.

Example 21

Preparation of N-[3-[[[(1,1-dimethylethyl)dimethylsilyl]oxy]phenyl]methyl]-3,5-dimethyl-4-hydroxybenzamide

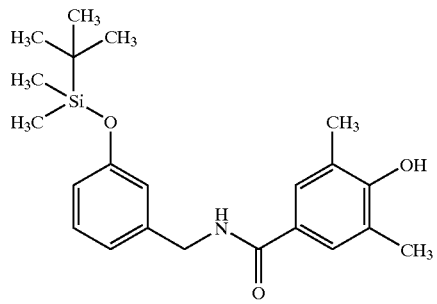

To a solution of 4-hydroxy-3,5-dimethylbenzoic acid (1.53 g, 9.2 mmol) in dichloromethane (30 mL) at 0° C. were added benzotriazol-1-yloxy-tris-(dimethylamino)-phosphonium hexafluorophosphate (BOP reagent, 4.45 g, 10 mmol) and 3-[[(1,1-dimethylethyl) dimethylsilyl]oxy]benzenemethanamine (Example 8; 3.28 g, 13.8 mmol), followed by diisopropylethylamine (4.9 mL, 27.6 mmol) slowly dropwise. After 1 h, the reaction was warmed to 25° C. and stirred for 1 h. The solvent was removed under reduced pressure and the residual oil was diluted with ethyl acetate (100 mL) and washed with 1N HCl (2×25 mL), saturated aqueous sodium bicarbonate (2×25 mL), water (25 mL), and brine (25 mL). The organic layer was dried (MgSO$_4$), filtered, evaporated and flash chromatographed (silica, 20–30% ethyl acetate in petroleum ether) to give N-[3-[[[(1,1-dimethylethyl)dimethylsilyl]oxy]phenyl]methyl]-3,5-dimethyl-4-hydroxybenzamide (3.1 g, 87%) as an off-white foam.

Also prepared by this route was the following:

Example 23

Preparation of trifluoromethanesulfonic acid, 2,6-dimethyl-4-[[[3-[[(1,1-dimethylethyl)dimethylsilyl]oxy]phenyl]methyl]amino]carbonyl]phenyl ester

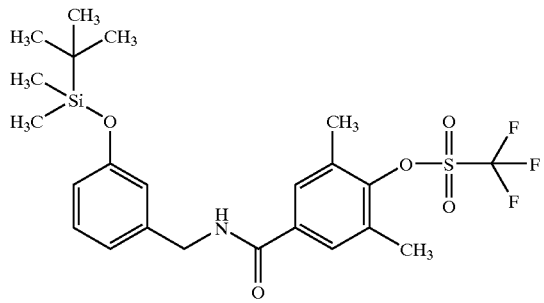

To a solution of N-[3-[[[(1,1-dimethylethyl)dimethylsilyl]oxy]phenyl]methyl]-3,5-dimethyl-4-hydroxybenzamide (Example 21; 0.5 g, 1.3 mmol) in dichloromethane (9 mL) at −78° C. was added triethylamine (0.72 mL, 5.2 mmol) followed by trifluoromethanesulfonic anhydride (0.26 mL, 1.56 mmol) slowly dropwise After stirring for 2 h, the reaction was quenched with saturated aqueous ammonium chloride (1 mL). The mixture was warmed to 25° C., diluted with ethyl acetate (70 mL) and washed with 1N HCl (25 mL), saturated aqueous sodium bicarbonate (25 mL), water (25 mL), and brine (25 mL). The organic layer was dried (MgSO$_4$), filtered, evaporated and quickly passed over a plug of silica (20% ethyl acetate in petroleum ether) to give trifluoromethanesulfonic acid, 2,6-dimethyl-4-[[[3-[[(1,1-dimethylethyl)dimethylsilyl]oxy]phenyl]methyl]amino]carbonyl]phenyl ester (577 mg, 86%) as an oil.

Also prepared by this route were the following:

| Example | Structure | Starting Material | Yield |
|---|---|---|---|
| 22[a] | 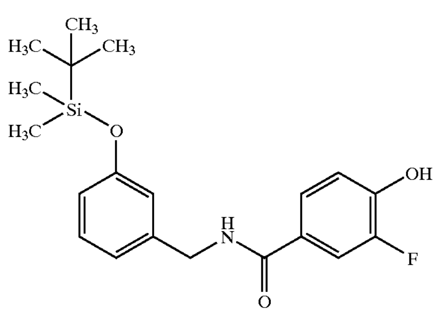 | Example 8 | 87% |

| Example | Structure | Starting Material | Yield |
|---|---|---|---|
| 24[a] | 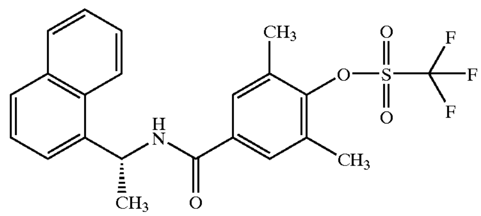 | Example 17 | 83% |
| 25[b] | 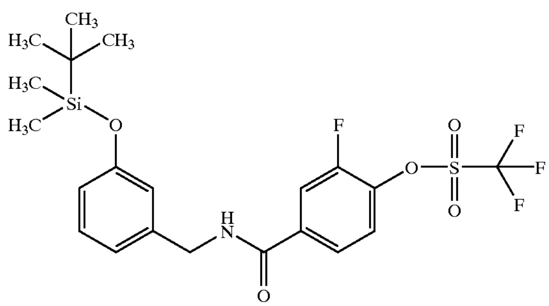 | Example 22 | 91% |

[a]The eluent used for chromatography was 10–25% ethyl acetate/petroleum ether; the product was obtained as a solid.
[b]The eluent used for chromatography was 10–15% ethyl acetate/petroleum ether; the product was obtained as a pale yellow oil.

Example 26

Preparation of 2-chloro-4-[[[(3-hydroxyphenyl)methyl]amino]carbonyl]benzoic acid

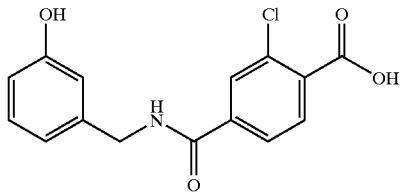

Crude 1-[[3-chloro-4-(methoxycarbonyl)benzoyl]oxy]-2,5-pyrrolidinedione (Example 5; ~35 g, ~0.1 mol) was charged to a 1L RB flask equipped with a magnetic stirrer, ice cooling bath, and a argon inlet tube, using dimethylformamide (350 mL) to complete the transfer. The mixture was cooled to about 10° C., then with stirring in an argon atmosphere, (3-hydroxyphenyl)methylamine hydrochloride salt (18.35 g, 0.115 mol) and triethylamine (35 mL, 0.25 mol) were added in rapid succession. A precipitate began to form immediately. After the reaction was stirred at ambient temperature overnight, the volatiles were removed under reduced pressure (<0.5 mm). The oily residue was taken up in ethyl acetate (600 mL) and washed in turn with 0.5N hydrochloric acid (400 mL), brine (300 mL), saturated sodium bicarbonate solution (2×300 mL) and brine (300 mL). Each aqueous layer was back-extracted in turn with ethyl acetate (2×300 mL), then the combined organic extracts were dried (MgSO$_4$), and evaporated to give crude 2-chloro-4-[[[(3-hydroxyphenyl)methyl]amino]carbonyl]benzoic acid methyl ester (~32g) as an off white solid. In a 2 L RB flask equipped with a magnetic stirrer, a slurry of crude 2-chloro-4-[[[(3-hydroxyphenyl)methyl]amino]carbonyl]benzoic acid methyl ester (~32 g, ~0.10 mol) in deionized water (300 mL) was treated with 1 N sodium hydroxide solution (300 mL, 0.3 mol). Most of the solids quickly dissolved, and the solution was stirred at room temperature overnight. The mixture was filtered through Celite to remove undissolved solids (residual DCU) and the filter cake was washed with deionized water (2×30 mL). The combined filtrates were transferred to a separatory funnel and extracted with diethyl ether (2×300 mL). Each ether extract was back-washed in turn with brine (50 mL). The combined aqueous phases were stirred as they were acidified by the addition of 6 N hydrochloric acid (55 mL, 0.33 mol). The resulting mixture was stirred overnight at room temperature, then the precipitated solids were collected by filtration and the filter cake was washed with deionized water (2×60 mL). The slightly off-white solid was dried in vacuo over P$_2$O$_5$ then was dissolved in warm ethyl acetate (400 mL), and the solution was treated with charcoal (4 g) and filtered through a bed of Celite. The filter cake was washed with ethyl acetate (2×40 mL). The combined filtrates were concentrated to about 250 mL then sufficient hexane was added to the hot stirred solution to produce a permanent cloud point. The mixture was cooled to room temperature, then was stored at −20° C. overnight. The solids were collected by filtration and were washed with hexane (2×50 mL) to give 2-chloro-4-[[[(3-hydroxyphenyl)methyl]amino]carbonyl]benzoic acid, mp 167–169° C. (27.1 g, 88.6% from 2-chloro-1,4-benzenedicarboxylic acid, 1-methyl ester).

Example 27

Preparation of 4-[[[(3-hydroxyphenyl)methyl]amino]carbonyl]-2-methylbenzoic acid

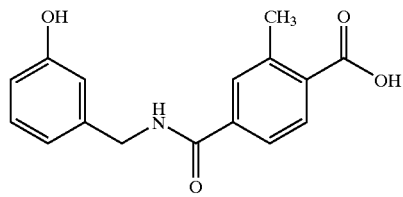

A. 4-[[[(3-Hydroxyphenyl)methyl]amino]carbonyl]-2-methylbenzoic acid, methyl ester A solution of 1-[[4-(methoxycarbonyl)-3-methylbenzoyl]oxy]-2,5-pyrrolidinedione (Example 6; 6.00 g, 20.6 mmol), 3-hydroxybenzylamine (2.92 g, 23.7 mmol) and triethylamine (2.61 g, 25.8 mmol) in N,N-dimethylformamide (100 mL) was stirred at room temperature overnight. The solvent was evaporated (<0.5 mm Hg, 40° C.) and ethyl acetate (200 mL) was added. The solution was washed with 0.5N hydrochloric acid (200 mL), brine (200 mL), saturated sodium bicarbonate solution (2×150 mL) and brine (200 mL). Each aqueous layer was back-extracted in turn with ethyl acetate (100 mL). The combined organic layers were dried (MgSO$_4$), filtered, and evaporated to give 4-[[[(3-hydroxyphenyl)methyl]amino]carbonyl]-2-methylbenzoic acid, methyl ester (5.63 g, 91%) as an orange liquid that solidified on standing, mp 100–103° C.

B. 4-[[[(3-Hydroxyphenyl)methyl]amino]carbonyl]-2-methylbenzoic acid

A solution of 4-[[[(3-hydroxyphenyl)methyl]amino]carbonyl]-2-methylbenzoic acid (5.63 g, 18.8 mmol) in water (60 mL) was treated with aqueous sodium hydroxide (1 M; 60 mL, 60 mmol) and the solution was stirred at room temperature overnight. The solution was acidified with 1 M HCl (100 mL), and extracted with ethyl acetate (2×100 mL). The combined extracts were washed with brine (100 mL). The solution was dried (MgSO$_4$), filtered, and evaporated to give 4-[[[(3-hydroxyphenyl)methyl]amino]carbonyl]-2-methylbenzoic acid (5.22 g, 97%) as an orange oil.

Example 29

Preparation of 2,6-dichloro-4-[[[(3-hydroxyphenyl)methyl]amino]carbonyl]benzoic acid

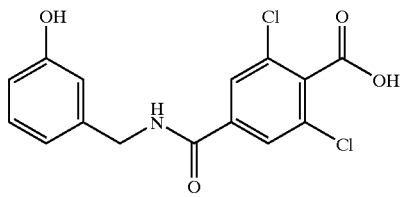

A solution of 2,6-dichlorobenzene-1,4-dicarboxylic acid, 1-methyl ester (Example 4; 18.75 g, 75.3 mmol), dicyclohexylcarbodiimide (16.46 g, 79.8 mmol), and N-hydroxysuccinimide (9.59 g, 83.3 mmol) in tetrahydrofuran (200 mL) was stirred at room temperature overnight. The solid was filtered off and discarded, and the solvent was evaporated from the filtrate to give a white solid (29.13 g). DMF (100 mL) was added, followed by 3-methoxybenzylamine (14.20 g, 103.5 mmol) and triethylamine (14.20 g, 140.3 mmol). The solution was stirred at room temperature overnight, then the solvent was evaporated (0.5 mm Hg, ~50° C.). 1 M HCl (200 mL) and dichloromethane (200 mL) were added. The mixture was swirled for 10 min and then allowed to stand until the layers separated. There was a white precipitate in the dichloromethane layer. Most of the aqueous layer was decanted off and the remaining material was heated until the solid dissolved. The remaining water was removed using a separating funnel, the dichloromethane solution was allowed to cool down, and the precipitate was filtered off and air-dried to give 2,6-dichloro-4-[[[(3-methoxyphenyl)methyl]amino]carbonyl]benzoic acid, methyl ester (23.67 g, 85%) as a white solid. A suspension of this material (11.83 g, 32.1 mmol) in dichloromethane (400 mL) was cooled to ~−78° C. (dry ice-acetone bath) and boron tribromide (1 M in dichloromethane; 100 mL, 100 mmol) was added. The mixture was stirred in the cooling bath for 3 h, and then allowed to stand at room temperature for 72 h. The supernatant was decanted off and water (300 mL) was added to each of the supernatant

| Example | Structure | Starting Materials | Yield (2 steps) |
|---|---|---|---|
| 28 | | Example 6 and (R)-(+)-1-(1-naphthyl)-ethylamine | 94% (white solid) | and the residue. The mixtures were stirred at ~40° C. for 1 h and then combined and filtered and air-dried to give 2,6-dichloro-4-[[[(3-hydroxyphenyl)methyl]amino]carbonyl]benzoic acid (8.73 g, 80%) as a cream-colored solid.

Example 30

Preparation of 2,6-dimethyl-4-[[[[3-[[(1,1-dimethylethyl)dimethylsilyl]oxy]phenyl]methyl]amino]carbonyl]benzoic acid

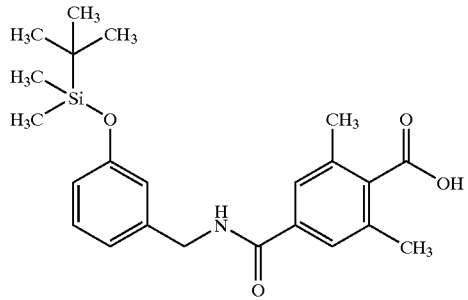

To a solution of trifluoromethanesulfonic acid, 2,6-dimethyl-4-[[[[3-[[(1,1-dimethylethyl)dimethylsilyl]oxy]phenyl]methyl]amino]carbonyl]phenyl ester (Example 23; 3.02 g, 5.83 mmol) in acetonitrile (49 mL) and water (7 mL) at 25° C. was added palladium (II) acetate (196 mg, 0.874 mmol), 1,3-bis(diphenylphosphino)propane (360 mg, 0.873 mmol), followed by triethylamine (2.03 mL, 14.5 mmol). The reaction was then pressurized to 40 psi with carbon monoxide and heated to 80° C. for 4 h. The mixture was diluted with ethyl acetate (300 mL) and washed with water (100 mL) containing 1 mL of triethylamine. The water layer was reextracted with ethyl acetate (2×50 mL) and the combined ethyl acetate layers were discarded. The water layer was acidified with 1 N HCl to pH 2, and extracted with ethyl acetate (200 mL). The ethyl acetate layer was washed with water (50 mL) and brine (50 mL), dried (MgSO$_4$), filtered and concentrated to yield 2,6-dimethyl-4-[[[[3-[[(1,1-dimethylethyl)dimethylsilyl]oxy]phenyl]methyl]amino]carbonyl]benzoic acid (1.7 g, 71%) as a white solid.

Also prepared by this route were the following:

| Example | Structure | Starting Material | Yield |
|---------|-----------|-------------------|-------|
| 31 | 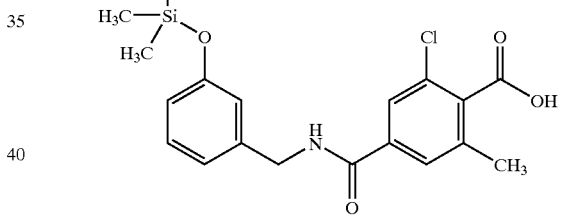 | Example 24 | 100% solid |
| 32 | 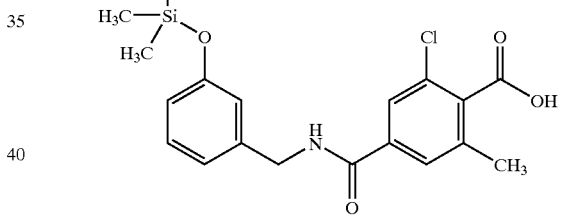 | Example 25 | 38% off-white foam |

Example 33

Preparation of 2-chloro-4-[[[[3-[[(1,1-dimethylethyl)dimethylsilyl]oxy]phenyl]methyl]amino]carbonyl]-6-methylbenzoic acid A. 3-Chloro-4-hydroxy-5-methylbenzaldehyde Hexamethylenetetramine (19.60 g, 139.8 mmol) was added in portions to a solution of 2-chloro-6-methylphenol (20.00 g, 117.2 mmol) in trifluoroacetic acid (200 mL). There was a slight exotherm and effervescence was noted. The reaction mixture was heated in an oil-bath at 84–86° C. for 5 h, then it was cooled and evaporated (~50° C., 0.2 mm). The residue was evaporated from hexane, then ice-water (500 mL) was added and the mixture was stirred for 20 min. Ether (100 mL) was added and the reaction was brought to approx. pH 5 by the careful portionwise addition of solid sodium hydrogen carbonate (49 g). The resulting mixture was extracted with ether (2×250 mL), and the ether layers were washed with brine, dried (MgSO$_4$), filtered and concentrated to about 100 mL. The mixture was then left to crystallize over the weekend to give a solid which was filtered off and washed with ice-cold ether to give 3-chloro-4-hydroxy-5-methylbenzaldehyde (6.9 g, 35%) as a yellow solid. The mother liquor was evaporated and dichloromethane (30 mL) was added. The yellow solid was filtered off (2.9 g, 14%). The remaining solution was purified by HPLC (7% ethyl acetate/hexanes) to give a yellow solid (7.8 g, 39%). The overall yield was 17.6 g (88%).

B. 3-Chloro-4-hydroxy-5-methylbenzoic acid

A solution of sulfamic acid (11.8 g, 121.5 mmol) in water (25 mL) was added with vigorous stirring to 3-chloro-4-hydroxy-5-methylbenzaldehyde (16.00 g, 93.8 mmol) in tert-butanol (100 mL). The mixture was cooled (~12° C.) and a solution of sodium chlorite (12.00 g, 106.1 mmol) in water (25 mL) was added in 5 mL portions with vigorous stirring. The reaction was exothermic and the temperature at the end of the addition was approximately 50° C. The two layers were separated and the aqueous layer was extracted with ether (2×50 mL). The organic layers were washed with brine and evaporated to dryness. Water was added, and the mixture was stirred and filtered. The solid was dissolved in warm ether (250 mL), and the solution was dried, filtered, concentrated to 100 mL, and cooled in the freezer (approx. −20° C.). Filtration and washing with cold ether gave 3-chloro-4-hydroxy-5-methylbenzoic acid (9.10 g, 52%), as a yellow solid, mp 242–244° C.

C. 2-Chloro-4-[[[[3-[[(1,1-dimethylethyl)dimethylsilyl]oxy]phenyl]methyl]amino]carbonyl]-6-methylphenol A suspension of 3-chloro-4-hydroxy-5-methylbenzoic acid (4.7 g, 25.2 mmol) in dichloromethane (50 mL) was cooled to 0° C. and BOP reagent (12.3 g, 27.8 mmol) was added, followed by diisopropylethylamine (13.2 mL, 75.6 mmol). A solution of 3-[[(1,1-dimethylethyl)dimethylsilyl]oxy]benzenemethanamine (Example 8; 6.59 g, 27.8 mmol) in dry dichloromethane (10 mL) was added by syringe and the resulting solution was stirred at ~0° C. for 3 h. The solvent was evaporated and ethyl acetate (200 mL) was added. The solution was washed with 1 M HCl (2×50 mL), aqueous sodium hydrogen carbonate (100 mL), brine (100 mL), and water (100 mL)dried (MgSO$_4$), filtered, evaporated, and chromatographed (30% ethyl acetate/hexanes) to give 2-chloro-4-[[[[3-[[(1,1-dimethylethyl)dimethylsilyl]oxy]phenyl]methyl]amino]carbonyl]-6-methylphenol (6.03 g, 59%) as a pale pink solid.

D. Trifluoromethanesulfonic acid, 2-chloro-4-[[[[3-[[(1,1-dimethylethyl)-dimethylsilyl]oxy]phenyl]methyl]amino]carbonyl]-6-methylphenyl ester Trifluoromethanesulfonic anhydride (3 mL, 17.7 mmol) was added to a cooled (−78° C.) solution of 2-chloro-4-[[[[3-[[(1,1-dimethylethyl)dimethylsilyl]oxy]-phenyl]methyl]amino]carbonyl]-6-methylphenol (6.00 g,14.8 mmol) and triethylamine (8.24 mL, 59.1 mmol) in dichloromethane (60 mL). After stirring for 2 h at −78° C. , the reaction was quenched with solid ammonium chloride (4 g). The mixture was diluted with ethyl acetate (200 mL) and washed with 1N HCl (100 mL), saturated aqueous sodium bicarbonate and brine. The organic layer was dried (MgSO$_4$), filtered, evaporated and chromatographed (20–30% ethyl acetate/hexanes) to give trifluoromethanesulfonic acid, 2-chloro-4-[[[[3-[[(1,1-dimethylethyl)dimethylsilyl]oxy]phenyl]methyl]amino]carbonyl]-6-methylphenyl ester (5.00 g, 63%) as pale orange oil.

E. 2-Chloro-4-[[[[3-[[(1,1-dimethylethyl)dimethylsilyl]oxy]phenyl]methyl]amino]carbonyl]-6-methylbenzoic acid A mixture of trifluoromethanesulfonic acid, 2-chloro-4-[[[[3-[[(1,1-dimethylethyl)dimethylsilyl]oxy]phenyl]methyl]amino]carbonyl]-6-methylphenyl ester (4.00 g, 7.4 mmol), water (10 mL), triethylamine (2.6 mL, 18.6 mmol), palladium(II) acetate (0.25 g, 1.1 mmol), and bis(diphenylphosphino)propane (0.46 g, 1.1 mmol) in acetonitrile (70 mL) was pressurized to 40 psi with carbon monoxide and the pressure was released. After four such cycles, the bottle was pressurized again and the contents were stirred at 80° C. for 3.5 h. The reaction mixture was cooled to room temperature and depressurized. The solvent was evaporated and ethyl acetate (200 mL) was added. The solution was extracted three times with aqueous sodium hydrogen carbonate. Water was then added to the organic layer, followed by triethylamine (3 mL), and the mixture was extracted with ethyl acetate. The aqueous layer was acidified with 2 M HCl and extracted three times with ethyl acetate. The combined ethyl acetate layers from this extraction were washed with brine, dried (MgSO$_4$), filtered, concentrated, and dried overnight under high vacuum to give 2-chloro-4-[[[[3-[[(1,1-dimethylethyl)dimethylsilyl]oxy]phenyl]methyl]amino]carbonyl]-6-methylbenzoic acid (2.30 g, 71%) as a yellow solid.

Example 34

Preparation of 2,6-dichloro-4-[[[[3-[[(1,1-dimethylethyl)dimethylsilyl]oxy]phenyl]methyl]amino]carbonyl]benzoic acid

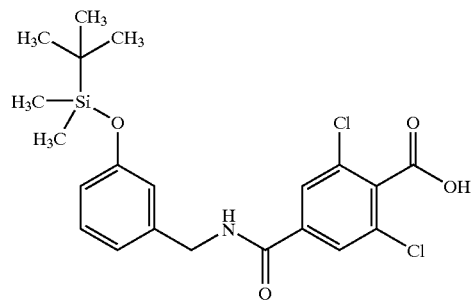

A. 2,6-Dichloro-4-[[[[3-[[(1,1-dimethylethyl)dimethylsilyl]oxy]phenyl]methyl]amino]carbonyl]phenol A solution of 3-[[(1,1-dimethylethyl)dimethylsilyl]oxy]benzenemethanamine (Example 8; 5.80 g, 24.5 mmol) in dry dichloromethane (20 mL) was added to a cooled (0° C.) suspension of 3,5-dichloro-4-hydroxybenzoic acid (4.2 g, 20.4 mmol) and BOP reagent (9.80 g, 22.3 mmol) in dry dichloromethane (50 mL). Diisopropylethylamine (10.6 mL, 60.9 mmol) was added slowly, and the cooling bath was removed. The solution was stirred at room temperature for 5 h, then the solvent was evaporated and the residue was dissolved in ethyl acetate. The solution was washed with 1 M HCl (2×100 mL), saturated aqueous sodium hydrogen carbonate (100 mL), and brine (100 mL), dried (MgSO$_4$), filtered, evaporated, and chromatographed (30% ethyl acetate/hexanes) to give 2,6-dichloro-4-[[[[3-[[(1,1-dimethylethyl)dimethylsilyl]oxy]phenyl]methyl]amino]carbonyl]phenol (7.50 g, 87%) as a white solid.

B. Trifluoromethanesulfonic acid, 2,6-dichloro-4-[[[[3-[[(1,1-dimethylethyl)dimethylsilyl]oxy]phenyl]methyl]amino]carbonyl]phenyl ester Trifluoromethanesulfonic anhydride (3.55 mL, 21.1 mmol) was added to a cooled (−75° C. ) solution of 2,6-dichloro-4-[[[[3-[[(1,1-dimethylethyl)dimethyl-silyl]oxy]phenyl]methyl]amino]carbonyl]phenol (7.50 g, 17.6 mmol) and triethylamine (9.8 mL, 70.4 mmol) in dry dichloromethane (70 mL). After stirring for 3 h at ~−70° C., the reaction was quenched with solid ammonium chloride (6 g). The solvent was evaporated and ethyl acetate was added. The solution was washed with 1 N HCl, saturated aqueous sodium bicarbonate and brine. The organic layer was dried (MgSO$_4$), filtered, evaporated and dried under high vacuum to give trifluoromethanesulfonic acid, 2,6-dichloro-4-[[[[3-[[(1,1-dimethylethyl)dimethyl-silyl]oxy]phenyl]methyl]amino]carbonyl]phenyl ester (9.46 g, 97%) as pale orange oil.

C. 2,6-Dichloro-4-[[[[3-[[(1,1-dimethylethyl)dimethylsilyl] oxy]phenyl]methyl]amino]carbonyl]benzoic acid A mixture of trifluoromethanesulfonic acid, 2,6-dichloro-4-[[[[3-[[(1,1-dimethylethyl)dimethylsilyl]oxy]phenyl] methyl]amino]carbonyl]phenyl ester (3.33 g, 6.0 mmol), water (7 mL), triethylamine (1.7 mL, 11.9 mmol), palladium (II) acetate (0.20 g, 0.9 mmol), and bis(diphenylphosphino) propane (0.37 g, 0.9 mmol) in acetonitrile (80 mL) was pressurized to 40 psi with carbon monoxide and the pressure was released. After three such cycles, the bottle was pressurized again and the contents were stirred at 80° C. for 5 h. The reaction mixture was cooled to room temperature and depressurized. The solvent was evaporated and ethyl acetate was added. The mixture was acidified with 1 M HCl and then the layers were separated. The organic solution was washed with brine, dried (MgSO$_4$), filtered, evaporated and chromatographed (70–100% ethyl acetate/hexanes then 10% methanol/ethyl acetate) to give 2,6-dichloro-4-[[[[3-[[(1,1-dimethylethyl)dimethylsilyl]oxy]phenyl]methyl]amino] carbonyl]benzoic acid (1.23 g, 45%) as a white solid.

ride (Example 9; 0.120 g, 0.60 mmol) in DMF (6 mL). The mixture was stirred a room temperature for 13 h and then filtered and diluted with water. The aqueous phase was extracted several times with ethyl acetate. The combined organic extracts were washed with water, concentrated and chromatographed (45% ethyl acetate/hexanes) to give 2-chloro-4-[[(2,3-dihydro-2-oxo-1H-indole-4-methyl) amino]carbonyl]benzoic acid, methyl ester (0.11 g, 50%). A solution of lithium hydroxide monohydrate (39 mg, 0.93 mmol) in water (1 mL) was added to a solution of the ester (0.11 g, 0.31 mmol) in tetrahydrofuran/methanol/water (3:1:1; 4 mL). The mixture was stirred for 3 h at room temperature and then acidified with 6 N HCl and diluted with water. The mixture was extracted several times with ethyl acetate and the combined organic layers were dried (Na$_2$SO$_4$) and concentrated to give 2-chloro-4-[[(2,3-dihydro-2-oxo-1H-indole-4-methyl)amino]carbonyl] benzoic acid as a brown solid (0.080 g, 75%).

Also prepared by this procedure were:

| Example | Structure | Starting Materials |
|---|---|---|
| 36 | 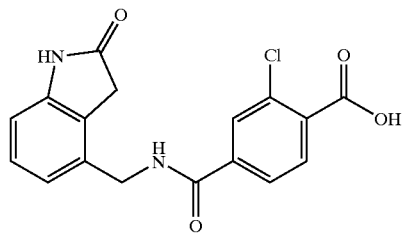 | Example 1 and Example 10 |
| 37 | 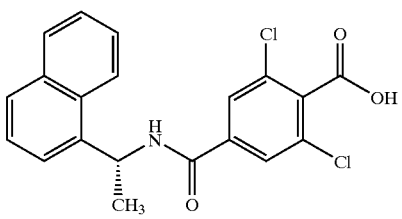 | Example 1 and (R)-(+)-1-(1-naphthyl)-ethylamine |

Example 35

Preparation of 2-chloro-4-[[(2,3-dihydro-2-oxo-1H-indole-4-methyl)amino]carbonyl]benzoic acid DCC (0.124 g, 0.60 mmol), HOBT (0.081 g, 0.60 mmol) and triethylamine (0.060 g, 0.060 mmol) were added successively to a solution of 2-chloro-1,4-benzenedicarboxylic acid, 1-methyl ester (Example 1; 0.129 g, 0.60 mmol) and 2,3-dihydro-2-oxo-1H-indole-4-methanamine hydrochlo- Example 38

Preparation of 2,6-dichloro-4-[[[(1R)-1-(1-naphthalenyl)ethyl]amino]carbonyl]benzoic acid A. 2,6-Dichloro-4-[[[(1R)-1-(1-naphthalenyl)ethyl]amino] carbonyl]benzoic acid, methyl ester A solution of 2,6-dichlorobenzene-1,4-dicarboxylic acid, 1-methyl ester (Example 4; 3.00 g, 12.0 mmol), (R)-(+)-1-(1-naphthyl)ethylamine (2.00 g, 11.7 mmol), HBTU (5.68 g, 15.0 mmol), HOBT (2.04 g, 15.1 mmol), and diisopropylethylamine (6.20 g, 48.0 mmol) in N,N-dimethylformamide (50 mL) was stirred at room temperature over the weekend. The solvent was evaporated and ethyl acetate (150 mL) was added. The solution was washed with 1 M HCl (100 mL) and the aqueous layer was back-extracted with ethyl, acetate (100 mL). The combined organic layers were washed with saturated aqueous sodium hydrogen carbonate and brine (200 mL each), then dried (MgSO$_4$), filtered, evaporated and chromatographed (30% ethyl acetate/hexanes) to give 2,6-dichloro-4-[[[(1R)-1-(1-naphthalenyl)ethyl]amino] carbonyl]benzoic acid, methyl ester (4.52 g, 96%) as a white foam.

B. 2,6-Dichloro-4-[[[(1R)-1-(1-naphthalenyl)ethyl]amino] carbonyl]benzoic acid

A solution of sodium hydroxide (0.62 g, 15.5 mmol) in water (100 mL) was added to a solution of 2,6-dichloro-4-[[[(1R)-1-(1-naphthalenyl)ethyl]amino]carbonyl]benzoic acid, methyl ester (5.62 g, 14.0 mmol) in tetrahydrofuran (100 mL). The solution was stirred overnight at room temperature. Tlc indicated that the reaction was not complete. 1 M NaOH (20 mL) was added and the mixture was heated at reflux for 6 h. Methanol (100 mL) was added and the mixture was stirred overnight at room temperature. Again, tlc indicated that the reaction was not complete so the reaction mixture was heated at reflux for 2 h, 1 M NaOH (100 mL) was added and the solution was heated at reflux for a further 4 h. The reaction mixture was allowed to stand overnight at room temperature, then the solvent was evaporated, and water (100 mL) and 1 M HCl (200 mL) were added. The mixture was stirred for 20 min and then the white solid was filtered off and dried overnight in a vacuum oven (25 mm Hg, 60° C.) to give 2,6-dichloro-4-[[[(1R)-1-(1-naphthalenyl)ethyl]amino]carbonyl]benzoic acid (4.84 g, 89%) as a white solid, mp 213–215° C. (dec.).

Example 39

Preparation of 2-chloro-4-[[[[1-(tetrahydro-2H-pyran-2-yl)-1H-indazol-4-yl]methyl]amino] carbonyl]benzoic acid

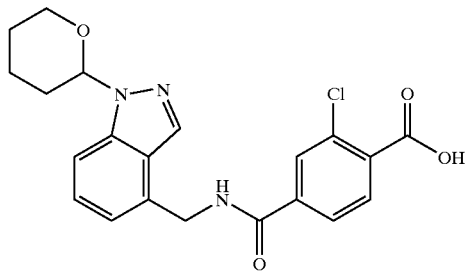

A. 2-Chloro-4-[[[[1-(tetrahydro-2H-pyran-2-yl)-1H-indazol-4-yl]methyl]amino]carbonyl]benzoic acid, methyl ester 2-Chloro-1,4-benzenedicarboxylic acid, 1-methyl ester (Example 1; 84.3 mg, 0.393 mmol) was suspended in dichloromethane (1.5 mL) and the mixture was cooled to 0° C. BOP reagent (191 mg, 0.432 mmol) was added in one portion, followed by 4-aminomethyl-1-(tetrahydro-2H-pyran-2-yl)-1H-indazole (Example 12; 91 mg, 0.393 mmol) with a 2×0.25 mL wash of dichloromethane. Diisopropylethylamine (0.21 g, 1.62 mmol) was added over 1 min at ~0° C. The mixture was stirred at ~0° C. for 30 min and then at room temperature for 3.5 h. The mixture was concentrated to remove dichloromethane, and ethyl acetate (60 mL) was added. The solution was washed with 1 M HCl, sodium hydrogen carbonate solution, and brine (10 mL each), then dried (MgSO$_4$), filtered, and concentrated. Ethyl acetate/ petroleum ether was added and the insoluble material was filtered off to give 2-chloro-4-[[[[1-(tetrahydro-2H-pyran-2-yl)-1H-indazol-4-yl]methyl]amino]carbonyl]benzoic acid, methyl ester (93 mg, 55%) as a white solid.

B. 2-Chloro-4-[[[[1-(tetrahydro-2H-pyran-2-yl)-1H-indazol-4-yl]methyl]amino]carbonyl]benzoic acid A suspension of 2-chloro-4-[[[[1-(tetrahydro-2H-pyran-2-yl)-1H-indazol-4-yl]methyl]amino]carbonyl]benzoic acid, methyl ester (87.8 mg, 0.206 mmol) in methanol (1 mL) was cooled to ~0° C. and 1 M sodium hydroxide (0.206 mL, 0.206 mmol) was added. The cooling bath was removed and the reaction mixture was allowed to stir overnight. A further portion of sodium hydroxide (1 M; 0.2 mL, 0.2 mmol) was added and the mixture was stirred at room temperature for 7 h. The solvent was evaporated and the residue was dissolved in water (25 mL) and washed with ethyl acetate (2×10 mL). The aqueous layer was made acidic with 1 M HCl and extracted with ethyl acetate (2×20 mL). These extracts were combined, washed with brine (10 mL), dried (MgSO$_4$), filtered, and concentrated to give 2-chloro-4-[[[[1-(tetrahydro-2H-pyran-2-yl)-1H-indazol-4-yl]methyl] amino]carbonyl]benzoic acid (77.3 mg, 91%) as a white solid.

Example 40

Preparation of 2-chloro-4-[[[(benzimidazol-4-yl) methyl]amino]-carbonyl]benzoic acid

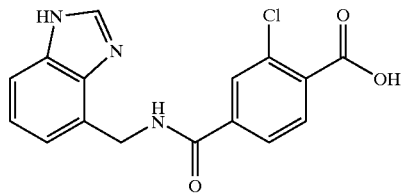

A mixture of 4-(azidomethyl)benzimidazole-1-carboxylic acid, 1,1-dimethylethyl ester (Example 13; 1.40, 5.1 mmol), 1-[[3-chloro-4-(methoxycarbonyl)benzoyl]oxy]-2,5-pyrrolidinedione (Example 5; 1.62 g, 5.2 mmol), and 10% palladium on charcoal (210 mg) in methanol (40 mL) and benzene (2 mL) was hydrogenated at atmospheric pressure for 105 min and then filtered through Celite. Tlc indicated that the reaction was not complete so more 10% palladium on charcoal (210 mg) was added and the mixture was hydrogenated at atmospheric pressure for 3 h and then shaken at 50 psi of hydrogen for 3 h. The reaction mixture was allowed to stand under hydrogen for 12 h, then filtered through Celite, evaporated, and chromatographed (20–100% ethyl acetate/hexanes) to give 2-chloro-4-[[[[1-[(1,1-dimethylethoxy)carbonyl]benzimidazol-4-yl]methyl] amino]carbonyl]benzoic acid, methyl ester (1.50 g, 66%). A solution of the ester (1.45 g, 3.3 mmol) in methanol (15 mL) and 3 M lithium hydroxide solution (5.5 mL) was stirred at room temperature overnight. A white solid was filtered off and discarded. The filtrate was evaporated to dryness. Water and 1 M HCl (16.6 mL) were added, and the mixture was filtered and washed with water to give 2-chloro-4-[[[(benzimidazol-4-yl)methyl]amino]carbonyl]-benzoic acid (925 mg, 86%).

Example 41

Preparation of 2-chloro-4-[1-oxo-3-(3-hydroxyphenyl)propyl]benzoic acid

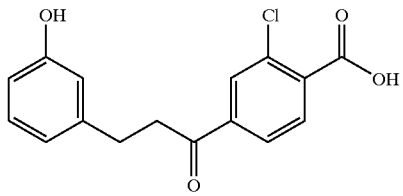

A mixture of 2-chloro-4-[1-oxo-3-(3-hydroxyphenyl)propyl]benzoic acid, methyl ester (Example 19; 2.1 g, 6.6 mmol) and 1 M sodium hydroxide solution was stirred for 4 h at room temperature. The solution was filtered through Celite and the filter cake was washed with water (5 mL). 1 M HCl (22 mL) was added to the stirred filtrate and the resulting mixture was stirred for 2 h and then filtered. The solid was washed with water, dried and recrystallized from ether/hexane to give 2-chloro-4-[1-oxo-3-(3-hydroxyphenyl)propyl]benzoic acid (1.59 g, 79%) as an off-white solid.

Example 42

Preparation of 2-chloro-4-[1-hydroxy-3-(3-hydroxyphenyl)propyl]benzoic acid

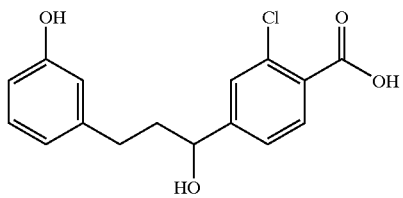

This compound was prepared in 90% yield from 2-chloro-4-[1-hydroxy-3-(3-hydroxyphenyl)propyl]benzoic acid, methyl ester (Example 19) by the procedure described for 2-chloro-4-[1-oxo-3-(3-hydroxyphenyl)propyl]benzoic acid (Example 41). The product was a racemic mixture and was not resolved.

Example 43

Preparation of 2-chloro-4-[5-[(3-hydroxy)phenylmethylamino]tetrazol-1-yl]benzoic acid

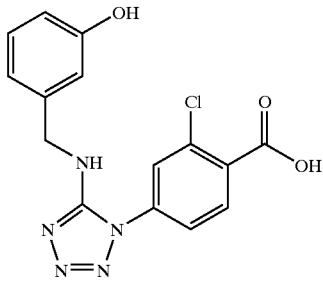

A. 4-[[[[(3-acetoxy)phenyl]methyl]amino]carbonyl]amino-2-chlorobenzoic acid, methyl ester A stirred suspension of 3-hydroxyphenylacetic acid (10.2 g, 67 mmol) in acetic anhydride (100 mL, 1.06 mol) under anhydrous conditions was treated with pyridine (0.5 mL). In the mildly exothermic reaction, the solids dissolved within several minutes and the mixture was maintained at 40° C. for 5 h. The reaction was concentrated in vacuo to about half volume, then water (30 g) in the form of ice chips was added at such a rate that the temperature remained <45° C. When the exotherm had subsided, a second portion of water (200 mL) was added slowly and the mixture was stirred for another 30 min. The precipitated solid was filtered, washed with water and dried to constant weight in vacuo over $P_2O_5$ to give 3-acetoxyphenylacetic acid (11.7 g, 90%) which was used without further purification. In an inert atmosphere, a solution of the above 3-acetoxyphenylacetic acid (1.942 g, 10 mmol), diphenylphosphoryl azide (2.8 g, 10.17 mmol) and diisopropylethylamine (1.92 mL, 11 mmol) in benzene (25 mL) was stirred at room temperature for 1 h, then the reaction temperature was slowly raised to 70° C. Evolution of gas began to be evident as the reaction temperature reached approximately 55° C. and became much more vigorous as the reaction temperature approached 70° C. Within 30 minutes at that temperature gas evolution had stopped and the reaction solution containing 3-acetoxybenzylisocyanate was cooled to 40° C. Another portion of DIPEA (3.84 mL, 22 mmol) was added, followed by 4-amino-2-chlorobenzoic acid methyl ester hydrochloride salt (2.95 g, 13.3 mmol) and the brownish purple solution was stirred and heated at reflux under argon overnight. The reaction mixture was cooled, diluted with benzene (50 mL) and washed in turn with 1N HCl (50 mL) and dilute brine. The aqueous layers were re-extracted with benzene, and the combined extracts were dried ($MgSO_4$), evaporated, and purified by HPLC (silica gel; 40% ethyl acetate/hexane). Evaporation of the appropriate fractions provided 3.24 g of the solid urea which was then crystallized from dichloromethane-ethyl acetate to give 4-[[[[(3-acetoxy)phenyl]methyl]amino]-carbonyl]amino-2-chlorobenzoic acid, methyl ester (2.71 g, 72%) as a colorless solid, mp 113–114° C.

B. 2-Chloro-4-[5-[[[(3-hydroxy)phenyl]methyl]amino]tetrazol-1-yl]benzoic acid

In a dry argon atmosphere, a solution of triphenylphosphine (1.684 g, 6.42 mmol), diethyl azodicarboxylate (1.13 g, 6.42 mmol) 4-[[[[(3-acetoxy)phenyl]methyl]amino]carbonyl]amino-2-chlorobenzoic acid, methyl ester (1.21 g, 3.21 mmol) in dry THF (30 mL) was treated with trimethylsilyl azide (0.86 mL, 6.48 mmol) and was stirred at room temperature for 24 hr. Examination of the reaction mixture by TLC suggested the presence of considerable starting material, so additional amounts of triphenylphosphine (0.842 g, 3.21 mmol), diethyl azodicarboxylate (0.565 g, 3.21 mmol) and trimethylsilyl azide (0.43 mL, 3.21 mmol) were added. The reaction was stirred at room temperature for an additional 40 hr. The solvents were removed under reduced pressure and the residue was taken up in dichloromethane (100 mL) and washed with water (2×50 mL). The aqueous layers were back-extracted in turn with dichloromethane (50 mL) and the combined organic phases were dried ($MgSO_4$, filtered and evaporated in vacuo. The residue was dissolved in a mixture of methanol (30 mL) and 1 N lithium hydroxide (15 mL) and the mixture was stirred at room temperature for 2 hr to complete the hydrolyses of both the ester and phenolic acetate groups. Most of the volatiles were removed under reduced pressure, then the basic solution was diluted with water (20 mL) and washed with dichloromethane (2×30 mL). The aqueous layer was then acidified with 1N HCl (16 mL) and extracted with ethyl acetate (2×50 mL). The dried ($MgSO_4$) ethyl acetate extracts were evaporated and the residual solid (810 mg), approximately a 4:1 mixture of the desired aminotetrazole and its positional isomer, was crystallized from ether to furnish 2-chloro-4-[5-[[[(3-hydroxy)phenyl]methyl]-amino]tetrazol-1-yl]benzoic acid (560 mg, 46%) as a colorless solid.

2-bromo-4-[[[3-[[(1,1-dimethylethoxy)carbonyl]aminophenyl]methyl]amino]carbonyl]benzoic acid (474 mg, 99%) as a white foam.

The following compounds were also prepared by this procedure, except that the reaction was allowed to proceed for 48 h at 25° C. rather than 24 h:

| Example | Structure | Starting Material | Yield |
|---|---|---|---|
| 45 | 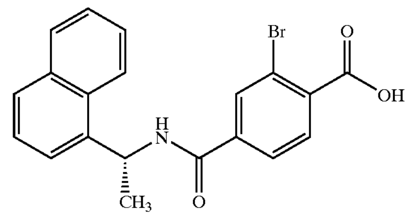 | Example 18 | 88% (white foam) |
| 46 | 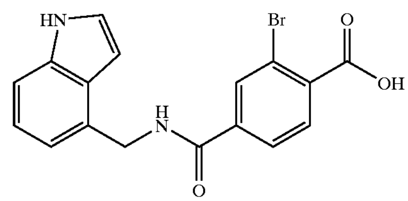 | Example 15 | 96% (off-white solid) |

Example 44

Preparation of 2-bromo-4-[[[3-[[(1,1-dimethylethoxy)carbonyl]aminophenyl]methyl]amino]carbonyl]benzoic-acid

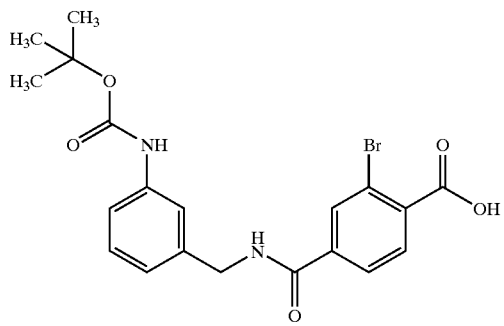

To a solution of 2-bromo-4-[[[3-[[(1,1-dimethylethoxy)carbonyl]aminophenyl]-methyl]amino]carbonyl]benzoic acid, methyl ester (Example 20; 495 mg, 1.07 mmol) in methanol (5 mL) at 0° C. was added 1 M NaOH (1.07 mL, 1.07 mmol). The reaction mixture was warmed to 25° C. and stirred for 24 h. TLC (10% methanol in dichloromethane) revealed that starting material was still present. 1 N NaOH (0.5 mL) was added at room temperature and the reaction was heated to 50° C. After stirring for 3 h, the solvents were evaporated under reduced pressure. The residue was diluted with ethyl acetate (100 mL) and washed with water (100 mL). The water layer was separated, acidified to pH 4 with 1 N HCl, and extracted with ethyl acetate (2×100 mL). The organic layers were combined, washed with brine (50 mL), dried with MgSO$_4$, filtered, and concentrated to yield

Example 47

Preparation of 2-bromo-4-[[[(3-hydroxyphenyl)methyl]amino]carbonyl]benzoic acid

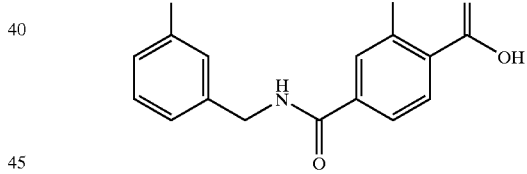

A solution of lithium hydroxide monohydrate (4.41 g, 105.1 mmol) in water (15 mL) was added to a solution of 2-bromo-4-[[[(3-hydroxyphenyl)methyl]amino]-carbonyl]benzoic acid, methyl ester (Example 14; 15.30 g, 42.0 mmol) in tetrahydrofuran/methanol (2:1, 21 mL). The solution was stirred at room temperature for 1 h, then it was concentrated to remove tetrahydrofuran and methanol. The remaining aqueous solution was extracted with ethyl acetate (15 mL) and the ethyl acetate extract was discarded. The aqueous layer was acidified with 1 M HCl (75 mL) and extracted with ethyl acetate (2×50 mL). The combined organic layers were washed with brine (15 mL), dried (MgSO$_4$), filtered, and evaporated to give 2-bromo-4-[[[(3-hydroxyphenyl)methyl]amino]carbonyl]benzoic acid (15.1 g, quantitative yield) which was used in the next step without further purification.

Example 48

Preparation of 1-(2-methoxyethyl) cyclopentanecarboxylic acid

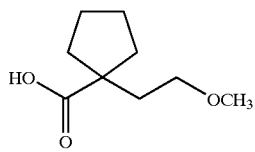

To a 3 L 3-necked round-bottomed flask equipped with a thermometer and dropping funnel were added diisopropylamine (136 mL, 0.98 mol) and tetrahydrofuran (750 mL). The solution was stirred under nitrogen and cooled in an ice-bath. Through the dropping funnel was added n-butyllithium (2.5 M in hexanes; 376 mL, 0.94 mol), and the solution was allowed to stir at 0° C. for 30 min and then cooled to −70° C. Through the dropping funnel was added a solution of cyclopentanecarboxylic acid, methyl ester (83.04 g, 0.65 mol) in tetrahydrofuran (135 mL). The solution was stirred at −70° C. for 1 h and then a solution of 2-bromoethyl methyl ether (55.5 mL, 0.59 mol) in tetrahydrofuran (135 mL) was added. The solution was stirred at −70° C. for 1 h and then the cooling bath was removed. The solution was stirred at room temperature overnight, then poured into saturated ammonium chloride solution (2 L) and extracted with ether (3×500 mL). The combined ether layers were washed with saturated brine (6×400 mL), dried ($Na_2SO_4$), filtered, evaporated, and distilled under vacuum to give 1-(2-methoxyethyl) cyclopentanecarboxylic acid, methyl ester (71.39 g, 59%) as a pale yellow liquid (bp 94–102° C. at 8 mm). This was dissolved in a mixture of tetrahydrofuran (340 mL), methanol (340 mL) and 1 M sodium hydroxide solution (425 mL). The mixture was stirred and heated at 55–60° C. for 24 h and then concentrated under reduced pressure to remove tetrahydrofuran and methanol. Water (400 mL) was added and the solution was extracted with ether (2×200 mL). The aqueous layer was acidified to pH 1 with 1 N HCl (500 mL), and extracted with ether (300 mL, then 2×200 mL). The combined ether layers were washed with saturated brine (2×200 mL), dried ($Na_2SO_4$), filtered, and evaporated to give 1-(2-methoxyethyl)cyclopentanecarboxylic acid (63.68 g, 97%) as a yellow liquid.

Example 49

Preparation of 1,4-dioxa-8-thiaspiro[4.5]decane-6-carboxylic acid

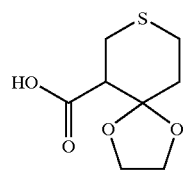

A solution of 1,4-dioxa-8-thiaspiro[4.5]decane-6-carboxylic acid, methyl ester (prepared according to Baldwin, J. J. et al. U.S. Pat. No. 4,803,286; 30.00 g, 0.137 mol) in ethanol (500 mL) and a solution of potassium hydroxide (16.80 g, 0.299 mol) in ethanol (300 mL) were combined and heated under reflux for 7 h. The solution was concentrated in vacuo and water was added. The mixture was extracted with ether, and the ether layer was discarded. The aqueous layer was made acidic and extracted with ether. The ether layers were washed, dried, and evaporated, and the residue was recrystallized from benzene/hexane to give 1,4-dioxa-8-thiaspiro[4.5]decane-6-carboxylic acid (17.8 g, 63%) as white crystals, mp 99–101° C.

Example 50

Preparation of (2S)-3-cyclohexyl-2-(pyrrol-1-yl) propanoic acid

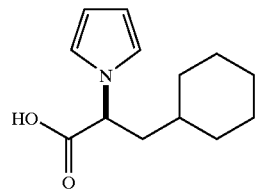

By analogy with the literature procedure (Ceccherelli, P. et al. *J. Org. Chem.* 1994, 59, 2882–4), to a refluxing solution of anhydrous sodium acetate (71.86 g, 0.876 mol) in acetic acid (609 mL) was added β-cyclohexyl-L-alanine (25.00 g, 0.146 mol) followed by 2,5-dimethoxytetrahydrofuran (18.9 mL, 0.146 mol). The solution was heated for 1 min and then concentrated. Saturated brine (250 mL) was added and the solution was extracted with ethyl acetate (2×400 mL). The combined extracts were washed with brine (250 mL), dried ($MgSO_4$), filtered, concentrated to dryness, and the residue was co-evaporated with toluene to remove traces of acetic acid. The dark residue (36.99 g) was dissolved in ethanol (125 mL) and charcoal (10 g) was added. The solution was stirred and filtered through Celite® and the filter cake was washed with ethanol (150 mL). Dicyclohexylamine (29.1 mL, 0.146 mol) was added to the filtrate and the tan precipitate was filtered off and washed with cold ethanol (2×18 mL) and ether (30 mL). The solid (40.22 g) was suspended in ethyl acetate (300 mL) and washed with 1 N citric acid (2×200 mL). The aqueous layer was back-extracted with ethyl acetate (300 mL) and the combined ethyl acetate layers were washed with saturated brine (200 mL), dried ($MgSO_4$), filtered and concentrated to give a dark liquid (26.1 g). An impurity (1.6 g) was removed by crystallization from ether/petroleum ether (1:1; 20 mL). Concentration of the filtrate gave (2S)-3-cyclohexyl-2-(pyrrol-1-yl)propionic acid (21.48 g, 66%) as a dark brown oil which solidified on standing, mp 78–80° C.

Example 51

Preparation of N-[(9H-fluoren-9-ylmethoxy) carbonyl]piperidine-4-carboxylic acid

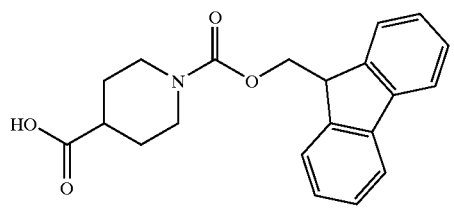

Piperidine-4-carboxylic acid (15.00 g, 116 mmol) was added to a solution of sodium hydrogen carbonate (12.7 g, 151 mmol) in water (200 mL) and the mixture was stirred for 10 min. A solution of 1-[[(9H-fluoren-9-ylmethoxy) carbonyl]oxy-2,5-pyrrolidinedione (Fmoc-OSu; 46.9 g, 139 mmol) in tetrahydrofuran (400 mL) was added. The solution was stirred at room temperature for 20 h and then acidified to pH 1 with 3 M HCl (500 mL). The mixture was extracted with ethyl acetate (200 mL then 100 mL) and the combined organic layers were washed with saturated brine (3×100 mL), dried (Na$_2$SO$_4$), filtered and concentrated to approximately 100 mL. Crystallization occurred on concentration. The mixture was allowed to stand for 2 h, then the solid was filtered off, washed with ethyl acetate and dried in a vacuum oven at 60° C. to give N-[(9H-fluoren-9-ylmethoxy) carbonyl]piperidine-4-carboxylic acid (34.51 g, 85%) as a white solid, mp 187–189° C.

The following can also be prepared by this procedure:

| Example | Structure | Starting material |
|---|---|---|
| 52 | 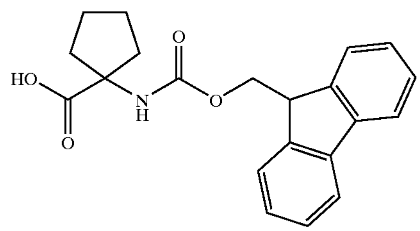 | 1-amino-1-cyclo-pentanecarboxylic acid |
| 53 | 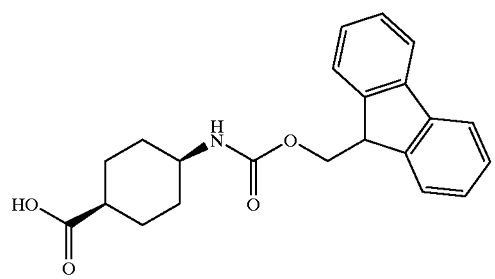 | cis-4-amino-1-cyclo-hexanecarboxylic acid |
| 54 | (racemic) | racemic-2-amino-4-cyclo-hexene-1-carboxylic acid |
| 55 | 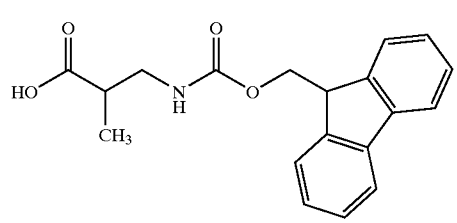 | DL-3-aminoisobutyric acid |

| Example | Structure | Starting material |
|---|---|---|
| 56 | 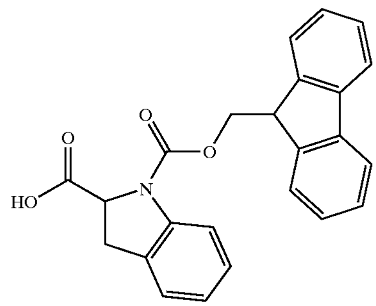 | DL-indoline-2-carboxylic acid |

Example 57

Preparation of 3-[N-[(9H-fluoren-9-ylmethoxy)carbonyl]amino]butanoic acid

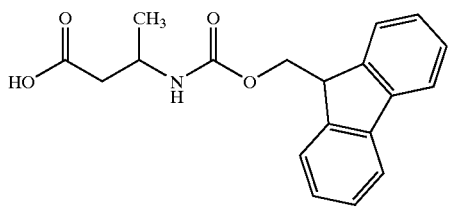

DL-3-aminobutyric acid (15 g, 145 mmol) was added to a solution of sodium hydrogen carbonate (15.9 g, 188.5 mmol) in water (200 mL). A solution of 1-[[(9H-fluoren-9-ylmethoxy) carbonyl]oxy-2,5-pyrrolidinedione (Fmoc-OSu; 58.7 g, 174 mmol) in tetrahydrofuran (400 mL) was added. The solution was stirred at room temperature for 20 h and then acidified to pH 1 with 3 M HCl (500 mL). The mixture was extracted with ethyl acetate (250 mL then 100 mL) and the combined organic layers were washed with saturated brine (3×100 mL), dried (Na$_2$SO$_4$), filtered and concentrated to dryness to give a white solid (56.22 g). This was triturated with boiling ether (500 mL), and allowed to cool. The mixture was filtered and the solid was washed with ether, and then dried in a vacuum oven at room temperature to give 3-[N-[(9H-fluoren-9-ylmethoxy)carbonyl]-amino]butanoic acid (35.33 g, 75%) as a white solid, mp 135–143° C.

Example 58

Preparation of 3-[N-[(9H-fluoren-9-ylmethoxy)carbonyl]amino]-4,4,4-trifluorobutyric acid

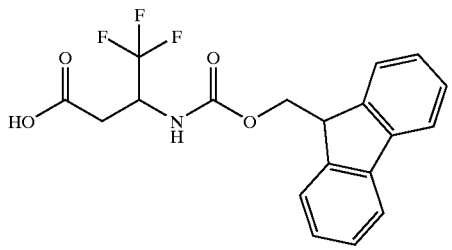

3-Amino-4,4,4-trifluorobutyric acid (10 g, 63.7 mmol) was added to a solution of sodium hydrogen carbonate (6.95 g, 82.8 mmol) in water (100 mL). A solution of 1-[[(9H-fluoren-9-ylmethoxy)carbonyl]oxy-2,5-pyrrolidinedione (Fmoc-OSu; 25.78 g, 76.4 mmol) in tetrahydrofuran (200 mL) was added. The solution was stirred at room temperature for 19 h and then acidified to pH 1 with 3 M HCl (250 mL). The mixture was extracted with ethyl acetate (250 mL then 100 mL) and the combined organic layers were washed with saturated brine (3×100 mL), dried (Na$_2$SO$_4$), filtered and concentrated to approximately 200 mL. Crystallization occurred on concentration. The mixture was allowed to stand for 10 min, then the solid was filtered off, washed with ethyl acetate and dried in a vacuum oven at 50° C. to give 3-[N-[(9H-fluoren-9-ylmethoxy)carbonyl]amino]-4,4,4-trifluorobutyric acid (11.47 g) as a white solid, mp 187–189° C. The mother liquor was concentrated to 80 mL. Crystallization occurred on concentration. The solid was filtered off, washed with ethyl acetate and dried in a vacuum oven at 50° C. to give a second batch of product (4.69 g). The overall yield was 16.16 g (67%).

Example 59

Preparation of 3-[N-[(9H-fluoren-9-ylmethoxy)carbonyl]amino]cyclohexanecarboxylic acid

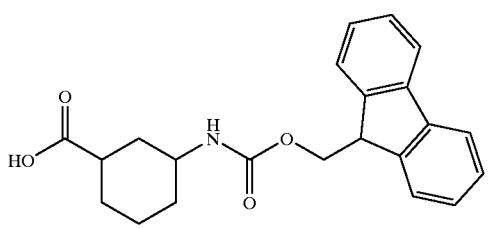

A. 3-Aminocyclohexanecarboxylic acid

A mixture of 3-aminobenzoic acid (66.12 g, 0.48 mol) and 10% palladium on-carbon (13.2 g) in 30% aqueous ethanol (1200 mL) was placed in a 4 L stainless steel high-pressure reactor and reduced at 50° C. and 500 psi of hydrogen for 30 h. The mixture was filtered through Celite and the filter cake was washed with ethanol. The solvent was evaporated, boiling ethanol (1 L) was added and the mixture was allowed to stand for 8 days at room temperature. The mixture was filtered and the product was washed with ethanol and then dried in a vacuum oven at 50° C., to give 3-aminocyclohexanecarboxylic acid (39.30 g, 57%) as a white solid.

B. 3-[N-[(9H-fluoren-9-ylmethoxy)carbonyl]amino]cyclohexanecarboxylic acid

3-Aminocyclohexanecarboxylic acid (10 g, 70 mmol) was added to a solution of sodium hydrogen carbonate (7.6 g, 91 mmol) in water (100 mL). A solution of 1-[[(9H-fluoren-9-ylmethoxy)carbonyl]oxy-2,5-pyrrolidinedione (Fmoc-OSu; 28.3 g, 84 mmol) in tetrahydrofuran (200 mL) was added. The solution was stirred at room temperature overnight and then poured into 3 M HCl (200 mL). The mixture was extracted with ethyl acetate (100 mL then 50 mL) and the combined organic layers were washed with saturated brine (3×100 mL), dried (Na$_2$SO$_4$), filtered, and concentrated to approximately 200 mL. Crystallization occurred on concentration. The mixture was allowed to stand overnight, then the solid was filtered off, washed with ethyl acetate and dried in a vacuum oven at 55° C. to give 3-[N-[(9H-fluoren-9-ylmethoxy)carbonyl]amino]cyclohexanecarboxylic acid (14.66, 57%) as a white solid.

Example 60

Preparation of 4-[N-[(9H-fluoren-9-ylmethoxy)carbonyl]amino]-1,3,4,5-tetrahydro-3-oxo-2H-2-benzazepine-2-acetic acid

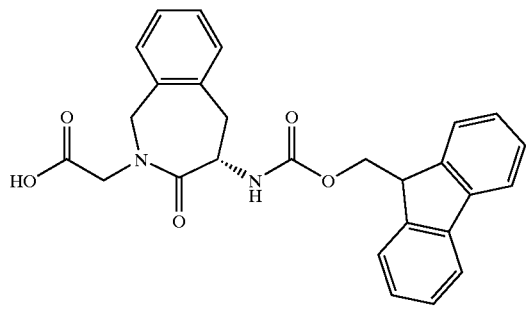

A. 4-Amino-1,3,4,5-tetrahydro-3-oxo-2H-2-benzazepine-2-acetic acid

Hydrazine monohydrate (36 mL, 0.742 mol) was added to a solution of (4S)-4-(1,3-dihydro-1,3-dioxo-2H-isoindol-2-yl)-1,3,4,5-tetrahydro-3-oxo-2H-2-benzazepine-2-acetic acid (prepared according to the procedure of Tourwe, D. et al. Bioorg. Med. Chem. Lett. 1992, 2, 1305–1308; 90.99 g, 0.245 mol) in ethanol (2.6 L) under argon with mechanical stirring. The solution was heated to reflux for 1 h, then cooled in an ice-water bath for 30 min. The white solid was filtered off and washed with cold ethanol (800 mL), then air-dried for 1 h, and dried at 0.3 mm Hg at 60° C. for 1.5 h to give a white solid (139 g). 3 N HCl (245 mL) was added and the mixture was stirred mechanically for 40 min and then allowed to stand overnight. The solid was filtered off and washed with water (2×180 mL). The aqueous layer was concentrated, then water (300 mL) was added and the mixture was stirred for 1.5 h and filtered. The filtrate was concentrated, first at aspirator pressure and then at 0.2 mm Hg 50° C. for 6 h to give a beige solid (80 g). Ethanol (300 mL) was added and the mixture was stirred for 30 min and filtered. The solid was washed with ethanol (50 mL). The solid was dried (0.15 mm Hg, 50° C. for 3 h) to give a white solid (73 g). Ethanol (300 mL) was added and the mixture was stirred for 1 h and filtered. The solid was washed with ethanol (50 mL). The solid was dried (0.2 mm Hg, 50° C. overnight) to give a white solid (69.21 g). Water (50 mL) and ethanol (20 mL) were added and the mixture was heated on a steam bath for 30 min. The supernatant was decanted and placed in the refrigerator overnight. The mixture was filtered and the filtrate was concentrated to give 60 g of solid. Water (50 mL) was added and the mixture was heated on the water bath for 1.5 h and then allowed to stand overnight at room temperature overnight. The solid was filtered, stored on the filter in the refrigerator for 4 h, washed with cold water (50 mL), and then dried (0.25 mm Hg, 50° C. overnight) to give 4-amino-1,3,4,5-tetrahydro-3-oxo-2H-2-benzazepine-2-acetic acid (34.57 g, 52%) as a white solid, mp 266–268° C.

B. 4-[N-[(9H-fluoren-9-ylmethoxy)carbonyl]amino]-1,3,4,5-tetrahydro-3-oxo-2H-2-benzazepine-2-acetic acid 4-Amino-1,3,4,5-tetrahydro-3-oxo-2H-2-benzazepine-2-acetic acid (15 g, 55 mmol) was added to a solution of sodium hydrogen carbonate (12 g, 143 mmol) in water (200 mL). A solution of 1-[[(9H-fluoren-9-ylmethoxy)carbonyl]oxy-2,5-pyrrolidinedione (Fmoc-OSu; 22.3 g, 66 mmol) in tetrahydrofuran (400 mL) was added. The solution was stirred at room temperature overnight and then poured into 3 M HCl (500 mL). The mixture was extracted with ethyl acetate (250 mL then 100 mL) and the combined organic layers were washed with saturated brine (3×100 mL), dried (Na$_2$SO$_4$), filtered and evaporated to give a white foam (29.62 g). This was dissolved in ethanol (150 mL), and the solution was allowed to stand at room temperature for 4 h. The white solid was filtered off, washed with ethanol and dried in a vacuum over at 60° C. to give 4-[N-[(9H-fluoren-9-ylmethoxy)carbonyl]amino]-1,3,4,5-tetrahydro-3-oxo-2H-2-benzazepine-2-acetic acid (25.19 g, 100%) as a white solid, mp 117–120° C.

Example 61

Preparation of 3-[[(9H-fluoren-9-ylmethoxy)carbonyl]amino]hexahydro-2-oxo-1H-azepine-1-acetic acid

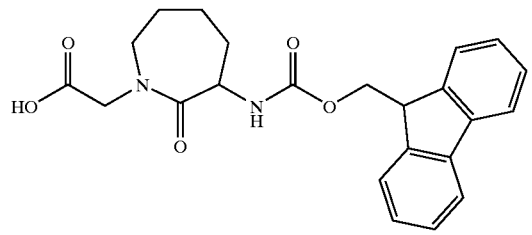

3-Aminohexahydro-2-oxo-1H-azepine-1-acetic acid (which can be prepared by the procedure of Thorsett, E. D. et al. J. Med. Chem. 1986, 29, 251–260; 9.3 g, 50 mmol) was added to a solution of sodium hydrogen carbonate (5 g, 60 mmol) in water (100 mL). A solution of 1-[[(9H-fluoren-9-ylmethoxy)carbonyl]oxy-2,5-pyrrolidinedione (Fmoc-OSu; 18.6 g, 55 mmol) in tetrahydrofuran (110 mL) was added. The solution was stirred at room temperature overnight and then ether (200 mL) was added. The layers were separated and the organic layer was back-extracted with saturated sodium hydrogen carbonate-water (1:1; 60 mL). The combined aqueous layers were acidified with 1 M HCl (110 mL). The solid was filtered off, washed with water (4×20 mL), and dried in vacuo to give 3-[[(9H-fluoren-9-ylmethoxy)carbonyl]amino]hexahydro-2-oxo-1H-azepine-1-acetic acid (20.1 g, 98%) as a white solid, mp 118° C. (dec.)

Example 62

Preparation of N-[(1,1-Dimethylethoxy)carbonyl]-3-[(9H-fluoren-9-ylmethoxy)carbonyl]amino-L-alanine, methyl ester.

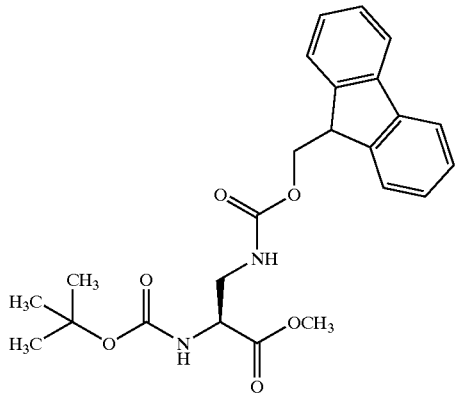

A. N-[(1,1-Dimethylethoxy)carbonyl]-3-[(9H-fluoren-9-ylmethoxy)carbonyl]amino-L-alanine Bis(trifluoroacetoxy)iodobenzene (44.4 g, 103.2 mmol) was added to a solution of N-[(1,1-dimethylethoxy)carbonyl]-L-asparagine (Boc-Asn; 20.00 g, 86.1 mmol) in N,N-dimethylformamide/water (2:1; 300 mL). The solution was stirred at room temperature for 30 min and then pyridine (10 mL, 123.6 mmol) was added. The solution was stirred at room temperature for 4.5 h and then the solvent was evaporated (45° C., ~0.5 mm Hg). The residue was dissolved in acetone/water (1:1; 400 mL) and sodium hydrogen carbonate (31.8 g, 378.5 mmol) and 1-[[(9H-fluoren-9-ylmethoxy)carbonyl]oxy]-2,5-pyrrolidinedione (Fmoc-OSu; 34.74 g, 103.0 mmol) were added. The mixture was stirred at room temperature overnight, then the acetone was evaporated and the mixture was acidified to pH 1 with 1 M HCl and extracted with ethyl acetate (200 mL, then 100 mL). The combined organic layers were washed with brine (3×50 mL), dried ($Na_2SO_4$), filtered, evaporated (45° C., ~0.5 mm Hg), and chromatographed (50–60% ethyl acetate/hexanes) to give N-[(1,1-dimethylethoxy)carbonyl]-3-[(9H-fluoren-9-ylmethoxy)carbonyl]amino-L-alanine (32.33 g, 88%) as a white solid.

B. N-[(1,1-Dimethylethoxy)carbonyl]-3-[(9H-fluoren-9-ylmethoxy)carbonyl]amino-L-alanine, methyl ester A solution of N-[(1,1-dimethylethoxy)carbonyl]-3-[(9H-fluoren-9-ylmethoxy)carbonyl]amino-L-alanine (5.00 g, 11.7 mmol) in N,N-dimethylformamide (10 mL) was treated with potassium hydrogen carbonate (1.4 g, 14.1 mmol) and iodomethane (0.8 ml, 12.9 mmol). The reaction mixture was stirred at room temperature for 2 h. Then water was added and the mixture was extracted three times with ethyl acetate. The combined organic layers were washed with brine, dried ($Na_2SO_4$), concentrated and chromatographed (10–40% ethyl acetate/hexanes) to give N-[(1,1-dimethylethoxy)carbonyl]-3-[(9H-fluoren-9-ylmethoxy)carbonyl]amino-L-alanine, methyl ester (4.20 g, 81%) as a white solid.

Example 63

Preparation of 3-carboxybenzamide

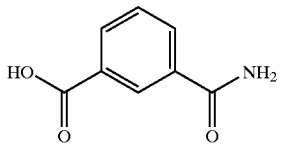

A. 3-Iodobenzamide

A solution of 3-iodobenzoic acid (5.00 g, 20.2 mmol) and thionyl chloride (5.00 g, 42 mmol) in benzene (100 mL) was heated at reflux for 1 h. The solvent was evaporated, and the residue was azeotroped with toluene. Ethyl ether (200 mL) was added and ammonia gas was bubbled through the solution for 10 min. The reaction mixture was diluted with ethyl acetate (200 mL) and water (200 mL). The mixture was filtered to give 3-iodobenzamide (0.88 g) as a cream-colored solid. The ethyl acetate layer was dried ($MgSO_4$), filtered and evaporated to give 3-iodobenzamide (3.40 g) as a cream-colored solid.

B. 3-Carboxybenzamide

A mixture of 3-iodobenzamide (4.28 g, 17.3 mmol), water (25.00 g, 1387.7 mmol), triethylamine (8.00 g, 79.1 mmol), palladium(II) acetate (0.28 g, 1.2 mmol), and bis(diphenylphosphino)propane (0.52 g, 1.3 mmol) in acetonitrile (50 mL) was pressurized to 40 psi with carbon monoxide and the pressure was released. After six such cycles, the bottle was pressurized again and the contents were stirred at 85° C. for 3 h. The reaction mixture was cooled to room temperature and depressurized. The solvent was evaporated and ethyl acetate (200 mL) was added. The solution was filtered and then extracted with water (2×200 mL). The combined aqueous layers were acidified with 12 M HCl to pH 0. The solid was filtered off and air-dried to give 3-carboxybenzamide (1.93 g, 87%) as a yellow solid

Example 64

Coupling of N-[(9H-fluoren-9-ylmethoxy)carbonyl]-3-[(2-propenyloxy)carbonyl]amino-L-alanine to Wang resin

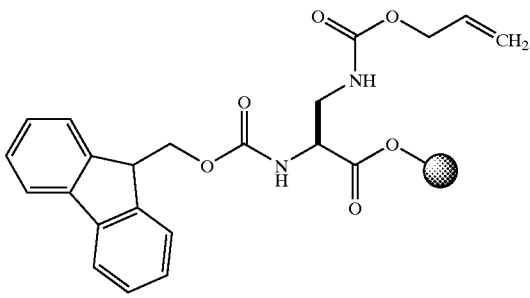

A 500 mL cylindrical glass vessel equipped with a coarse glass frit was charged with 30 g of Wang resin (loading factor: 1.1 mmol/g, 300 mesh). The resin was washed with dichloromethane, methanol and dimethylformamide. To the swollen resin was added N-[(9H-fluoren-9-ylmethoxy)carbonyl]-3-[(2-propenyloxy)carbonyl]amino-L-alanine (20.4 g, 49.7 mmol) and 2,6-dichlorobenzoyl chloride (23.6 mL, 163 mmol) in N-methylpyrrolidone (300 mL) and the mixture was agitated for 30 min. Pyridine (18.6 mL, 230 mmol) was added and the resulting mixture was agitated for 4 hr. The resin was filtered and washed with dimethylformamide, dichloromethane and methanol extensively, and dried under vacuum. The substitution was determined to be 0.92 mmol of N-[(9H-fluoren-9-ylmethoxy)carbonyl]-3-[(2-propenyloxy)carbonyl]amino-L-alanine per gram of resin by quantitative UV measurement of the Fmoc group present on the resin.

Example 65

Preparation of N-[2-chloro-4-[[[(3-hydroxyphenyl)methyl]amino]carbonyl]benzoyl]-3-[(2-propenyloxy)carbonyl]amino-L-alanine on Wang resin

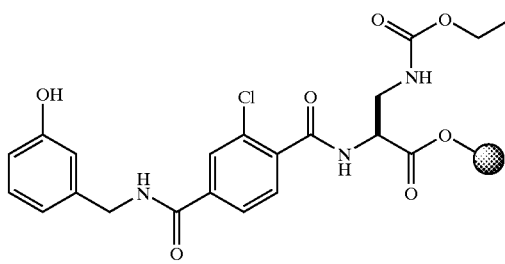

A 150 mL cylidrical glass vessel equipped with a coarse glass frit was charged with N-[(9H-fluoren-9-ylmethoxy)carbonyl]-3-[(2-propenyloxy)carbonyl]amino-L-alanine resin (Example 64; 5 g) and 25% piperidine in N-methylpyrrolidinone (50 mL). The mixture was agitated at room temperature for 30 min. The resin was filtered and treated again with fresh 25% piperidine in N-methylpyrrolidinone (50 mL) at room temperature for 30 min. After filtration, the resin was washed with dichloromethane and methanol. To the resin was added a solution prepared from 2-chloro-4-[[[(3-hydroxyphenyl)methyl]amino]carbonyl]benzoic acid (Example 26; 2.5 g, 8.2 mmol), HOAT (3.7 g, 27.2 mmol) and DICI (4.3 mL, 27.5 mmol) in N-methylpyrrolidinone (50 mL). The reaction mixture was agitated at room temperature for 1 h, and then filtered. The resin was washed with dichloromethane and methanol, and dried under vacuum to afford resin-bound N-[2-chloro-4-[[[(3-hydroxyphenyl)methyl]amino]carbonyl]benzoyl]-3-[(2-propenyloxy)carbonyl]amino-L-alanine.

Example 66

Preparation of 3-amino-N-[2-chloro-4-[[[(3-hydroxyphenyl)methyl]amino]carbonyl]benzoyl]-L-alanine on Wang resin

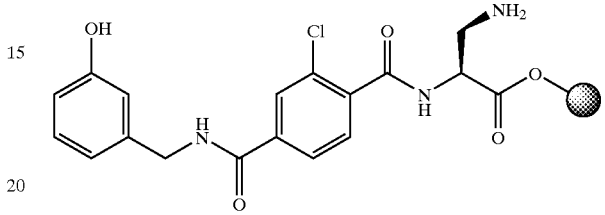

To N-[2-chloro-4-[[[(3-hydroxyphenyl)methyl]amino]carbonyl]benzoyl]-3-[(2-propenyloxy)carbonyl]amino-L-alanine-substituted Wang resin obtained from Example 65 was added a solution prepared from bis(triphenylphosphine)-palladium dichloride (0.8 g, 1.15 mmol) and acetic acid (2.5 mL, 42.0 mmol) in dry dichloromethane (40 mL). The slurry was agitated at room temperature for 30 min and then tri-n-butyltin hydride (10 mL, 37 mmol) was added. More tri-n-butyltin hydride (5 mL) was added to the mixture after 1 h. Agitation was continued for 1 h. The resin was filtered and the procedure was repeated. After the second deprotection cycle, the resin was washed with dimethylformamide, dichloromethane and methanol to give 3-amino-N-[2-chloro-4-[[[(3-hydroxyphenyl)methyl]amino]carbonyl]benzoyl]-L-alanine-substituted Wang resin.

Also prepared by this procedure were:

| Example | Structure | Starting Materials |
| --- | --- | --- |
| 67 | 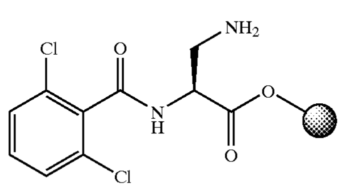 | Example 64; 2,6-dichlorobenzoic acid |
| 68 | 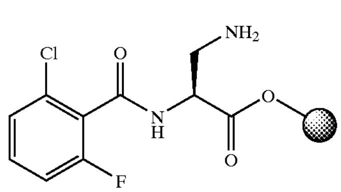 | Example 64; 2-chloro-6-fluorobenzoic acid |

-continued

| Example | Structure | Starting Materials |
|---|---|---|
| 69 | 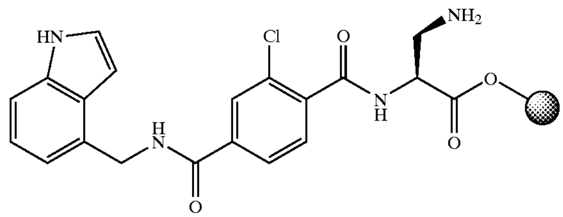 | Example 64; Example 36 |
| 70 | 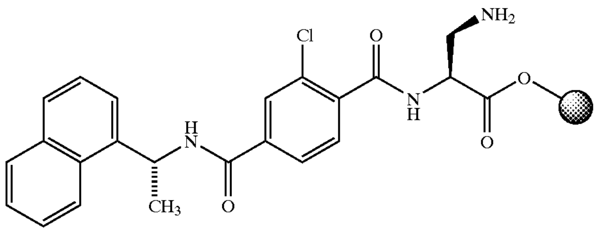 | Example 64; Example 37 |
| 71 | 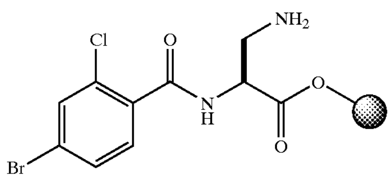 | Example 64; 4-bromo-2-chloro-benzoic acid |

Example 72

Preparation of 3-amino-N-[2-chloro-4-[[[(3-hydroxyphenyl)methyl]amino]carbonyl]benzoyl]-L-alanine, methyl ester

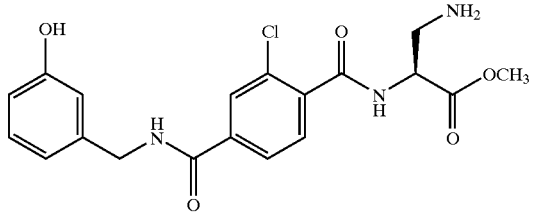

A. N-[2-chloro-4-[[[(3-hydroxyphenyl)methyl]amino]carbonyl]benzoyl]-3-[(9H-fluoren-9-ylmethoxy)carbonyl]amino-L-alanine, methyl ester A solution of N-[(1,1-dimethylethoxy)carbonyl]-3-[(9H-fluoren-9-ylmethoxy)carbonyl]amino-L-alanine, methyl ester (Example 62; 1.50 g, 3.4 mmol) was converted to crude 3-[(9H-fluoren-9-ylmethoxy)carbonyl]amino-L-alanine, methyl ester (1.30 g, 112% of the theoretical amount) by treatment with trifluoroacetic acid/dichloromethane (1:1). A portion of this material (0.50 g) was combined with 2-chloro-4-[[[(3-hydroxyphenyl)methyl]amino]carbonyl]benzoic acid (449 mg, 1.5 mmol), HOAT (219 mg, 1.6 mmol) and dicyclohexylcarbodiimide (363 mg, 1.8 mmol) in N,N-dimethylformamide (5 mL) and the reaction mixture was stirred at room temperature over the weekend. Water was added and the mixture was extracted three times with ethyl acetate. The combined organic layers were washed with water and brine, dried, filtered, evaporated, and chromatographed (2–10% methanol/dichloromethane) to give N-[2-chloro-4-[[[(3-hydroxyphenyl)methyl]amino]carbonyl]benzoyl]-3-[(9H-fluoren-9-ylmethoxy)carbonyl]amino-L-alanine, methyl ester (0.57 g, 62%) as a white solid.

B. 3-Amino-N-[2-chloro-4-[[[(3-hydroxyphenyl)methyl]amino]carbonyl]benzoyl]-L-alanine, methyl ester A solution of N-[2-chloro-4-[[[(3-hydroxyphenyl)methyl]amino]carbonyl]benzoyl]-3-[(9H-fluoren-9-ylmethoxy)carbonyl]amino-L-alanine, methyl ester (1.17 g, 1.9 mmol) in dichloromethane/methanol (2:1) was added to piperidine (1.1 mL, 11.2 mmol). The reaction mixture was stirred for 4 h at room temperature and then more piperidine (1.1 mL, 11.2 mmol) was added. The solution was stirred at room temperature overnight, then it was concentrated and the residue was chromatographed (0–40% methanol/dichloromethane) to give 3-amino-N-[2-chloro-4-[[[(3-hydroxyphenyl)methyl]amino]carbonyl]benzoyl]-L-alanine, methyl ester (760 mg, 100%) as a pale yellow solid.

C. Example 73

Preparation of 3-amino-N-[2,6-dimethyl-4-[[[(3-hydroxyphenyl)methyl]amino]carbonyl]benzoyl]-L-alanine, methyl ester

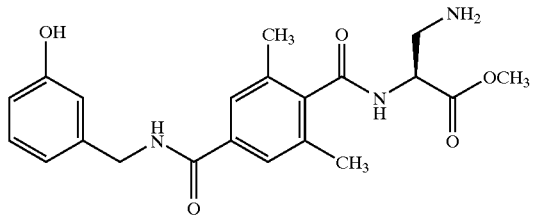

A. N-[2,6-Dimethyl-4-[[[(3-hydroxyphenyl)methyl]amino]carbonyl]benzoyl]-3-[[(1,1-dimethylethoxy)carbonyl]amino]-L-alanine, methyl ester Diisopropylethylamine (0.211 mL, 1.21 mmol) was added to a solution of 2,6-dimethyl-4-[[[[3-[[(1,1-dimethylethyl)dimethylsilyl]oxy]phenyl]methyl]amino]carbonyl]benzoic acid (Example 30; 100 mg, 0.242 mmol), HOBT (39 mg, 0.29 mmol), and HBTU (110 mg, 0.29 mmol) in N,N-dimethylformamide (1 mL). The mixture was stirred at room temperature overnight. The solvent was evaporated and ethyl acetate (50 mL) was added. The solution was washed with 1 M HCl (25 mL), saturated aqueous sodium hydrogen carbonate (25 mL), and brine (25 mL), dried (MgSO$_4$), filtered, and evaporated to give crude N-[2,6-dimethyl-4-[[[(3-hydroxyphenyl)methyl]amino]carbonyl]benzoyl]-3-[[(1,1-dimethylethoxy)carbonyl]amino]-L-alanine, methyl ester (144 mg, 97%). This was used without further purification.

B. 3-Amino-N-[2,6-dimethyl-4-[[[(3-hydroxyphenyl)methyl]amino]carbonyl]benzoyl]-L-alanine, methyl ester A solution of crude N-[2,6-dimethyl-4-[[[(3-hydroxyphenyl)methyl]amino]carbonyl]benzoyl]-3-[[(1,1-dimethylethoxy)carbonyl]amino]-L-alanine, methyl ester (144 mg, 0.235 mmol) in trifluoroacetic acid (2 mL) and dichloromethane (2 mL) was stirred at room temperature for 1 h. The reaction mixture was concentrated and ethyl acetate was added. The solution was washed with saturated aqueous sodium hydrogen carbonate, and the aqueous layer was back-extracted seven times with ethyl acetate. The combined organic layers were dried (MgSO$_4$), filtered, and evaporated to give crude 3-amino-N-[2,6-dimethyl-4-[[[(3-hydroxyphenyl)methyl]amino]carbonyl]benzoyl]-L-alanine, methyl ester (104 mg, 110% of the theoretical amount).

Example 74

Preparation of 3-amino-N-[2-chloro-4-[[[(3-hydroxyphenyl)methyl]amino]carbonyl]-6-methylbenzoyl]-L-alanine, methyl ester

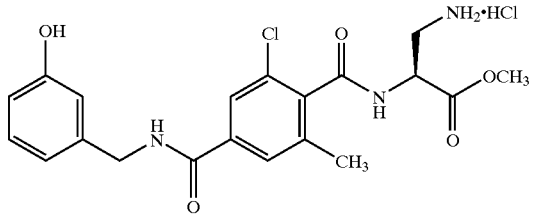

A. N-[2-Chloro-4-[[[[3-[[(1,1-dimethylethyl)dimethylsilyl]oxy]phenyl]methyl]-amino]carbonyl]-6-methylbenzoyl]-3-[[(1,1-dimethylethoxy)carbonyl]amino]-L-alanine, methyl ester Diisopropylethylamine (2.11 mL, 12.1 mmol) was added to a solution of 2-chloro-4-[[[[3-[[(1,1-dimethylethyl)dimethylsilyl]oxy]phenyl]methyl]amino]carbonyl]-6-methylbenzoic acid (Example 33; 1.32 g, 3.04 mmol) and 3-[[(1,1-dimethylethoxy)carbonyl]amino]-L-alanine, methyl ester, hydrochloride (1.54 g, 6.05 mmol) in dichloromethane (15 mL). Benzotriazol-1-yloxy-tris-(dimethylamino)-phosphonium hexafluorophosphate (BOP reagent; 1.48 g, 3.35 mmol) was added and the mixture was stirred at room temperature for 4 h. The solution was diluted with ethyl acetate, washed with 1 M HCl, water, saturated aqueous sodium hydrogen carbonate, and water. The solution was then dried (MgSO$_4$), filtered, evaporated, and chromatographed (40% ethyl acetate/petroleum ether) to give N-[2-chloro-4-[[[[3-[[(1,1-dimethylethyl)dimethylsilyl]oxy]phenyl]methyl]amino]carbonyl]-6-methylbenzoyl]-3-[[(1,1-dimethylethoxy)carbonyl]amino]-L-alanine, methyl ester (1.57 g, 81%) as a white foam B. N-[2-Chloro-4-[[[(3-hydroxyphenyl)methyl]amino]carbonyl]-6-methylbenzoyl]-3-[[(1,1-dimethylethoxy)carbonyl]amino]-L-alanine, methyl ester A solution of tetra-n-butylammonium fluoride in tetrahydrofuran (1 M; 1.78 mL, 1.78 mmol) was added in two portions to a solution of N-[2-chloro-4-[[[[3-[[(1,1-dimethylethyl) dimethylsilyl]oxy]phenyl]methyl]amino]carbonyl]-6-methylbenzoyl]-3-[[(1,1-dimethylethoxy)carbonyl]amino]-L-alanine, methyl ester (1.03 g, 1.62 mmol) in dry tetrahydrofuran (20 mL). The solution was stirred at room temperature for 30 min, then diluted with ethyl acetate (100 mL) and washed with water (25 mL) and brine (25 mL). The solution was dried (MgSO$_4$), filtered, evaporated, held under high vacuum for 2.5 h, and then chromatographed (60–70% ethyl acetate/petroleum ether) to give N-[2-chloro-4-[[[(3-hydroxyphenyl)methyl]amino]carbonyl]-6-methylbenzoyl]-3-[[(1,1-dimethylethoxy)carbonyl]amino]-L-alanine, methyl ester (0.82 g, 97%) as a white foam.

C. 3-Amino-N-[2-chloro-4-[[[(3-hydroxyphenyl)methyl]amino]carbonyl]-6-methylbenzoyl]-L-alanine, methyl ester hydrochloride Trifluoroacetic acid (20 mL) was added to a solution of N-[2-chloro-4-[[[(3-hydroxyphenyl)methyl]amino]carbonyl]-6-methylbenzoyl]-3-[[(1,1-dimethylethoxy)carbonyl]amino]-L-alanine, methyl ester (800 mg, 1.54 mmol) in dichloromethane (20 mL). The solution was stirred at room temperature for 1 h. The reaction mixture was concentrated, azeotroped three times with dichloromethane/hexanes, and then held under high vacuum for 35 min. 1 M HCl (4.6 mL, 4.6 mmol) was added, along with acetonitrile (4 mL) and the mixture was freeze-dried overnight to give crude 3-amino-N-[2-chloro-4-[[[(3-hydroxyphenyl)methyl]amino]carbonyl]-6-methylbenzoyl]-L-alanine, methyl ester hydrochloride (0.85 g, 120% of the theoretical amount).

Example 75

Preparation of 3-amino-N-[2,6-dichloro-4-[[[(3-hydroxyphenyl)methyl]amino]carbonyl]benzoyl]-L-alanine, methyl ester hydrochloride

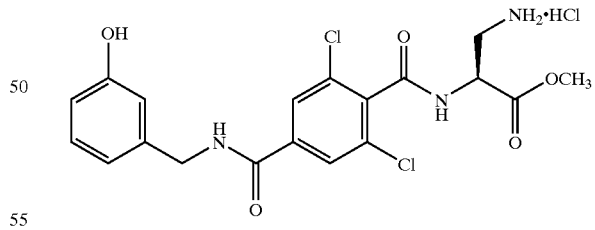

A. N-[2,6-dichloro-4-[[[(3-hydroxyphenyl)methyl]amino]carbonyl]benzoyl]-3-[[(1,1-dimethylethoxy)carbonyl]amino]-L-alanine, methyl ester Diisopropylethylamine (14 mL, 80.6 mmol) was added to a cooled (~0° C.) solution of 2,6-dichloro-4-[[[(3-hydroxyphenyl)methyl]amino]carbonyl]benzoic acid (Example 29; 7.44 g, 21.9 mmol), 3-[[(1,1-dimethylethoxy)carbonyl]amino]-L-alanine, methyl ester, hydrochloride (6.15 g, 24.1 mmol), HOBT (3.12 g, 22.8 mmol), and HBTU (8.64 g, 22.8 mmol) in N,N-dimethylformamide (200 mL). The mixture was stirred at room temperature for 16 h. The solvent was evaporated and ethyl acetate (200 mL) was added. The solution was washed with 1 M HCl (100 mL) and the aqueous layer was extracted with ethyl acetate (100 mL). The combined organic layers were washed with saturated aqueous sodium hydrogen carbonate, and brine (200 mL each), dried (MgSO$_4$), filtered, evaporated, and chromatographed (70% ethyl acetate/hexanes) to give N-[2,6-dichloro-4-[[[(3-hydroxyphenyl)methyl]amino]carbonyl]benzoyl]-3-[[(1,1-dimethylethoxy)carbonyl]amino]-L-alanine, methyl ester (8.64 g, 73%) as a white foam.

B. 3-Amino-N-[2,6-dichloro-4-[[[(3-hydroxyphenyl)methyl]amino]carbonyl]benzoyl]-L-alanine, methyl ester hydrochloride A solution of acidic methanol was prepared by adding acetyl chloride (25 mL, 351.6 mmol) to cooled (~0° C.) methanol (200 mL) and stirring for 10 min. This solution was added to N-[2,6-dichloro-4-[[[(3-hydroxyphenyl)methyl]amino]-carbonyl]benzoyl]-3-[[(1,1-dimethylethoxy)carbonyl]amino]-L-alanine, methyl ester (8.64 g, 16.0 mmol) and the resulting solution was stirred at room temperature for 16 h. The solvent was evaporated to give 3-amino-N-[2,6-dichloro-4-[[[(3-hydroxyphenyl)methyl]amino]carbonyl]benzoyl]-L-alanine, methyl ester hydrochloride (7.40 g, 97%) as a cream-colored foam.

Example 76

Preparation of N-[2-chloro-4-[[[(3-hydroxyphenyl)methyl]amino]carbonyl]benzoyl]-3-(3-methoxybenzoylamino)-L-alanine

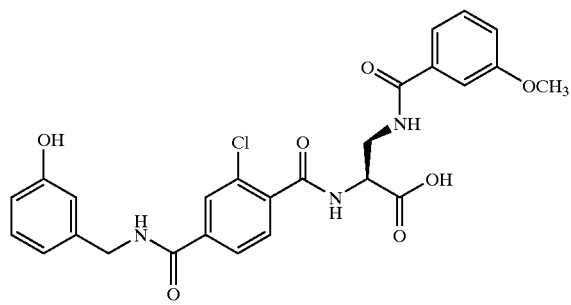

3-Amino-N-[2-chloro-4-[[[(3-hydroxyphenyl)methyl]amino]carbonyl]benzoyl]-L-alanine-substituted Wang resin (Example 66; 100 mg) was slurried in a solution prepared from HOAT (75 mg, 0.55 mmol), DICI (86 µL, 0.55 mmol) and 3-methoxybenzoic acid (700 mg, 4.6 mmol) in N-methyl-pyrrolidinone (1 mL) and agitated for 2 h until the ninhydrin test was negative. The resin was then filtered and washed extensively with N-methylpyrrolidinone, dichloromethane and methanol. Cleavage of the product was effected with 50% trifluoroacetic acid in dichloromethane for 30 min. The cleavage solution was collected by filtration and the solvent was evaporated under high vacuum. The residue was purified by reverse phase HPLC to give N-[2-chloro-4-[[[(3-hydroxyphenyl)methyl]amino]-carbonyl]benzoyl]-3-(3-methoxybenzoylamino)-L-alanine.

The procedures used to prepare Example 76 were also used to prepare Examples 77–227 (see Tables 1 and 2).

TABLE 1

[[[[(3-hydroxyphenyl)methyl]amino]carbonyl]benzoyl] Derivatives (Examples 77–203)

| Example | R | Prepared by reaction of Example 66 with: |
|---|---|---|
| 77 | cyclopentyl-CH$_2$– | cyclopentaneacetic acid |
| 78 | cyclohexyl-CH$_2$– | cyclohexaneacetic acid |
| 79 | phenyl-CH$_2$– | phenylacetic acid |
| 80 | 4-methoxyphenyl-CH$_2$– | 4-methoxyphenylacetic acid |
| 81 | 4-nitrophenyl-CH$_2$– | 4-nitrophenylacetic acid |
| 82 | 3-trifluoromethylphenyl-CH$_2$– | 3-trifluoromethylphenylacetic acid |
| 83 | 2,4-dinitrophenyl-CH$_2$– | 2,4-dinitrophenylacetic acid |
| 84 | 2-thienyl-CH$_2$– | 2-thiopheneacetic acid |
| 85 | 3-pyridyl-CH$_2$– | 2-pyridineacetic acid hydrochloride |

TABLE 1-continued

[[[[(3-hydroxyphenyl)methyl]amino]carbonyl]benzoyl] Derivatives (Examples 77–203)

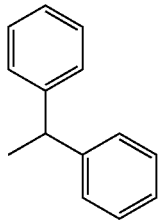

| Example | R | Prepared by reaction of Example 66 with: |
|---|---|---|
| 86 | 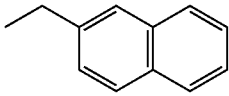 | diphenylacetic acid |
| 87 | 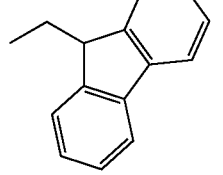 | 2-naphthylacetic acid |
| 88 | 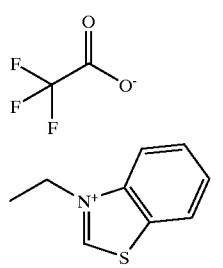 | 9-fluoreneacetic acid |
| 89 | 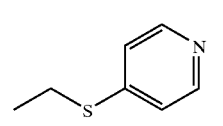 | 3-(carboxymethyl)-benzothiazolium bromide |
| 90 | 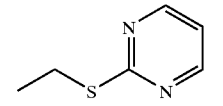 | 4-pyridylthioacetic acid |
| 91 | 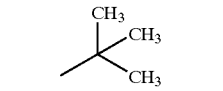 | 2-(pyrimidylthio)-acetic acid |
| 92 | 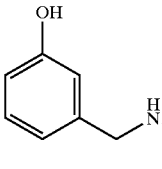 | trimethylacetic acid |

TABLE 1-continued

[[[[(3-hydroxyphenyl)methyl]amino]carbonyl]benzoyl] Derivatives (Examples 77–203)

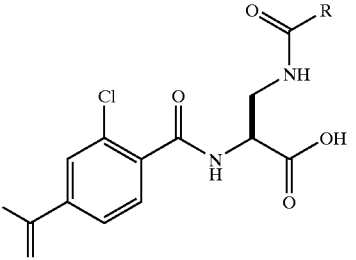

| Example | R | Prepared by reaction of Example 66 with: |
|---|---|---|
| 93 | 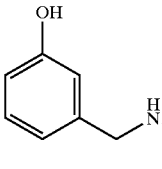 | 1-adamantane-carboxylic acid |
| 94 | 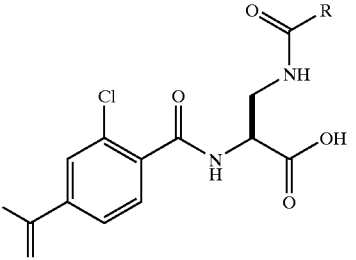 | hydrocinnamic acid |
| 95[a] | 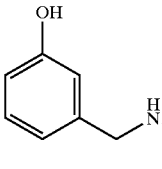 | 3-phenylbutyric acid |
| 96 | 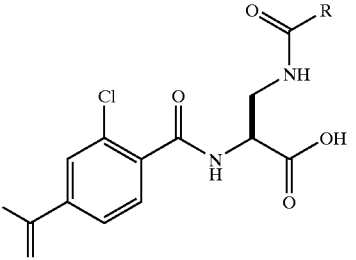 | (S)-(+)-5-oxo-2-tetra-hydrofurancarboxylic acid |
| 97 |  | cyclopropane-carboxylic acid |
| 98[a] | 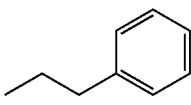 | 2,2-dichloro-1-methylcyclopropane-carboxylic acid |
| 99 | 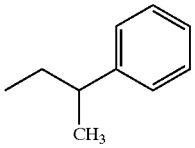 | 1-phenyl-1-cyclopropane-carboxylic acid |
| 100 | 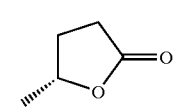 | cyclobutanecarboxylic acid |
| 101 |  | cyclopentane-carboxylic acid |
| 102 | 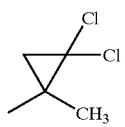 | Example 48 |

TABLE 1-continued

[[[[(3-hydroxyphenyl)methyl]amino]carbonyl]benzoyl] Derivatives
(Examples 77–203)

| Example | R | Prepared by reaction of Example 66 with: |
|---|---|---|
| 103 | 1-phenyl-1-cyclopentyl (phenyl-substituted cyclopentane) | 1-phenyl-1-cyclopentanecarboxylic acid |
| 104 | cyclohexyl | cyclohexanecarboxylic acid |
| 105 | 1-methylcyclohexyl | 1-methyl-1-cyclohexanecarboxylic acid |
| 106[a] | thiopyranyl-dioxolane spiro | Example 49 |
| 107[a] | tetrahydronaphthyl | 1,2,3,4-tetrahydro-naphthoic acid |
| 108[a] | 7-methoxy-octahydrophenanthrenyl | 7-methoxy-1,2,3,4,4ab,9,10,10ab-octahydro-2b-phenanthrene-carboxylic acid, which can be prepared by the procedure of Goldberg, M. W. et al US 3314871 |
| 109[a] | 6-bromo-4-methyl-2-oxo-tetrahydroquinolinyl | bromo-2-oxo-1,2,3,4-tetrahydroquinoline-4-carboxylic acid, which can be prepared by the procedure of Aeschlimann, J. A. J. Chem. Soc. 1926, 2902–2911 |
| 110 | pyrrolylmethylcyclohexyl | Example 50 |
| 111 | 3,5-dimethyl-4-propyl-isoxazolyl | dimethyl-4-isoxazole-propanoic acid, which can be prepared by the procedure of Ceccherelli, P. et al. J. Org. Chem. 1994, 59, 2882–4 |
| 112 | piperidinylpropyl | 1-piperidinepropionic acid |
| 113 | propenyl (CH₃) | crotonic acid |
| 114 | 4-methoxystyryl | 4-methoxycinnamic acid |
| 115 | 3-pyridylvinyl | trans-3-(3-pyridyl)-acrylic acid |
| 116 | 2-thienylvinyl | 3-(2-thienyl)acrylic acid |
| 117 | 2-(acetoxy)phenyl | acetylsalicylic acid |
| 118 | 3-aminophenyl | 3-aminobenzoic acid |

TABLE 1-continued

[[[[(3-hydroxyphenyl)methyl]amino]carbonyl]benzoyl] Derivatives (Examples 77–203)

| Example | R | Prepared by reaction of Example 66 with: |
|---|---|---|
| 119 | 4-methylbenzenesulfonamide (p-tolyl-SO2NH2) | 4-carboxybenzene-sulfonamide |
| 120 | 2-bromotoluene (methyl, Br ortho) | 2-bromobenzoic acid |
| 121 | 3-bromotoluene | 3-bromobenzoic acid |
| 122 | 2-chlorotoluene | 2-chlorobenzoic acid |
| 123 | 3-chlorotoluene | 3-chlorobenzoic acid |
| 124 | 4-chlorotoluene | 4-chlorobenzoic acid |
| 125 | 4-chloro-2-nitrotoluene | 2-amino-4-chloro-benzoic acid |
| 126 | 3-cyanotoluene | 3-cyanobenzoic acid |
| 127 | 3-(dimethylamino)toluene | 3-dimethylamino-benzoic acid |
| 128 | 4-(dimethylamino)toluene | 4-dimethylamino-benzoic acid |
| 129 | 3,5-dinitrotoluene | 3,5-dinitrobenzoic acid |
| 130 | 4-ethoxytoluene | 4-ethoxybenzoic acid |
| 131 | 3-fluorotoluene | 3-fluorobenzoic acid |
| 132 | 3-hydroxytoluene | 3-hydroxybenzoic acid |
| 133 | 3-iodotoluene | 3-iodobenzoic acid |
| 134 | 2-methoxytoluene | 2-methoxybenzoic acid |
| 135 | 4-methoxytoluene | 4-methoxybenzoic acid |

TABLE 1-continued

[[[[(3-hydroxyphenyl)methyl]amino]carbonyl]benzoyl] Derivatives
(Examples 77–203)

| Example | R | Prepared by reaction of Example 66 with: |
|---|---|---|
| 136 | 3-methyl benzoate methyl ester (m-CH₃-C₆H₄-C(O)OCH₃) | monomethyl isophthalate |
| 137 | o-tolyl (2-CH₃-C₆H₄-) | o-toluoyl chloride |
| 138 | m-tolyl (3-CH₃-C₆H₄-) | m-toluoyl chloride |
| 139 | p-tolyl (4-CH₃-C₆H₄-) | p-toluoyl chloride |
| 140 | 2-nitrophenyl | 2-nitrobenzoic acid |
| 141 | 3-nitrophenyl | 3-nitrobenzoic acid |
| 142 | 4-nitrophenyl | 4-nitrobenzoic acid |
| 143 | 4-(pentyloxy)phenyl | 4-(pentyloxy)benzoic acid |
| 144 | 2-(phenoxy)phenyl | 2-phenoxybenzoic acid |
| 145 | 2,4,5-trifluorophenyl (with methyl) | 2,4,5-trifluorobenzoic acid |
| 146 | 3-(trifluoromethyl)phenyl | 3-(trifluoromethyl)-benzoic acid |
| 147 | 3,4,5-trimethoxyphenyl | 3,4,5-trimethoxy-benzoic acid |
| 148 | 2-furyl | 2-furoic acid |
| 149 | 5-nitro-2-furyl | 5-nitro-2-furoic acid |
| 150 | 5-bromo-2-furyl | 5-bromo-2-furoic acid |
| 151 | pyrrol-2-yl | pyrrole-2-carboxylic acid |

TABLE 1-continued

[[[[(3-hydroxyphenyl)methyl]amino]carbonyl]benzoyl] Derivatives
(Examples 77–203)

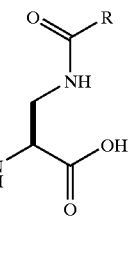

| Example | R | Prepared by reaction of Example 66 with: |
|---|---|---|
| 152 | 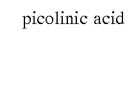 | 5-nitro-3-pyrazolecarboxylic acid |
| 153 | 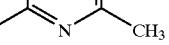 | 3,5-dimethylisoxazole-4-carboxylic acid |
| 154 |  | 3-bromothiophene-2-carboxylic acid |
| 155 | 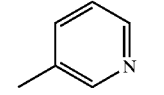 | 5-bromo-2-thiophene-carboxylic acid |
| 156 | 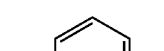 | 3-chlorothiophene-2-carboxylic acid |
| 157 | 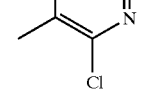 | 5-chlorothiophene-2-carboxylic acid |
| 158 | 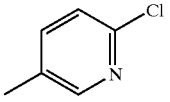 | 4,5-dibromothiophene-2-carboxylic acid |
| 159 | 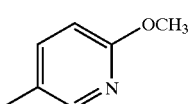 | 3-methylthiophene-2-carboxylic acid |
| 160 | 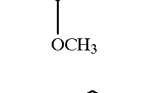 | 5-methylthiophene-2-carboxylic acid |
| 161 | 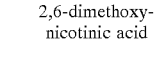 | thiophene-3-carboxylic acid |
| 162 | 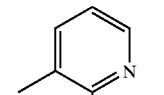 | picolinic acid |
| 163 | 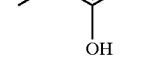 | 6-methylpicolinic acid |
| 164[a] | 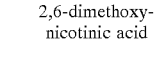 | 3,4-dibromobutyl)-pyridine-2-carboxylic acid was obtained from Banyu Pharmaceutical Company, Tokyo, Japan |
| 165 | 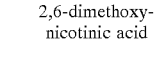 | nicotinic acid |
| 166 | 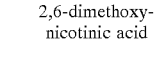 | 2-chloronicotinic acid |
| 167 | 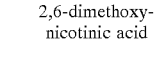 | 6-chloronicotinic acid |
| 168 | 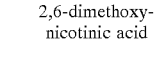 | 2,6-dimethoxy-nicotinic acid |
| 169 | 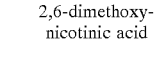 | 6-hydroxynicotinic acid |

TABLE 1-continued

[[[[(3-hydroxyphenyl)methyl]amino]carbonyl]benzoyl] Derivatives
(Examples 77–203)

| Example | R | Prepared by reaction of Example 66 with: |
|---|---|---|
| 170 | 3-methylpyrazin-2-yl | pyrazine-2-carboxylic acid |
| 171 | 5-chloro-2-[(3-methylpyrazin-2-yl)carbonylamino]pyridinyl | 5-chloro-2-pyridinyl)amino]carbonyl] pyrazinecarboxylic acid, which can be prepared by the procedure of Cotrel, C. et al. US 4220646 |
| 172 | 5-methyl-2,4-dihydroxypyrimidin-5-yl | 2,4-dihydroxy-pyrimidine-5-carboxylic acid |
| 173 | 6-methyl-2,4-dihydroxypyrimidin-5-yl | orotic acid |
| 174 | 2-methylbenzofuran-5-yl | benzofuran-2-carboxylic acid |
| 175 | 2-methylbenzo[b]thiophen-5-yl | benzo[b]thiophene-2-carboxylic acid |
| 176 | 5-methylbenzimidazol-2-yl | benzimidazole-5-carboxylic acid |
| 177 | 6-methylbenzothiazol-2-yl | benzothiazole-6-carboxylic acid |
| 178 | 1-methylnaphthyl | 1-naphthoic acid |
| 179 | 2-methylnaphthyl | 2-naphthoic acid |
| 180 | 1-methylisoquinolinyl | 1-isoquinoline-carboxylic acid |
| 181 | 2-methylquinolinyl | quinoline-2-carboxylic acid |
| 182 | 4-methoxy-2-methylquinolinyl | 4-methoxyquinoline-2-carboxylic acid |
| 183 | 3-methylquinolinyl | quinoline-3-carboxylic acid |
| 184 | 4-methylquinolinyl | quinoline-4-carboxylic acid |

TABLE 1-continued

[[[[(3-hydroxyphenyl)methyl]amino]carbonyl]benzoyl] Derivatives
(Examples 77–203)

| Example | R | Prepared by reaction of Example 66 with: |
|---|---|---|
| 185 | 4-methylcinnoline | cinnoline-4-carboxylic acid |
| 186 | 3-hydroxy-2-methylquinoxaline | 3-hydroxyquinoxaline-2-carboxylic acid |
| 187 | 2-methylchromone | chromone-2-carboxylic acid |
| 188 | 3-methylcoumarin | coumarin-3-carboxylic acid |
| 189 | 10-methylanthracene | anthracene-9-carboxylic acid |
| 190 | 9-methyl-1,2,3,4-tetrahydroacridine | 1,2,3,4-tetrahydroacridine-9-carboxylic acid dihydrate |
| 191 | methoxy-methyl-pyrido[2,1-b]quinazolinone | methoxy-11-oxo-11H-pyrido[2,1-b]quinazoline-8-carboxylic acid, which can be prepared by the procedure of Kierstead, R. W. et al. US 4348396 |
| 192 | methyl-thioxanthone-S,S-dioxide | 9-oxo-9H-thioxanthene-3-carboxylic acid 10,10-dioxide |
| 193 | —CH$_3$ | acetic acid |
| 194 | —CH(CH$_3$)$_2$ | isobutyric acid |
| 195 | —CH$_2$CH(CH$_3$)$_2$ (sec-butyl shown) | isovaleric acid |
| 196 | 2-methylpyrrolidine | Boc-L-proline |
| 197 | —CH(NH$_2$)CH$_2$CH$_2$SCH$_3$ | Boc-L-methionine |
| 198 | —CH(NH$_2$)(CH$_2$)$_3$CH(CH$_3$)NH$_2$ | bis-Boc-L-lysine |

TABLE 1-continued

[[[[(3-hydroxyphenyl)methyl]amino]carbonyl]benzoyl] Derivatives (Examples 77–203)

| Example | R | Prepared by reaction of Example 66 with: |
|---|---|---|
| 199 | (1-phenylpropan-2-yl)amine group | Boc-L-Phe |
| 200 | 3-amino-butanamide group | Boc-L-asparagine |
| 201 | (1-(1H-indol-3-yl)propan-2-yl)amine group | Boc-L-tryptophan |
| 202 | 2-amino-pentanedioic acid group | Boc-L-glutamic acid alpha-tert-butyl ester |
| 203 | methyl pentanoate group | mono-methyl glutarate |

[a]The starting material for this substance was racemic. The diastereomeric products were not separated.

TABLE 2

Truncated Compounds (Examples 204–227)

| Example | R | X | Starting Materials |
|---|---|---|---|
| 204 | benzyl | Cl | Example 67 and phenylacetic acid |
| 205 | 4-nitrobenzyl | Cl | Example 67 and 4-nitrophenylacetic acid |
| 206[a] | 1-phenylethyl (with CH₃) | Cl | Example 67 and 3-phenylbutyric acid |
| 207[a] | 1-phenylethyl (with CH₃) | F | Example 68 and 3-phenylbutyric acid |
| 208 | (S)-5-oxo-tetrahydrofuran-2-yl | Cl | Example 67 and (S)-(+)-5-oxo-2-tetrahydrofurancarboxylic acid |
| 209 | (S)-5-oxo-tetrahydrofuran-2-yl | F | Example 68 and (S)-(+)-5-oxo-2-tetrahydrofurancarboxylic acid |
| 210 | cyclopropyl | Cl | Example 67 and cyclopropanecarboxylic acid |
| 211 | cyclopropyl | F | Example 68 and cyclopropanecarboxylic acid |
| 212 | cyclobutyl | Cl | Example 67 and cyclobutanecarboxylic acid |
| 213 | cyclopentyl | Cl | Example 67 and cyclopentanecarboxylic acid |
| 214 | cyclopentyl | F | Example 68 and cyclopentanecarboxylic acid |

TABLE 2-continued

Truncated Compounds (Examples 204–227)

| Example | R | X | Starting Materials |
|---|---|---|---|
| 215 | methylcyclohexyl | Cl | Example 67 and cyclohexanecarboxylic acid |
| 216 | methylcyclohexyl | F | Example 68 and cyclohexanecarboxylic acid |
| 217[a] | 4-methyl-6-bromo-2-oxo-1,2,3,4-tetrahydroquinolin-4-yl | Cl | Example 67 and bromo-2-oxo-1,2,3,4-tetrahydroquinoline-4-carboxylic acid, which can be prepared by the procedure of Aeschlimann, J. A. J. Chem. Soc. 1926, 2902–2911 |
| 218 | (E)-1-(2-thienyl)propenyl | Cl | Example 67 and 3-(2-thienyl)acrylic acid |
| 219 | methylphenyl | Cl | Example 67 and benzoic acid |
| 220 | methylphenyl | F | Example 68 and benzoic acid |
| 221 | methyl-3-methoxyphenyl | Cl | Example 67 and 3-methoxybenzoic acid |
| 222 | methyl-3-methoxyphenyl | F | Example 68 and 3-methoxybenzoic acid |
| 223 | 5-bromo-2-methylthienyl | Cl | Example 67 and 5-bromo-2-thiophenecarboxylic acid |
| 224 | 5-bromo-2-methylthienyl | F | Example 68 and 5-bromo-2-thiophenecarboxylic acid |
| 225 | 5-methylindolyl | Cl | Example 67 and indole-5-carboxylic acid |
| 226 | 5-methylbenzotriazolyl | F | Example 68 and benzotriazole-5-carboxylic acid |
| 227 | 2,6-dimethylpyridyl | Cl | Example 67 and 6-methylpicolinic acid |

[a]The starting material for this substance was racemic. The diastereomeric products were not separated.

Example 228

Preparation of N-[2-chloro-4-[[[(8-hydroxyphenyl)methyl]amino]carbonyl]benzoyl]-3-(3,5-dibromobenzoyl)amino-L-alanine

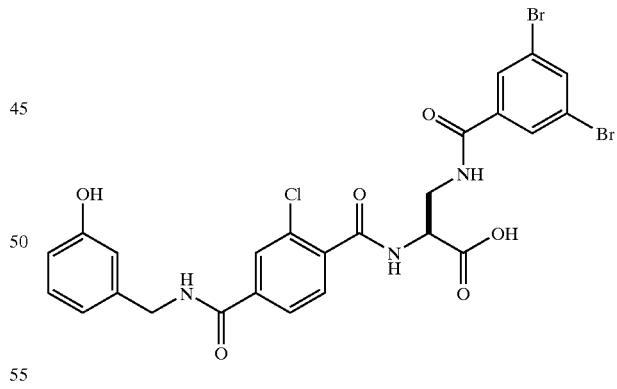

Diisopropylethylamine (0.4 mL, 2.47 mmol) was added to a cooled (~0° C.) solution of 3-amino-N-[2-chloro-4-[[[(3-hydroxyphenyl)methyl)methyl]amino]-carbonyl]benzoyl]-L-alanine, methyl ester (Example 72; 200 mg, 0.49 mmol), 3,5-dibromobenzoic acid (125 mg, 0.45 mmol), HBTU (187 mg, 0.49 mmol), and HOBT (66.5 mg, 0.49 mmol) in N,N-dimethylformamide (3 mL). The solution was stirred at ~0° C. for 10 min, and then the cooling bath was removed and the solution was stirred overnight at room temperature. The solvent was evaporated. Ethyl acetate (20 mL) was added and the solution was washed with 0.5 M HCl (5 mL), sodium hydrogen carbonate solution (5 mL) and brine (10 mL). The ethyl acetate solution was dried (MgSO$_4$) and evaporated to give a brown oil (237 mg). This was dissolved in tetrahydrofuran/methanol (1:1; 2 mL) and the solution was added to a solution of lithium hydroxide monohydrate (100 mg, 2.38 mmol) in water (1 mL). The resulting solution was allowed to stir at room temperature over the weekend, and then it was concentrated. Water was added and the solution was made acidic to pH 2 with 1 M HCl. The resulting mixture was extracted with ethyl acetate, and the ethyl acetate solution was washed with brine, dried (MgSO$_4$), filtered, evaporated and purified by HPLC to give N-[2-chloro-4-[[[(3-hydroxyphenyl)methyl]amino]carbonyl]benzoyl]-3-(3,5-dibromobenzoyl)amino-L-alanine (94.2 mg, 40%) as a white solid.

The following compounds were prepared by the same procedure:

| Example | Structure | Yield | Prepared by reaction of Example 72 with: |
|---|---|---|---|
| 229 | 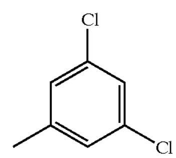 | 28% | 3,5-dichlorobenzoic acid |
| 230 | 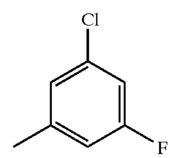 | 20% | 3-chloro-5-fluorobenzoic acid (available from Butt Park, Ltd., Bath, UK) |
| 231 | 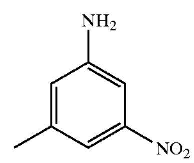 | 8% | 3-amino-5-nitrobenzoic acid |
| 232 | 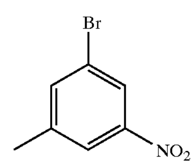 | 17% | 3-bromo-5-nitrobenzoic acid (this can be prepared according to the procedure of Hübner et al. Liebigs Ann. Chem. 1884, 222, 166) |
| 233 | 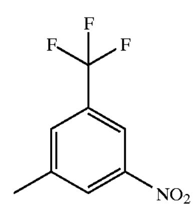 | 7% | 3-nitro-5-(trifluoromethyl)benzoic acid |
| 234 | 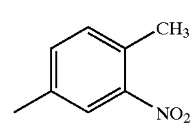 | 13% | 4-methyl-3-nitrobenzoic acid |
| 235 | 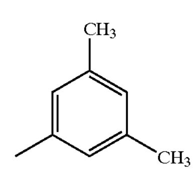 | 11% | 3,5-dimethylbenzoic acid |
| 236 | 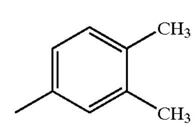 | 10% | 3,4-dimethylbenzoic acid |

-continued

| Example | Structure | Yield | Prepared by reaction of Example 72 with: |
|---------|-----------|-------|------------------------------------------|
| 237 | 4-methyl-2-nitro-1-methylbenzene derivative (NO₂, CH₃) | 17% | 3-methyl-4-nitrobenzoic acid |
| 238 | 4-methyl-2-amino derivative (NH₂, CH₃) | 2% | 4-amino-3-methylbenzoic acid |
| 239 | 4-methyl-2-bromo derivative (Br, CH₃) | 2% | 4-bromo-3-methylbenzoic acid |
| 240 | 3,5-dimethoxy derivative (OCH₃, OCH₃) | 11% | 3,5-dimethoxybenzoic acid |
| 241 | NO₂, OCH₃ derivative | 2% | 3-methoxy-4-nitrobenzoic acid |
| 242 | OCH₃, OCH₃ derivative | 2% | 3,4-dimethoxybenzoic acid |
| 243 | OH, OH derivative | 10% | 3,5-dihydroxybenzoic acid |
| 244 | OCH₃, OH derivative | 2% | 3-hydroxy-4-methoxybenzoic acid |
| 245 | CH₃, OH derivative | 10% | 3-hydroxy-4-methylbenzoic acid |
| 246 | CH₃, NO₂ derivative | 2% | 2-methyl-3-nitrobenzoic acid |
| 247 | CH₃, OH derivative | 3% | 4-methylsalicylic acid |

-continued

| Example | Structure | Yield | Prepared by reaction of Example 72 with: |
|---|---|---|---|
| 248 | 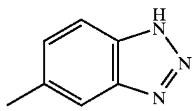 | 2% | benzotriazole-5-carboxylic acid |
| 249 | 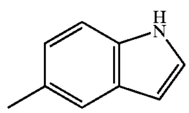 | 4% | indole-5-carboxylic acid |
| 250 | 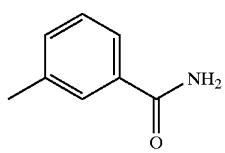 | 4% | Example 63 |
| 251 | 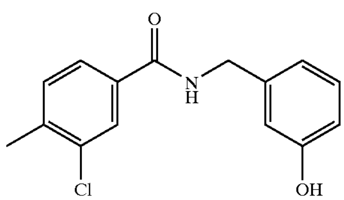 | 1% | Example 26 |

Example 252

Preparation of N-[2-chloro-4-[[[(3-hydroxyphenyl)methyl]amino]carbonyl]benzoyl]-3-(3,5-difluorobenzoyl)amino-L-alanine

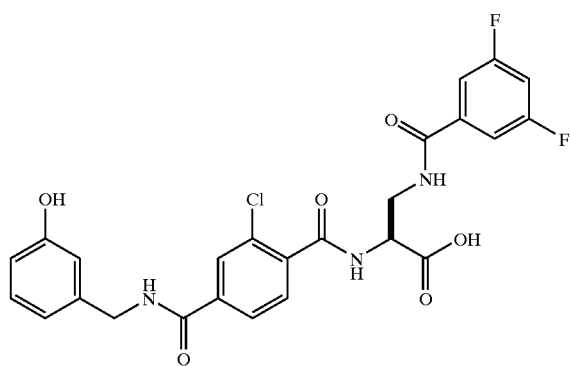

To a suspension of 3-amino-N-[2-chloro-4-[[[(3-hydroxyphenyl)methyl]amino]-carbonyl]benzoyl]-L-alanine-substituted Wang resin (Example 66; 100 mg, 0.111 mmol) in DMF (3 mL) were added 3,5-difluorobenzoic acid (26 mg, 0.166 mmol), HOAT (44 mg, 0.333 mmol), and then DICI (26 μL, 0.166 mmol). The reaction mixture was shaken for 1 h. The solvent was removed by air pressure with filtration and the resin was washed with dichloromethane (3 times) followed by methanol (once) and this was repeated a total of five times. The ninhydrin test was negative. Cleavage of the product was effected by shaking the resin with 50% trifluoroacetic acid in dichloromethane (3 mL) for 30 min. The cleavage solution was collected by filtration and the solvent was evaporated under reduced pressure. The residue was purified by reverse phase HPLC (acetonitrile, water, 0.075% TFA) to give N-[2-chloro-4-[[[(3-hydroxyphenyl)methyl]amino]carbonyl]benzoyl]-3-(3,5-difluorobenzoyl)amino-L-alanine (11 mg, 19%) as a white solid.

The following compounds were prepared by the same procedure. All were obtained as white solids.

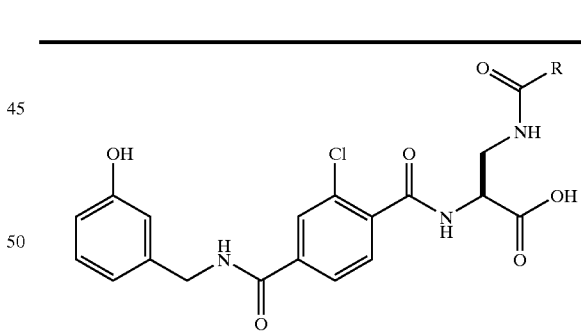

| Example | R | Starting materials | Yield |
|---|---|---|---|
| 253[a] | | Example 66 and 2,4-dimethylthiazole-5-carboxylic acid, which can be prepared according to Roubleff, T. Liebigs Ann. Chem. 1890, 259, 253–276 | 22% |
| 254 | | Example 66 and 1,2,3-thiadiazole-4-carboxylic acid | 25% |

-continued

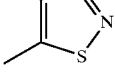

| Example | R | Starting materials | Yield |
|---|---|---|---|
| 255 | 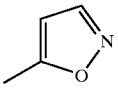 | Example 66 and 4-methyl-1,2,3-thiadiazole-5-carboxylic acid | 16% |
| 256 | 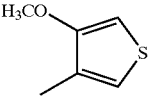 | Example 66 and isoxazole-5-carboxylic acid | 22% |
| 257 | H₃CO— (thiophene) | Example 66 and 4-methoxythiophene-3-carboxylic acid | 18% |

Example 258

Preparation of N-[2-chloro-4-[[[(3-hydroxyphenyl)methyl]amino]carbonyl]benzoyl]-3-(5-chloro-4-methoxythiophene-3-carbonyl)amino-L-alanine

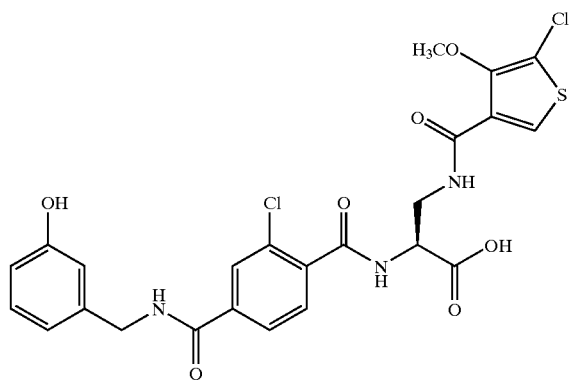

To a suspension of 3-amino-N-[2-chloro-4-[[[(3-hydroxyphenyl)methyl]amino]-carbonyl]benzoyl]-L-alanine-substituted Wang resin (Example 66; 100 mg, 0.111 mmol) in DMF (3 mL) were added 2-chloro-3-methoxythiophene-4-carboxylic acid (32 mg, 0.166 mmol), HOAT (44 mg, 0.333 mmol), and then DICI (26 μL, 0.166 mmol). The reaction mixture was shaken for 1 h. The solvent was removed by air pressure with filtration and the resin was washed with dichloromethane (3 times) followed by methanol (once) and this was repeated a total of five times. The ninhydrin test was positive, so DMF (3 mL), HBTU (84 mg, 0.222 mmol), and 2-chloro-3-methoxythiophene-4-carboxylic acid (32 mg, 0.166 mmol) were added, followed by DIPEA (0.444 mmol, 77 μL) and the reaction mixture was shaken for 1.5 hr. The solvent was removed by air pressure with filtration and the resin was washed with dichloromethane (3 times) followed by methanol (once) and this was repeated a total of five times. The ninhydrin test was negative. Cleavage of the product was effected by shaking the resin with 50% trifluoroacetic acid in dichloromethane (3 mL) for 30 min. The cleavage solution was collected by filtration and the solvent was evaporated under reduced pressure. The residue was purified by reverse phase HPLC (acetonitrile, water, 0.075% TFA) to give N-[2-chloro-4-[[[(3-hydroxyphenyl)methyl]amino]carbonyl]benzoyl]-3-(5-chloro-4-methoxythiophene-3-carbonyl)amino-L-alanine (9 mg, 15%) as an off-white solid.

Example 259

Preparation of N-[2-chloro-4-[[[(3-hydroxyphenyl)methyl]-amino]carbonyl]benzoyl]-3-(furan-3-carbonyl)amino-L-alanine

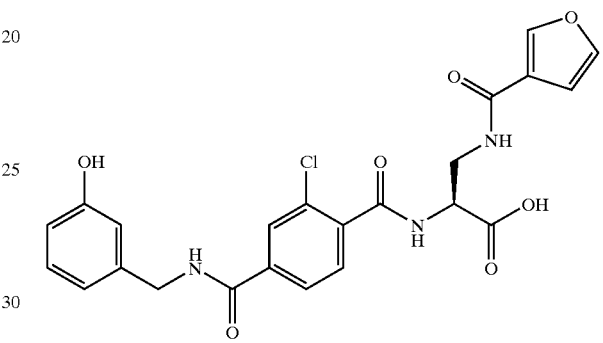

3-Amino-N-[2-chloro-4-[[[(3-hydroxyphenyl)methyl]amino]carbonyl]benzoyl]-L-alanine-substituted Wang resin (Example 66; 100 mg, 0.111 mmol) was washed three times with DMF, then it was suspended in DMF and 3-furoic acid (14.9 mg, 0.13 mmol), HBTU (55 mg, 0.15 mmol), and diisopropylethylamine (77 μL, 0.44) were added. The reaction mixture was shaken for 3 h. The solvent was removed by air pressure with filtration and the resin was washed with dichloromethane (3 times) followed by methanol (once) and this was repeated a total of five times. The ninhydrin test was positive, so DMF, 3-furoic acid (14.9 mg, 0.13 mmol), HBTU (55 mg, 0.15 mmol), and diisopropylethylamine (77 μL, 0.44) were added and the reaction mixture was shaken for 2 hr. The solvent was removed by air pressure with filtration and the resin was washed with dichloromethane (3 times) followed by methanol (once) and this was repeated a total of five times. The ninhydrin test was negative. Cleavage of the product was effected by shaking the resin with 50% trifluoroacetic acid in dichloromethane (3 mL) for 1 h. The cleavage solution was collected by filtration and the solvent was evaporated under reduced pressure. The residue was purified by reverse phase HPLC (acetonitrile, water, 0.075% TFA) and then freeze-dried to give N-[2-chloro-4-[[[[[(furan-3-carbonyl)oxy]phenyl]methyl]amino]carbonyl]benzoyl]-3-[(furan-3-carbonyl)amino]-L-alanine. This was dissolved in methanol (1 mL) and treated with 2 equivalents of 1 M NaOH. The solution was stirred for 8 h, then concentrated, purified by HPLC and freeze-dried to give N-[2-chloro-4-[[[(3-hydroxyphenyl)methyl]amino]carbonyl]benzoyl]-3-(furan-3-carbonyl)amino-L-alanine (3 mg, 5.5%) as a white solid.

The following compound was also prepared from Example 66 and 3-fluoro-3-(trifluoromethyl) benzoic acid by this procedure:

| Example | R | Yield |
|---|---|---|
| 260 | 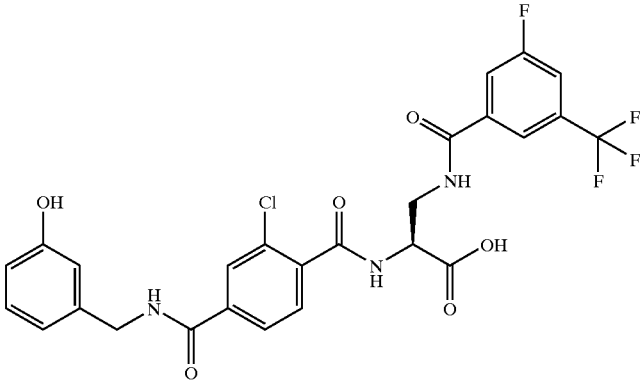 | 8% |

Example 261

Preparation of N-[2-chloro-4-[[[(3-hydroxyphenyl)methyl]amino]carbonyl]benzoyl]-3-(4-aminobutanoylamino)-L-alanine 3-Amino-2-[2-chloro-4-[[[(3-hydroxyphenyl)methyl]amino]carbonyl]benzoyl]-L-alanine-substituted Wang resin (Example 66; 100 mg) was slurried in a solution prepared from HOAT (68 mg, 0.5 mmol), DICI (78 μL, 0.5 mmol) and 4-[(9H-fluoren-9-ylmethoxy)carbonyl]amino]butanoic acid (163 mg, 0.5 mmol) in N-methylpyrrolidinone (1 mL) and agitated for 1 h. The resin was then filtered and washed extensively with dichloromethane and methanol. The resin was then treated with a solution of piperidine in N-methylpyrrolidone (1:3; 2 mL) and the mixture was shaken for 1 h. The resin was then filtered and washed extensively with dichloromethane and methanol. Cleavage of the product was effected with 50% trifluoroacetic acid in dichloromethane (1:1; 2 mL) for 30 min. The cleavage solution was collected by filtration and the solvent was evaporated under high vacuum. The residue was purified by reverse phase HPLC to give 2-[2-chloro-4-[[[(3-hydroxyphenyl)methyl]amino]carbonyl]benzoyl]-3-(4-aminobutanoylamino)-L-alanine.

The following compounds were prepared by the same procedure:

| Example | R | Prepared by reaction of Example 66 with: |
|---|---|---|
| 262 | 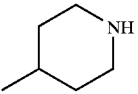 | Example 51 |
| 263 | 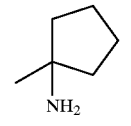 | Example 52 |
| 264 | 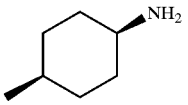 | Example 53 |
| 265a | 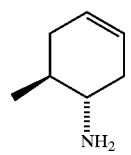 | Example 54 |
| 266 | 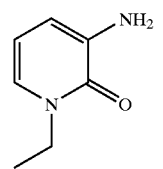 | Fmoc-3-amino-1-carboxymethyl-pyridin-2-one |

| # | Structure | Name |
|---|---|---|
| 267 | 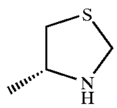 | Fmoc-L-thiazolidine-4-carboxylic acid |
| 268 | 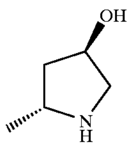 | Fmoc-L-4-hydroxyproline |
| 269[a] | 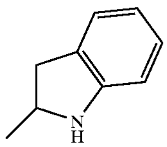 | Example 56 |
| 270 | 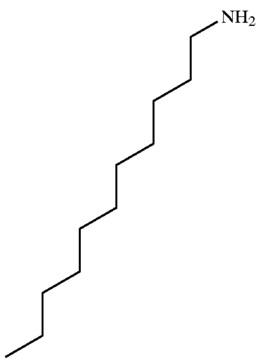 | Fmoc-11-amino-undecanoic acid |
| 271 | 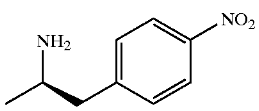 | Fmoc-4-nitro-L-phenylalanine |
| 272[a] | 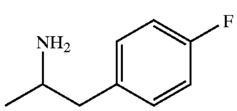 | Fmoc-4-fluoro-DL-phenylalanine |
| 273 | 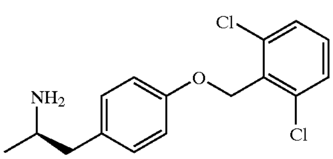 | Fmoc-O-(2,6-dichlorobenzyl)-L-tyrosine |
| 274 | 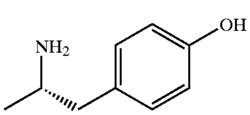 | Fmoc-D-tyrosine |
| 275 | 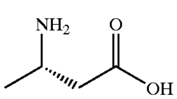 | Fmoc-D-aspartic acid β-tert-butyl ester |
| 276 | 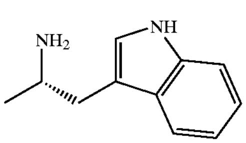 | Fmoc-D-tryptophan |
| 277 | 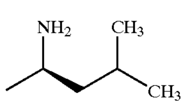 | Fmoc-L-leucine |
| 278 | 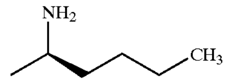 | Fmoc-L-norleucine |
| 279 | 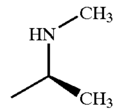 | Fmoc-N-methyl-L-alanine |
| 280 | 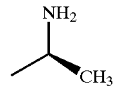 | Fmoc-L-alanine |
| 281 | 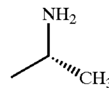 | Fmoc-D-alanine |
| 282 | 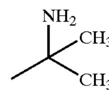 | Fmoc-aminoisobutyric acid |
| 283 | 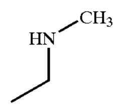 | Fmoc-sarcosine |
| 284 | 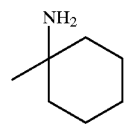 | Fmoc-1-aminocyclohexane-carboxylic acid |
| 285 | 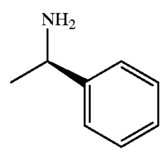 | Fmoc-L-phenylglycine |
| 286 | 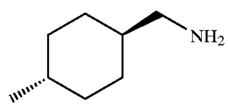 | Fmoc-tranexamic acid |
| 287[b] | 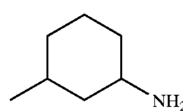 | Example 59 |
| 288 | 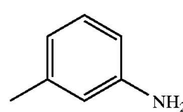 | Fmoc-3-aminobenzoic acid |
| 289[a] | 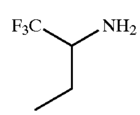 | Example 58 |
| 290[a] | 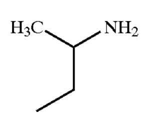 | Example 57 |
| 291[a] | 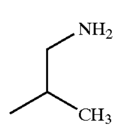 | Example 55 |

| | | |
|---|---|---|
| 292 | 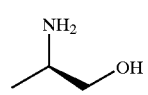 | Fmoc-O-tert-butyl-L-serine |
| 293 | 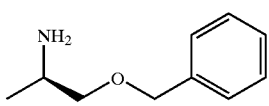 | Fmoc-O-benzyl-L-serine |
| 294[a] | 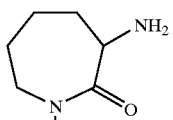 | Example 61 |
| 295 | 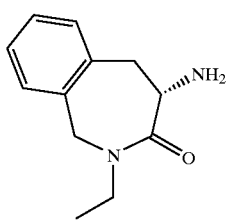 | Example 60 |
| 296 | 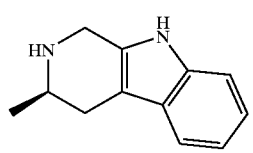 | Fmoc-L-1,2,3,4-tetra-hydronorharman-3-carboxylic acid |

[a]The carboxylic acid was racemic and the diastereoisomeric products were not separated
[b]The diastereoisomeric products were not separated

Example 297

Preparation of 3-(3-carboxybenzoyl)amino-N-[2-chloro-4-[[(3-hydroxyphenyl)methyl]amino]carbonyl]benzoyl]-L-alanine

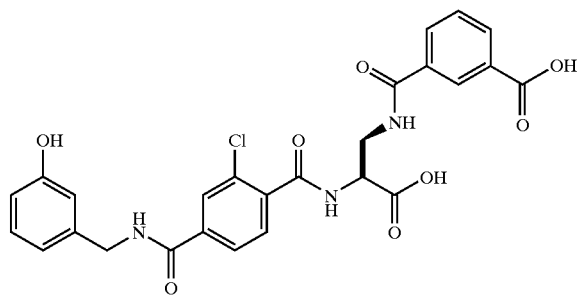

Lithium hydroxide monohydrate (2 mg, 0.048 mmol) was added to a solution of 3-[3-(methoxycarbonyl)benzoyl]amino-N-[2-chloro-4-[[(3-hydroxyphenyl)methyl]amino]carbonyl]benzoyl]-L-alanine (Example 136; 7 mg, 0.012 mmol) in tetrahydrofuran/methanol/water (3:1:1; 0.5 mL). The solution was stirred at room temperature for 3 h and then purified by HPLC to give 3-(3-carboxybenzoyl)amino-N-[2-chloro-4-[[(3-hydroxyphenyl)methyl]amino]carbonyl]benzoyl]-L-alanine (5.6 mg, 82%) as a white powder.

Also prepared by this procedure from Example 203 was:

| Example | Structure |
|---|---|
| 298 | 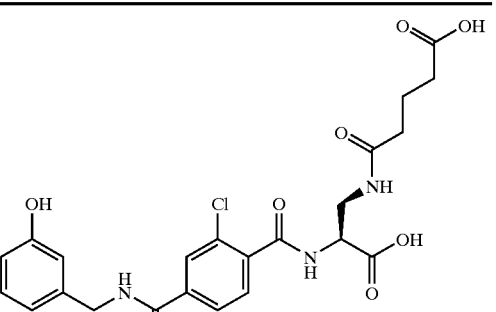 |

Example 299

Preparation of 3-(benzoylamino)-L-alanine methyl ester

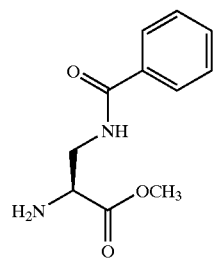

Bromine (10 mL, 194.1 mmol) was added to a solution of sodium hydroxide (40.00 g, 1000 mmol) in water (330 mL) cooled in a bath at −10° C. The clear yellow solution was stirred for 15 min, and then 2-[(1,1-dimethylethoxy)carbonyl]-L-asparagine (Boc-Asn; 39.50 g, 170.1 mmol) was added as a solid. The resulting solution was heated at ~70° C. for 1 h. After cooling, a solution of benzoyl chloride (25.30 g, 180.0 mmol) in ether (50 mL) was added and the reaction mixture was allowed to stir at room temperature overnight. The pH of the solution was adjusted to ~10 with 1 M NaOH solution and the solution was extracted with ethyl acetate (200 mL). The organic layer was discarded and the aqueous layer was made acidic to pH ~2 with 1 M HCl solution. The resulting solution was extracted with ethyl acetate (2×200 mL), washed with brine (200 mL), dried (MgSO4), filtered, and evaporated to give a white solid (31.5 g). This was dissolved in dichloromethane (200 mL) and ethereal diazomethane was added until the yellow color persisted. Acetic acid (ca 2 mL) was added to quench the excess diazomethane and the solution was washed with water and brine (200 mL each), dried (MgSO$_4$), filtered, evaporated, and chromatographed (30–50% ethyl acetate/hexanes) to give methyl benzoate (13.86 g, Rf 0.75 in 30% ethyl acetate/hexanes) and of 3-(benzoylamino)-N-[(1,1-dimethylethoxy)carbonyl]-L-alanine methyl ester (Rf 0.12 in 30% ethyl acetate/hexanes) as a colorless oil (6.39 g, 11.5%) that solidified on standing along with 3.54 g of less pure fractions (6.5%). A solution of pure 3-(benzoylamino)-N-[(1,1-dimethylethoxy)carbonyl]-L-alanine methyl ester (200 mg, 0.62 mmol) in dichloromethane/trifluoroacetic acid (1:1; 2.5 mL) was stirred at room temperature for 30 min. The solvent was evaporated under reduced pressure. Ethyl acetate (10 mL) was added and the solution was washed with saturated aqueous $NaHCO_3$ solution (10 mL), dried ($Na_2SO_4$), filtered, concentrated and then dried under high vacuum to give 3-(benzoylamino)-L-alanine methyl ester (77 mg, 56%).

Example 300

Preparation of 3-(benzoylamino)-L-alanine methyl ester hydrochloride

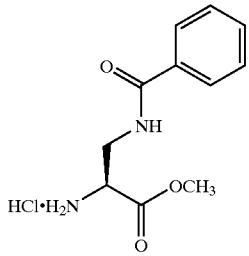

Bromine (20 mL, 388.2 mmol) was added to a solution of sodium hydroxide (80.00 g, 2000 mmol) in water (660 mL) cooled in a bath at –10° C. The clear yellow solution was stirred for 15 min, and then 2-[(1,1-dimethylethoxy)carbonyl]-L-asparagine (Boc-Asn; 79.00 g, 340.2 mmol) was added as a solid. The resulting solution was heated at ~70° C. for 1 h. After cooling to ~0° C., a solution of benzoyl chloride (50.80 g, 361.6 mmol) in ether (100 mL) was added and the reaction mixture was allowed to stir at room temperature for 48 h. The pH of the solution was adjusted to ~10 with 3 M NaOH solution and the solution was extracted with ethyl acetate (200 mL). The organic layer was discarded and the aqueous layer was made acidic to pH ~2 with 3 M HCl solution. The resulting solution was extracted with ethyl acetate (2×300 mL), washed with brine, dried (MgSO4), filtered, and evaporated to give a white solid (64.87 g). To this was added a solution prepared by adding acetyl chloride (50 g) dropwise to a cooled (~0° C.) solution of methanol and stirring for 10 min. The resulting solution was stirred at room temperature for 24 h, then the solvents were evaporated and water (250 mL) was added. The mixture was extracted with ethyl acetate (300 mL) and the organic extract was discarded. A white precipitate formed in the aqueous layer on concentration. This was filtered off to give 3-(benzoylamino)-L-alanine methyl ester hydrochloride (11.62 g, 15%) as a white solid.

Example 301

Preparation of 3-(thiophene-2-carbonyl)amino-L-alanine methyl ester hydrochloride

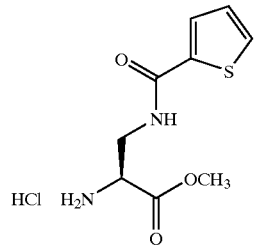

Bromine (25.25 mL, 0.49 mol) was added to a solution of sodium hydroxide (100.8 g, 2.52 mol) in water (830 mL) cooled in an acetone/ice bath at –10° C. The clear yellow solution was stirred for 15 min, and then 2-[(1,1-dimethylethoxy)carbonyl]-L-asparagine (Boc-Asn; 100.0 g, 0.43 mol mmol) was added as a solid. The resulting solution was heated at ~75° C. for 1.5 h. After cooling, a solution of thiophene-2-carbonyl chloride (66.7 g, 0.455 mol) in ether (125 mL) was added and the reaction mixture was allowed to stir at room temperature for 3 d. The pH of the solution was adjusted to ~10 with 3 M NaOH solution and the solution was extracted with ethyl acetate (500 mL). The organic layer was discarded and the aqueous layer was made acidic to pH ~2 with 6 M HCl solution. The resulting solution was extracted with ethyl acetate (2×500 mL), washed with brine (200 mL), dried ($MgSO_4$), filtered to give 1400 mL of solution. Of this solution, 1100 mL was evaporated to dryness and dissolved in methanolic HCl (prepared by the addition of acetyl chloride (45 mL) to methanol (600 mL)). The mixture was stirred at 50° C. overnight, then cooled and evaporated. The residue was evaporated twice from ethyl acetate (200 mL). Water (150 mL) was added, and the solution was extracted with ethyl acetate (3×250 mL). The organic extracts were backwashed with water (50 mL). The combined aqueous layers were concentrated in vacuo to ~150 mL then lyophilized to give 3-(thiophene-2-carbonyl)amino-L-alanine methyl ester hydrochloride (21.7 g, 24%) as a colorless solid.

Example 302

Preparation of 3-benzoylamino-N-[2-chloro-4-[[[(3-hydroxyphenyl)methyl]amino]carbonyl]benzoyl]-L-alanine

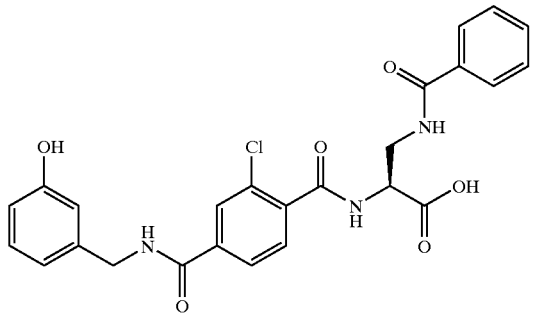

A. 3-Benzoylamino-N-[2-chloro-4-[[[(3-hydroxyphenyl) methyl]amino]carbonyl]benzoyl]-L-alanine, methyl ester Diisopropylethylamine (27 mL, 147.2 mmol) was added dropwise to a cooled (~0° C.) solution of 2-chloro-4-[[[(3-hydroxyphenyl)methyl]amino]carbonyl]benzoic acid (Example 26; 9.00 g, 29.4 mmol), 3-benzoylamino-L-alanine methyl ester hydrochloride (Example 300; 11.4 g, 44.2 mmol), HTBU (13.4 g, 35.3 mmol) and HOBT (4.8 g, 35.3 mmol) in N,N-dimethylformamide (125 mL). The reaction was allowed to warm to room temperature and to stir for 18 h. The solvent was concentrated under vacuum to remove most of the N,N-dimethylformamide. Ethyl acetate was added and the solution was washed with water (2×150 mL). 1 M HCl (3×100 mL) and brine. The solution was dried (MgSO$_4$), filtered, evaporated, and chromatographed (0–50% acetone/dichloromethane) to give 3-benzoylamino-N-[2-chloro-4-[[[(3-hydroxyphenyl)methyl]amino] carbonyl]benzoyl]-L-alanine, methyl ester (10.7 g, 71%).

B. 3-Benzoylamino-N-[2-chloro-4-[[[(3-hydroxyphenyl) methyl]amino]carbonyl]benzoyl]-L-alanine A solution of 3-benzoylamino-N-[2-chloro-4-[[[(3-hydroxyphenyl)methyl]amino]carbonyl]benzoyl]-L-alanine, methyl ester (10.7 g, 21.0 mmol) in tetrahydrofuran/methanol (3:1; 80 mL) was added to a stirred solution of lithium hydroxide monohydrate (2.65 g, 63.0 mmol) in water (40 mL) at room temperature. The reaction was stirred at room temperature overnight and then concentrated to remove methanol and tetrahydrofuran. Water (150 mL) was added and the mixture was cooled to between 0 and –5° C. The mixture was acidified to pH 3 with concentrated HCl and stirred for 10 min. The mixture was extracted twice with ethyl acetate, and the combined organic layers were washed with brine, dried (MgSO$_4$), filtered and evaporated to give 3-benzoylamino-N-[2-chloro-4-[[[(3-hydroxyphenyl) methyl]amino]carbonyl]benzoyl]-L-alanine (7.1 g). The drying agent was extracted with ethyl acetate/methanol (50:3; 2×106 mL) to give a further quantity of the product (3.3 g). Overall yield: 10.4 g (quantitative).

Example 303

Preparation of N-[2-chloro-4-[[[(3-hydroxyphenyl) methyl]amino]carbonyl]benzoyl]-3-(thiophene-2-carbonyl)amino-L-alanine

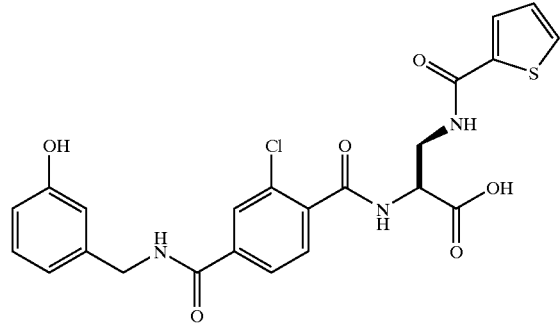

A. N-[2-Chloro-4-[[[(3-hydroxyphenyl)methyl]amino] carbonyl]benzoyl]-3-(thiophene-2-carbonyl)amino-L-alanine, methyl ester Diisopropylethylamine (7.00 g, 64.2 mmol) was added to a solution of 3-(thiophene-2-carbonyl)amino-L-alanine, methyl ester hydrochloride (Example 301; 7.00 g, 26.4 mmol), 2-chloro-4-[[[(3-hydroxyphenyl)methyl]amino] carbonyl]benzoic acid (Example 26; 7.00 g, 22.9 mmol), and HBTU (13.00 g, 34.3 mmol) in DMF (75 mL). The solution was allowed to stir at room temperature for 4 days, and it was then concentrated to remove most of the DMF. Ethyl acetate (200 mL) was added, followed by water (200 mL) and 1 M HCl (100 mL). The layers were separated; the ethyl acetate layer was evaporated, and the residue was chromatographed (50–100% ethyl acetate/hexanes) to give N-[2-chloro-4-[[[(3-hydroxyphenyl)methyl]amino]carbonyl] benzoyl]-3-(thiophene-2-carbonyl)amino-L-alanine, methyl ester (8.30 g, 70%) as a white solid.

B. N-[2-Chloro-4-[[[(3-hydroxyphenyl)methyl]amino] carbonyl]benzoyl]-3-(thiophene-2-carbonyl)amino-L-alanine A solution of N-[2-chloro-4-[[[(3-hydroxyphenyl)methyl] amino]carbonyl]benzoyl]-3-(thiophene-2-carbonyl)amino-L-alanine, methyl ester (8.30 g, 16.1 mmol) and lithium hydroxide monohydrate (2.05 g, 48.9 mmol) in tetrahydrofuran (60 mL), methanol (20 mL), and water (40 mL) was stirred at room temperature overnight. The solution was concentrated to remove tetrahydrofuran and methanol, and ethyl acetate (200 mL) and 1 M HCl (100 mL) were added. The aqueous layer was extracted with ethyl acetate (100 mL) and the combined organic layers were washed with brine (200 mL), dried (MgSO$_4$), filtered, and evaporated to give N-[2-chloro-4-[[[(3-hydroxyphenyl)methyl]amino] carbonyl]benzoyl]-3-(thiophene-2-carbonyl)amino-L-alanine (7.75 g, 96%) as a white solid.

Example 304

Preparation of 3-benzoylamino-N-[2-chloro-4-[[[(3-hydroxyphenyl)methyl]amino]carbonyl]benzoyl]-L-alanine, sodium salt

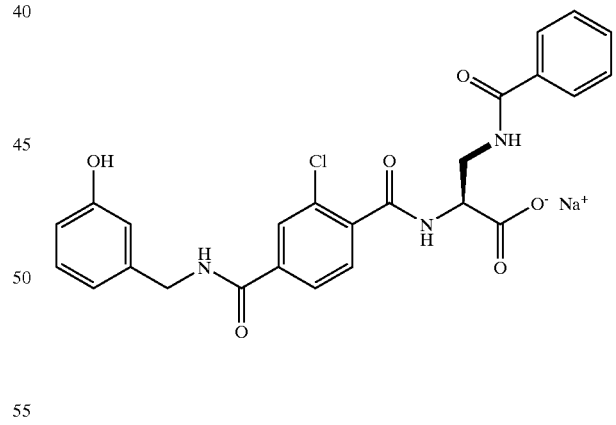

A solution of sodium hydroxide (1 M; 13.5 mL, 13.5 mmol) was added to a suspension of 3-benzoylamino-N-[2-chloro-4-[[[(3-hydroxyphenyl)methyl]amino]carbonyl] benzoyl]-L-alanine (Example 302; 6.68 g, 13.5 mmol) in water (200 mL). The reaction mixture was stirred at room temperature for 15 min, and filtered. The filtrate was lyophilized. The lyophilized material was relyophilized a further two times after dissolution in HPLC grade water (200 mL) to give 3-benzoylamino-N-[2-chloro-4-[[[(3-hydroxyphenyl)methyl]amino]carbonyl]benzoyl]-L-alanine, sodium salt (5.78 g, 83%) as a white solid.

Example 305

Preparation of N-[2-chloro-4-[[[(3-hydroxyphenyl)methyl]amino]carbonyl]benzoyl]-3-(thiophene-2-carbonyl)amino-L-alanine, sodium salt

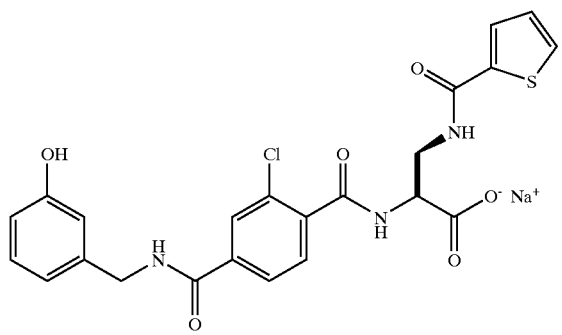

A solution of sodium hydroxide (1 M; 25 mL, 25 mmol) was added to a suspension of N-[2-chloro-4-[[[(3-hydroxyphenyl)methyl]amino]carbonyl]benzoyl]-3-(thiophene-2-carbonyl)amino-L-alanine (Example 303; 12.53 g, 25.0 mmol) in water (200 mL). The reaction mixture was stirred at room temperature for 2 h, and filtered. The filtrate was lyophilized. The lyophilized material was relyophilized a further two times after dissolution in HPLC grade water (100 mL) to give N-[2-chloro-4-[[[(3-hydroxyphenyl)methyl]amino]carbonyl]benzoyl]-3-(thiophene-2-carbonyl)amino-L-alanine, sodium salt (12.43 g, 95%) as a white solid.

Example 306

Preparation of N-[2-bromo-4-[[[(3-hydroxyphenyl)methyl]amino]carbonyl]benzoyl]-3-(thiophene-2-carbonyl)amino-L-alanine, methyl ester

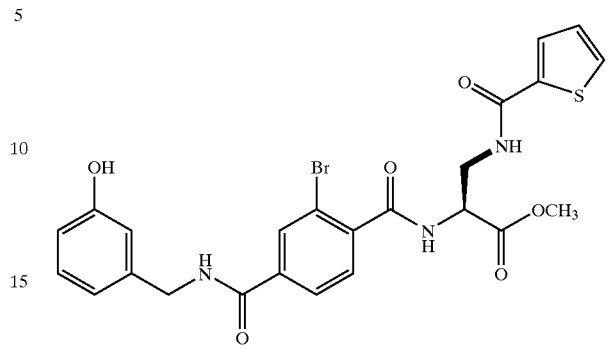

Diisopropylethylamine (305 μL, 1.71 mmol) was added dropwise to a solution of 2-bromo-4-[[[(3-hydroxyphenyl)methyl]amino]carbonyl]benzoic acid (Example 47; 150 mg, 0.428 mmol), HBTU (179 mg, 0.471 mmol), 3-(thiophene-2-carbonyl)amino-L-alanine methyl ester HCl salt (Example 301; 125 mg, 0.471 mmol), and HOBT (64 mg, 0.471 mmol) in N,N-dimethylformamide (6.5 mL) at 25° C. The solution was stirred for 6 h. The solvent was concentrated under vacuum to remove most of the N,N-dimethylformamide. The residue was diluted with ethyl acetate (60 mL) and washed with 1 N HCl (10 mL), water (10 mL), saturated aqueous NaHCO3 (10 mL) and brine (10 mL). The organic layer was dried (MgSO₄), filtered, evaporated and flash chromatographed (silica, 60–75% ethyl acetate in petroleum ether) to give N-[2-bromo-4-[[[(3-hydroxyphenyl)methyl]amino]carbonyl]benzoyl]-3-(thiophene-2-carbonyl)amino-L-alanine, methyl ester (198 mg, 83%) as an off-white foam.

Also prepared by this route were the following:

| Example | Structure | Starting Materials | Yield |
|---|---|---|---|
| 307[a] | 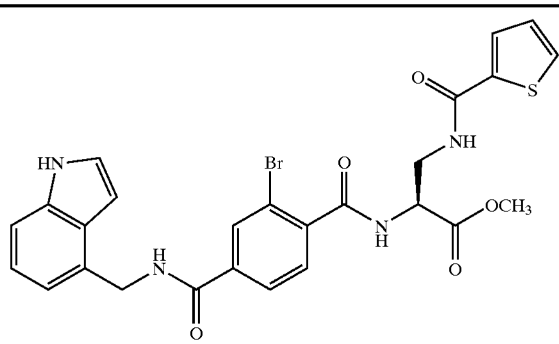 | Example 46 and Example 301 | 97% |
| 308[b] | 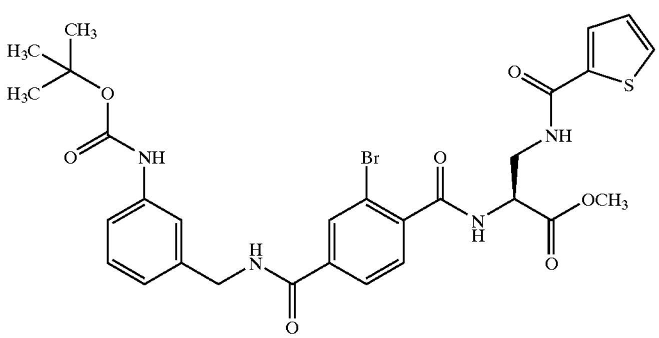 | Example 44 and Example 301 | 94% |

| Example | Structure | Starting Materials | Yield |
|---|---|---|---|
| 309[c] | (structure: 1-naphthyl(CH₃)CH-NH-C(O)-phenyl(Br)-C(O)-NH-CH(CO₂CH₃)-CH₂-NH-C(O)-thiophene) | Example 45 and Example 301 | 88% |
| 310[d] | (structure: 3-hydroxybenzyl-NH-C(O)-phenyl(F)-C(O)-NH-CH(CO₂CH₃)-CH₂-NH-C(O)-thiophene) | Example 32 and Example 301 | 72% |
| 311[e] | (structure: 3-hydroxybenzyl-NH-C(O)-phenyl(2,6-diCH₃)-C(O)-NH-CH(CO₂CH₃)-CH₂-NH-C(O)-thiophene) | Example 30 and Example 301 | 100% |

[a] The reaction time was 4 h at 25° C.; the eluent used for chromatography was 60–70% ethyl acetate/petroleum ether; the product was obtained as a white solid.

[a] The reaction time was 2 h at 25° C.; the eluent used for chromatography was 60–70% ethyl acetate/petroleum ether; the product was obtained as a white foam.

[a] The reaction time was 6 h at 25° C.; the eluent used for chromatography was 60–70% ethyl acetate/petroleum ether; the product was obtained as an off-white foam.

[a] The reaction time was 24 h at 25° C.; the eluent used for chromatography was 2% methanol/dichloromethane; the product was obtained as a yellow oil.

[e] The reaction time was 24 h at 25° C.; the product was obtained as a white foam, and was used without chromatography.

Example 312

Preparation of N-[2,6-dimethyl-4-[[[(1R)-1-(1-naphthalenyl)ethyl]amino]carbonyl]benzoyl]-3-(thiophene-2-carbonyl)amino-L-alanine, methyl ester

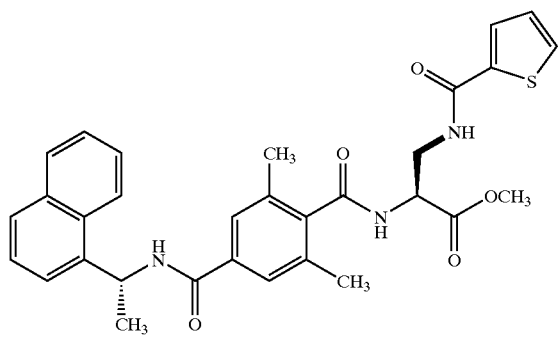

To a solution of 2,6-dimethyl-4-[[[(1R)-1-(1-naphthalenyl)ethyl]amino]carbonyl]benzoic acid (Example 31; 100 mg, 0.29 mmol) in dichloromethane (1 mL) at 25° C. was added benzotriazol-1-yloxy-tris-(dimethylamino) phosphonium hexafluorophosphate (BOP reagent, 140 mg, 0.32 mmol), 3-(thiophene-2-carbonyl)amino-L-alanine methyl ester HCl salt (Example 301; 114 mg, 0.43 mmol), followed by diisopropylethylamine (250 μL, 1.4 mmol) slowly dropwise. After stirring for 2 h, the reaction was diluted with ethyl acetate (50 mL) and washed with 1N HCl (10 mL), saturated aqueous sodium bicarbonate (10 mL) and brine (15 mL). The organic layer was dried (MgSO$_4$), filtered, evaporated and flash chromatographed (silica, 50% ethyl acetate in petroleum ether) to give N-[2,6-dimethyl-4-[[[(1R)-1-(1-naphthalenyl)ethyl]amino]carbonyl]benzoyl]-3-(thiophene-2-carbonyl)amino-L-alanine methyl ester (88 mg, 54%) as an off-white solid.

Example 313

Preparation of N-[2-chloro-4-[[(2,3-dihydro-2-oxo-1H-indole-4-methyl)amino]carbonyl]benzoyl]-3-(3-methoxybenzoylamino)-L-alanine

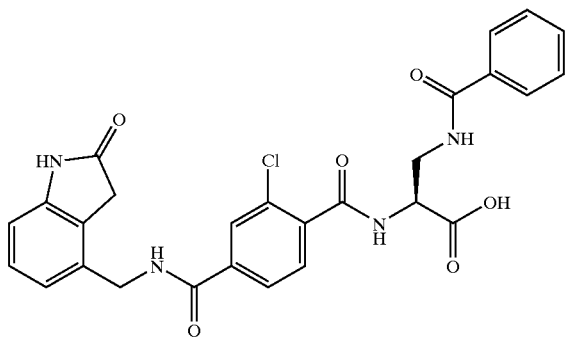

DCC (0.072 g, 0.352 mmol) and HOAT (0.087 g, 0.64 mmol) were added to a solution of 2-chloro-4-[[(2,3-dihydro-2-oxo-1H-indole-4-methyl)amino]carbonyl] benzoic acid (Example 35; 0.111 g, 0.32 mmol) and 3-(benzoylamino)-L-alanine methyl ester (Example 299; 0.142 g, 0.64 mmol) in DMF (5 mL). The solution was stirred at room temperature for 48 h, then filtered and diluted with ethyl acetate. The resulting solution was washed with water several times, evaporated, and chromatographed (70% ethyl acetate/hexanes to elute DCC, then 10% methanol/dichloromethane then 100% ethanol) to give N-[2-chloro-4-[[(2,3-dihydro-2-oxo-1H-indole-4-methyl)amino] carbonyl]benzoyl]-3-(3-methoxybenzoylamino)-L-alanine, methyl ester as a light brown solid (27 mg, 15%). A solution of lithium hydroxide monohydrate (5 mg, 0.1 mmol) was added to a solution of the ester (27 mg, 0.05 mmol) in tetrahydrofuran/methanol/water (3:1:1; 3 mL). The mixture was stirred for 5 h at room temperature and then acidified with 6 N HCl. The solvent was evaporated and the residue was suspended in water. The product was filtered off, washed with diethyl ether and water, and purified by HPLC to give N-[2-chloro-4-[[(2,3-dihydro-2-oxo-1H-indole-4-methyl)amino]carbonyl]benzoyl]-3-(3-methoxybenzoylamino)-L-alanine (10.7 mg, 42%).

Example 314

Preparation of 3-(benzoylamino)-N-[2-chloro-4-[[(1H-indol-4-ylmethyl)amino]carbonyl]benzoyl]-L-alanine

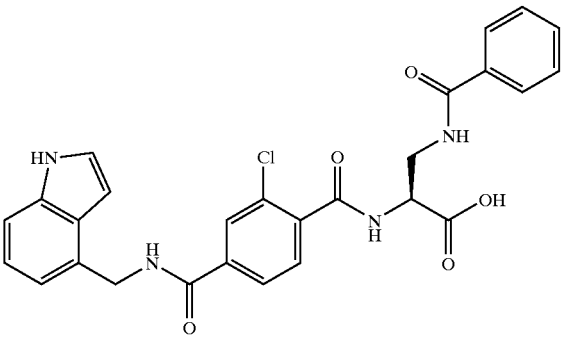

3-(Benzoylamino)-L-alanine methyl ester (Example 299; 77 mg, 0.35 mmol) was mixed with 2-chloro-4-[[(1H-indol-4-yl-methyl)amino]carbonyl]benzoic acid (Example 36; 115 mg, 0.35 mmol), HOBT (57 mg, 0.42 mmol) and EDCl (80.5 mg, 0.42 mmol) in DMF (4 mL). The reaction mixture was stirred at room temperature for 16 h and then diluted with water (about 20 ml). The solution was extracted with ethyl acetate (3×10 ml) and the ethyl acetate layer was washed with dilute aqueous NaCl solution and then brine, dried (Na$_2$SO$_4$), concentrated, and chromatographed (40–80% ethyl acetate/hexanes) to give 3-(benzoylamino)-N-[2-chloro-4-[[(1H-indol-4-ylmethyl)amino]carbonyl]benzoyl]-L-alanine methyl ester (88 mg, 47%). A solution of the ester (51 mg, 0.096 mmol) and lithium hydroxide monohydrate (8 mg, 0.19 mmol) in tetrahydrofuran/methanol/water (3:1:1; 2 mL) was stirred at room temperature for 3 h. The solvent was removed and the product was purified by HPLC to give 3-(benzoylamino)-N-[2-chloro-4-[[(1H-indol-4-ylmethyl)amino]carbonyl]benzoyl]-L-alanine (37 mg, 75%) as a white fluffy powder.

Example 315

Preparation of 3-(thiophene-2-carbonyl)amino-N-[2-chloro-4-[[(1H-indol-4-ylmethyl)amino]carbonyl]benzoyl]-L-alanine

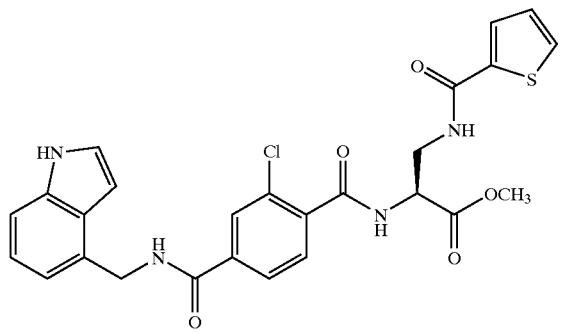

A. 3-[(9H-Fluoren-9-ylmethoxy)carbonyl]amino-N-[2-chloro-4-[[(1H-indol-4-ylmethyl)amino]carbonyl]benzoyl]-L-alanine, methyl ester A solution of N-[(1,1-dimethylethoxy)carbonyl]-3-[(9H-fluoren-9-ylmethoxy)carbonyl]amino-L-alanine, methyl ester (Example 62; 200 mg, 0.45 mmol) in trifluoroacetic acid/dichloromethane (1:1; 2 mL) was stirred at room temperature for 40 min. The solvent was evaporated and ethyl acetate (10 mL) was added. The solution was washed with saturated aqueous sodium hydrogen carbonate, dried (Na$_2$SO$^4$), filtered and evaporated to give 3-[(9H-fluoren-9-ylmethoxy) carbonyl]amino-L-alanine, methyl ester. HOAT (73 mg, 0.45 mmol), DCC (111 mg, 0.45 mmol), 2-chloro-4-[[(1H-indol-4-ylmethyl)amino]carbonyl]-benzoic acid (Example 36; 148 mg, 0.45 mmol) and N,N-dimethylformamide (5 mL) were added and the solution was stirred at room temperature for 1.5 h. Water was added and the solution was extracted three times with ethyl acetate. The combined extracts were washed with brine, dried (Na$_2$SO$_4$), filtered, evaporated, and chromatographed (40–80% ethyl acetate/hexanes) to give 3-[(9H-fluoren-9-ylmethoxy)carbonyl]amino-N-[2-chloro-4-[[(1H-indol-4-ylmethyl)amino]carbonyl]benzoyl]-L-alanine, methyl ester (116 mg, 40%).

B. 3-(Thiophene-2-carbonyl)amino-N-[2-chloro-4-[[(1H-indol-4-ylmethyl)amino]carbonyl]benzoyl]-L-alanine Piperidine (88 μL, 0.89 mmol) was added to a solution of 3-[(9H-fluoren-9-ylmethoxy)carbonyl]amino-N-[2-chloro-4-[[(1H-indol-4-ylmethyl)amino]carbonyl]benzoyl]-L-alanine, methyl ester (116 mg, 0.18 mmol) in N,N-dimethylformamide (5 mL). The solution was stirred at room temperature for 30 min and then the solvent was evaporated. The resulting white solid was triturated with ether five times and dried in vacuo to give 3-amino-N-[2-chloro-4-[[(1H-indol-4-ylmethyl)amino]carbonyl]benzoyl]-L-alanine, methyl ester as an off-white solid (59 mg, 81%). N,N-Dimethylformamide (5 mL) was added, followed by HOAT (23 mg, 0.17 mmol), 1-(3-dimethylaminopropyl)-3-ethylcarbodiimide hydrochloride (32 mg, 0.17 mmol), and thiophene-2-carboxylic acid (18 mg, 0.14 mmol). The reaction mixture was stirred at room temperature for 18 h. Water was added, and the mixture was extracted three times with ethyl acetate. The combined extracts were washed with brine, dried (Na$_2$SO$_4$), filtered, evaporated, and chromatographed (40–80% ethyl acetate/hexanes) to give 3-[(thiophene-2-carbonyl)amino)-N-[2-chloro-4-[[(1H-indol-4-ylmethyl)amino]carbonyl]benzoyl]-L-alanine, methyl ester (58 mg, 78%). A solution of lithium hydroxide monohydrate (13 mg, 0.32 mmol) in tetrahydrofuran/methanol/water (3:1:1) was added, and the solution was stirred at room temperature for 20 min. The solvent was evaporated and the residue was purified by HPLC to give 3-(thiophene-2-carbonyl)amino-N-[2-chloro-4-[[(1H-indol-4-ylmethyl)amino]carbonyl]benzoyl]-L-alanine (45 mg, 80% from ester, 48% for three steps) as a white powder.

Also prepared by this procedure were:

| Example | Structure | Starting Materials |
|---|---|---|
| 316 | 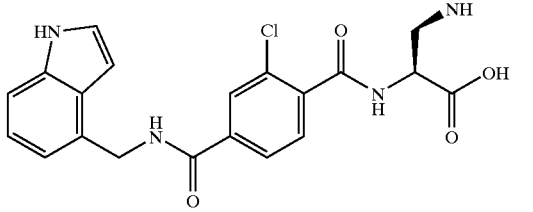 | Example 62; Example 36; thiophene-3-carboxylic acid |

-continued

| Example | Structure | Starting Materials |
|---|---|---|
| 317 | 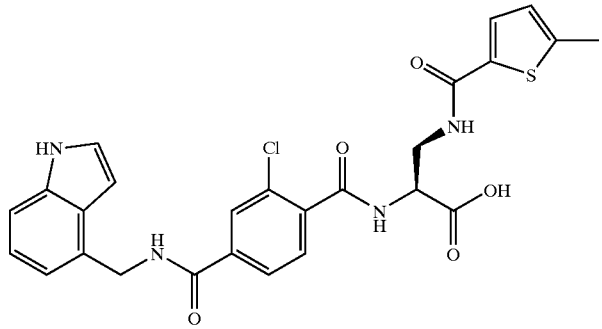 | Example 62; Example 36; 5-methylthiophene-2-carboxylic acid |

Example 318

Preparation of 3-(thiophene-2-carbonyl)amino-N-[2-chloro-4-[[(2,3-dihydro-1H-indol-4-ylmethyl)amino]carbonyl]benzoyl]-L-alanine

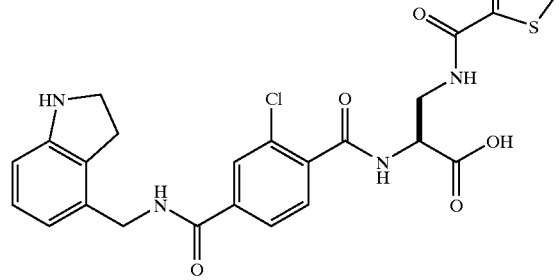

To 3-amino-N-[2-chloro-4-[[(1H-indol-4-ylmethyl)amino]carbonyl]benzoyl]-L-alanine on Wang resin (Example 69; 100 mg) was added a solution of HOAT (70 mg, 0.51 mmol), diisopropylcarbodiimide (80 μL, 0.51 mmol), and thiophene-2-carboxylic acid (70 mg, 0.55 mmol) in 1-methyl-2-pyrrolidinone (1 mL). The mixture was agitated for 2 h and then the resin was filtered and washed extensively with dichloromethane and methanol. Cleavage of the product was effected with triethylsilane/trifluoroacetic acid/dichloromethane (2:1:1; 1 mL) at room temperature for 30 min. The solvent was evaporated and the residue was purified by HPLC to give 3-(thiophene-2-carbonyl)amino-N-[2-chloro-4-[[(2,3-dihydro-1H-indol-4-ylmethyl)amino]carbonyl]benzoyl]-L-alanine (10.7 mg).

Example 319

Preparation of N-[2-chloro-4-[1-oxo-3-(3-hydroxyphenyl)propyl]benzoyl]-3-(thiophene-2-carbonyl)amino-L-alanine

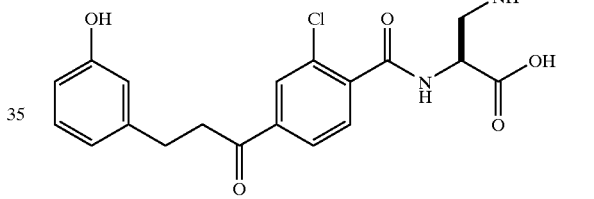

A. N-[2-chloro-4-[1-hydroxy-3-(3-hydroxyphenyl)propyl]benzoyl]-3-(thiophene-2-carbonyl)amino-L-alanine, methyl ester A solution of 2-chloro-4-[1-oxo-3-(3-hydroxyphenyl)propyl]benzoic acid (Example 41; 75.8 mg, 0.25 mmol), 3-(thiophene-2-carbonyl)amino-L-alanine, methyl ester hydrochloride (Example 301; 73 mg, 0.28 mmol), HBTU (113 mg, 0.30 mmol), HOBT (41 mg, 0.27 mmol) and diisopropylethylamine (0.22 mL, 1.26 mmol) in N,N-dimethylformamide (6 mL) was stirred overnight at room temperature. The solvent was evaporated. Ethyl acetate (30 mL) was added and the solution was washed with sodium hydrogen carbonate solution and 0.5 M HCl. Each of the aqueous layers was extracted with ethyl acetate (10 mL) and the combined organic layers were dried (Na$_2$SO$_4$), filtered, evaporated, and chromatographed (10–100% ethyl acetate/hexanes) to give N-[2-chloro-4-[1-hydroxy-3-(3-hydroxyphenyl)propyl]benzoyl]-3-(thiophene-2-carbonyl)amino-L-alanine, methyl ester (125 mg, 98%).

B. N-[2-chloro-4-[1-hydroxy-3-(3-hydroxyphenyl)propyl]benzoyl]-3-(thiophene-2-carbonyl)amino-L-alanine A solution of N-[2-chloro-4-[1-oxo-3-(3-hydroxyphenyl)propyl]benzoyl]-3-(thiophene-2-carbonyl)amino-L-alanine, methyl ester (120 mg, 0.23 mmol) and lithium hydroxide monohydrate (40 mg, 0.95 mmol) in tetrahydrofuran/methanol/water (2:2:1; 2.5 mL) was stirred at room temperature for 90 min. The solvent was evaporated, then water was added, followed by 1 M HCl (1.1 mL). The resulting solid was filtered off, washed with water, dried, and purified by HPLC to give N-[2-chloro-4-[1-oxo-3-(3-hydroxyphenyl)propyl]-benzoyl]-3-(thiophene-2-carbonyl) amino-L-alanine (95 mg, 81%).

Also prepared by this route were the following:

| Example | Structure | Starting Materials | Yield |
|---------|-----------|--------------------|-------|
| 320[a]  | 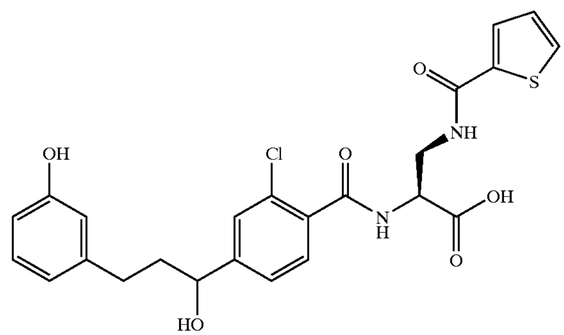          | Example 42 and Example 301 | 62% |
| 321     | 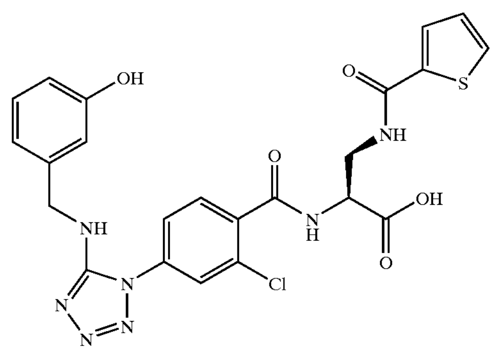          | Example 43 and Example 301 | 60% |
| 322     | 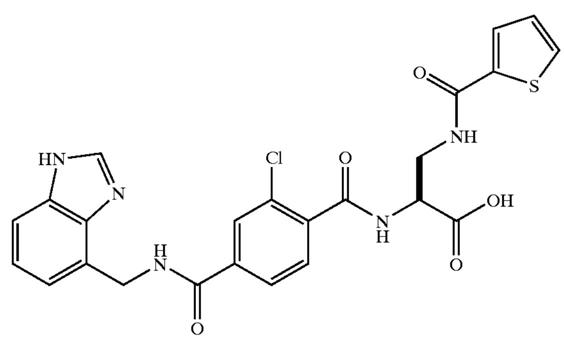          | Example 40 and Example 301 | 38% |
| 323     | 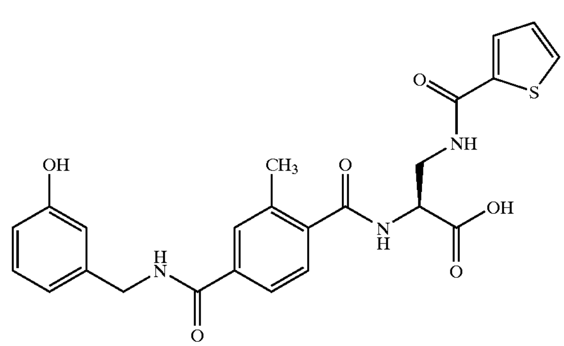          | Example 27 and Example 301 | 23% |

-continued

| Example | Structure | Starting Materials | Yield |
|---|---|---|---|
| 324 | 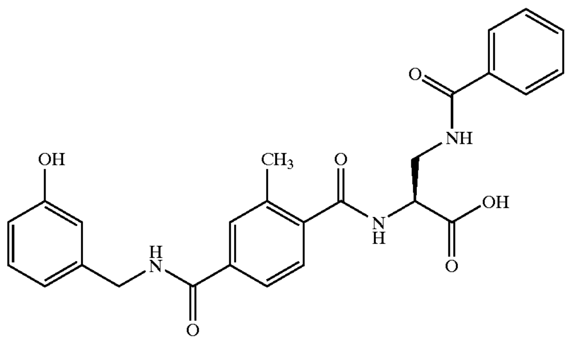 | Example 27 and Example 300 | 22% |
| 325 | 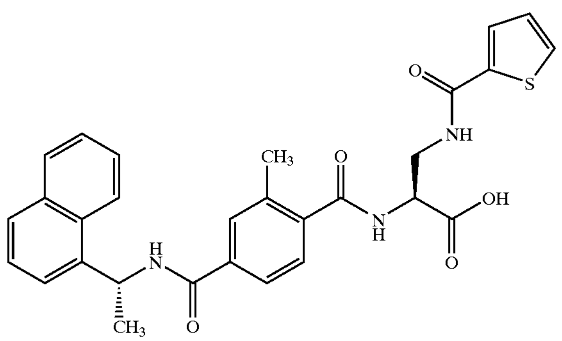 | Example 28 and Example 301 | 50% |
| 326 | 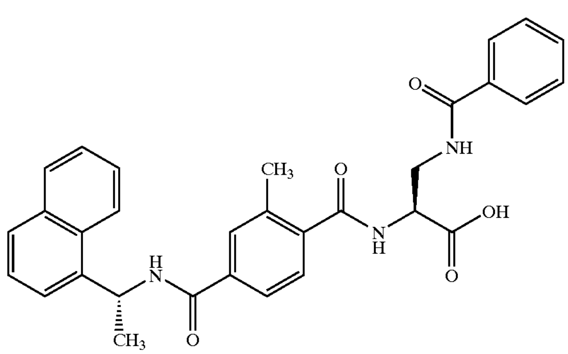 | Example 28 and Example 300 | 27% |

<sup>a</sup>This product was a mixture of diastereoisomers which were not separated.

Example 327

Preparation of N-[2-chloro-4-[[[(1H-indazol-4-yl)methyl]amino]carbonyl]benzoyl]-3-(thiophene-2-carbonyl)amino-L-alanine

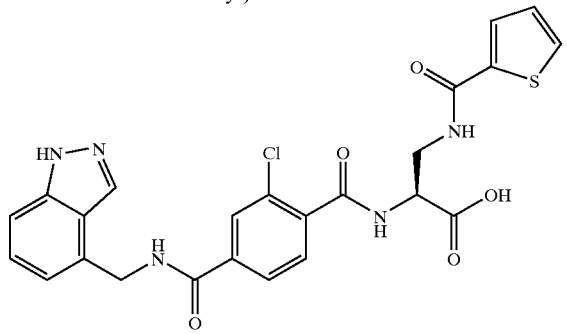

A. N-[2-chloro-4-[[[[1-(tetrahydro-2H-pyran-2-yl)-1H-indazol-4-yl]methyl]amino]carbonyl]benzoyl]-3-(thiophene-2-carbonyl)amino-L-alanine, methyl ester Diisopropylethylamine (0.147 mL, 0.84 mmol) was added to a solution of 3-(thiophene-2-carbonyl)amino-L-alanine, methyl ester hydrochloride (Example 301; 58 mg, 0.22 mmol), 2-chloro-4-[[[[1-(tetrahydro-2H-pyran-2-yl)-1H-indazol-4-yl]methyl]amino]carbonyl]benzoic acid (Example 39; 70 mg, 0.169 mmol), HBTU (78 mg, 0.21 mmol), and HOBT (27 mg, 0.20 mmol) in DMF (2 mL). The solution was allowed to stir at room temperature overnight, and it was then concentrated to remove most of the DMF. Ethyl acetate was added, and the solution was washed with saturated aqueous sodium hydrogen carbonate (twice), dilute acid, and brine, dried (MgSO$_4$), filtered, evaporated and chromatographed (2% methanol/dichloromethane) to give N-[2-chloro-4-[[[[1-(tetrahydro-2H-pyran-2-yl)-1H-indazol-4-yl]methyl]amino]carbonyl]benzoyl]-3-(thiophene-2-carbonyl)amino-L-alanine, methyl ester (108 mg, 102%) as a tan solid.

B. N-[2-Chloro-4-[[[[1-(tetrahydro-2H-pyran-2-yl)-1H-indazol-4-yl]methyl]amino]carbonyl]benzoyl]-3-(thiophene-2-carbonyl)amino-L-alanine An aqueous solution of sodium hydroxide (1 M, 190 µL, 0.19 mmol) was added to a solution of N-[2-chloro-4-[[[[1-(tetrahydro-2H-pyran-2-yl)-1H-indazol-4-yl]methyl]amino]carbonyl]benzoyl]-3-(thiophene-2-carbonyl)amino-L-alanine, methyl ester (108 mg, ~0.169 mmol) in methanol (1 mL). The solution was allowed to stir at room temperature for 2 days, then it was concentrated and held under high vacuum for 1 h to give N-[2-chloro-4-[[[[1-(tetrahydro-2H-pyran-2-yl)-1H-indazol-4-yl]methyl]amino]carbonyl]benzoyl]-3-(thiophene-2-carbonyl)amino-L-alanine (100 mg, 97%) as a yellow solid.

C. N-[2-Chloro-4-[[[(1H-indazol-4-yl)methyl]amino]carbonyl]benzoyl]-3-(thiophene-2-carbonyl)amino-L-alanine A solution of N-[2-chloro-4-[[[[1-(tetrahydro-2H-pyran-2-yl)-1H-indazol-4-yl]methyl]amino]carbonyl]benzoyl]-3-(thiophene-2-carbonyl)amino-L-alanine (35 mg, 0.057 mmol) in 2 M HCl (2 mL) and methanol (2 mL) was heated at reflux for 3 h. The solution was concentrated, diluted with aqueous acetic acid and purified by HPLC to give N-[2-chloro-4-[[[(1H-indazol-4-yl)methyl]amino]carbonyl]benzoyl]-3-(thiophene-2-carbonyl)amino-L-alanine (8 mg, 26%) along with N-[2-chloro-4-[[[(1H-indazol-4-yl)methyl]amino]carbonyl]benzoyl]-3-(thiophene-2-carbonyl)amino-L-alanine, methyl ester (13 mg, 42%).

Example 328

Preparation of N-[2-bromo-4-[[[(3-hydroxyphenyl)methyl]amino]carbonyl]benzoyl]-3-(thiophene-2-carbonyl)amino-L-alanine To a solution of N-[2-bromo-4-[[[(3-hydroxyphenyl)methyl]amino]carbonyl]benzoyl]-3-(thiophene-2-carbonyl)amino-L-alanine methyl ester (Example 306; 195 mg, 0.348 mmol) in methanol (2 mL) at 25° C. was added 1 N NaOH (350 µL, 0.348 mmol). The reaction mixture was stirred for 24 h and TLC (10% methanol in dichloromethane) revealed that starting material was still present. 1 N NaOH (350 µL) was added at room temperature and the reaction was stirred for 24 h. The solvents were evaporated under reduced pressure, the residue was placed under vacuum for 1 h, and then purified by HPLC (gradient of acetonitrile, water, 0.075% TFA). The pure fractions were combined, concentrated under vacuum and then freeze dried for 24 h to yield N-[2-bromo-4-[[[(3-hydroxyphenyl)methyl]amino]carbonyl]benzoyl]-3-(thiophene-2-carbonyl)amino-L-alanine (144 mg, 76%) as a white solid.

The following compounds were prepared by the same procedure. In each case, the product was a white solid.

| Example | Structure | Starting Material | Yield |
|---|---|---|---|
| 329 | 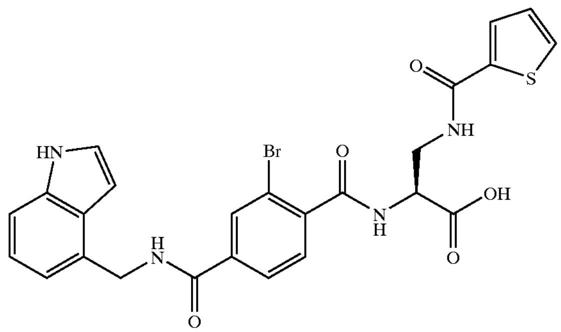 | Example 307 | 72% |

-continued

| Example | Structure | Starting Material | Yield |
|---|---|---|---|
| 330 | 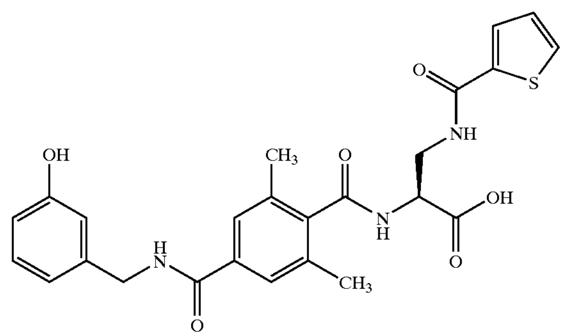 | Example 311 | 54% |
| 331 | 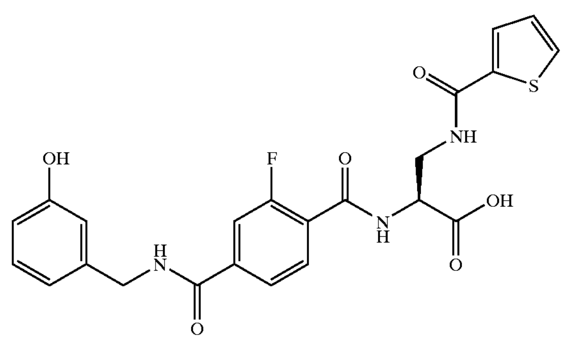 | Example 310 | 79% |
| 332 | 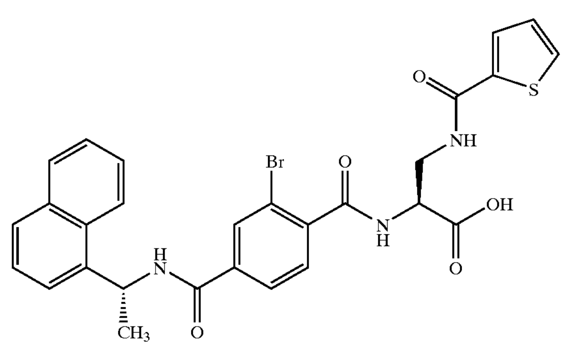 | Example 309 | 73% |
| 333 | 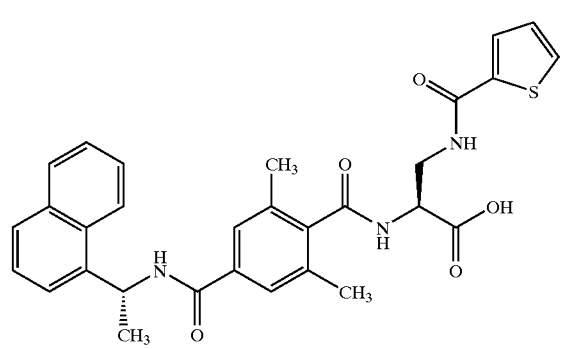 | Example 312 | 67% |

Example 334

Preparation of N-[4-[[[(3-aminophenyl)methyl]amino]carbonyl]-2-bromobenzoyl]-3-(thiophene-2-carbonyl)amino-L-alanine

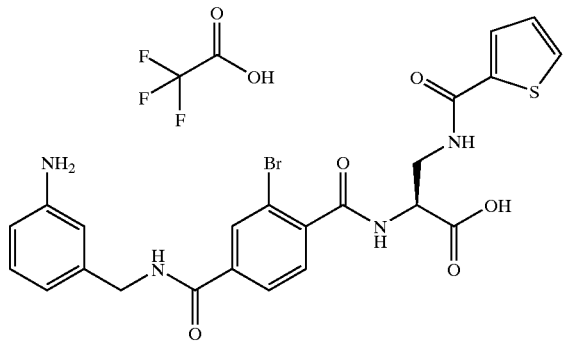

A. N-[2-bromo-4-[[[3-[[(1,1-dimethylethoxy)carbonyl]aminophenyl]methyl]amino]carbonyl]benzoyl]-3-(thiophene-2-carbonyl)amino-L-alanine To a solution of N-[2-bromo-4-[[[3-[[(1,1-dimethylethoxy)carbonyl]aminophenyl]methyl]amino]carbonyl]benzoyl]-3-(thiophene-2-carbonyl)amino-L-alanine, methyl ester (Example 308; 320 mg, 0.485 mmol) in methanol (2.5 mL) at 0° C. was added 1 N NaOH (534 µL, 0.533 mmol). The reaction mixture was warmed to 25° C. and stirred for 24 h The solvents were evaporated under reduced pressure, the residue was diluted with ethyl acetate (50 mL) and washed with water (100 mL). The water layer was separated, acidified to pH 4 with 1 N HCl, and extracted with ethyl acetate (3×50 mL). The organic layers were combined, washed with brine (50 mL), dried with MgSO4, filtered, and concentrated to give N-[2-bromo-4-[[[3-[[(1,1-dimethylethoxy)carbonyl]aminophenyl]methyl]-amino]carbonyl]benzoyl]-3-(thiophene-2-carbonyl)amino-L-alanine (260 mg, 83%) as a white foam.

B. N-[4-[[[(3-aminophenyl)methyl]amino]carbonyl]-2-bromobenzoyl]-3-(thiophene-2-carbonyl)amino-L-alanine, trifluoroacetate salt To a solution of N-[2-bromo-4-[[[3-[[(1,1-dimethylethoxy)carbonyl]aminophenyl]methyl]amino]carbonyl]benzoyl]-3-(thiophene-2-carbonyl)amino-L-alanine (260 mg, 0.40 mmol) in dichloromethane (2 mL) at 25° C. was added trifluoroacetic acid (2 mL). The reaction mixture was stirred for 1.5 h. The solvents were evaporated under reduced pressure, the residue was placed under vacuum for 1 h, and then purified by HPLC (gradient of acetonitrile, water, 0.075% TFA). The pure fractions were combined, concentrated under vacuum and then freeze dried for 24 h to yield N-[4-[[[(3-aminophenyl)methyl]amino]carbonyl]-2-bromobenzoyl]-3-(thiophene-2-carbonyl)amino-L-alanine TFA salt (182 mg, 69%) as a white solid.

Example 335

Synthesis of N-[2-chloro-4-[[[(3,5-dihydroxyphenyl)methyl]amino]carbonyl]benzoyl]-3-[thiophene-2-carbonyl]amino-L-alanine

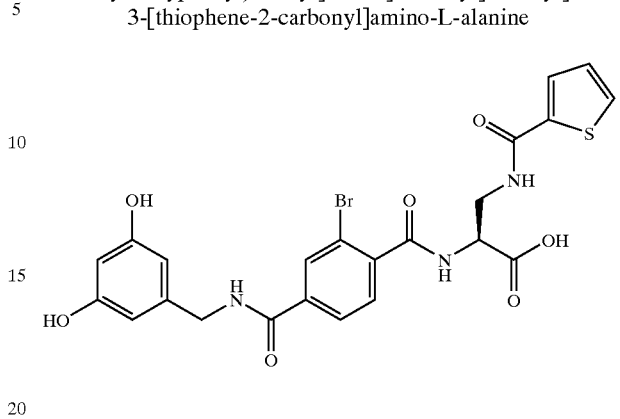

A. 2-Chloro-4-[[(3,5-dimethoxybenzyl)amino]carbonyl]benzoic acid, methyl ester A solution of 1-[[3-chloro-4-(methoxycarbonyl)benzoyl]oxy]-2,5-pyrrolidinedione (Example 5; 2.00 g, 6.4 mmol), 3,5-dimethoxybenzylamine (1.25 g, 7.5 mmol) and triethylamine (1.00 g, 9.9 mmol) in N,N-dimethylformamide (100 mL) was stirred at room temperature overnight. The solvent was evaporated (<0.5 mm Hg, 40° C.), ethyl acetate (200 mL) was added, and the solution was allowed to stand over the weekend at room temperature. The white solid was filtered off and discarded. Silica gel was added, the solvent was evaporated and the residue was chromatographed (30–50% ethyl acetate/hexanes) to give 2-chloro-4-[[[(3,5-dimethoxyphenyl)methyl]amino]carbonyl]benzoic acid, methyl ester (1.69 g, 72%) as a white solid, mp 101–103° C.

B. 2-Chloro-4-[[[(3,5-dihydroxyphenyl)methyl]amino]carbonyl]benzoic acid, methyl ester A solution of 2-chloro-4-[[(3,5-dimethoxybenzyl)amino]carbonyl]benzoic acid, methyl ester (0.50 g, 1.4 mmol) in dry dichloromethane (20 mL) was cooled to −78° C. A solution of boron tribromide (1 M in dichloromethane; 10 mL, 10 mmol) was added and the solution was allowed to warm to room temperature and stir overnight. The reaction mixture was poured into water (200 mL) and extracted with ethyl acetate (2×100 mL). The combined organic layers were washed with brine (200 mL), dried (MgSO4), filtered, and evaporated to give 2-chloro-4-[[[(3,5-dihydroxyphenyl)methyl]amino]carbonyl]benzoic acid, methyl ester (400 mg, 90%) as a white solid, mp 152–155° C.

C. N-[2-Chloro-4-[[[(3,5-dihydroxyphenyl)methyl]amino]carbonyl]benzoyl]-3-[thiophene-2-carbonyl]amino-L-alanine, methyl ester Diisopropylethylamine (0.40 g, 3.09 mmol) was added to an ice-bath cooled solution of 3-(thiophene-2-carbonyl)-L-alanine methyl ester hydrochloride (Example XX; 0.33 g, 1.25 mmol), 2-chloro-4-[[[(3,5-dihydroxy)phenyl]methyl]amino]carbonylbenzoic acid (0.40 g,1.24 mmol), HBTU (500 mg, 1.3 mmol), and HOBT (180 mg, 1.3 mmol) in N,N-dimethylformamide (10 mL). The solution was allowed to stir at room temperature overnight. It was then concentrated to remove most of the N,N-dimethylformamide. Ethyl acetate (200 mL) was added, followed by water (200 mL) and 1 M HCl (100 mL). The layers were separated; the ethyl acetate layer was washed with brine (200 mL), dried (MgSO4), and evaporated to give N-[2-chloro-4-[[[(3,5-dihydroxyphenyl)methyl]amino]carbonyl]benzoyl]-3-[thiophene-2-carbonyl]amino-L-alanine, methyl ester as a white solid (270 mg, 41%), mp 120–123° C.

D. N-[2-Chloro-4-[[[(3,5-dihydroxyphenyl)methyl]amino]carbonyl]benzoyl]-3-[thiophene-2-carbonyl]amino-L-alanine A solution of N-[2-chloro-4-[[[(3,5-dihydroxyphenyl)methyl]amino]carbonyl]benzoyl]-3-[thiophene-2-carbonyl]amino-L-alanine, methyl ester (250 mg, 0.47 mmol), and lithium hydroxide monohydrate (200 mg, 4.8 mmol) in tetrahydrofuran (30 mL), methanol (10 mL), and water (10 mL) was stirred at room temperature overnight. The solution was concentrated to remove methanol and tetrahydrofuran, and then water (50 mL) and 1 M HCl (20 mL) were added. The mixture was extracted with ethyl acetate (2×30 mL), and the solvent was evaporated from the extracts. The residue was dissolved in methanol (30 mL) and 10 mL of this solution was purified by HPLC to give N-[2-chloro-4-[[[(3,5-dihydroxyphenyl)methyl]amino]carbonyl]benzoyl]-3-[thiophene-2-carbonyl]amino-L-alanine (21.2 mg, 26%) as an off-white solid.

Example 336

Preparation of N-[2,6-dimethyl-4-[[[(3-hydroxyphenyl)methyl]amino]carbonyl]benzoyl]-3-(thiophene-3-carbonyl)amino-L-alanine

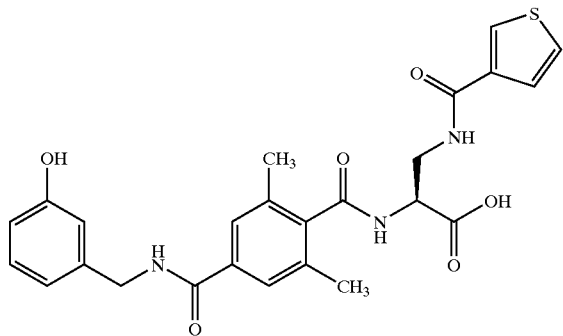

To a cooled (~0° C.) solution of crude N-[2,6-dimethyl-4-[[[(3-hydroxyphenyl)methyl]amino]carbonyl]benzoyl]-3-amino-L-alanine, methyl ester (Example 73; 50 mg, approx. 0.125 mmol) in N,N-dimethylformamide (1 mL) were added HBTU (57 mg, 0.150 mmol), HOBT (20 mg, 0.148 mmol), diisopropylethylamine (109 µL, 0.626 mmol), and finally thiophene-3-carboxylic acid (18 mg, 0.140 mmol). The solution was stirred for 1 h at 0° C. and then for 5 h at room temperature. The N,N-dimethylformamide was evaporated. The residue was diluted with ethyl acetate and the solution was washed with 1 M HCl (twice) and sodium hydrogen carbonate (twice). The solution was dried (MgSO₄), filtered, and concentrated to give a yellow oil (52 mg). This contained two major components: N-[2,6-dimethyl-4-[[[(3-hydroxyphenyl)methyl]amino]carbonyl]benzoyl]-3-(thiophene-3-carbonyl)amino-L-alanine, methyl ester and N-[2,6-dimethyl-4-[[[[3-(thiophene-3-carbonyl)oxyphenyl]methyl]amino]carbonyl]benzoyl]-3-(thiophene-3-carbonyl)amino-L-alanine, methyl ester. A solution of sodium hydroxide (1 M; 196 µL; 0.196 mmol) was added to a solution of this yellow oil (50 mg) in methanol (1 mL). The reaction mixture was stirred at room temperature overnight. Tlc indicated the presence of some starting material so a further 50 µL (0.05 mmol) of sodium hydroxide was added and the solution was stirred overnight again. The solvent was evaporated (using a rotary evaporator and then a vacuum pump) and the residue was purified by HPLC and lyophilized to give N-[2,6-dimethyl-4-[[[(3-hydroxyphenyl)methyl]amino]carbonyl]benzoyl]-3-(thiophene-3-carbonyl)amino-L-alanine (3.7 mg, 6% overall from 2,6-dimethyl-4-[[[3-[[(1,1-dimethylethyl)dimethylsilyl]oxy]phenyl]methyl]amino]carbonyl]benzoic acid) as a white solid.

Example 337

Preparation of N-[2,6-dimethyl-4-[[[(3-hydroxyphenyl)methyl]amino]carbonyl]benzoyl]-3-(3,5-difluorobenzoylamino)-L-alanine

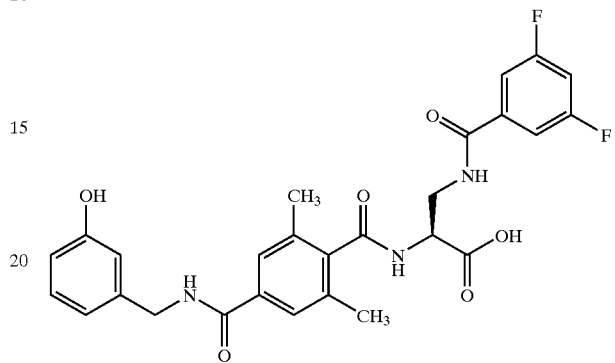

To a cooled (~0° C.) solution of crude N-[2,6-dimethyl-4-[[[(3-hydroxyphenyl)methyl]amino]carbonyl]benzoyl]-3-amino-L-alanine, methyl ester (Example 73; 50 mg, approx. 0.125 mmol) in N,N-dimethylformamide (1 mL) were added HBTU (57 mg, 0.150 mmol), HOBT (20 mg, 0.148 mmol), diisopropylethylamine (109 µL, 0.626 mmol), and finally 3,5-difluorobenzoic acid (22 mg, 0.14 mmol). The solution was stirred for 1 h at 0° C. and then for 5 h at room temperature. The N,N-dimethylformamide was evaporated. The residue was diluted with ethyl acetate and the solution was washed with 1 M HCl (twice) and sodium hydrogen carbonate (twice). The solution was dried (MgSO₄), filtered, and concentrated to give a yellow oil (48 mg). This was dissolved in methanol (1 mL), and an aqueous solution of sodium hydroxide (1 M; 117 µL, 117 µmol) was added. The solution was stirred at room temperature overnight and then the solvents were evaporated. The residue was purified by HPLC and lyophilized to give N-[2,6-dimethyl-4-[[[(3-hydroxyphenyl)methyl]amino]-carbonyl]benzoyl]-3-(3,5-difluorobenzoylamino)-L-alanine (4 mg, 6%).

Example 338

Preparation of N-[2-chloro-4-[[[(3-hydroxyphenyl)methyl]amino]carbonyl]-6-methylbenzoyl]-3-[(thiophene-2-carbonyl)amino]-L-alanine

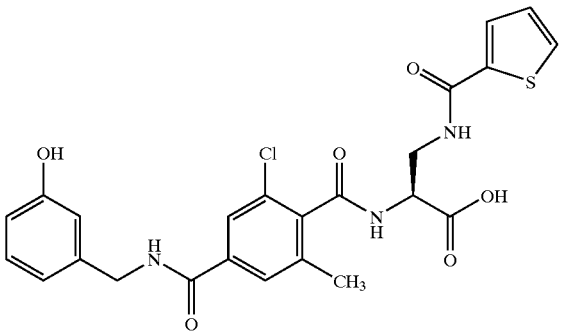

189

A. N-[2-Chloro-4-[[[[3-[[(1,1-dimethylethyl)dimethylsilyl]oxy]phenyl]methyl]amino]-carbonyl]-6-methylbenzoyl]-3-[(thiophene-2-carbonyl)amino]-L-alanine, methyl ester Diisopropylethylamine (4.6 mL, 26.5 mmol) was added to a solution of 2-chloro-4-[[[[3-[[(1,1-dimethylethyl)dimethylsilyl]oxy]phenyl]methyl]amino]carbonyl]-6-methylbenzoic acid (Example 33; 2.30 g, 5.3 mmol), 3-(thiophene-2-carbonyl)amino-L-alanine, methyl ester hydrochloride (Example 301; 1.80 g, 6.9 mmol), HOBT (0.80 g, 6.4 mmol), and HBTU (2.40 g, 6.4 mmol) in N,N-dimethylformamide (10 mL). The reaction mixture was allowed to stir at room temperature overnight. The solvent was evaporated (<0.5 mm Hg, 40° C.), and ethyl acetate was added. The solution was washed with 1 M HCl, saturated sodium hydrogen carbonate and brine, dried (MgSO$_4$), filtered, evaporated and chromatographed (50–100% ethyl acetate/hexanes then 5% methanol/ethyl acetate) to give N-[2-chloro-4-[[[[3-[[(1,1-dimethylethyl)dimethylsilyl]oxy]phenyl]methyl]amino]carbonyl]-6-methylbenzoyl]-3-[(thiophene-2-carbonyl)amino]-L-alanine, methyl ester (2.00 g, 59% of the theoretical amount) and N-[2-chloro-4-[[[(3-hydroxyphenyl)methyl]amino]carbonyl]-6-methylbenzoyl]-3-[(thiophene-2-carbonyl)amino]-L-alanine, methyl ester (850 mg, 30% of the theoretical amount).

B. N-[2-Chloro-4-[[[(3-hydroxyphenyl)methyl]amino]carbonyl]-6-methylbenzoyl]-3-[(thiophene-2-carbonyl)amino]-L-alanine, methyl ester Tetra-n-butylammonium fluoride (1 M in tetrahydrofuran; 3.4 mL, 3.4 mmol) was added to a solution of N-[2-chloro-4-[[[[3-[[(1,1-dimethylethyl)dimethylsilyl]oxy]phenyl]methyl]amino]carbonyl]-6-methylbenzoyl]-3-[(thiophene-2-carbonyl)amino]-L-alanine (2.0 g, 3.1 mmol) in tetrahydrofuran (10 mL). The solution was stirred at room temperature for 20 min, then diluted with ethyl acetate and washed with water and then brine. The solution was dried (MgSO4), filtered, evaporated, concentrated, evaporated, dried overnight under high vacuum and then crystallized from methanol to give N-[2-chloro-4-[[[(3-hydroxyphenyl)methyl]amino]carbonyl]-6-methylbenzoyl]-3-[(thiophene-2-carbonyl)amino]-L-alanine, methyl ester (1.06 g) as a solid. The mother liquors were concentrated and chromatographed (70% ethyl acetate/hexanes then methanol/ethyl acetate/hexanes 10:133:57) to give a further portion of the product (0.16 g). The overall yield was 1.22 g (74%).

C. N-[2-Chloro-4-[[[(3-hydroxyphenyl)methyl]amino]carbonyl]-6-methylbenzoyl]-3-[(thiophene-2-carbonyl)amino]-L-alanine A mixture of N-[2-chloro-4-[[[(3-hydroxyphenyl)methyl]amino]carbonyl]-6-methylbenzoyl]-3-[(thiophene-2-carbonyl)amino]-L-alanine, methyl ester (2.06 g, 3.9 mmol) in methanol (100 mL) and sodium hydroxide (0.31 g, 7.8 mmol) in water (2 mL) was stirred at room temperature overnight and then the solvents were evaporated. The residue was partitioned between water and ethyl acetate and the ethyl acetate layer was discarded. The aqueous layer was poured into 2 M HCl, and extracted twice with ethyl acetate. The combined organic extracts were washed with brine, concentrated, and dried under high vacuum to give N-[2-chloro-4-[[[(3-hydroxyphenyl)methyl]amino]carbonyl]-6-methylbenzoyl]-3-[(thiophene-2-carbonyl)amino]-L-alanine (1.50 g, 75%) as a white solid.

190

Example 339

Preparation of N-[2-chloro-4-[[[(3-hydroxyphenyl)methyl]amino]carbonyl]-6-methylbenzoyl]-3-[(thiophene-3-carbonyl)amino]-L-alanine

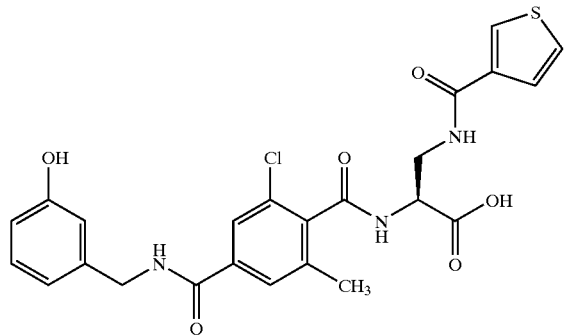

A. N-[2-Chloro-4-[[[[3-[(thiophene-3-carbonyl)oxy]phenyl]methyl]amino]carbonyl]-6-methylbenzoyl]-3-[(thiophene-3-carbonyl)amino]-L-alanine, methyl ester Diisopropylethylamine (0.286 mL, 1.64 mmol) was added to a cooled (~0° C.) solution of 3-amino-N-[2-chloro-4-[[[(3-hydroxyphenyl)methyl]amino]carbonyl]-6-methylbenzoyl]-L-alanine, methyl ester hydrochloride (Example 74; 150 mg, 0.329 mmol), thiophene-3-carboxylic acid (92.7 mg, 0.72 mmol), HOBT (97.8 mg, 0.72 mmol), and HBTU (275 mg, 0.73 mmol) in N,N-dimethylformamide (3 mL). The reaction mixture was allowed to stir at room temperature over the weekend. The solvent was evaporated. Ethyl acetate (100 mL) was added and the solution was washed with 1 M HCl, saturated aqueous sodium hydrogen carbonate, and brine (25 mL each). The solution was dried (MgSO$_4$), filtered, evaporated and chromatographed (60% ethyl acetate/petroleum ether) to give N-[2-chloro-4-[[[[3-[(thiophene-3-carbonyl)oxy]phenyl]methyl]amino]carbonyl]-6-methylbenzoyl]-3-[(thiophene-3-carbonyl)amino]-L-alanine, methyl ester (170 mg, 81%) as an orange foam. N-[2-Chloro-4-[[[(3-hydroxyphenyl)methyl]amino]carbonyl]-6-methylbenzoyl]-3-[(thiophene-3-carbonyl)amino]-L-alanine An aqueous solution of sodium hydroxide (1 M; 0.5 mL, 0.5 mmol) was added to a solution of N-[2-chloro-4-[[[[3-[(thiophene-3-carbonyl)oxy]phenyl]methyl]amino]carbonyl]-6-methylbenzoyl]-3-[(thiophene-3-carbonyl)amino]-L-alanine, methyl ester (160 mg, 0.25 mmol) in methanol (2 mL). The solution was allowed to stir overnight and then concentrated. The residue was purified by HPLC and lyophilized to give N-[2-chloro-4-[[[(3-hydroxyphenyl)methyl]amino]carbonyl]-6-methylbenzoyl]-3-[(thiophene-3-carbonyl)amino]-L-alanine (76.5 mg, 59%) as a white solid.

Example 340

Preparation of N-[2-chloro-4-[[[(3-hydroxyphenyl)methyl]amino]carbonyl]-6-methylbenzoyl]-3-[(3,5-difluorobenzoyl)amino]-L-alanine

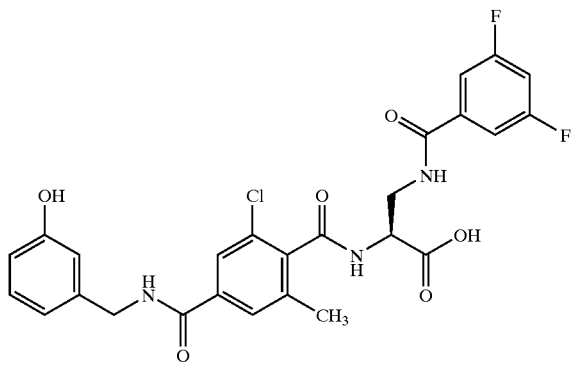

A. N-[2-Chloro-4-[[[[3-[(3,5-difluorobenzoyl)oxy]phenyl]methyl]amino]carbonyl]-6-methylbenzoyl]-3-[(3,5-difluorobenzoyl)amino]-L-alanine, methyl ester and N-[2-chloro-4-[[[(3-hydroxyphenyl)methyl]amino]carbonyl]-6-methylbenzoyl]-3-[(3,5-difluorobenzoyl)amino]-L-alanine, methyl ester Diisopropylethylamine (0.287 mL, 1.65 mmol) was added to a cooled (~0° C.) solution of 3-amino-N-[2-chloro-4-[[[(3-hydroxyphenyl)methyl]amino]carbonyl]-6-methylbenzoyl]-L-alanine, methyl ester hydrochloride (Example 74; 150 mg, 0.329 mmol), 3,5-difluorobenzoic acid (114 mg, 0.72 mmol), HOBT (98 mg, 0.73 mmol), and HBTU (275 mg, 0.73 mmol) in N,N-dimethylformamide (3 mL). The reaction mixture was allowed to stir at room temperature overnight. The solvent was evaporated. Ethyl acetate (100 mL) was added and the solution was washed with 1 M HCl, saturated aqueous sodium hydrogen carbonate, and brine (25 mL each). The solution was dried (MgSO$_4$), filtered, evaporated and chromatographed (40–60% ethyl acetate/petroleum ether) to give N-[2-chloro-4-[[[[3-[(3,5-difluorobenzoyl)oxy]phenyl]methyl]amino]carbonyl]-6-methylbenzoyl]-3-[(3,5-difluorobenzoyl)amino]-L-alanine, methyl ester (48.9 mg, 21%) as an off-white solid, and N-[2-chloro-4-[[[(3-hydroxyphenyl)methyl]amino]carbonyl]-6-methylbenzoyl]-3-[(3,5-difluorobenzoyl)amino]-L-alanine, methyl ester (44.6 mg, 24%) as an off-white solid.

B. N-[2-Chloro-4-[[[(3-hydroxyphenyl)methyl]amino]carbonyl]-6-methylbenzoyl]-3-[(3,5-difluorobenzoyl)amino]-L-alanine An aqueous solution of sodium hydroxide (1 M; 0.123 mL, 0.123 mmol) was added to a solution of N-[2-chloro-4-[[[3-[(3,5-difluorobenzoyl)oxy]phenyl]methyl]amino]carbonyl]-6-methylbenzoyl]-3-[(3,5-difluorobenzoyl)amino]-L-alanine, methyl ester (43 mg, 0.0614 mmol) in methanol (1 mL). The solution was allowed to stir overnight and then concentrated. The residue was purified by HPLC and lyophilized to give N-[2-chloro-4-[[[(3-hydroxyphenyl)methyl]amino]carbonyl]-6-methylbenzoyl]-3-[(3,5-difluorobenzoyl)amino]-L-alanine (14.6 mg, 43%) as a white solid.

Example 341

Preparation of N-[2-chloro-4-[[[(3-hydroxyphenyl)methyl]amino]carbonyl]-6-methylbenzoyl]-3-(3,5-dihydroxybenzoylamino)-L-alanine

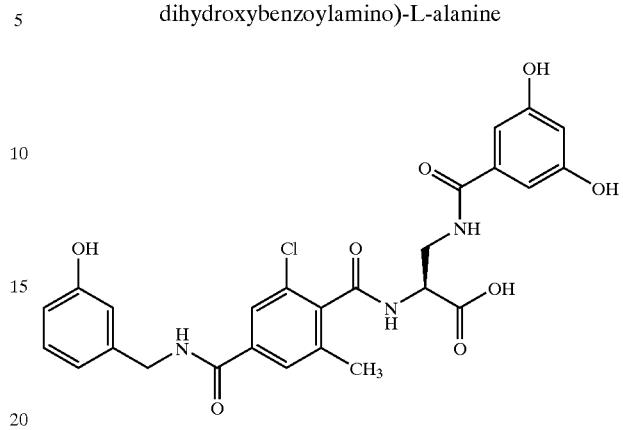

A. N-[2-Chloro-4-[[[(3-hydroxyphenyl)methyl]amino]carbonyl]-6-methylbenzoyl]-3-(3,5-dihydroxybenzoylamino)-L-alanine, methyl ester Diisopropylethylamine (0.68 mL, 3.9 mmol) was added to a cooled (~0° C.) solution of 2-chloro-4-[[[[3-[[(1,1-dimethylethyl)dimethylsilyl]oxy]phenyl]methyl]-amino]carbonyl]-6-methylbenzoic acid (Example 33; 400 mg, 0.92 mmol), 3-[[(1,1-dimethylethoxy)carbonyl]amino]-L-alanine, methyl ester, hydrochloride (259 mg, 1.02 mmol), HOBT (138 mg, 1.02 mmol), and HBTU (380 mg, 1.02 mmol) in N,N-dimethylformamide (6 mL). The reaction mixture was allowed to warm to room temperature and stir overnight. The solvent was evaporated (<0.5 mm Hg, 40° C.), and ethyl acetate (10 mL), water (10 mL) and 1 M HCl (4 mL) were added. The layers were separated and the aqueous layer was extracted with ethyl acetate (2×15 mL). The combined organic layers were washed with saturated sodium hydrogen carbonate and brine, dried (MgSO$_4$), filtered, evaporated and chromatographed (0–66% ethyl acetate/hexanes) to give N-[2-chloro-4-[[[[3-[[(1,1-dimethylethyl)dimethylsilyl]oxy]phenyl]methyl]amino]-carbonyl]-6-methylbenzoyl]-3-[[(1,1-dimethylethoxy)carbonyl]amino]-L-alanine, methyl ester (299 mg, 51% of the theoretical amount) and N-[2-chloro-4-[[[(3-hydroxyphenyl)methyl]amino]carbonyl]-6-methylbenzoyl]-3-[[(1,1-dimethylethoxy)carbonyl]amino]-L-alanine, methyl ester (242 mg, 51% of the theoretical amount). The two products were combined. A portion (510 mg) of the resulting material was dissolved in dichloromethane (5 mL) and the solution was cooled to 0° C. A solution of trifluoroacetic acid (3.5 mL) in dichloromethane (3 mL) was added dropwise. The cooling bath was removed and the solution was allowed to stir at room temperature for 2 h. The solvent was evaporated and the residue was azeotroped three times with hexanes/dichloromethane (1:1) and then held under high vacuum to give the deprotected amine (466 mg). This material was dissolved in N,N-dimethylformamide (10 mL) and 3,5-dihydroxybenzoic acid (284 mg, 1.84 mmol), HOBT (248 mg, 1.84 mmol), and HBTU (383 mg, 1.84 mmol) were added. The solution was cooled to ~0° C. and diisopropylethylamine (1.4 mL, 7.4 mmol) was added. The solution was allowed to stir overnight at room temperature and the solvent was evaporated. The residue was dissolved in tetrahydrofuran (10 mL) and tetra-n-butylammonium fluoride (1 M in tetrahydrofuran; 5 mL, 5 mmol) was added. The mixture was stirred at room temperature for 3 h and then the solvent was evaporated. Water (10 mL) and ethyl acetate (10 mL) were added and the mixture was acidified with 1 M HCl. The layers were separated and the aqueous layer was extracted with ethyl acetate (2×15 mL). The combined ethyl acetate layers were washed with saturated aqueous sodium hydrogen carbonate and brine, and then dried (MgSO₄). A precipitate started to form on the magnesium sulfate so methanol was added, the mixture was filtered and the filter cake was washed with 10% methanol/ethyl acetate. The filtrate was evaporated to give N-[2-chloro-4-[[[(3-hydroxyphenyl)methyl]amino]carbonyl]-6-methylbenzoyl]-3-(3,5-dihydroxybenzoylamino)-L-alanine, methyl ester (790 mg)

B. N-[2-Chloro-4-[[[(3-hydroxyphenyl)methyl]amino]carbonyl]-6-methylbenzoyl]-3-(3,5-dihydroxybenzoylamino)-L-alanine A solution of N-[2-chloro-4-[[[(3-hydroxyphenyl)methyl]amino]carbonyl]-6-methylbenzoyl]-3-(3,5-dihydroxybenzoylamino)-L-alanine, methyl ester (790 mg, 0.87 mmol) in tetrahydrofuran/methanol (1:1; 8 mL) was added to a solution of lithium hydroxide monohydrate (183 mg, 4.4 mmol) in water (4 mL). The solution was stirred at room temperature overnight and then the solvents were evaporated. Water (15 mL) was added and the solution was acidified with 3 M HCl. The mixture was extracted with ethyl acetate (3×20 mL) and the combined extracts were washed with brine and evaporated. The residue was dissolved in methanol (14 mL) and purified in two portions by HPLC to give N-[2-chloro-4-[[[(3-hydroxyphenyl)methyl]amino]carbonyl]-6-methylbenzoyl]-3-(3,5-dihydroxybenzoylamino)-L-alanine (65 mg, 14%).

Example 342

Preparation of N-[2,6-dichloro-4-[[[(3-hydroxyphenyl)methyl]amino]carbonyl]benzoyl]-3-[(thiophene-2-carbonyl)amino]-L-alanine

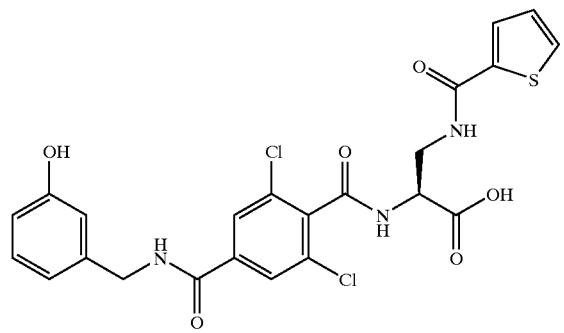

A. N-[2,6-Dichloro-4-[[[[3-[[(1,1-dimethylethyl)dimethylsilyl]oxy]phenyl]methyl]amino]carbonyl]benzoyl]-3-[(thiophene-2-carbonyl)amino]-L-alanine, methyl ester Diisopropylethylamine (3.49 mL, 20.0 mmol) was added to a solution of 2,6-dichloro4-[[[[3-[[(1,1-dimethylethyl)dimethylsilyl]oxy]phenyl]methyl]amino]carbonyl]benzoic acid (Example 34; 1.82 g, 4.0 mmol), 3-[(thiophene-2-carbonyl)amino]-L-alanine, methyl ester hydrochloride (Example 301; 1.27 g, 4.8 mmol), HOBT (0.65 g, 4.8 mmol), and HBTU (1.82 g, 4.8 mmol) in N,N-dimethylformamide (10 mL). The reaction mixture was allowed to stir at room temperature overnight. The solvent was evaporated (<0.5 mm Hg, 40° C.), and ethyl acetate was added. The solution was washed with 1 M HCl, saturated sodium hydrogen carbonate and brine, dried (MgSO₄), filtered, evaporated and chromatographed (50–100% ethyl acetate/hexanes then 5% methanol/ethyl acetate) to give N-[2,6-dichloro-4-[[[[3-[[(1,1-dimethylethyl)dimethylsilyl]oxy]phenyl]methyl]amino]carbonyl]benzoyl]-3-[(thiophene-2-carbonyl)amino]-L-alanine, methyl ester (1.09 g, 42%) as a white solid, and N-[2,6-dichloro-4-[[[(3-hydroxyphenyl)methyl]amino]carbonyl]benzoyl]-3-[(thiophene-2-carbonyl)amino]-L-alanine, methyl ester (510 mg, 23%) as a white solid.

B. N-[2,6-Dichloro-4-[[[(3-hydroxyphenyl)methyl]amino]carbonyl]benzoyl]-3-[(thiophene-2-carbonyl)amino]-L-alanine, methyl ester Tetra-n-butylammonium fluoride (1 M in tetrahydrofuran; 3.94 mL, 3.94 mmol) was added to a solution of N-[2,6-dichloro-4-[[[[3-[[(1,1-dimethylethyl)dimethylsilyl]oxy]phenyl]methyl]amino]carbonyl]benzoyl]-3-[(thiophene-2-carbonyl)amino]-L-alanine (2.38 g, 3.6 mmol) in tetrahydrofuran (30 mL). The solution was stirred at room temperature for 3 h, then diluted with ethyl acetate and concentrated. The residue was chromatographed (50–100% ethyl acetate/hexanes then 10% methanol/ethyl acetate) to give N-[2,6-dichloro-4-[[[(3-hydroxyphenyl)methyl]amino]carbonyl]benzoyl]-3-[(thiophene-2-carbonyl)amino]-L-alanine, methyl ester (1.68 g, 85%) as a white solid.

C. N-[2,6-Dichloro-4-[[[(3-hydroxyphenyl)methyl]amino]carbonyl]benzoyl]-3-[(thiophene-2-carbonyl)amino]-L-alanine A mixture of N-[2,6-dichloro-4-[[[(3-hydroxyphenyl)methyl]amino]carbonyl]benzoyl]-3-[(thiophene-2-carbonyl)amino]-L-alanine, methyl ester (2.41 g, 4.4 mmol) in methanol (100 mL) and sodium hydroxide (0.35 g, 8.8 mmol) in water (2 mL) was stirred at room temperature overnight and then the solvents were evaporated. The residue was partitioned between water and ethyl acetate and the ethyl acetate layer was discarded. The aqueous layer was acidified with 1 M HCl, and extracted twice with ethyl acetate. The combined organic extracts were washed with brine, and the product started to precipitate. The solvents were evaporated from the organic layer, and dichloromethane/hexanes was added to the residue. The solid was filtered off, dried overnight under high vacuum, and taken up again in dichloromethane/hexanes. The solid was filtered off, and then dried overnight under high vacuum to give N-[2,6-dichloro-4-[[[(3-hydroxyphenyl)methyl]amino]carbonyl]benzoyl]-3-[(thiophene-2-carbonyl)amino]-L-alanine (2.10 g, 89%) as a white solid.

Example 343

Preparation of N-[2,6-dichloro-4-[[[(3-hydroxyphenyl)methyl]amino]carbonyl]benzoyl]-3-[(thiophene-3-carbonyl)amino]-L-alanine

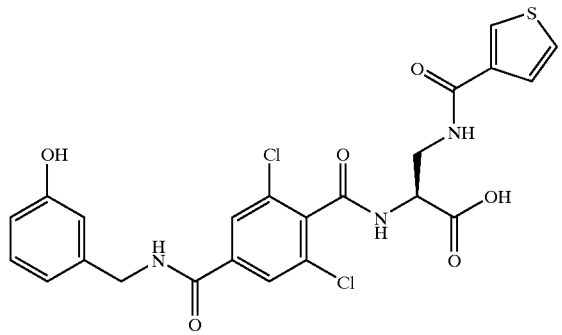

A. N-[2,6-Dichloro-4-[[[3-[(thiophene-3-carbonyl)oxy]phenyl]methyl]amino]carbonyl]benzoyl]-3-[(thiophene-3-carbonyl)amino]-L-alanine, methyl ester and N-[2,6-dichloro-4-[[[(3-hydroxyphenyl)methyl]amino]carbonyl]benzoyl]-3-[(thiophene-3-carbonyl)amino]-L-alanine, methyl ester Diisopropylethylamine (0.274 mL, 1.57 mmol) was added to a solution of 3-amino-N-[2,6-dichloro-4-[[[(3-hydroxyphenyl)methyl]amino]carbonyl]benzoyl]-L-alanine, methyl ester hydrochloride (Example 75; 150 mg, 0.315 mmol), thiophene-3-carboxylic acid (85 mg, 0.66 mmol), HOBT (89 mg, 0.66 mmol), and HBTU (251 mg, 0.66 mmol) in N,N-dimethylformamide (2 mL). The reaction mixture was allowed to stir at room temperature overnight. Tlc indicated that the reaction was not complete so a further equivalent each of thiophene-3-carboxylic acid, HOBT, and HBTU, and 2 equivalents of diisopropylethylamine were added and the reaction was allowed to stir overnight. The solvent was evaporated. Ethyl acetate was added and the solution was washed with 1 M HCl, brine, saturated aqueous sodium hydrogen carbonate, and brine. The solution was dried (MgSO₄), filtered, evaporated and chromatographed (40–60% ethyl acetate/petroleum ether) to give N-[2,6-dichloro-4-[[[3-[(thiophene-3-carbonyl)oxy]phenyl]methyl]amino]carbonyl]benzoyl]-3-[(thiophene-3-carbonyl)amino]-L-alanine, methyl ester (101 mg, 49%) and N-[2,6-dichloro-4-[[[(3-hydroxyphenyl)methyl]amino]carbonyl]benzoyl]-3-[(thiophene-3-carbonyl)amino]-L-alanine, methyl ester (58 mg, 33%).

B. N-[2,6-Dichloro-4-[[[(3-hydroxyphenyl)methyl]amino]carbonyl]benzoyl]-3-[(thiophene-3-carbonyl)amino]-L-alanine An aqueous solution of sodium hydroxide (1 M; 0.305 mL, 0.305 mmol) was added to a solution of N-[2,6-dichloro-4-[[[3-[(thiophene-3-carbonyl)oxy]phenyl]methyl]amino]carbonyl]benzoyl]-3-[(thiophene-3-carbonyl)amino]-L-alanine, methyl ester (101 mg, 0.153 mmol) in methanol (2 mL). The solution was allowed to stir overnight and then concentrated. An aqueous solution of sodium hydroxide (1 M; 0.210 mL, 0.210 mmol) was added to a solution of N-[2,6-dichloro-4-[[[(3-hydroxyphenyl)methyl]amino]carbonyl]-benzoyl]-3-[(thiophene-3-carbonyl)amino]-L-alanine, methyl ester (58 mg, 0.105 mmol) in methanol (2 mL). The solution was allowed to stir overnight and then concentrated. The residues from the two reactions were purified by HPLC and lyophilized to give N-[2,6-dichloro-4-[[[(3-hydroxyphenyl)methyl]amino]carbonyl]-benzoyl]-3-[(thiophene-3-carbonyl)amino]-L-alanine (107 mg, 78%) as a white solid.

Example 344

Preparation of N-[2,6-dichloro-4-[[[(3-hydroxyphenyl)methyl]amino]carbonyl]benzoyl]-3-[(3,5-difluorobenzoyl)amino]-L-alanine

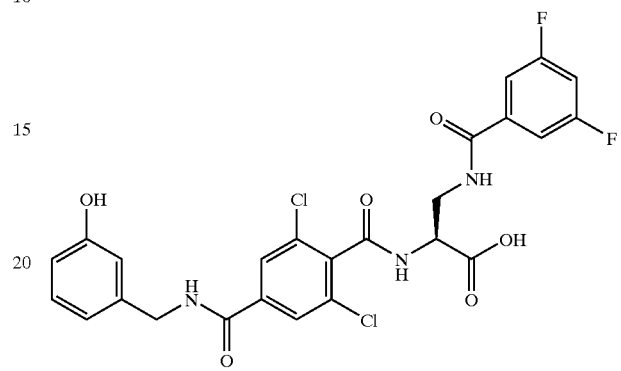

A. N-[2,6-Dichloro-4-[[[3-[(3,5-difluorobenzoyl)oxy]phenyl]methyl]amino]carbonyl]benzoyl]-3-[(3,5-difluorobenzoyl)amino]-L-alanine, methyl ester and N-[2,6-dichloro-4-[[[(3-hydroxyphenyl)methyl]amino]carbonyl]benzoyl]-3-[(3,5-difluorobenzoyl)amino]-L-alanine, methyl ester Diisopropylethylamine (0.343 mL, 1.97 mmol) was added to a cooled (~0° C.) solution of 3-amino-N-[2,6-dichloro-4-[[[(3-hydroxyphenyl)methyl]amino]-carbonyl]benzoyl]-L-alanine, methyl ester hydrochloride (Example 75; 188 mg, 0.394 mmol), 3,5-difluorobenzoic acid (137 mg, 0.87 mmol), HOBT (117 mg, 0.87 mmol), and HBTU (328 mg, 0.86 mmol) in N,N-dimethylformamide (3.5 mL). The cooling bath was removed and the reaction mixture was allowed to stir at room temperature overnight. The solvent was evaporated. Ethyl acetate (100 mL) was added and the solution was washed with 1 M HCl, saturated aqueous sodium hydrogen carbonate, and brine (25 mL each). The solution was dried (MgSO₄), filtered, evaporated and chromatographed (40–60% ethyl acetate/petroleum ether) to give N-[2,6-dichloro-4-[[[3-[(3,5-difluorobenzoyl)oxy]phenyl]methyl]-amino]carbonyl]benzoyl]-3-[(3,5-difluorobenzoyl)amino]-L-alanine, methyl ester (54.8 mg, 19%) and N-[2,6-dichloro-4-[[[(3-hydroxyphenyl)methyl]amino]carbonyl]benzoyl]-3-[(3,5-difluorobenzoyl)amino]-L-alanine, methyl ester (121 mg, 53%).

B. N-[2,6-Dichloro-4-[[[(3-hydroxyphenyl)methyl]amino]carbonyl]benzoyl]-3-[(3,5-difluorobenzoyl)amino]-L-alanine An aqueous solution of sodium hydroxide (1 M; 0.386 mL, 0.386 mmol) was added to a solution of N-[2,6-dichloro-4-[[[(3-hydroxyphenyl]methyl]amino]-carbonyl]benzoyl]-3-[(3,5-difluorobenzoyl)amino]-L-alanine, methyl ester (112 mg, 0.193 mmol) in methanol (2 mL). The solution was allowed to stir overnight and then concentrated. The residue was purified by HPLC and lyophilized to give N-[2,6-dichloro-4-[[[(3-hydroxyphenyl)methyl]amino]carbonyl]benzoyl]-3-[(3,5-difluorobenzoyl)amino]-L-alanine (43 mg, 39%) as a white solid.

Example 345

Preparation of N-[2,6-dichloro-4-[[[(3-hydroxyphenyl)methyl]amino]carbonyl]benzoyl]-3-(3,5-dihydroxybenzoylamino)-L-alanine

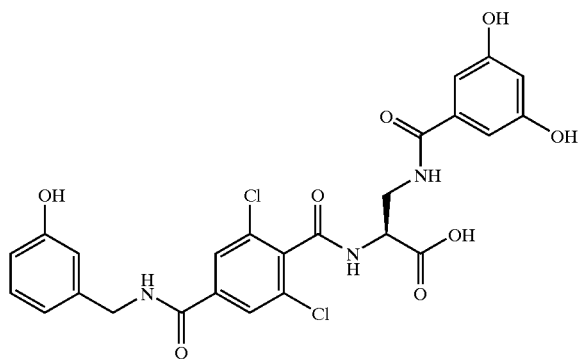

A. 3,5-Bis[(tetrahydro-2H-pyran-2-yl)oxy]benzoic acid

A mixture of methyl 3,5-dihydroxybenzoate (10.00 g, 59.5 mmol), 3,4-dihydro-2H-pyran (15.00 g, 178.3 mmol), and pyridinium p-toluenesulfonate (1.50 g, 6.0 mmol) in dichloromethane/tetrahydrofuran (1:1; 60 mL) was stirred at room temperature overnight. The solution was washed with 0.5 M sodium hydroxide solution (200 mL) and the aqueous wash was back-extracted with dichloromethane (200 mL). The combined organic layers were washed with brine (200 mL), dried (MgSO$_4$), filtered, and evaporated to give crude 3,5-bis[(tetrahydro-2H-pyran-2-yl)oxy]benzoic acid, methyl ester (19.53 g) as a yellow oil. Tetrahydrofuran (100 mL) was added, followed by a solution of sodium hydroxide (3.00 g, 75 mmol) in water (100 mL). The mixture was stirred at room temperature overnight and the solvent was evaporated. Ethyl acetate (200 mL) was added. The solution was washed with 0.5 M HCl (200 mL) and the aqueous wash was back-extracted with ethyl acetate (100 mL). The combined organic layers were washed with brine (200 mL), dried (MgSO$_4$), filtered, and evaporated to give 3,5-bis[(tetrahydro-2H-pyran-2-yl)oxy]benzoic acid (15.62 g, 84%) as a pale yellow solid.

B. 1-[[3,5-Bis[(tetrahydro-2H-pyran-2-yl)oxy]benzoyl]oxy]-2,5-pyrrolidinedione

A mixture of 3,5-bis[(tetrahydro-2H-pyran-2-yl)oxy]benzoic acid (5.00 g, 15.5 mmol), 1,3-dicyclohexylcarbodiimide (3.72 g, 18.1 mmol) and N-hydroxysuccinimide (2.08 g, 18.0 mmol) in tetrahydrofuran (100 mL) was stirred at room temperature for 40 h. Ether (100 mL) was added and the mixture was stirred for 20 min. The white solid was filtered off and discarded. The solvent was evaporated from the filtrate, and the residue was coated onto silica gel and chromatographed (50–75% ethyl acetate/hexanes) to give 1-[[3,5-bis[(tetrahydro-2H-pyran-2-yl)oxy]benzoyl]oxy]-2,5-pyrrolidinedione (5.84 g, 90%) as a white solid.

C. 3-[[3,5-Bis[(tetrahydro-2H-pyran-2-yl)oxy]benzoyl]amino]-N-[2,6-dichloro-4-[[[(3-hydroxyphenyl)methyl]amino]carbonyl]benzoyl]-L-alanine, methyl ester A solution of 1-[[3,5-bis[(tetrahydro-2H-pyran-2-yl)oxy]benzoyl]oxy]-2,5-pyrrolidinedione (2.10 g, 5.0 mmol), 3-amino-N-[2,6-dichloro-4-[[[(3-hydroxyphenyl)methyl]amino]carbonyl]benzoyl]-L-alanine, methyl ester hydrochloride (Example 75; 2.00 g, 4.2 mmol), and triethylamine (500 mg, 4.9 mmol) in N,N-dimethylformamide (20 mL) was stirred at room temperature overnight. The solvent was evaporated and ethyl acetate (125 mmol) was added. The solution was washed with 0.2 M HCl (125 mL) and the aqueous wash was back-extracted with ethyl acetate (100 mL). The combined organic layers were washed with saturated aqueous sodium hydrogen carbonate and brine (30 mL each), evaporated, and chromatographed (50–100% ethyl acetate/hexanes) to give 3-[[3,5-bis[(tetrahydro-2H-pyran-2-yl)oxy]benzoyl]amino]-N-[2,6-dichloro-4-[[[(3-hydroxyphenyl)methyl]amino]-carbonyl]benzoyl]-L-alanine, methyl ester (1.61 g, 52%) as a white foam.

D. N-[2,6-Dichloro-4-[[[(3-hydroxyphenyl)methyl]amino]carbonyl]benzoyl]-3-(3,5-dihydroxybenzoylamino)-L-alanine, methyl ester A solution of HCl in methanol was prepared by adding acetyl chloride (10 mL) to methanol at approx. 0° C. The solution was allowed to stir for 10 min and then it was added to 3-[[3,5-bis[(tetrahydro-2H-pyran-2-yl)oxy]benzoyl]amino]-N-[2,6-dichloro-4-[[[(3-hydroxyphenyl)methyl]amino]carbonyl]benzoyl]-L-alanine, methyl ester (1.60 g, 2.1 mmol). The resulting solution was allowed to stir overnight at room temperature and then the volatiles were evaporated to give N-[2,6-dichloro-4-[[[(3-hydroxyphenyl)methyl]amino]carbonyl]benzoyl]-3-(3,5-dihydroxybenzoylamino)-L-alanine, methyl ester (1.26 g, quantitative yield) as an off-white solid.

E. N-[2,6-Dichloro-4-[[[(3-hydroxyphenyl)methyl]amino]carbonyl]benzoyl]-3-(3,5-dihydroxybenzoylamino)-L-alanine A solution of lithium hydroxide monohydrate (160 mg, 3.8 mmol) in water (10 mL) was added to a solution of N-[2,6-dichloro-4-[[[(3-hydroxyphenyl)methyl]amino]-carbonyl]benzoyl]-3-(3,5-dihydroxybenzoylamino)-L-alanine, methyl ester (490 mg, 0.85 mmol) in tetrahydrofuran/methanol (3:1; 40 mL). The solution was stirred at room temperature overnight and then the solvent was evaporated. Tetrahydrofuran and water (75 mL each) were added followed by 1 M HCl (10 mL). The cloudy white solution was heated at approx. 50° C. for 10 min and then allowed to stand overnight at room temperature. The solvents were evaporated and the residue was dissolved in methanol/water (1:4; 60 mL) and purified by HPLC in 10 mL portions. Fractions homogeneous for the product were pooled and lyophilized to give N-[2,6-dichloro-4-[[[(3-hydroxyphenyl)methyl]amino]carbonyl]benzoyl]-3-(3,5-dihydroxybenzoylamino)-L-alanine (308.5 mg, 65%) as a white solid.

Example 346

Preparation of N-[2,6-dichloro-4-[[[(1R)-1-(1-naphthalenyl)ethyl]amino]carbonyl]benzoyl]-3-[(thiophene-2-carbonyl)amino]-L-alanine

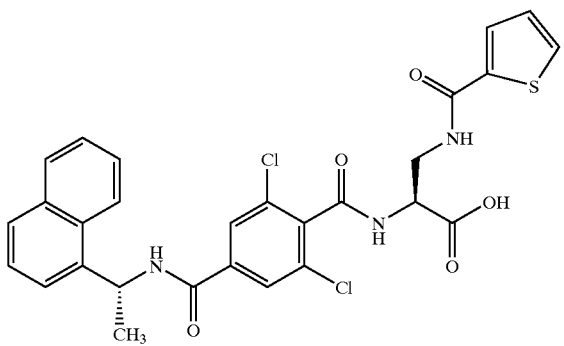

A. N-[2,6-Dichloro-4-[[[(1R)-1-(1-naphthalenyl)ethyl]amino]carbonyl]benzoyl]-3-[(thiophene-2-carbonyl)amino]-L-alanine, methyl ester A solution of 2,6-dichloro-4-[[[(1R)-1-(1-naphthalenyl)ethyl]amino]carbonyl]benzoic acid (Example 38; 1.00 g, 2.6 mmol), 3-(thiophene-2-carbonyl)amino-L-alanine, methyl ester hydrochloride (Example 301; 680 mg, 2.6 mmol), HBTU (1.27 g, 3.35 mmol), HOBT (450 mg, 3.3 mmol), and diisopropylethylamine (1.33 g, 10.3 mmol) in N,N-dimethylformamide (20 mL) was stirred at room temperature over the weekend. The solvent was evaporated and ethyl acetate (200 mL) was added. The solution was washed with 1 M HCl (100 mL), saturated aqueous sodium hydrogen carbonate (Note: some material was lost due to effervescence at this stage) and brine (200 mL each), then dried (MgSO$_4$), filtered, evaporated and chromatographed (70% ethyl acetate/hexanes) to give N-[2,6-dichloro-4-[[[(1R)-1-(1-naphthalenyl)ethyl]amino]carbonyl]benzoyl]-3-[(thiophene-2-carbonyl)amino]-L-alanine, methyl ester (260 mg, 17%) as a white solid.

B. N-[2,6-Dichloro-4-[[[(1R)-1-(1-naphthalenyl)ethyl]amino]carbonyl]benzoyl]-3-[(thiophene-2-carbonyl)amino]-L-alanine A solution of lithium hydroxide monohydrate (100 mg, 2.38 mmol) in water (5 mL) was added to a solution of N-[2,6-dichloro-4-[[[(1R)-1-(1-naphthalenyl)ethyl]amino]carbonyl]benzoyl]-3-[(thiophene-2-carbonyl)amino]-L-alanine, methyl ester (260 mg, 0.434 mmol) in tetrahydrofuran (15 mL) and methanol (5 mL), and the resulting mixture was stirred at room temperature overnight. The solution was evaporated, and the residue was partitioned between ethyl acetate (40 mL) and 1M HCl (10 mL). The organic layer was evaporated and the residue was dissolved in methanol (~1 mL), purified by HPLC, and lyophilized to give N-[2,6-dichloro-4-[[[(1R)-1-(1-naphthalenyl)ethyl]amino]carbonyl]benzoyl]-3-[(thiophene-2-carbonyl)amino]-L-alanine (170 mg, 67%).

Also prepared by this route was the following:

Example 348

Preparation of 3-[(3-chlorobenzoyl)amino]-N-[2,6-dichloro-4-[[[(3-hydroxyphenyl)methyl]amino]carbonyl]benzoyl]-L-alanine

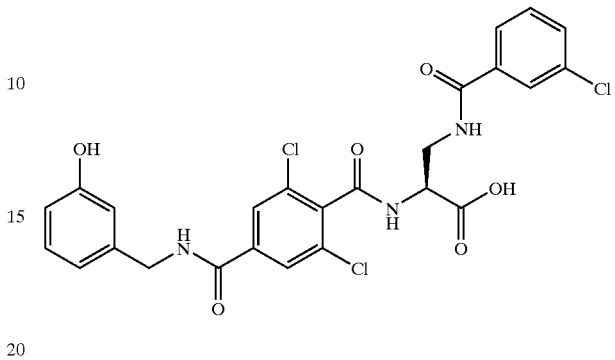

Diisopropylethylamine (220 mg, 1.7 mmol) was added to a cooled (~0° C.) solution of 3-amino-N-[2,6-dichloro-4-[[[(3-hydroxyphenyl)methyl]amino]carbonyl]benzoyl]-L-alanine, methyl ester hydrochloride (Example 75; 135 mg, 0.28 mmol), 3-chlorobenzoic acid (53 mg, 0.34 mmol), HBTU (136 mg, 0.36 mmol), and HOBT (49 mg, 0.36 mmol) in N,N-dimethylformamide (2 mL). The solution was allowed to stir at room temperature for 4 days, and then the solvent was evaporated. Ethyl acetate (50 mL) was added, and the solution was washed with 1 M HCl, saturated aqueous sodium hydrogen carbonate, and brine (10 mL each), and evaporated.

Tetrahydrofuran/methanol (3:1; 4 mL) was added, followed by 10% aqueous lithium hydroxide monohydrate (1 mL, 2.38 mmol). The solution was stirred at room temperature overnight, then the solvent was evaporated and the residue

| Example | Structure | Starting Materials | Yield |
|---|---|---|---|
| 347 | | Example 38 and Example 300 | 20% | was partitioned between ethyl acetate (30 mL) and 1 M HCl (10 mL). The ethyl acetate layer was evaporated and the residue was dissolved in methanol (~1 mL), purified by HPLC, and lyophilized to give 3-[(3-chlorobenzoyl)amino]-N-[2,6-dichloro-4-[[[(3-hydroxyphenyl)methyl]amino] carbonyl]benzoyl]-L-alanine (81.1 mg, 51%) as a white solid.

The following compounds were also prepared by this route, by reacting 3-amino-N-[2,6-dichloro-4-[[[(3-hydroxyphenyl)methyl]amino]carbonyl]benzoyl]-L-alanine, methyl ester hydrochloride (Example 75) with the carboxylic acids indicated:

| Example | Structure | Carboxylic Acid | Yield |
|---|---|---|---|
| 349 | 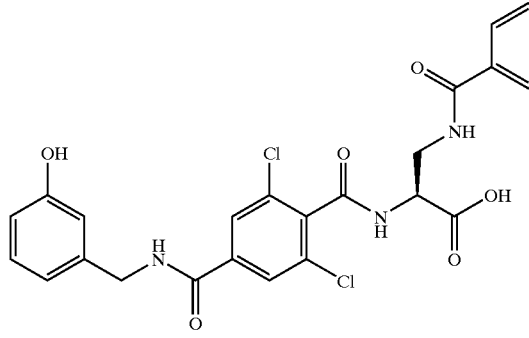 | 3-fluorobenzoic acid | 52% |
| 350 | 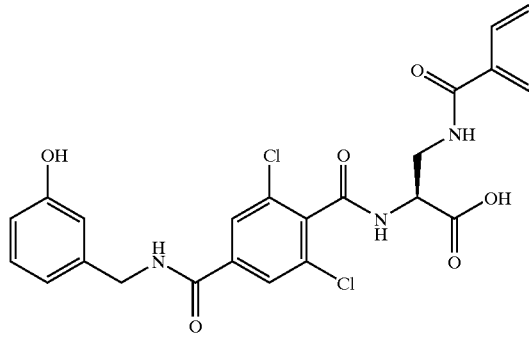 | 3-hydroxybenzoic acid | 52% |
| 351 | 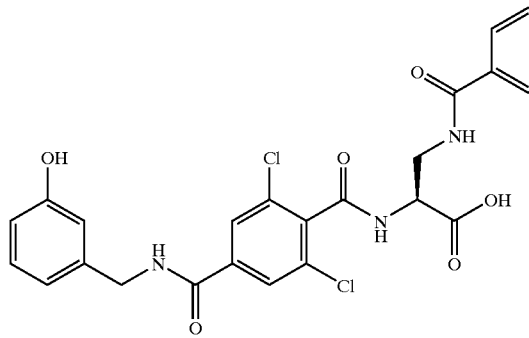 | 3-hydroxy-4-methoxybenzoic acid | 49% |
| 352 | 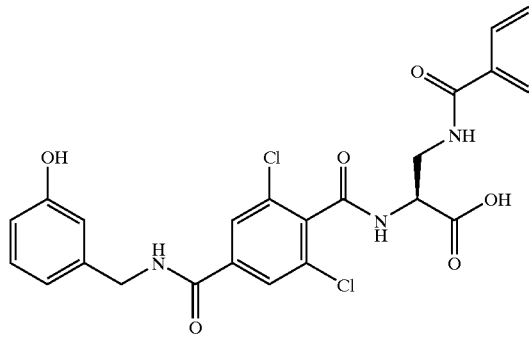 | m-toluic acid | 55% |

| Example | Structure | Carboxylic Acid | Yield |
|---|---|---|---|
| 353 | 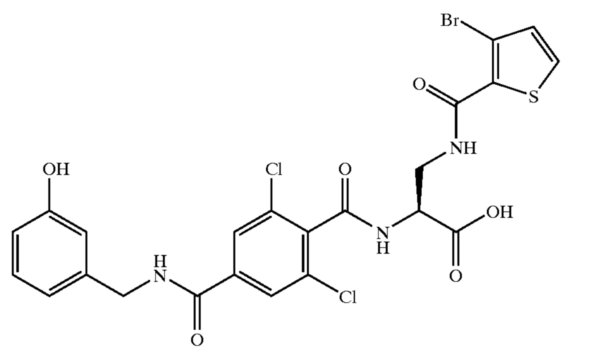 | 3-bromothiophene-2-carboxylic acid | 28% |
| 354 | 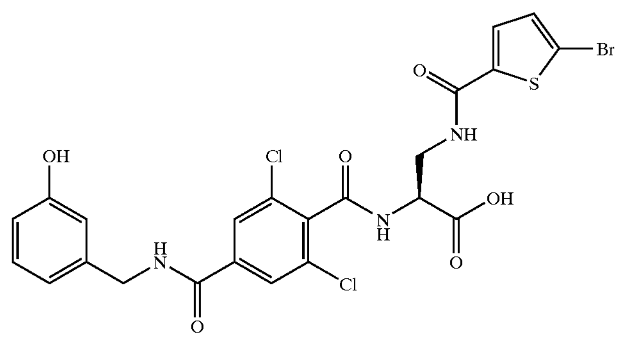 | 5-bromothiophene-2-carboxylic acid | 47% |
| 355 | 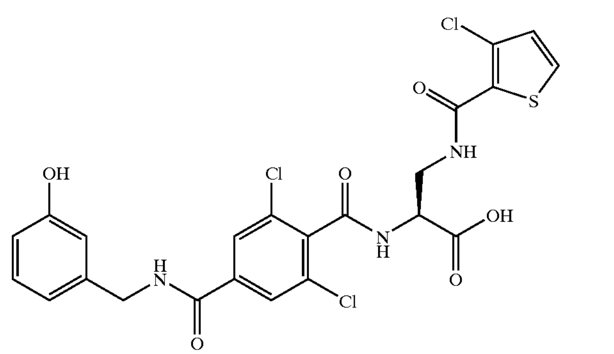 | 3-chlorothiophene-2-carboxylic acid | 41% |
| 356 | 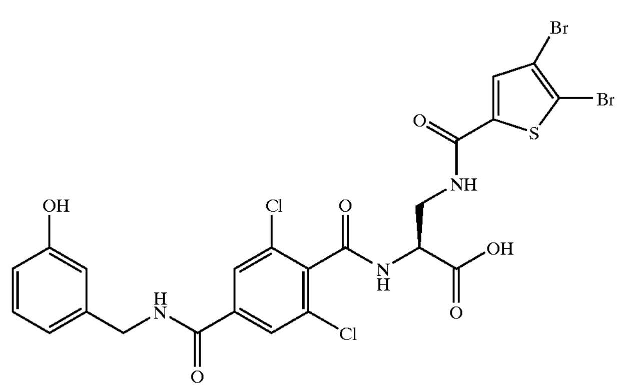 | 4,5-dibromothiophene-2-carboxylic acid | 29% |

| Example | Structure | Carboxylic Acid | Yield |
|---|---|---|---|
| 357 | 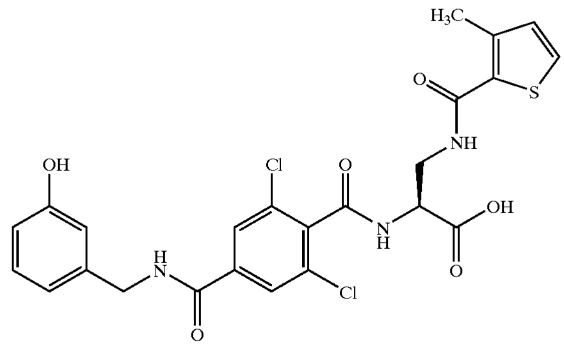 | 3-methylthiophene-2-carboxylic acid | 42% |
| 358 | 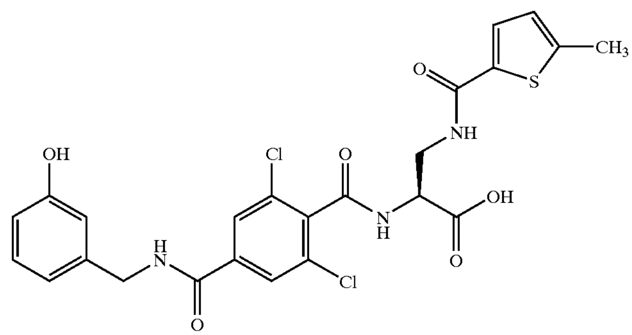 | 5-methylthiophene-2-carboxylic acid | 49% |

Example 359

Preparation of 3-(phenylmethyl)amino-N-[2-chloro-4-[[(1H-indol-4-ylmethyl)amino]carbonyl]benzoyl]-L-alanine To 3-amino-N-[2-chloro-4-[[[(3-hydroxyphenyl)methyl]amino]carbonyl]benzoyl]-L-alanine-substituted Wang resin (Example 66; 1.00 g) was added a solution of benzaldehyde (1.16 g, 10.9 mmol) and benzotriazole (0.20 g, 1.7 mmol) in tetrahydrofuran/trimethyl orthoformate (1:1; 10 mL). The mixture was agitated at room temperature for 18 h and then twice washed briefly with dichloromethane. 100 mg of this resin was treated with a solution of sodium cyanoborohydride (80 mg, 1.3 mmol) in acetic acid/N,N-dimethylacetamide (9:1; 1 mL), and the mixture was agitated at room temperature for 5 h. The resin was filtered and washed extensively with dichloromethane and methanol. Cleavage of the product was effected with trifluoroacetic acid/dichloromethane (1:1; 1 mL) at room temperature for 30 min. The solvent was evaporated and the residue was purified by HPLC to give 3-(phenylmethyl)amino-N-[2-chloro-4-[[(1H-indol-4-ylmethyl)amino]carbonyl]benzoyl]-L-alanine (15 mg).

Example 360

Preparation of 3-(phenylsulfonylamino)-N-[2-chloro-4-[[[(3-hydroxyphenyl)methyl]amino]carbonyl]benzoyl]-L-alanine 3-Amino-N-[2-chloro-4-[[[(3-hydroxyphenyl)methyl]amino]carbonyl]benzoyl]-L-alanine-substituted Wang resin (Example 66; 100 mg, 1.1 mmol/g) was slurried in pyridine (1 mL), and benzenesulfonyl chloride (0.12 g, 0.67 mmol) was added. The mixture was agitated at room temperature for 1 h. The resin was then filtered and washed extensively with dichloromethane and methanol. Cleavage of the product was effected with 50% trifluoroacetic acid in dichloromethane for 30 min. The cleavage solution was collected by filtration and the solvent was evaporated under high vacuum. The compound was purified by reverse phase HPLC to give 3-(phenylsulfonylamino)-N-[2-chloro-4-[[[(3-hydroxyphenyl)methyl]amino]carbonyl]benzoyl]-L-alanine.

Example 361

Preparation of 3-(1-butanesulfonylamino)-N-[2-chloro-4-[[[(1R)-1-(1-naphthalenyl)ethyl]amino]carbonyl]benzoyl]-L-alanine.

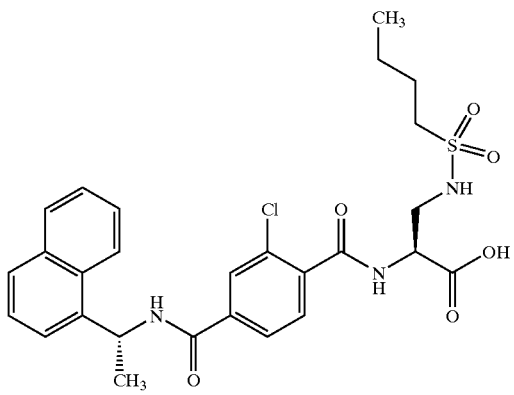

3-Amino-N-[2-chloro-4-[[[(1R)-1-(1-naphthalenyl)ethyl]amino]carbonyl]benzoyl]-L-alanine-substituted Wang resin (Example 70; 100 mg, 1.1 mmol/g) was slurried in pyridine (1 mL), and 1-butanesulfonyl chloride (0.10 g, 0.66 mmol) was added. The mixture was agitated at room temperature for 1 h. The resin was then filtered and washed extensively with dichloromethane and methanol. Cleavage of the product was effected with 50% trifluoroacetic acid in dichloromethane for 30 min. The cleavage solution was collected by filtration and the solvent was evaporated under high vacuum. Purification by reverse phase HPLC gave 3-(1-butane-sulfonylamino)-N-[2-chloro-4-[[[(1R)-1-(1-naphthalenyl)ethyl]amino]carbonyl]benzoyl]-L-alanine.

Also prepared by this route was the following:

Example 363

Preparation of N-[4-(aminomethyl)-2-chlorobenzoyl]-3-(benzoyl)amino-L-alanine, methyl ester

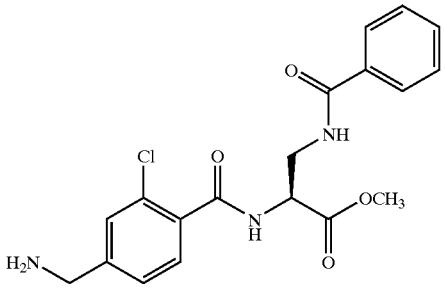

A. 2-Chloro-4-(hydroxymethyl)benzoic acid, methyl ester

Borane-methyl sulfide complex (10 M; 10 mL, 100 mmol) was added to a solution of 2-chloro-1,4-benzenedicarboxylic acid, 1-methyl ester (Example 1; 11.98 g, 55.8 mmol) in tetrahydrofuran (100 mL). The solution was heated at reflux for 2 h and then allowed to stand at room temperature overnight. It was poured into water and ethyl acetate (200 mL each). The layers were separated and the aqueous layer was extracted with ethyl acetate (100 mL). The combined organic layers were washed with brine (200 mL), dried (MgSO$_4$), filtered, and evaporated to give 2-chloro-4-(hydroxymethyl)benzoic acid, methyl ester (11.09 g, 99%) as a colorless oil.

B. 4-(Azidomethyl)-2-chlorobenzoic acid, methyl ester

A solution of 2-chloro-4-(hydroxymethyl)benzoic acid, methyl ester (11.09 g, 55.3 mmol), diphenylphosphoryl azide (22.58 g, 82.0 mmol) and 1,8-diazabicyclo[5.4.0]undec-7-ene (8.57 g, 56.3 mmol) in tetrahydrofuran was stirred overnight at room temperature. Silica gel was added and the solvent was evaporated. The residue was chromatographed (10% ethyl acetate/hexanes) to give 4-(azidomethyl)-2-chlorobenzoic acid, methyl ester (12.17 g, 98%) as a white solid.

C. 4-(Azidomethyl)-2-chlorobenzoic acid

A solution of lithium hydroxide monohydrate (7.00 g, 166.8 mmol) in water (100 mL) was added to a solution of

| Example | Structure | Starting materials |
|---|---|---|
| 362 | 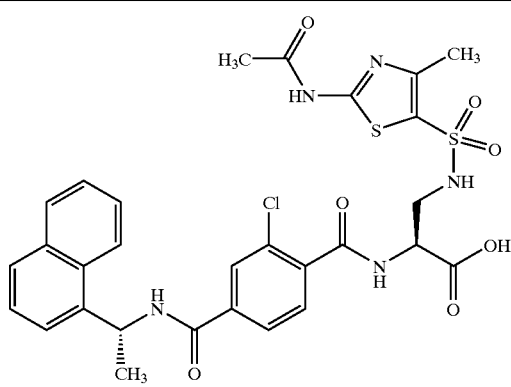 | Example 70 and 2-acetamido-4-methyl-5-thiazolesulfonyl chloride |

4-(azidomethyl)-2-chlorobenzoic acid, methyl ester (12.17 g, 53.9 mmol) in tetrahydrofuran (100 mL) and the resulting solution was stirred at room temperature overnight. The reaction mixture was concentrated to remove some of the tetrahydrofuran. The solution was extracted with ethyl acetate (200 mL) and the extract was discarded. Then 1 M HCl (100 mL) was added and the mixture was extracted with ethyl acetate (2×200 mL). The combined organic layers were dried (MgSO$_4$), filtered, and evaporated to give 4-(azidomethyl)-2-chlorobenzoic acid (6.82 g, 60%) as a white solid, mp 87–88° C.

D. 1-[[4-(Azidomethyl)-2-chlorobenzoyl]oxy]-2,5-pyrrolidinedione

A solution of 4-(azidomethyl)-2-chlorobenzoic acid (6.82 g, 32.2 mmol), N-hydroxysuccinimide (5.19 g, 45.1 mmol) and dicyclohexylcarbodiimide (9.31 g, 45.1 mmol) in tetrahydrofuran (250 mL) was stirred overnight at room temperature. The dicyclohexylurea (7.70 g, 76%) was filtered off and discarded. Silica gel was added, the solvent was evaporated and the residue was chromatographed (40–60% ethyl acetate/hexanes) to give 1-[[4-(azidomethyl)-2-chlorobenzoyl]oxy]-2,5-pyrrolidinedione (9.64 g, 97%) as a white solid.

E. N-[4-(Azidomethyl)-2-chlorobenzoyl]-3-(benzoyl)amino-L-alanine, methyl ester

A solution of 1-[[4-(azidomethyl)-2-chlorobenzoyl]oxy]-2,5-pyrrolidinedione (4.64 g, 15.0 mmol), 3-(benzoyl)amino-L-alanine, methyl ester hydrochloride (4.00 g, 15.5 mmol), and triethylamine (4.00 g, 39.5 mmol) in N,N-dimethylformamide (50 mL) was stirred at room temperature for 3 h. The solvent was evaporated, and 1 M HCl (100 mL) was added. The mixture was extracted with ethyl acetate (2×100 mL), washed with brine (100 mL), dried (MgSO$_4$), filtered, evaporated, and chromatographed (50–75% ethyl acetate/hexanes) to give N-[4-(azidomethyl)-2-chlorobenzoyl]-3-(benzoyl)amino-L-alanine, methyl ester (4.34 g, 69%) as a colorless oil that solidified on standing, mp 112–114° C.

F. N-[4-(Aminomethyl)-2-chlorobenzoyl]-3-(benzoyl)amino-L-alanine, methyl ester

A mixture of N-[4-(azidomethyl)-2-chlorobenzoyl]-3-(benzoylamino)-L-alanine, methyl ester (4.34 g, 10.4 mmol) and 10% palladium on carbon (0.20 g, 0.2 mmol) in ethanol (200 mL) was hydrogenated at atmospheric pressure for 1 h. The mixture was filtered through Celite and the filter cake was washed with ethanol (100 mL). The combined filtrates were evaporated to give N-[4-(aminomethyl)-2-chlorobenzoyl]-3-benzoylamino-L-alanine, methyl ester (3.65 g, 90%) as a colorless foam.

Example 364

Preparation of N-[2-chloro-4-[[(3-hydroxyphenyl)carbonyl]aminomethyl]benzoyl]-3-benzoylamino-L-alanine

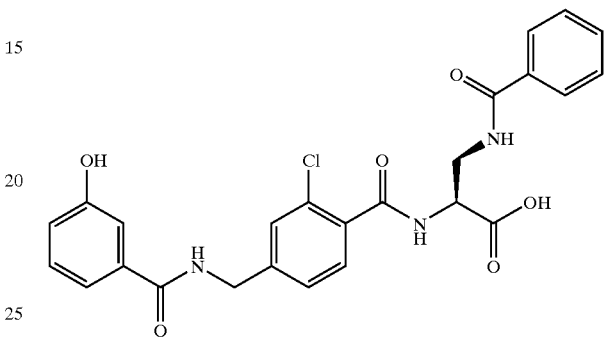

A mixture of N-[4-(aminomethyl)-2-chlorobenzoyl]-3-benzoylamino-L-alanine (Example 363; 100 mg, 0.26 mmol), 3-hydroxybenzoic acid (40 mg, 0.29 mmol) and dicyclohexylcarbodiimide (60 mg, 0.29 mmol) in tetrahydrofuran/DMF (4:1; 2.5 mL) was stirred at room temperature overnight. Methanol (1 mL) and a solution of lithium hydroxide monohydrate (100 mg, 2.4 mmol) in water (1 mL) were added and the solution was stirred at room temperature overnight. The solution was made acidic with 1 M HCl and extracted with ethyl acetate. The ethyl acetate was evaporated and the residue purified by HPLC to give N-[2-chloro-4-[[(3-hydroxyphenyl)carbonyl]aminomethyl]benzoyl]-3-benzoylamino-L-alanine (12.2 mg, 9%) as a white solid.

Also prepared by this route were:

| Example | Structure | Starting materials | Yield |
|---|---|---|---|
| 365 | 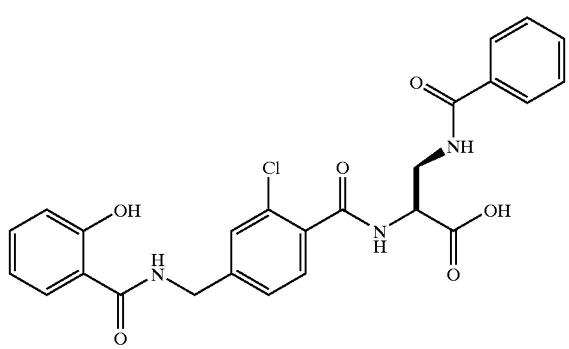 | Example 363 and salicylic acid | 4% |

-continued

| Example | Structure | Starting materials | Yield |
|---------|-----------|--------------------|-------|
| 366 | 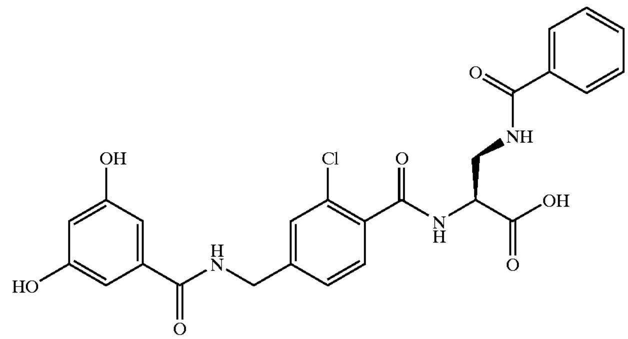 | Example 363 and 3,5-dihydroxybenzoic acid | 18% |
| 367 | 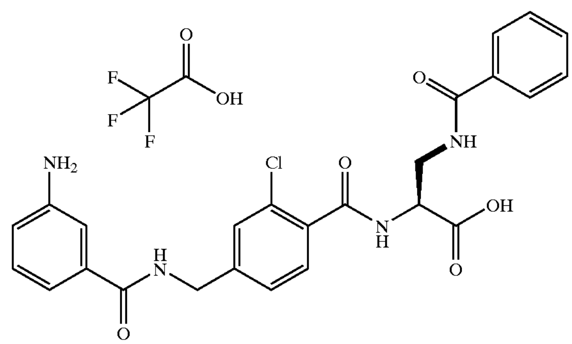 | Example 363 and 3-aminobenzoic acid | 16% |
| 368 | 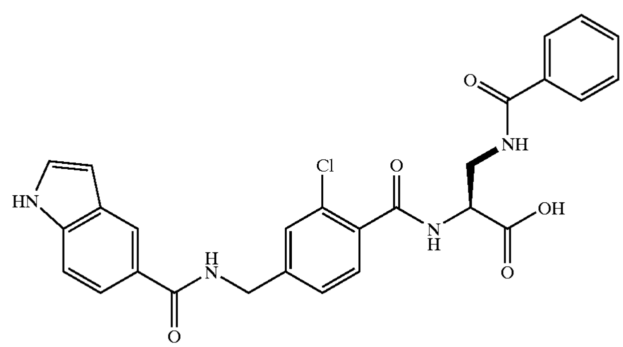 | Example 363 and indole 5-carboxylic acid | 16% |
| 369 | 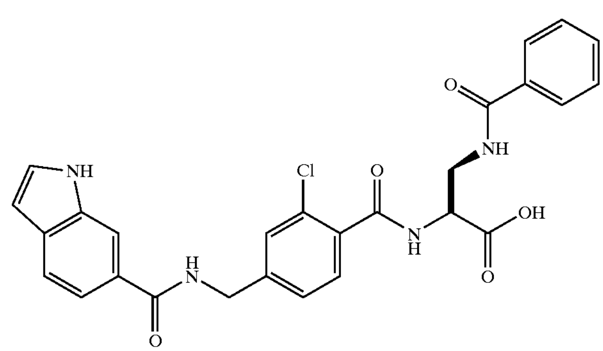 | Example 363 and indole 6-carboxylic acid | 8% |

-continued

| Example | Structure | Starting materials | Yield |
|---|---|---|---|
| 370 | 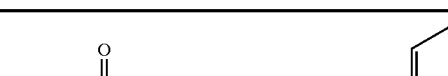 | Example 363 and quinoline-3-carboxylic acid | 18% |

Example 371

Preparation of N-[2-chloro-4-[[[(3-hydroxyphenyl)methyl]amino]carbonyl]benzoyl]-3-(aminoiminomethyl)amino-L-alanine

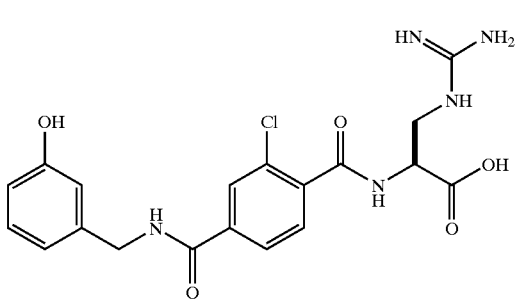

To a solution of 3-amino-N-[2-chloro-4-[[[(3-hydroxyphenyl)methyl]amino]carbonyl]benzoyl]-L-alanine, methyl ester (Example 72; 50 mg, 0.123 mmol) in methanol (2 mL) were added triethylamine (3 drops) and aminoiminomethanesulfonic acid (prepared according to Kim, K. et al. *Tetrahedron Lett.* 1988, 29, 3183–3186; 37 mg, 0.30 mmol). The reaction was stirred at room temperature overnight, and then the solvent was evaporated. The residue was suspended in tetrahydrofuran/methanol/water (3:1:1; 2 mL) and lithium hydroxide monohydrate (20 mg, 0.48 mmol) was added. The reaction mixture was stirred at room temperature for 1 h, then the solvent was evaporated and the residue was purified by reverse phase HPLC to give N-[2-chloro-4-[[[(3-hydroxyphenyl)methyl]amino]carbonyl]benzoyl]-3-(aminoiminomethyl)amino-L-alanine (17 mg, 33%) as a white powder.

Example 372

Preparation of N-(4-bromo-2-chlorobenzoyl)-3-(thiophene-2-carbonyl)amino-L-alanine on Wang resin

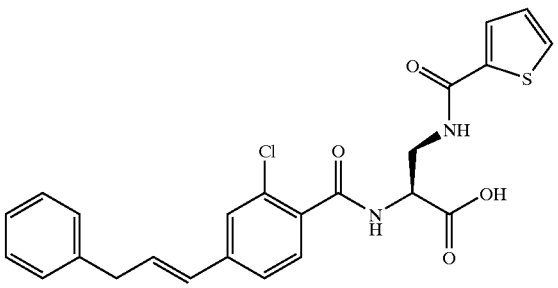

3-Amino-N-(4-bromo-2-chlorobenzoyl)-L-alanine-substituted Wang resin (Example 71, 15 g) was slurried in a solution prepared from HOAT (11.22 g, 82.4 mmol), DICI (12.9 mL, 82.4 mmol) and thiophene-2-carboxylic acid (10.6 g, 82.7 mmol) in N-methylpyrrolidinone and the mixture was agitated for 2 h. The resin was then filtered and washed extensively with N-methyl-pyrrolidinone, dichloromethane and methanol to give N-(4-bromo-2-chlorobenzoyl)-3-(thiophene-2-carbonyl)amino-L-alanine on Wang resin.

Example 373

Preparation of N-[2-chloro-4-(3-phenyl-1-propenyl)benzoyl]-3-(thiophene-2-carbonyl)amino-L-alanine A mixture of N-(4-bromo-2-chlorobenzoyl)-3-(thiophene-2-carbonyl)amino-L-alanine on Wang resin (Example 372; 100 mg), allylbenzene (73 μL, 0.55 mmol), palladium(II) acetate (12 mg, 0.05 mmol), triphenylphosphine (58 mg, 0.22 mmol) and tetra-n-butylammonium chloride (61 mg, 0.22 mmol) in N,N-dimethylacetamide was shaken overnight. The resin was then filtered and washed extensively with dichloromethane and methanol. The product was cleaved from the resin using 50% trifluoroacetic acid in dichloromethane. The cleavage solution was collected by filtration and the solvent was evaporated under high vacuum. The residue was purified by reverse phase HPLC to give N-[2-chloro-4-[[[(3-hydroxyphenyl)methyl]amino]carbonyl]benzoyl]-3-(thiophene-2-carbonyl)amino-L-alanine.

Example 374

Preparation of 1-[[2-chloro-4-(tributylstannyl)benzoyl]oxy]-2,5-pyrrolidinedione

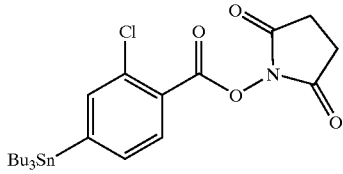

A. 1-[(4-Bromo-2-chlorobenzoyl)oxy]-2,5-pyrrolidinedione

A solution of 4-bromo-2-chlorobenzoic acid (2.00 g, 8.5 mmol), N-hydroxysuccinimide (1.07 g, 9.3 mmol) and EDCl (1.79 g, 9.3 mmol) in tetrahydrofuran/N,N-dimethylformamide (3:1; 40 mL) was stirred at room temperature for 18 h. The reaction was concentrated and water (50 mL) was added. The mixture was extracted with ethyl acetate (3×50 mL) and the combined organic layers were washed with brine, dried (Na₂SO₄), concentrated, and dried in vacuo to give 1-[(4-bromo-2-chlorobenzoyl)oxy]-2,5-pyrrolidinedione (2.59 g, 92%) as an off-white solid which was used directly in the next step without further purification.

B. 1-[[2-Chloro-4-(tributylstannyl)benzoyl]oxy]-2,5-pyrrolidinedione

Hexabutyldistannane (3.9 mL, 7.7 mmol) and tetrakis(triphenyl-phosphine)palladium(0) (103 mg, 0.09 mmol) were added to a solution of 1-[(4-bromo-2-chlorobenzoyl)oxy]-2,5-pyrrolidinedione (1.78 g, 5.4 mmol) in toluene (50 mL), and the solution was stirred at reflux for 6 h. The solvent was removed under reduced presure, and the oily residue was loaded onto a short plug of SiO₂, washed with hexane, then eluted with 30% ethyl acetate hexanes. The solvent was evaporated and the residue was chromotagraphed (30% % ethyl acetate hexane) to give 1-[[2-chloro-4-(tributylstannyl)benzoyl]oxy]-2,5-pyrrolidinedione (1.74 g, 60%) as a colorless oil.

Example 375

Preparation of N-[2-chloro-4-(tri-n-butylstannyl)benzoyl]-3-(thiophene-2-carbonyl)amino-L-alanine on Wang resin

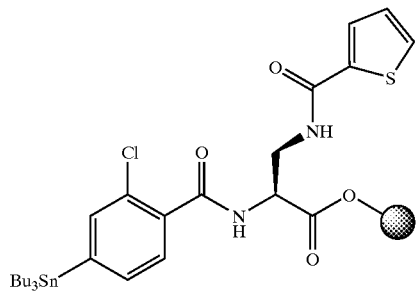

A. 3-Amino-N-[(9H-fluoren-9-ylmethoxy)carbonyl]-L-alanine on Wang resin

A mixture of N-[(9H-fluoren-9-ylmethoxy)carbonyl]-3-[(2-propenyloxy)carbonyl]amino-L-alanine resin (Example 64; 2 g), tetrakis(triphenylphosphine)palladium(0) (509 mg, 0.45 mmol), and phenylsilane (21.9 mmol) in dichloromethane (20 mL) was shaken for 35 min. The resin was washed with dichloromethane and methanol, then vortexed with dimethylformamide/water (1:1) at room temperature for 10 min, and washed again with dichloromethane and methanol to give 3-amino-N-[(9H-fluoren-9-ylmethoxy)carbonyl]-L-alanine on Wang resin.

B. 3-(Thiophene-2-carbonyl)amino-L-alanine on Wang resin

A mixture of 3-amino-N-[(9H-fluoren-9-ylmethoxy)carbonyl]-L-alanine on Wang resin (2 g), thiophene-2-carboxylic acid (1.41 g, 11.0 mmol), HOAT (1.50 g, 11.0 mmol) and diisopropylcarbodiimide (1.68 mL, 10.7 mmol) in N-methylpyrrolidinone (20 mL) was shaken for 3 h and then washed with dichloromethane and methanol to give N-[(9H-fluoren-9-ylmethoxy)carbonyl]-3-(thiophene-2-carbonyl)amino-L-alanine on Wang resin. The Fmoc group was cleaved by treatment with 25% piperidine in N-methylpyrrolidinone, followed by shaking for 1 h. The resin was washed with dichloromethane and methanol to give 3-(thiophene-2-carbonyl)amino-L-alanine on Wang resin.

C. N-[2-Chloro-4-(tri-n-butylstannyl)benzoyl]-3-thiopene-2-carbonyl)amino-L-alanine on Wang resin A mixture of 3-(thiophene-2-carbonyl)amino-L-alanine on Wang resin (2.00 g) and 1-[[2-chloro-4-(tributylstannyl)benzoyl]oxy]-2,5-pyrrolidinedione (Example 374; 2.50 g, 4.6 mmol) in N,N-dimethylformamide was shaken for 72 h. The resin was washed with dichloromethane and methanol to give N-[2-chloro-4-(tri-n-butylstannyl)benzoyl]-3-(thiophene-2-carbonyl)amino-L-alanine on Wang resin.

Example 376

Preparation of N-[2-chloro-4-(phenoxyacetyl)benzoyl]-3-(thiophene-2-carbonyl)amino-L-alanine

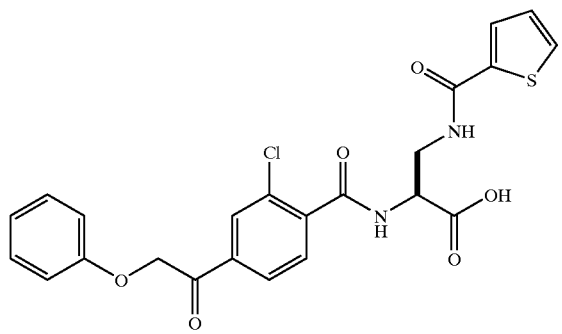

A mixture of N-[2-chloro-4-(tri-n-butylstannyl)benzoyl]-3-(thiophene-2-carbonyl)amino-L-alanine on Wang resin (Example 375; 100 mg), phenoxyacetyl chloride (100 μL, 0.72 mmol), tris(dibenzylidene-acetone)dipalladium(0) (18 mg, 0.02 mmol), potassium carbonate (50 mg, 0.36 mmol) and diisopropylethylamine (100 μL, 0.57 mmol) in tetrahydrofuran (2 mL) was shaken for 2 h, then washed with water, dichloromethane, and methanol. Cleavage was effected by treatment with trifluoroacetic acid/dichloromethane (1:1; 4 mL) and shaking for an hour. The cleavage solution was collected by filtration and the solvent was evaporated. The residue was purified by reverse phase HPLC to give N-[2-chloro-4-(phenoxyacetyl)benzoyl]-3-(thiophene-2-carbonyl)amino-L-alanine.

Also prepared by this procedure were:

| Example | Structure | Starting Materials |
|---|---|---|
| 377[a] | 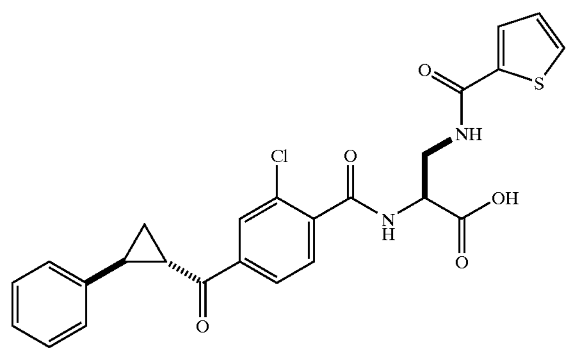 | Example 375 and trans-2-phenyl-1-cyclopropanecarbonyl chloride |
| 378 | 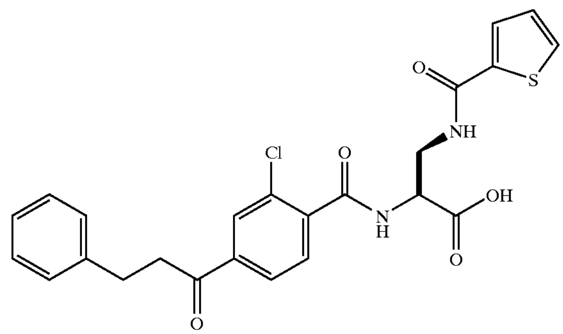 | Example 375 and hydrocinnamoyl chloride |

[a]The carboxylic acid was racemic and the diastereoisomeric products were not separated.

Example 379

Preparation of N-[2-chloro-4-[[[(3-hydroxyphenyl)methyl]amino]carbonyl]benzoyl]-3-(thiophene-2-carbonyl)amino-L-alanine, 2-(dimethyl-amino)ethyl ester

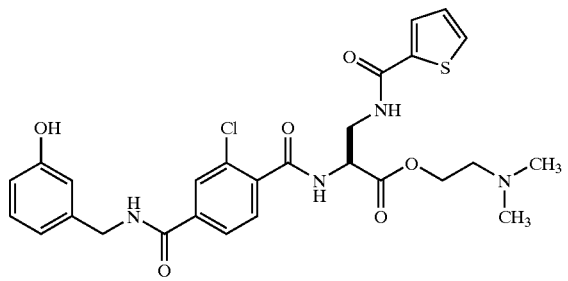

A mixture of N-[2-chloro-4-[[[(3-hydroxyphenyl)methyl]amino]carbonyl]benzoyl]-3-(thiophene-2-carbonyl)amino-L-alanine (Example 303; 1 mmol), potassium carbonate (2.1 mmol), potassium iodide (0.2 mmol), and (2-chloroethyl)dimethylamine hydrochloride (1.1 mmol) in N,N-dimethylformamide (10 mL) is heated at 60° C. for 3 h. The reaction mixture is concentrated to remove N,N-dimethylformamide. Water (50 mL) is added and the pH is adjusted to 9. The mixture is extracted with ethyl acetate (3×50 mL). The combined ethyl acetate layers are washed with brine (100 mL), dried (MgSO$_4$), filtered, evaporated and chromatographed to give N-[2-chloro-4-[[[(3-hydroxyphenyl)methyl]amino]carbonyl]benzoyl]-3-(thiophene-2-carbonyl)amino-L-alanine, 2-(dimethylamino) ethyl ester.

Example 380

Preparation of N-[2-chloro-4-[[[(3-hydroxyphenyl)methyl]amino]carbonyl]benzoyl]-3-(thiophene-2-carbonyl)amino-L-alanine, [(ethoxycarbonyl)oxy]methyl ester

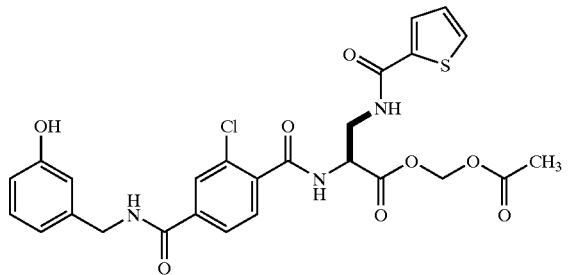

A mixture of N-[2-chloro-4-[[[(3-hydroxyphenyl)methyl]amino]carbonyl]benzoyl]-3-(thiophene-2-carbonyl)amino-L-alanine (Example 303; 1 mmol), potassium carbonate (1.1 mmol), potassium iodide (0.2 mmol), and chloromethyl ethyl carbonate (which is prepared according to Boehme, H. et al. *Synthesis* 1971, 588–590; 1.1 mmol) in N,N-dimethylformamide (10 mL) is heated at 60° C. for 3 h. The reaction mixture is concentrated to remove N,N-dimethylformamide. Water (50 mL) is added and the mixture is extracted with ethyl acetate (3×50 mL). The combined ethyl acetate layers are washed with brine (100 mL), dried (MgSO$_4$), filtered, evaporated and chromatographed to give N-[2-chloro-4-[[[(3-hydroxyphenyl)methyl]amino]carbonyl]benzoyl]-3-(thiophene-2-carbonyl)amino-L-alanine, [(ethoxycarbonyl)oxy]methyl ester.

Example 381

LFA-1/ICAM-1 Protein-Protein Assay

LFA-1/ICAM-1 antagonist activity, defined as the ability to block LFA-1 binding to immobilized ICAM-1, was quantitated using a solid-phase ELISA. Typically, fusion protein consisting of the entire extracellular domain of human ICAM-1 and the Fc domain of human IgG (5dICAM-Ig) was coated onto 96-well microtiter plates (0.15 μg in 100 μL PBS) overnight at 4° C. The plates were then blocked with 150 μL of 1% BSA/1 mM MnCl$_2$/0.14 M NaCl/20 mM HEPES, pH 7.2 for 1 h at 37° C. and washed 3 times (150 μL each) with Wash Buffer (50 mM Tris, pH 7.4/100 mM NaCl/1 mM MnCl$_2$/0.05% Tween 20). Stock solutions (100 μM in 100% DMSO) of test compounds were diluted 50 fold with 150 μL of Binding Buffer (0.05% BSA/0.05% Tween 20/1 mM MnCl$_2$/0.14 M NaCl/20 mM HEPES, pH 7.2) plus 10% DMSO. A series of 1:4 dilutions were performed to achieve a concentration range of 0.12 nM–2 μM. Fifty μL per well of each dilution was added to the ICAM-1 coated plates, followed by 50 μL per well of membrane-bound LFA-1 (280 ng/mL in Binding Buffer) derived from transfected 293 cells. The plates were shaken vigorously for 1 min (room temperature) and gently for 2 h (37° C.). After incubation, the plates were washed 3 times (150 μL each) with Wash Buffer. Mouse anti-human integrin β2 monoclonal antibody was added (100 μL/well, 1 μg/mL in Binding Buffer) and allowed to incubate for 1 h (37° C.) with gentle agitation. The plates were then washed 3 times with Wash Buffer. HRP-conjugated goat anti-mouse IgG (100 μL/well, 1:1500 dilution in Binding Buffer) was added to each well, followed by incubation for 1 h (37° C.), and concluded by three washes (150 μL each) with Wash Buffer. TMB solution (100 μL per well) was added for color development (10 min). The reaction was stopped by the addition of 100 μL of 1 M H$_3$PO$_4$ to each well. The plates were then read at 450 nm. The inhibitory activities of test compounds were determined by the IC$_{50}$s and are presented in Table 4.

Example 382

Mixed Lymphocyte Reaction (MLR)

Admixture of murine spleen cells from two different inbred strains of mice induces proliferation of T lymphocytes. The magnitude of T cell proliferation depends on the extent of disparity in the major histocompatibility antigens between the two strains. Splenic T lymphocytes from both strains proliferate due to alloantigen recognition, a process for which the interaction of ICAM-1 on antigen-presenting cells with LFA-1 on lymphocytes is necessary. The ability of antagonists to inhibit T lymphocyte proliferation following recognition of alloantigens was assessed in a one-way MLR, where cells from one strain were irradiated to permit measurement of the proliferative response of cells from the other strain. Spleen cells were washed three times in tissue culture medium (TCM; see below). Fifty microliters of a spleen cell suspension (prepared at 10×10$^6$ cells/ml in TCM) obtained from C57Bl/6 mice were added to an equal number of lethally-irradiated (2000 rads) spleen cells obtained from BALB/c mice in a 96-well U-bottom tissue culture plate (Costar, 3799). One hundred microliters of serial dilutions of antagonists or TCM were added to the spleen cell mixture. The total volume in each well was 200 μL. TCM was RPMI1640 containing 10% heat-inactivated fetal bovine serum, 200 mM L-glutamine, 100 Units/ml each of penicillin and streptomycin and $5\times10^{-5}$ M 2-mercaptoethanol. Dilutions of antagonists were prepared in TCM. Plates were incubated in 5% $CO_2$ for 3 days. On the third day, 0.5 μCi of tritiated thymidine (10 μCi/mL) was added to all the wells. Cells were harvested 6 h later on a 96-well plate harvester and the amount of tritiated thymidine incorporated was assessed in a liquid scintillation counter. $IC_{50}$s were calculated and are presented in Table 4. The $IC_{50}$s for anti-LFA-1 (M17) and anti-CD18 (HB226) antibodies are 0.138 nM and 3.35 nM respectively. Anti-Mac-1 antibody (M1/70) was not found to inhibit the mixed lymphoctye reaction.

Example 383

Mac-1/ICAM-1 Screening Assay

Mac-1/ICAM-1 antagonist activity, defined as the ability to compete with ICAM-1 binding to immobilized Mac-1, was quantitated by a solid-phase ELISA. Membrane-bound Mac-1 derived from transfected 293 cells was coated onto 96-well microtiter plates (50 μL/well, 3 μg/mL Mac-1 in 20 mM Hepes, pH 7.2/0.14 M NaCl/1 mM $MnCl_2$) overnight at 4° C. The plates were blocked with 100 μL/well of 0.5% BSA in 20 mM Hepes, pH 7.2/0.14 M NaCl/1 mM $MnCl_2$ at 37° C. for 1 h and washed 3 times (120 μL each) with Binding Buffer (20 mM Hepes, pH 7.2/0.14 M NaCl/1 mM $MnCl_2$/0.05% Tween 20). Test compounds were dissolved in 100% DMSO and diluted 1:50 in Binding Buffer plus 10% DMSO. A series of 1:4 dilutions were performed for each compound (concentration range, 0.12 nM-20 μM). Each dilution (25 μL/well) was added to the plates, followed by 25 μL/well of 5dICAM-Ig (40 μg/mL in Binding Buffer). The plates were shaken vigorously for 1 min (room temperature), followed by gentle agitation for 2 h (37° C.), and washed with Binding Buffer (3 times, 120 μL each). HRP-conjugated goat anti-human IgG(Fc-specific) antibody (0.125 μg/mL in Binding Buffer plus 0.05% BSA) was added to each well (50 μL/well), followed by incubation for 1 h at 37° C. The plates were then washed 3 times with Binding Buffer (120 μL each). TMB solution (100 μL/well) was added to each well for color development for 10 min. The reaction was stopped with 1 M $H_3PO_4$ (100 μL/well) and the plates were read at 450 nm. $IC_{50}$s were calculated and are presented in Table 4.

Example 384

Mac-1/Fibrinogen Cell-Based Screening Assay

Cellular Mac-1/Fibrinogen antagonist activity, defined as the ability to inhibit cell-surface Mac-1 adhesion to immobilized fibrinogen, was quantitated by a cell based assay. Human fibrinogen was coated onto 96 well microtiter plates (1 μg in 100 μL TBS) overnight at 4° C. The plates were then blocked with 150 μL of 10% polyvinyl pyrrolidone (PVP) in TBS for 1 h at 37° C. Plates were washed 3 times (150 μL each) with TBS. HL-60 cells ($8\times10^6$/mL), differentiated for 62–72 h with 1.5% DMSO were fluorescently labeled with 6-carboxyfluorescein (a stock solution of 5 mg/mL in acetone was added to cells to achieve a final concentration of 100 μg/mL) for 40 min in IMDM/1 mM $MgCl_2$/1.2 mM $CaCl_2$. A ten-fold excess of volume of the same buffer was added and cells were centrifuged. The medium was decanted and cells were resuspended at a concentration of $2\times10^6$ cells/mL in RPMI/0.05% BSA/0.2 mM $MnCl_2$. Stock solutions (10 mM in DMSO) of test compounds were diluted to 2.5 mM with DMSO. A series of 1:4 dilutions in DMSO were performed to achieve a concentration range of 38.2 nM–2.5 mM. Each sample was further diluted 50-fold with RPMI/0.05% BSA/0.2 mM $MnCl_2$. Equal volumes of labeled cells were then added to assay tubes containing diluted compounds. Final concentrations of compounds tested in the assay ranged from 0.38 nM–25 μM with cell concentrations of $1\times10^6$ per mL. Cells were incubated for 10 min at 37° C. with gentle shaking, then dispensed (100 μL per well) onto fibrinogen coated plates and incubated for 30 min at 37° C./5% $CO_2$. Unbound cells were gently washed with TBS two times. Plates were read on a Cytofluor™ 2300 (Millipore) at an excitation wavelength of 485 nm and emittance wavelength of 530 nm. The inhibitory activities of test compounds were determined by the $IC_{50}$s and are presented in Table 4.

Example 385

Neutrophil (Mac-1 and LFA-1)/ICAM-1 Cell-Based Screening Assay

Both Mac-1 and LFA-1 are expressed on the cell surface of neutrophils. The ability of antagonists to inhibit Mac-1 and LFA-1-mediated neutrophil binding to immobilized ICAM-1 was quantitated by a cell based assay. Typically, fusion protein consisting of the entire extracellular domain of human ICAM-1 and the Fc domain of human IgG (5dICAM-Ig) was coated onto 96 well microtiter plates (1 μg in 100 μL TBS) overnight at 4° C. The plates were then blocked with 150 μL of 10% PVP in TBS for 1 h at 37° C. Plates were washed 3 times (150 μL each) with TBS. Human neutrophils were purified from whole blood from healthy volunteers using LSM (ICN). Cells ($8\times10^6$/mL) were fluorescently labeled with 6-carboxyfluorescein (100 μg/mL) for 40 min in IMDM/1 mM $MgCl_2$/1.2 mM $CaCl_2$ as described in Example 287. Cells ($8\times10^6$/mL) were stimulated with f-Met-Leu-Phe (10 μM) for 5 min at room temperature just prior to being used in the assay, and diluted to $2\times10^6$ cells/mL with RPMI/0.05% BSA/0.2 mM $MnCl_2$. Stock solutions (10 mM) of test compounds were diluted to 2.5 mM with DMSO. A series of 1:4 dilutions in DMSO were performed to achieve a concentration range of 38.2 nM–2.5 mM. Each sample was further diluted 50-fold with RPMI/0.05% BSA/0.2 mM $MnCl_2$. Equal volumes of labeled cells were then added to assay tubes containing diluted compound. Final concentrations of compound tested in the assay ranged from 0.38 nM–25 μM with a cell concentration of $1\times10^6$ per mL. Cells were incubated for 10 min at 37° C. with gentle shaking, then dispensed (100 μL per well) onto ICAM-1 coated plates and incubated for 30 min at 37° C./5% $CO_2$. Unbound cells were washed and plates were read on a Cytofluor™ 2300 (Millipore) as described in Example 384. The inhibitory activities of test compounds were determined by the $IC_{50}$s and are presented in the Table 4.

TABLE 4

Results from protein-protein and cell-based assays.

| Example | LFA-1/ICAM-1 Protein-Protein Assay IC50 (nM) | MLR IC50 (nM) | Mac-1/ICAM-1 Protein-Protein Assay IC50 (nM) | Mac-1/Fgn Cell based Assay IC50 (nM) | Neutrophil/ICAM Assay IC50 (nM) |
|---|---|---|---|---|---|
| 76 | 1.2 | 310 | 6.8 | 43 | 63 |
| 77 | 2.1 | 700 | 25 | 312 | ND |
| 78 | 1.0 | 1025 | 94 | ND | 253 |
| 79 | 2.9 | 2500 | 74 | ND | ND |
| 80 | 6.0 | 1800 | 134 | ND | ND |
| 81 | 4.0 | 1650 | 58 | ND | ND |
| 82 | 4.3 | 1700 | 62 | ND | ND |
| 83 | 2.3 | 460 | 58 | ND | ND |
| 84 | 1.0 | 1300 | 60 | ND | ND |
| 85 | 3.2 | 1125 | 48 | ND | ND |
| 86 | 3.3 | 4150 | 179 | ND | ND |
| 87 | 4.8 | 1300 | 87 | ND | ND |
| 88 | 1.8 | 12500 | 273 | ND | ND |
| 89 | 5.9 | 10500 | 464 | ND | ND |
| 90 | 2.4 | 1450 | 29 | 711 | ND |
| 91 | 5.0 | 2450 | 174 | ND | ND |
| 92 | 2.1 | 900 | 48 | ND | ND |
| 93 | 0.5 | 525 | 57 | ND | ND |
| 94 | 1.5 | 1400 | 42 | ND | ND |
| 95 | 2.7 | 2850 | 48 | ND | ND |
| 96 | 3.1 | 1300 | 56 | ND | ND |
| 97 | 1.9 | 1550 | 121 | ND | ND |
| 98 | 3.1 | 800 | 38 | ND | ND |
| 99 | 7.5 | 2000 | 50 | ND | ND |
| 100 | 2.9 | 705 | 32 | ND | ND |
| 101 | 1.9 | 565 | 29 | 79 | ND |
| 102 | 2.2 | 400 | 50 | ND | ND |
| 103 | 1.6 | 520 | 21 | 123 | ND |
| 104 | 3.5 | 775 | 25 | 82 | ND |
| 105 | 1.9 | 280 | 22 | 151 | 94 |
| 106 | 2.4 | 680 | 30 | ND | ND |
| 107 | 1.2 | 900 | 32 | ND | ND |
| 108 | 3.7 | 1400 | 63 | ND | ND |
| 109 | 1.2 | ND | 105 | ND | ND |
| 110 | 3.7 | 10000 | 272 | ND | ND |
| 111 | 2.0 | 500 | 44 | ND | ND |
| 112 | 1.5 | 375 | 18 | 161 | ND |
| 113 | 1.7 | 350 | 30 | ND | ND |
| 114 | 1.8 | 1650 | 48 | ND | ND |
| 115 | 2.2 | 1350 | 43 | ND | ND |
| 116 | 1.8 | 1300 | 18 | 86 | ND |
| 117 | 3.6 | 290 | 33 | 131 | ND |
| 118 | 1.9 | 145 | 23 | 16 | 37 |
| 119 | 3.0 | 420 | 26 | 468 | 220 |
| 120 | 4.9 | 890 | 114 | ND | ND |
| 121 | 1.6 | 530 | 9.0 | 80 | ND |
| 122 | 2.8 | 925 | 32 | ND | ND |
| 123 | 0.8 | 300 | 6.9 | 20 | 21 |
| 124 | 3.3 | 2500 | 35 | ND | ND |
| 125 | 2.2 | 515 | 78 | ND | ND |
| 126 | 1.2 | 400 | 11 | 27 | ND |
| 127 | 2.2 | 455 | 23 | 71 | ND |
| 128 | 4.2 | 4900 | 124 | ND | ND |
| 129 | 4.2 | 3000 | 37 | ND | ND |
| 130 | 5.0 | 3000 | 53 | ND | ND |
| 131 | 0.8 | 215 | 9.7 | 12 | 27 |
| 132 | 0.6 | 82 | 7.0 | 3.3 | 4.9 |
| 133 | 1.5 | 625 | 10 | 32 | ND |
| 134 | 2.1 | 1550 | 26 | 218 | ND |
| 135 | 6.3 | 2635 | 61 | ND | ND |
| 136 | 2.0 | 490 | 16 | 121 | ND |
| 137 | 1.1 | 325 | 22 | 84 | ND |
| 138 | 0.7 | 205 | 10 | 17 | 31 |
| 139 | 4.8 | 1750 | 47 | ND | ND |
| 140 | 1.8 | 350 | 47 | 98 | ND |
| 141 | 1.9 | 450 | 9.6 | 47 | ND |
| 142 | 2.0 | 500 | 13 | 275 | ND |
| 143 | 11 | 12000 | 62 | ND | ND |
| 144 | 6.6 | 1800 | 53 | ND | ND |
| 145 | 1.7 | 1450 | 24 | 131 | ND |
| 146 | 2.6 | 490 | 27 | 153 | ND |
| 147 | 15 | 4600 | 119 | ND | ND |
| 148 | 1.4 | 335 | 18 | 76 | ND |
| 149 | 2.9 | 950 | 35 | ND | ND |
| 150 | 2.5 | 800 | 21 | 65 | ND |
| 151 | 2.8 | 265 | 33 | 46 | ND |
| 152 | 6.4 | ND | 101 | 1221 | ND |
| 153 | 7.7 | ND | 203 | 804 | ND |
| 154 | 0.9 | 365 | 11 | 58 | ND |
| 155 | 0.7 | 750 | 13 | 51 | 65 |
| 156 | 1.0 | 465 | 12 | 64 | ND |
| 157 | 1.2 | 700 | 7.7 | 34 | ND |
| 158 | 7.5 | 7600 | 20 | 70 | ND |
| 159 | 0.9 | 165 | 13 | 36 | ND |
| 160 | 0.9 | 220 | 6.6 | 11 | 23 |
| 161 | 1.0 | 94 | 12 | 17 | 44 |
| 162 | 1.0 | ND | 105 | ND | ND |
| 163 | 3.2 | 1550 | 40 | ND | ND |
| 164 | 5.0 | ND | 373 | ND | ND |
| 165 | 1.3 | 800 | 39 | ND | ND |
| 166 | 3.0 | ND | 68 | ND | ND |
| 167 | 2.2 | ND | 39 | ND | ND |
| 168 | 12 | ND | 224 | ND | ND |
| 169 | 2.7 | ND | 248 | ND | ND |
| 170 | 1.9 | 560 | 116 | ND | ND |
| 171 | 1.0 | ND | 136 | ND | ND |
| 172 | 7.0 | ND | 538 | ND | ND |
| 173 | 0.6 | ND | 36 | ND | ND |
| 174 | 3.4 | ND | 91 | ND | ND |
| 175 | 2.6 | 4000 | 23 | 345 | ND |
| 176 | 1.2 | ND | 54 | ND | ND |
| 177 | 1.0 | 950 | 19 | 157 | ND |
| 178 | 2.3 | 900 | 19 | 125 | ND |
| 179 | 3.6 | 5400 | 31 | 314 | ND |
| 180 | 0.6 | ND | 48 | ND | ND |
| 181 | 12 | ND | 176 | ND | ND |
| 182 | 15 | ND | 521 | ND | ND |
| 183 | 12 | 4600 | 222 | ND | ND |
| 184 | 2.5 | ND | 91 | ND | ND |
| 185 | 1.3 | ND | 187 | ND | ND |
| 186 | 1.6 | ND | 167 | ND | ND |
| 187 | 12 | 2800 | 56 | ND | ND |
| 188 | 3.4 | ND | 146 | ND | ND |
| 189 | 18 | ND | 1052 | ND | ND |
| 190 | 13 | ND | 417 | 4853 | ND |
| 191 | 2.2 | ND | 130 | ND | ND |
| 192 | 1.3 | 1700 | 40 | ND | 634 |
| 193 | 0.7 | 830 | 49 | ND | ND |
| 194 | 1.9 | 800 | 36 | ND | ND |
| 195 | 2.0 | 840 | 47 | ND | ND |
| 196 | 2.8 | 5500 | 16 | 63 | ND |
| 197 | 4.9 | 22500 | 38 | ND | ND |
| 198 | 12 | 21500 | 48 | ND | ND |
| 199 | 7.4 | 19000 | 36 | ND | ND |
| 200 | 2.9 | 3100 | 33 | ND | ND |
| 201 | 7.6 | 17300 | 49 | ND | ND |
| 202 | 1.8 | 500 | 37 | ND | ND |
| 204 | 42 | ND | ND | ND | ND |
| 205 | 31 | ND | ND | ND | ND |
| 206 | 19 | 5500 | ND | ND | ND |
| 207 | 60% @ 100 nM | ND | ND | ND | ND |
| 208 | 23 | ND | ND | ND | ND |
| 209 | 73% @ 100 nM | ND | ND | ND | ND |
| 210 | 36 | ND | ND | ND | ND |
| 211 | 56% @ 100 nM | ND | ND | ND | ND |

TABLE 4-continued

Results from protein-protein and cell-based assays.

| Example | LFA-1/ICAM-1 Protein-Protein Assay IC50 (nM) | MLR IC50 (nM) | Mac-1/ICAM-1 Protein-Protein Assay IC50 (nM) | Mac-1/Fgn Cell based Assay IC50 (nM) | Neutrophil/ICAM Assay IC50 (nM) |
|---|---|---|---|---|---|
| 212 | 36 | ND | ND | ND | ND |
| 213 | 31 | ND | ND | ND | ND |
| 214 | 57% @ 100 nM | ND | ND | ND | ND |
| 215 | 35 | ND | ND | ND | ND |
| 216 | 54% @ 100 nM | ND | ND | ND | ND |
| 217 | 34 | 31000 | ND | ND | ND |
| 218 | 33 | ND | ND | ND | ND |
| 219 | 13 | 7250 | 319 | ND | ND |
| 220 | 14 | ND | 304 | ND | ND |
| 221 | 24 | ND | ND | ND | ND |
| 222 | 62% @ 100 nM | ND | ND | ND | ND |
| 223 | 6.4 | 3600 | 82 | ND | ND |
| 224 | 24 | 11100 | 377 | ND | ND |
| 225 | 31 | ND | ND | ND | ND |
| 226 | 47 | ND | 273 | ND | ND |
| 227 | 21 | 8550 | ND | ND | ND |
| 228 | 7.1 | 5000 | ND | 149 | ND |
| 229 | 3.7 | 1850 | ND | 88 | ND |
| 230 | 1.4 | 485 | ND | 48 | ND |
| 231 | 1.9 | 350 | ND | ND | ND |
| 232 | 3.9 | 3250 | ND | 115 | ND |
| 233 | 7.4 | 7500 | ND | 286 | ND |
| 234 | 5.8 | 3150 | ND | 331 | ND |
| 235 | 3.8 | 2250 | ND | 318 | ND |
| 236 | 4.4 | 5250 | ND | 273 | ND |
| 237 | 3.7 | 3050 | ND | 463 | ND |
| 238 | 2.0 | 325 | ND | 81 | ND |
| 239 | 10 | 6000 | ND | 725 | ND |
| 240 | 12 | 7000 | ND | 497 | ND |
| 241 | 5.4 | 2300 | ND | 453 | ND |
| 242 | 8.3 | 1350 | ND | 522 | ND |
| 243 | 0.7 | 31 | ND | 2.2 | 3 |
| 244 | 0.8 | 140 | ND | 19 | 22 |
| 245 | 3.4 | 1550 | ND | 109 | ND |
| 246 | 3.5 | 1750 | ND | 78 | ND |
| 247 | 5.1 | 6500 | ND | 315 | ND |
| 248 | 3.5 | 2400 | ND | 58 | ND |
| 249 | 1.5 | 180 | ND | 25 | 50 |
| 250 | 1.4 | 140 | ND | 15 | 59 |
| 251 | 4.1 | 7500 | ND | 1477 | ND |
| 252 | 0.9 | 340 | 6.8 | 19 | 34 |
| 253 | 6.8 | 3750 | 55 | ND | ND |
| 254 | 0.7 | 460 | 11 | 31 | ND |
| 255 | 2.9 | 1850 | 41 | ND | ND |
| 256 | 0.8 | 525 | 14 | 24 | ND |
| 257 | 1.2 | 1400 | 23 | 87 | ND |
| 258 | 2.2 | 3750 | 26 | ND | ND |
| 259 | 1.2 | 260 | ND | 63 | 21 |
| 260 | 5.4 | 1950 | ND | 330 | ND |
| 261 | 2.2 | 780 | 11 | 46 | ND |
| 262 | 4.8 | 1800 | 15 | 49 | ND |
| 263 | 4.2 | 2100 | 27 | ND | ND |
| 264 | 4.6 | 1950 | 25 | ND | ND |
| 265 | 2.9 | 1000 | 18 | 107 | ND |
| 266 | 4.6 | 3050 | 306 | ND | ND |
| 267 | 2.9 | 490 | ND | 71 | ND |
| 268 | 1.7 | 900 | ND | 148 | ND |
| 269 | 2.6 | 3100 | ND | 358 | ND |
| 270 | 7.9 | 4750 | ND | 357 | ND |
| 271 | 3.8 | 4100 | ND | 547 | ND |
| 272 | 7.2 | 13000 | ND | 1155 | ND |
| 273 | 7.4 | 12000 | ND | 1740 | ND |
| 274 | 4.4 | 3700 | ND | ND | ND |
| 275 | 2.2 | 540 | ND | ND | ND |
| 276 | 6.9 | 7250 | ND | 235 | ND |
| 277 | 4.3 | 8700 | ND | 282 | ND |
| 278 | 8.5 | 13500 | ND | 311 | ND |
| 279 | 8.0 | 2200 | ND | 371 | ND |
| 280 | 3.1 | 4200 | ND | 77 | ND |
| 281 | 3.7 | 4450 | ND | 291 | ND |
| 282 | 4.6 | 1050 | ND | 162 | ND |
| 283 | 3.1 | 1500 | ND | 166 | ND |
| 284 | 5.7 | 1130 | ND | 198 | ND |
| 285 | 3.1 | 3100 | ND | 135 | ND |
| 286 | 4.1 | 1520 | ND | 74 | ND |
| 287 | 2.7 | 1635 | ND | 82 | ND |
| 288 | 1.2 | 210 | ND | ND | ND |
| 289 | 4.9 | 2400 | ND | 581 | ND |
| 290 | 3.3 | 1800 | ND | 155 | ND |
| 291 | 1.2 | 900 | ND | 135 | ND |
| 292 | 5.4 | 3650 | ND | ND | ND |
| 293 | 6.3 | 13500 | ND | 290 | ND |
| 294 | 3.0 | 650 | ND | 52 | ND |
| 295 | 1.9 | 1624 | ND | 89 | ND |
| 296 | 3.4 | 4600 | ND | 167 | ND |
| 297 | 0.8 | 1650 | 81 | ND | ND |
| 298 | 4.8 | 1800 | 298 | ND | ND |
| 302 | 0.9 | 310 | 31 | 74 | 41 |
| 303 | 0.5 | 70 | 6.4 | 8.7 | 16 |
| 304 | 1.1 | 270 | ND | ND | ND |
| 305 | 1.0 | 100 | 19 | ND | ND |
| 313 | 7.3 | 2750 | 90 | ND | ND |
| 314 | 1.9 | 625 | 40 | 162 | ND |
| 315 | 1.3 | 445 | 22 | ND | ND |
| 316 | 1.3 | 425 | 24 | ND | ND |
| 317 | 3.5 | 1750 | 36 | ND | ND |
| 318 | 1.9 | 1850 | 98 | ND | ND |
| 319 | 1.4 | 665 | 43 | ND | ND |
| 320 | 1.0 | 145 | ND | 64 | ND |
| 321 | 2.6 | 775 | 76 | ND | ND |
| 322 | 8.5 | 3600 | 51 | ND | ND |
| 323 | 1.3 | 325 | ND | 26 | 61 |
| 324 | 1.5 | 460 | ND | 32 | ND |
| 325 | 2.6 | 965 | ND | 59 | ND |
| 326 | 4.1 | 1500 | ND | 93 | ND |
| 327 | 1.8 | 180 | ND | 18 | 20 |
| 328 | 1.3 | 160 | ND | 28 | ND |
| 329 | 2.7 | 420 | 25 | ND | ND |
| 330 | 1.4 | 32 | ND | 6 | 6.7 |
| 331 | 1.1 | 710 | ND | 68 | ND |
| 332 | 4.8 | 1535 | 68 | ND | ND |
| 333 | 3.5 | 180 | ND | 12 | 14 |
| 334 | 3.0 | 495 | 71 | ND | ND |
| 335 | 1.1 | 85 | ND | 27 | 35 |
| 336 | 2.1 | 33 | ND | 5.4 | 6.1 |
| 337 | 3.7 | 59 | ND | 12 | 12 |
| 338 | 1.5 | 21 | 21 | 2.2 | 3.9 |
| 339 | 1.7 | 29 | ND | 3.1 | 3.0 |
| 340 | 0.3 | 36 | ND | 6.2 | 4 |
| 341 | 0.3 | 3 | ND | ND | 0.3 |
| 342 | 1.6 | 27 | ND | 1 | 2.3 |
| 343 | 2.5 | 30 | ND | 1.7 | 1.9 |
| 344 | 0.3 | 34 | ND | 4.8 | 1.7 |
| 345 | 0.2 | 2 | ND | 0.3 | 0.1 |
| 346 | 2.1 | 68 | ND | 4.0 | 9.7 |
| 347 | 3.4 | 250 | ND | 13.1 | 16.1 |
| 348 | 1.3 | 173 | ND | 19.8 | ND |
| 349 | 1.1 | 42 | ND | 6.2 | 4.7 |
| 350 | 1.0 | 12 | ND | 0.5 | 0.7 |
| 351 | 0.8 | 23 | ND | 3.0 | 2.7 |
| 352 | 1.2 | 91 | ND | 28.0 | ND |
| 353 | 1.6 | 52 | ND | 13.0 | 18.6 |
| 354 | 1.0 | 203 | ND | 12.0 | 4.7 |
| 355 | 0.9 | 86 | ND | 17.7 | ND |
| 356 | 3.4 | 1760 | ND | 81.0 | ND |

TABLE 4-continued

Results from protein-protein and cell-based assays.

| Example | LFA-1/ ICAM-1 Protein-Protein Assay IC50 (nM) | MLR IC50 (nM) | Mac-1/ ICAM-1 Protein-Protein Assay IC50 (nM) | Mac-1/Fgn Cell based Assay IC50 (nM) | Neutrophil/ ICAM Assay IC50 (nM) |
|---|---|---|---|---|---|
| 357 | 0.5 | 21 | ND | 23.0 | ND |
| 358 | 0.2 | 64 | ND | 6.5 | 4.3 |
| 359 | 12 | 6000 | 1413 | ND | ND |
| 360 | 5.2 | 4600 | 600 | ND | ND |
| 361 | 42 | 21500 | ND | ND | ND |
| 362 | 8.8 | 15000 | 1533 | ND | ND |
| 364 | 7.7 | 2850 | 167 | ND | ND |
| 365 | 18 | 9500 | 208 | ND | ND |
| 366 | 3.4 | 1400 | 61 | ND | ND |
| 367 | 41 | 17000 | ND | ND | ND |
| 368 | 11 | 3850 | 765 | ND | ND |
| 369 | 8.5 | 3200 | 403 | ND | ND |
| 370 | 40 | 11000 | ND | ND | ND |
| 371 | 10 | 3500 | 73 | ND | ND |
| 373 | 7.7 | 12500 | 68 | ND | ND |
| 376 | 37 | ND | 152 | ND | ND |
| 377 | 19 | 9500 | 160 | ND | ND |
| 378 | 9.7 | 6400 | 75 | ND | ND |

Example 386

Delayed Type Hypersensitivity in Mice

Sensitization: On day 0, adult female C57BI/6 mice (20–25 g) received 50 µl each of a 1:1 mixture of 10 mg/ml methylated bovine serum albumin (mBSA) in phosphate buffered saline (PBS) and complete Freund's adjuvant (CFA) intradermally at two sites on shaved bellies (total volume 100 µl per mouse). Control mice received an equal volume of a PBS/CFA mixture (unsensitized).

Challenge: On day 7, the mice received 20 µl I of 5 mg/ml mBSA in PBS injected into the right hind paw. The contralateral left paw of each mouse was injected with an identical volume of PBS. After 24 hours, the paw swelling of both the hind feet of all mice was measured with microcalipers. To determine the paw swelling response, measurements of the left paw were subtracted from that of the right paw for each individual mouse.

At the time of challenge, anaesthetized mice were implanted on their backs with Alzet osmotic minipumps which delivered a constant volume per hour of the inhibitors (e.g. Example 226) subcutaneously. The pumps delivered a volume 200 µl over a period of 1 day. Different doses of the compounds were tested viz. 850, 250 and 85 mg/kg/day. The inhibitors were formulated in distilled water. Control mice received pumps containing distilled water. For antibody treatment groups, mice received 200 µg of anti-mouse LFA-1 (Mi7), anti-mouse Mac-1 (M1/70) or control rat IgG intraperitoneally on the day of challenge.

The results show that Mac-1/LFA-1 inhibitors inhibit the paw swelling response in a dose-dependent manner in this model of DTH. Measurement of circulating serum drug levels demonstrate that the inhibitor is efficacious at 9 µM and at 3 µM (850 mg/kg/day and 250 mg/kg/day, respectively). In parallel studies, anti-LFA-1 and anti-Mac-1 antibodies were also found to be effective in inhibiting the response.

In table 10, the swelling response in antibody-treated animals is compared to the swelling response in rat IgG-treated animals. The swelling response in compound-treated animals is compared to the swelling-response in mice that had received pumps containing distilled water

TABLE 5

Percentage inhibition of paw swelling in response to challenge with methylated bovine serum albumin

| Antagonist | Inhibition |
|---|---|
| Anti-LFA-1 | 75% |
| Anti-Mac-1 | 40% |
| Example 226 (9 µM) | 77% |
| Example 226 (3 µM) | 52% |
| Example 226 (1 µM) | −2% |

Example 387

Croton Oil-Induced Dermatitis in Mice

Adult female BALB/c mice (20–25 g) received 10 µl of 20 mg/ml of croton oil in 80% acetone:20% olive oil vehicle on each side of the right ear (total of 20 µl per mouse). All the mice received a similar volume of the acetone/olive oil vehicle on the contralateral left ear. Negative control mice received vehicle on both ears. Six hours thereafter, the ear swelling on both ears was measured with microcalipers. The ear swelling response was determined by subtraction of the swelling measurements of the left ear from that of the right ear for each individual mouse.

Inhibitors were administered to mice via 3 day Alzet osmotic minipumps. Pumps containing different concentrations of the inhibitors were implanted on the backs of anaesthetized mice 2 days prior to croton oil application. Additional mice received an equal volume of distilled water in pumps. For mice receiving antibodies, anti-CD18 antibody (HB226) or control rat IgG were administered i.p. at 200 µg per mouse 18 hours prior to croton oil application.

The results demonstrate that Mac-1/LFA-1 antagonists inhibit the ear swelling response in a dose-dependent manner in this acute model of inflammation. Measurement of circulating serum drug levels show that the inhibitors are efficacious at 4 µM and at 2 µM (250 mg/kg/day and 64 mg/kg/day, respectively). In parallel studies, anti-CD18 antibody was also found to be effective in inhibiting the ear swelling response.

In table 11, the swelling response in antibody-treated animals is compared to the swelling response in rat IgG-treated animals. The swelling response in compound-treated animals is compared to the swelling-response in mice that had received pumps containing distilled water

TABLE 6

Percentage inhibition of ear swelling in response to croton oil application

| Antagonist | Inhibition |
|---|---|
| Anti-CD18 | 65% |
| Example 226 (4 µM) | 62% |
| Example 226 (2 µM) | 48% |
| Example 226 (1 µM) | 8% |

What is claimed is:

1. A compound of formula

1d wherein U is chlorine, bromine, fluorine, or methyl; $R_3$ is hydrogen, carboxy, or lower alkyl;

X is carbonyl, phenyl-substituted loweralkylene, or sulfonyl;

Y is lower alkylene which may be substituted by one or more of amino, substituted amino, loweralkyl, or cyclo lower alkyl, or Y is lower alkenylene or lower alkylenethio, k is 0 or 1; when k is 1, Z is hydrogen, lower alkylthio, —COOH, —CONH$_2$, or amino, or when k is 0 or 1, Z is: 1-adamantyl, diphenylmethyl,3-[[(5-chloropyridin-2-yl)amino]carbonyl] pyrazin-2-yl, hydroxy, phenylmethoxy, 2-chloro-4-[[[(3-hydroxyphenyl)methyl]amino]carbonyl]phenyl, [(2,6-dichlorophenyl)methoxy]phenyl or Z is one of the following:

cycloalkyl or aryl containing 0 to 3 heteroatoms which may be the same or different, or a fused ring system containing two or three rings which rings are independently cycloalkyl or aryl containing 0 to 3 heteroatoms which may be the same or different, any of which rings may be unsubstituted, or substituted with at least one of:

halogen, cyano, amino, substituted amino, aminosulfonyl, nitro, oxo, hydroxy, aryl, aryloxy, unsubstituted lower alkyl, halogen-substituted lower alkyl, lower alkoxy-substituted lower alkyl, lower alkoxy, lower alklanesulfonyl, lower alkylthio, acetyl, aminocarbonyl, hydrazino, carboxy, lower alkoxycarbonyl, acetoxy, or amino loweralkyl;

or a pharmaceutically acceptable salt or ester thereof.

2. Compounds of claim 1 which are:

N-[2-chloro-4-[[[(3-hydroxyphenyl)methyl]amino] carbonyl]benzoyl]-3-(phenylsulfonyl)amino-L-alanine;

3-[(3-carboxybenzoyl)amino-N-[2-chloro-4-[[(3-hydroxyphenyl)methyl]amino]carbonyl]benzoyl]-L-alanine;

N-[2-bromo-4-[[[(3-hydroxyphenyl)methyl]amino] carbonyl]benzoyl]-3-(thiophene-2-carbonyl)amino-L-alanine; and N-[2-fluoro-4-[[[(3-hydroxyphenyl)methyl]amino] carbonyl]benzoyl]-3-(thiophene-2-carbonyl)amino-L-alanine.

3. A compound of claim 1 which is 3-(11-aminoundecanoyl)amino-N-[2-chloro-4-[[[(3-hydroxyphenyl)methyl]amino]carbonyl]benzoyl]-L-alanine.

4. A compound of claim 1 which has formula

1e wherein Z is 1-adamantyl, diphenylmethyl, 3-[[(5-chloropyridin-2-yl)amino]carbonyl]pyrazin-2-yl,2-chloro-4-[[[(3-hydroxyphenyl)methyl]amino]carbonyl]phenyl, [(2,6-dichlorophenyl)methoxy]phenyl or Z is one of the following:

cycloalkyl or aryl containing 0 to 3 heteroatoms which may be the same or different, or a fused ring system containing two or three rings which rings are independently cycloalkyl or aryl containing 0 to 3 heteroatoms which may be the same or different, any of which rings may be unsubstituted, or substituted with at least one of:

halogen, cyano, amino, substituted amino, aminosulfonyl, nitro, oxo, hydroxy, aryl, aryloxy, unsubstituted lower alkyl, halogen-substituted lower alkyl, lower alkoxy-substituted lower alkyl, lower alkoxy, lower alkanesulfonyl, lower alkylthio, acetyl, aminocarbonyl, hydrazino, carboxy, lower alkoxycarbonyl, acetoxy, or aminomethyl;

or a pharmaceutically acceptable salt or ester thereof.

5. A compound of claim 4 wherein Z is cycloalkyl.

6. Compounds of claim 5 which are

N-[2-chloro-4-[[[(3-hydroxyphenyl)methyl]amino] carbonyl]benzoyl]-3-(cyclopropylcarbonyl)amino-L-alanine;

N-[2-chloro-4-[[[(3-hydroxyphenyl)methyl]amino] carbonyl]benzoyl]-3-[(2,2-dichloro-1-methylcyclopropyl)carbonyl]amino-L-alanine;

N-[2-chloro-4-[[[(3-hydroxyphenyl)methyl]amino] carbonyl]benzoyl]-3-[(1-phenylcyclopropyl)carbonyl] amino-L-alanine;

N-[2-chloro-4-[[[(3-hydroxyphenyl)methyl]amino] carbonyl]benzoyl]-3-(cyclobutylcarbonyl)amino-L-alanine;

N-[2-chloro-4-[[[(3-hydroxyphenyl)methyl]amino] carbonyl]benzoyl]-3-(cyclopentylcarbonyl)amino-L-alanine;

N-[2-chloro-4-[[[(3-hydroxyphenyl)methyl]amino] carbonyl]benzoyl]-3-[1-(2-methoxyethyl) cyclopentylcarbonyl]amino-L-alanine;

N-[2-chloro-4-[[[(3-hydroxyphenyl)methyl]amino] carbonyl]benzoyl]-3-[(1-phenylcyclopentyl)carbonyl] amino-L-alanine;

N-[2-chloro-4-[[[(3-hydroxyphenyl)methyl]amino] carbonyl]benzoyl]-3-(cyclohexylcarbonyl)amino-L-alanine;

N-[2-chloro-4-[[[(3-hydroxyphenyl)methyl]amino] carbonyl]benzoyl]-3-(1-methylcyclohexylcarbonyl) amino-L-alanine;

N-[2-chloro-4-[[[(3-hydroxyphenyl)methyl]amino] carbonyl]benzoyl]-3-[1-aminocyclopentyl)carbonyl] amino-L-alanine;

N-[2-chloro-4-[[[(3-hydroxyphenyl)methyl]amino] carbonyl]benzoyl]-3-[cis-4-aminocyclohexyl) carbonyl]amino-L-alanine;

N-[2-chloro-4-[[[(3-hydroxyphenyl)methyl]amino] carbonyl]benzoyl]-3-[trans-6-amino-3-cyclohexene-1-carbonyl]amino-L-alanine;

3-[[trans-4-(aminomethyl)cyclohexyl]carbonyl]amino-N-[2-chloro-4-[[[(3-hydroxyphenyl)methyl]amino] carbonyl]benzoyl]-L-alanine;

3-[(1-aminocyclohexyl)carbonyl]amino-N-[2-chloro-4-[[[(3-hydroxyphenyl)methyl]amino]carbonyl] benzoyl]-L-alanine; and 3-[(3-aminocyclohexyl)carbonyl]amino-N-[2-chloro-4-[[[(3-hydroxyphenyl)methyl]amino]carbonyl] benzoyl]-L-alanine.

7. Compounds of claim 4 which are:

N-[2-chloro-4-[[[(3-hydroxyphenyl)methyl]amino] carbonyl]benzoyl]-3-(diphenylacetyl)amino-L-alanine;

3-(1-adamantylcarbonyl)amino-N-[2-chloro-4-[[[(3-hydroxyphenyl)methyl]amino]carbonyl]benzoyl]-L-alanine;

N-[2-chloro-4-[[[(3-hydroxyphenyl)methyl]amino] carbonyl]benzoyl]-3-[(2S)-5-oxotetrahydrofuran-2-carbonyl]amino-L-alanine;

N-[2-chloro-4-[[[(3-hydroxyphenyl)methyl]amino] carbonyl]benzoyl]-3-(1,4-dioxa-8-thiaspiro[4.5] decane-6-carbonyl)amino-L-alanine;

N-[2-chloro-4-[[[(3-hydroxyphenyl)methyl]amino] carbonyl]benzoyl]-3-(2-phenoxybenzoyl)amino-L-alanine;

N-[2-chloro-4-[[[(3-hydroxyphenyl)methyl]amino] carbonyl]benzoyl]-3-(furan-2-carbonyl)amino-L-alanine;

N-[2-chloro-4-[[[(3-hydroxyphenyl)methyl]amino] carbonyl]benzoyl]-3-(5-nitrofuran-2-carbonyl)amino-L-alanine;

N-[2-chloro-4-[[[(3-hydroxyphenyl)methyl]amino] carbonyl]benzoyl]-3-(5-bromofuran-2-carbonyl) amino-L-alanine;

N-[2-chloro-4-[[[(3-hydroxyphenyl)methyl]amino] carbonyl]benzoyl]-3-[(3,5-dimethylisoxazol-4-yl) carbonyl]amino-L-alanine;

N-[2-chloro-4-[[[(3-hydroxyphenyl)methyl]amino] carbonyl]benzoyl]-3-(piperidine-4-carbonyl)amino-L-alanine;

N-[2-chloro-4-[[[(3-hydroxyphenyl)methyl]amino] carbonyl]benzoyl]-3-(L-prolyl)amino-L-alanine;

N-[2-chloro-4-[[[(3-hydroxyphenyl)methyl]amino] carbonyl]benzoyl]-3-(1,2,3-thiadiazol-4-carbonyl) amino-L-alanine;

N-[2-chloro-4-[[[(3-hydroxyphenyl)methyl]amino] carbonyl]benzoyl]-3-(4-methyl-1,2,3-thiadiazol-5-carbonyl)amino-L-alanine;

N-[2-chloro-4-[[[(3-hydroxyphenyl)methyl]amino] carbonyl]benzoyl]-3-(isoxazole-5-carbonyl)amino-L-alanine;

N-[2-chloro-4-[[[(3-hydroxyphenyl)methyl]amino] carbonyl]benzoyl]-3-(4-chloro-2-nitrobenzoyl)amino-L-alanine;

N-[2-chloro-4-[[[(3-hydroxyphenyl)methyl]amino] carbonyl]benzoyl]-3-(2,4-dimethylthiazole-5-carbonyl)amino-L-alanine;

N-[2-chloro-4-[[[(3-hydroxyphenyl)methyl]amino] carbonyl]benzoyl]-3-[[2-chloro-4-[[[(3-hydroxyphenyl)methyl]amino]carbonyl]benzoyl] amino]-L-alanine; and N-[2-chloro-4-[[[(3-hydroxyphenyl)methyl]amino] carbonyl]benzoyl]-3-[[[(3S)-2,3,4,9-tetrahydro-1H-pyrido[3,4-b]indol-3-yl]carbonyl]amino]-L-alanine.

8. A compound of claim 4 wherein Z is thiophene, or Z is phenyl, or Z is thiophene substituted with at least one of halogen or methyl, or Z is phenyl substituted with at least one of halogen, hydroxy, cyano, lower alkyl, lower alkoxy, amino, substituted amino, aminocarbonyl, nitro, aminosulfonyl, acetoxy, or substituted lower alkyl, or Z is a five- or six-membered ring with 0 to 3 heteroatoms selected from O, N, and S which may be the same or different, which ring may be unsubstituted or substituted with hydroxy, or Z is a fused ring system containing at least one benzene ring and containing one or two other rings which are independently 5 or 6-membered cycloalkyl or aryl with 0 to 3 heteroatoms selected from O, N, and S which may be the same or different, any of which may be unsubstituted or substituted with at least one of lower alkoxy, halogen, oxo, or hydroxy.

9. Compounds of claim 8 which are 3-(3-amino-5-nitrobenzoyl)amino-N-[2-chloro-4-[[[(3-hydroxyphenyl)methyl]amino]carbonyl]benzoyl]-L-alanine;

3-(3-bromo-5-nitrobenzoyl)amino-N-[2-chloro-4-[[[(3-hydroxyphenyl)methyl]amino]carbonyl]benzoyl]-L-alanine;

N-[2-chloro-4-[[[(3-hydroxyphenyl)methyl]amino] carbonyl]benzoyl]-3-(3-nitro-5-trifluoromethylbenzoyl)amino-L-alanine;

N-[2-chloro-4-[[[(3-hydroxyphenyl)methyl]amino] carbonyl]benzoyl]-3-(3-methyl-5-nitrobenzoyl)amino-L-alanine;

N-[2-chloro-4-[[[(3-hydroxyphenyl)methyl]amino] carbonyl]benzoyl]-3-(3-methyl-4-nitrobenzoyl)amino-L-alanine;

3-(4-amino-3-methylbenzoyl)amino-N-[2-chloro-4-[[[(3-hydroxyphenyl)methyl]amino]carbonyl]benzoyl]-L-alanine;

3-(4-bromo-3-methylbenzoyl)amino-N-[2-chloro-4-[[[(3-hydroxyphenyl)methyl]amino]carbonyl]benzoyl]-L-alanine;

N-[2-chloro-4-[[[(3-hydroxyphenyl)methyl]amino] carbonyl]benzoyl]-3-(3-methoxy-4-nitrobenzoyl) amino-L-alanine;

N-[2-chloro-4-[[[(3-hydroxyphenyl)methyl]amino] carbonyl]benzoyl]-3-(3-hydroxy-4-methoxybenzoyl) amino-L-alanine;

N-[2-chloro-4-[[[(3-hydroxyphenyl)methyl]amino] carbonyl]benzoyl]-3-(2-methyl-3-nitrobenzoyl)amino-L-alanine;

3-(1H-benzotriazole-5-carbonyl)amino-N-[2-chloro-4-[[[(3-hydroxyphenyl)methyl]amino]carbonyl] benzoyl]-L-alanine;

3-(3-aminocarbonylbenzoyl)amino-N-[2-chloro-4-[[[(3-hydroxyphenyl)methyl]amino]carbonyl]benzoyl]-L-alanine;

N-[2-chloro-4-[[[(3-hydroxyphenyl)methyl]amino] carbonyl]benzoyl]-3-(furan-3-carbonyl)amino-L-alanine;

N-[2-chloro-4-[[[(3-hydroxyphenyl)methyl]amino] carbonyl]benzoyl]-3-(3-fluoro-5-trifluoromethylbenzoyl)amino-L-alanine;

N-[2-chloro-4-[[[(3-hydroxyphenyl)methyl]amino] carbonyl]benzoyl]-3-[(4R)-thiazolidine-4-carbonyl] amino-L-alanine;

N-[2-chloro-4-[[[(3-hydroxyphenyl)methyl]amino]carbonyl]benzoyl]-3-[(4R)-4-hydroxy-L-prolyl]amino-L-alanine; and N-[2-chloro-4-[[[(3-hydroxyphenyl)methyl]amino]carbonyl]benzoyl]-3-[2,3-dihydro-1H-indole-2-carbonyl]amino-L-alanine.

10. A compound of claim 8 wherein Z is thiophene, or thiophene substituted with at least one of halogen or methyl.

11. Compounds of claim 10 which are:

N-[2-chloro-4-[[[(3-hydroxyphenyl)methyl]amino]carbonyl]benzoyl]-3-[(thiophene-2-carbonyl)amino]-L-alanine;

3-(3-bromothiophene-2-carbonyl)amino-N-[2-chloro-4-[[[(3-hydroxyphenyl)methyl]amino]carbonyl]benzoyl]-L-alanine;

3-(5-bromothiophene-2-carbonyl)amino-N-[2-chloro-4-[[[(3-hydroxyphenyl)methyl]amino]carbonyl]benzoyl]-L-alanine;

N-[2-chloro-4-[[[(3-hydroxyphenyl)methyl]amino]carbonyl]benzoyl]-3-(3-chlorothiophene-2-carbonyl)amino-L-alanine;

N-[2-chloro-4-[[[(3-hydroxyphenyl)methyl]amino]carbonyl]benzoyl]-3-(5-chlorothiophene-2-carbonyl)amino-L-alanine;

N-[2-chloro-4-[[[(3-hydroxyphenyl)methyl]amino]carbonyl]benzoyl]-3-(4,5-dibromothiophene-2-carbonyl)amino-L-alanine;

N-[2-chloro-4-[[[(3-hydroxyphenyl)methyl]amino]carbonyl]benzoyl]-3-(3-methylthiophene-2-carbonyl)amino-L-alanine;

N-[2-chloro-4-[[[(3-hydroxyphenyl)methyl]amino]carbonyl]benzoyl]-3-(5-methylthiophene-2-carbonyl)amino-L-alanine; and N-[2-chloro-4-[[[(3-hydroxyphenyl)methyl]amino]carbonyl]benzoyl]-3-(thiophene-3-carbonyl)amino-L-alanine.

12. A compound of claim 8 wherein Z is a five- or six-membered ring with one to three nitrogens.

13. Compounds of claim 12 which are:

N-[2-chloro-4-[[[(3-hydroxyphenyl)methyl]amino]carbonyl]benzoyl]-3-(pyrrole-2-carbonyl)amino-L-alanine;

N-[2-chloro-4-[[[(3-hydroxyphenyl)methyl]amino]carbonyl]benzoyl]-3-(5-nitropyrazole-3-carbonyl)amino-L-alanine;

N-[2-chloro-4-[[[(3-hydroxyphenyl)methyl]amino]carbonyl]benzoyl]-3-(pyridine-2-carbonyl)amino-L-alanine;

N-[2-chloro-4-[[[(3-hydroxyphenyl)methyl]amino]carbonyl]benzoyl]-3-(6-methylpyridine-2-carbonyl)amino-L-alanine;

N-[2-chloro-4-[[[(3-hydroxyphenyl)methyl]amino]carbonyl]benzoyl]-3-[5-(3,4-dibromobutyl)pyridine-2-carbonyl]amino-L-alanine;

N-[2-chloro-4-[[[(3-hydroxyphenyl)methyl]amino]carbonyl]benzoyl]-3-(pyridine-3-carbonyl)amino-L-alanine;

N-[2-chloro-4-[[[(3-hydroxyphenyl)methyl]amino]carbonyl]benzoyl]-3-(2-chloropyridine-3-carbonyl)amino-L-alanine;

N-[2-chloro-4-[[[(3-hydroxyphenyl)methyl]amino]carbonyl]benzoyl]-3-(6-chloropyridine-3-carbonyl)amino-L-alanine;

N-[2-chloro-4-[[[(3-hydroxyphenyl)methyl]amino]carbonyl]benzoyl]-3-(2,6-dimethoxypyridine-3-carbonyl)amino-L-alanine;

N-[2-chloro-4-[[[(3-hydroxyphenyl)methyl]amino]carbonyl]benzoyl]-3-(2-hydroxypyridine-3-carbonyl)amino-L-alanine;

N-[2-chloro-4-[[[(3-hydroxyphenyl)methyl]amino]carbonyl]benzoyl]-3-(pyrazine-2-carbonyl)amino-L-alanine;

N-[2-chloro-4-[[[(3-hydroxyphenyl)methyl]amino]carbonyl]benzoyl]-3-[3-[[(5-chloro-2-pyridinyl)amino]carbonyl]pyrazine-2-carbonyl]amino-L-alanine;

N-[2-chloro-4-[[[(3-hydroxyphenyl)methyl]amino]carbonyl]benzoyl]-3-(2,4-dihydroxypyrimidine-5-carbonyl)amino-L-alanine; and N-[2-chloro-4-[[[(3-hydroxyphenyl)methyl]amino]carbonyl]benzoyl]-3-(2,4-dihydroxypyrimidine-6-carbonyl)amino-L-alanine.

14. A compound of claim 8 wherein Z is phenyl, or phenyl substituted with at least one of hydroxy, cyano, lower alkyl or substituted lower alkyl.

15. Compounds of claim 14 which are:

3-benzoylamino-N-[2-chloro-4-[[[(3-hydroxyphenyl)methyl]amino]carbonyl]benzoyl]-L-alanine;

N-[2-chloro-4-[[[(3-hydroxyphenyl)methyl]amino]carbonyl]benzoyl]-3-(3-cyanobenzoyl)amino-L-alanine;

N-[2-chloro-4-[[[(3-hydroxyphenyl)methyl]amino]carbonyl]benzoyl]-3-(3-hydroxybenzoyl)amino-L-alanine;

N-[2-chloro-4-[[[(3-hydroxyphenyl)methyl]amino]carbonyl]benzoyl]-3-(2-methylbenzoyl)amino-L-alanine;

N-[2-chloro-4-[[[(3-hydroxyphenyl)methyl]amino]carbonyl]benzoyl]-3-(3-methylbenzoyl)amino-L-alanine;

N-[2-chloro-4-[[[(3-hydroxyphenyl)methyl]amino]carbonyl]benzoyl]-3-(4-methylbenzoyl)amino-L-alanine;

N-[2-chloro-4-[[[(3-hydroxyphenyl)methyl]amino]carbonyl]benzoyl]-3-[3-(trifluoromethyl)benzoyl]amino-L-alanine;

N-[2-chloro-4-[[[(3-hydroxyphenyl)methyl]amino]carbonyl]benzoyl]-3-(3,5-dimethylbenzoyl)amino-L-alanine;

N-[2-chloro-4-[[[(3-hydroxyphenyl)methyl]amino]carbonyl]benzoyl]-3-(3,4-dimethylbenzoyl)amino-L-alanine;

N-[2-chloro-4-[[[(3-hydroxyphenyl)methyl]amino]carbonyl]benzoyl]-3-(3-hydroxy-4-methylbenzoyl)amino-L-alanine; and N-[2-chloro-4-[[[(3-hydroxyphenyl)methyl]amino]carbonyl]benzoyl]-3-(2-hydroxy-4-methylbenzoyl)amino-L-alanine.

16. A compound of claim 8 wherein Z is phenyl substituted with at least one hydroxy.

17. Compounds of claim 16 which are

N-[2-chloro-4-[[[(3-hydroxyphenyl)methyl]amino]carbonyl]benzoyl]-3-(3-hydroxybenzoyl)amino-L-alanine; and N-[2-chloro-4-[[[(3-hydroxyphenyl)methyl]amino]carbonyl]benzoyl]-3-(3,5-dihydroxybenzoyl)amino-L-alanine.

18. A compound of claim 17 which is N-[2-chloro-4-[[[(3-hydroxyphenyl)methyl]amino]carbonyl]benzoyl]-3-(3-hydroxybenzoyl)amino-L-alanine.

19. A compound of claim 17 which is N-[2-chloro-4-[[[(3-hydroxyphenyl)methyl]amino]carbonyl]benzoyl]-3-(3,5-dihydroxybenzoyl)amino-L-alanine.

20. A compound of claim 8 wherein Z is phenyl substituted with at least one of lower alkoxy, lower alkoxy carbonyl, —O—C(O)—CH$_3$, or —C(O)—O—CH$_3$.

21. Compounds of claim 38 which are:
N-[2-chloro-4-[[[(3-hydroxyphenyl)methyl]amino]carbonyl]benzoyl]-3-(3-methoxybenzoyl)amino-L-alanine;
3-(2-acetoxybenzoyl)amino-N-[2-chloro-4-[[[(3-hydroxyphenyl)methyl]amino]carbonyl]benzoyl]-L-alanine;
N-[2-chloro-4-[[[(3-hydroxyphenyl)methyl]amino]carbonyl]benzoyl]-3-(4-ethoxybenzoyl)amino-L-alanine;
N-[2-chloro-4-[[[(3-hydroxyphenyl)methyl]amino]carbonyl]benzoyl]-3-(2-methoxybenzoyl)amino-L-alanine;
N-[2-chloro-4-[[[(3-hydroxyphenyl)methyl]amino]carbonyl]benzoyl]-3-(4-methoxybenzoyl)amino-L-alanine;
N-[2-chloro-4-[[[(3-hydroxyphenyl)methyl]amino]carbonyl]benzoyl]-3-[3-(methoxycarbonyl)benzoyl]amino-L-alanine;
N-[2-chloro-4-[[[(3-hydroxyphenyl)methyl]amino]carbonyl]benzoyl]-3-(4-pentyloxybenzoyl)amino-L-alanine;
N-[2-chloro-4-[[[(3-hydroxyphenyl)methyl]amino]carbonyl]benzoyl]-3-(3,4,5-trimethoxybenzoyl)amino-L-alanine;
N-[2-chloro-4-[[[(3-hydroxyphenyl)methyl]amino]carbonyl]benzoyl]-3-(3,5-dimethoxybenzoyl)amino-L-alanine; and
N-[2-chloro-4-[[[(3-hydroxyphenyl)methyl]amino]carbonyl]benzoyl]-3-(3,4-dimethoxybenzoyl)amino-L-alanine.

22. A compound of claim 8 wherein Z is phenyl substituted with at least one halogen.

23. Compounds of claim 22 which are:
3-(2-bromobenzoyl)amino-N-[2-chloro-4-[[[(3-hydroxyphenyl)methyl]amino]carbonyl]benzoyl]-L-alanine;
3-(3-bromobenzoyl)amino-N-[2-chloro-4-[[[(3-hydroxyphenyl)methyl]amino]carbonyl]benzoyl]-L-alanine;
3-(2-chlorobenzoyl)amino-N-[2-chloro-4-[[[(3-hydroxyphenyl)methyl]amino]carbonyl]benzoyl]-L-alanine;
3-(3-chlorobenzoyl)amino-N-[2-chloro-4-[[[(3-hydroxyphenyl)methyl]amino]carbonyl]benzoyl]-L-alanine;
3-(4-chlorobenzoyl)amino-N-[2-chloro-4-[[[(3-hydroxyphenyl)methyl]amino]carbonyl]benzoyl]-L-alanine;
N-[2-chloro-4-[[[(3-hydroxyphenyl)methyl]amino]carbonyl]benzoyl]-3-(3-fluorobenzoyl)amino-L-alanine;
N-[2-chloro-4-[[[(3-hydroxyphenyl)methyl]amino]carbonyl]benzoyl]-3-(3-iodobenzoyl)amino-L-alanine;
N-[2-chloro-4-[[[(3-hydroxyphenyl)methyl]amino]carbonyl]benzoyl]-3-(2,4,5-trifluorobenzoyl)amino-L-alanine;
3-(3-chloro-5-fluorobenzoyl)amino-N-[2-chloro-4-[[[(3-hydroxyphenyl)methyl]amino]carbonyl]benzoyl]-L-alanine;
N-[2-chloro-4-[[[(3-hydroxyphenyl)methyl]amino]carbonyl]benzoyl]-3-(3,5-dichlorobenzoyl)amino-L-alanine;
N-[2-chloro-4-[[[(3-hydroxyphenyl)methyl]amino]carbonyl]benzoyl]-3-(3,5-dibromobenzoyl)amino-L-alanine; and
N-[2-chloro-4-[[[(3-hydroxyphenyl)methyl]amino]carbonyl]benzoyl]-3-(3,5-difluorobenzoyl)amino-L-alanine.

24. A compound of claim 8 wherein Z is phenyl substituted with at least one of amino, substituted amino, nitro, or aminosulfonyl.

25. Compounds of claim 24 which are:
3-(3-aminobenzoyl)amino-N-[2-chloro-4-[[[(3-hydroxyphenyl)methyl]amino]carbonyl]benzoyl]-L-alanine;
3-(4-aminosulfonylbenzoyl)amino-N-[2-chloro-4-[[[(3-hydroxyphenyl)methyl]amino]carbonyl]benzoyl]-L-alanine;
N-[2-chloro-4-[[[(3-hydroxyphenyl)methyl]amino]carbonyl]benzoyl]-3-(3-dimethylaminobenzoyl)amino-L-alanine;
N-[2-chloro-4-[[[(3-hydroxyphenyl)methyl]amino]carbonyl]benzoyl]-3-(4-dimethylaminobenzoyl)amino-L-alanine;
N-[2-chloro-4-[[[(3-hydroxyphenyl)methyl]amino]carbonyl]benzoyl]-3-(3,5-dinitrobenzoyl)amino-L-alanine;
N-[2-chloro-4-[[[(3-hydroxyphenyl)methyl]amino]carbonyl]benzoyl]-3-(2-nitrobenzoyl)amino-L-alanine;
N-[2-chloro-4-[[[(3-hydroxyphenyl)methyl]amino]carbonyl]benzoyl]-3-(3-nitrobenzoyl)amino-L-alanine; and
N-[2-chloro-4-[[[(3-hydroxyphenyl)methyl]amino]carbonyl]benzoyl]-3-(4-nitrobenzoyl)amino-L-alanine.

26. A compound of claim 8 wherein Z is a fused ring system containing at least one benzene ring and containing one or two other rings which are independently 5 or 6-membered cycloalkyl or aryl with 0 to 2 heteroatoms selected from O, N, and S which may be the same or different, any of which may be unsubstituted or substituted with at least one of lower alkoxy, halogen, oxo, or hydroxy.

27. Compounds of claim 26 which are:
N-[2-chloro-4-[[[(3-hydroxyphenyl)methyl]amino]carbonyl]benzoyl]-3-[(1,2,3,4-tetrahydronaphthalene-2-carbonyl)amino]-L-alanine;
N-[2-chloro-4-[[[(3-hydroxyphenyl)methyl]amino]carbonyl]benzoyl]-3-[(DL-7-methoxy-1,2,3,4,4aβ,9,10,10aβ-octahydro-2β-phenanthrenecarbonyl)amino]-L-alanine;
3-[(6-bromo-2-oxo-1,2,3,4-tetrahydroquinoline-4-carbonyl)amino]-N-[2-chloro-4-[[[(3-hydroxyphenyl)methyl]amino]carbonyl]benzoyl]-L-alanine;
N-[2-chloro-4-[[[(3-hydroxyphenyl)methyl]amino]carbonyl]benzoyl]-3-[benzofuran-2-carbonyl)amino-L-alanine;
N-[2-chloro-4-[[[(3-hydroxyphenyl)methyl]amino]carbonyl]benzoyl]-3-(benzothiophene-2-carbonyl)amino-L-alanine;
N-[2-chloro-4-[[[(3-hydroxyphenyl)methyl]amino]carbonyl]benzoyl]-3-(benzimidazole-5-carbonyl)amino-L-alanine;
N-[2-chloro-4-[[[(3-hydroxyphenyl)methyl]amino]carbonyl]benzoyl]-3-(benzothiazole-6-carbonyl)amino-L-alanine;

N-[2-chloro-4-[[[(3-hydroxyphenyl)methyl]amino] carbonyl]benzoyl]-3-(naphthalene-1-carbonyl)amino-L-alanine;
N-[2-chloro-4-[[[(3-hydroxyphenyl)methyl]amino] carbonyl]benzoyl]-3-(naphthalene-2-carbonyl)amino-L-alanine;
N-[2-chloro-4-[[[(3-hydroxyphenyl)methyl]amino] carbonyl]benzoyl]-3-(isoquinoline-1-carbonyl)amino-L-alanine;
N-[2-chloro-4-[[[(3-hydroxyphenyl)methyl]amino] carbonyl]benzoyl]-3-(quinoline-2-carbonyl)amino-L-alanine;
N-[2-chloro-4-[[[(3-hydroxyphenyl)methyl]amino] carbonyl]benzoyl]-3-(4-methoxyquinoline-2-carbonyl) amino-L-alanine;
N-[2-chloro-4-[[[(3-hydroxyphenyl)methyl]amino] carbonyl]benzoyl]-3-(quinoline-3-carbonyl)amino-L-alanine;
N-[2-chloro-4-[[[(3-hydroxyphenyl)methyl]amino] carbonyl]benzoyl]-3-(quinoline-4-carbonyl)amino-L-alanine;
N-[2-chloro-4-[[[(3-hydroxyphenyl)methyl]amino] carbonyl]benzoyl]-3-(cinnoline-4-carbonyl)amino-L-alanine;
N-[2-chloro-4-[[[(3-hydroxyphenyl)methyl]amino] carbonyl]benzoyl]-3-(2-hydroxyquinoxaline-3-carbonyl)amino-L-alanine;
N-[2-chloro-4-[[[(3-hydroxyphenyl)methyl]amino] carbonyl]benzoyl]-3-(4-oxo-4H-1-benzopyran-2-carbonyl)amino-L-alanine;
N-[2-chloro-4-[[[(3-hydroxyphenyl)methyl]amino] carbonyl]benzoyl]-3-(2-oxo-2H-1-benzopyran-3-carbonyl)amino-L-alanine;
3-(anthracene-9-carbonyl)amino-N-[2-chloro-4-[[[(3-hydroxyphenyl)methyl]amino]carbonyl]benzoyl]-L-alanine;
N-[2-chloro-4-[[[(3-hydroxyphenyl)methyl]amino] carbonyl]benzoyl]-3-(1,2,3,4-tetrahydroacridine-9-carbonyl)amino-L-alanine;
N-[2-chloro-4-[[[(3-hydroxyphenyl)methyl]amino] carbonyl]benzoyl]-3-(2-methoxy-11-oxo-11H-pyrido[2,1]quinazoline-8-carbonyl)amino-L-alanine; and
N-[2-chloro-4-[[[(3-hydroxyphenyl)methyl]amino] carbonyl]benzoyl]-3-(9-oxo-9H-thioxanthene-3-carbonyl)amino-L-alanine.

28. A compound of claim 1 which has formula

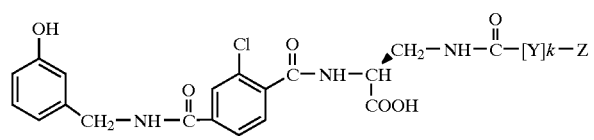

1f wherein Y is lower alkylene which may be substituted by one or more of amino, substituted amino, loweralkyl, or cyclo lower alkyl, or Y is lower alkenylene or lower alkylenethio; k is 1;
Z is hydrogen, lower alkylthio, —COOH, —CONH$_2$, amino, 1-adamantyl, diphenylmethyl, 3-[[(5-chloropyridin-2-yl)amino]carbonyl]pyrazin-2-yl, 2-chloro-4-[[[(3-hydroxyphenyl)methyl]amino]carbonyl]phenyl, [(2,6-dichlorophenyl)-methoxy]phenyl, phenylmethoxy, hydroxy or Z is one of the following:
cycloalkyl or aryl containing 0 to 3 heteroatoms which may be the same or different, or a fused ring system containing two or three rings which rings are independently cycloalkyl or aryl containing 0 to 3 heteroatoms which may be the same or different, any of which rings may be unsubstituted, or substituted with at least one of:
halogen, cyano, amino, substituted amino, aminosulfonyl, nitro, oxo, hydroxy, aryl, aryloxy, unsubstituted lower alkyl, halogen-substituted lower alkyl, lower alkoxy-substituted lower alkyl, lower alkoxy, lower alkanesulfonyl, lower alkylthio, acetyl, aminocarbonyl, hydrazino, carboxy, lower alkoxycarbonyl, or acetoxy;
or a pharmaceutically acceptable salt thereof.

29. A compound of claim 28 wherein Y is methylene.
30. Compounds of claim 29 which are:
3-acetylamino-N-[2-chloro-4-[[[(3-hydroxyphenyl)methyl]amino]carbonyl]benzoyl]-L-alanine;
N-[2-chloro-4-[[[(3-hydroxyphenyl)methyl]amino] carbonyl]benzoyl]-3-(cyclopentylacetyl)amino-L-alanine;
N-[2-chloro-4-[[[(3-hydroxyphenyl)methyl]amino] carbonyl]benzoyl]-3-(cyclohexylacetyl)amino-L-alanine;
N-[2-chloro-4-[[[(3-hydroxyphenyl)methyl]amino] carbonyl]benzoyl]-3-(phenylacetyl)amino-L-alanine;
N-[2-chloro-4-[[[(3-hydroxyphenyl)methyl]amino] carbonyl]benzoyl]-3-(4-methoxyphenylacetyl)amino-L-alanine;
N-[2-chloro-4-[[[(3-hydroxyphenyl)methyl]amino] carbonyl]benzoyl]-3-(4-nitrophenylacetyl)amino-L-alanine;
N-[2-chloro-4-[[[(3-hydroxyphenyl)methyl]amino] carbonyl]benzoyl]-3-(3-trifluoromethylphenylacetyl) amino-L-alanine;
N-[2-chloro-4-[[[(3-hydroxyphenyl)methyl]amino] carbonyl]benzoyl]-3-(3,5-dinitrophenylacetyl)amino-L-alanine;
N-[2-chloro-4-[[[(3-hydroxyphenyl)methyl]amino] carbonyl]benzoyl]-3-(2-thienylacetyl)amino-L-alanine;
N-[2-chloro-4-[[[(3-hydroxyphenyl)methyl]amino] carbonyl]benzoyl]-3-(3-pyridylacetyl)amino-L-alanine;
N-[2-chloro-4-[[[(3-hydroxyphenyl)methyl]amino] carbonyl]benzoyl]-3-(2-naphthylacetyl)amino-L-alanine;
N-[2-chloro-4-[[[(3-hydroxyphenyl)methyl]amino] carbonyl]benzoyl]-3-(9H-fluoren-9-ylacetyl)amino-L-alanine;
3-[[(2S)-2-carboxy-2-[2-chloro-4-[(3-hydroxyphenyl) methyl]amino]carbonyl]benzoylamino] ethylaminocarbonyl]methyl]benzothiazol-3-ium salt;
N-[2-chloro-4-[[[(3-hydroxyphenyl)methyl]amino] carbonyl]benzoyl]-3-[3-amino-2-oxo-1(2H)-pyridineacetyl]amino-L-alanine;
3-(3-aminohexahydro-2-oxo-1H-azepine-1-acetyl) amino-N-[2-chloro-4-[[[(3-hydroxyphenyl)methyl] amino]carbonyl]benzoyl]-L-alanine; and
3-(4-amino-1,3,4,5-tetrahydro-3-oxo-2H-2-benzazepine-2-acetyl)amino-N-[2-chloro-4-[[[(3-hydroxyphenyl) methyl]amino]carbonyl]benzoyl]-L-alanine.
31. A compound of claim 28 wherein Y is —CH$_2$CH$_2$—, —C(CH$_3$)$_2$CH$_2$—, —CH(CH$_3$)CH$_2$, —CH$_2$CH(CH$_3$)

—CH$_2$—, —CH$_2$CH(CH$_3$)—, or

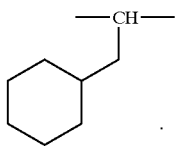

32. Compounds of claim 31 which are:
N-[2-chloro-4-[[[(3-hydroxyphenyl)methyl]amino]carbonyl]benzoyl]-3-(3-phenylpropanoyl)amino-L-alanine;
N-[2-chloro-4-[[[(3-hydroxyphenyl)methyl]amino]carbonyl]benzoyl]-3-[(3,5-dimethylisoxazol-4-yl)propanoyl]amino-L-alanine;
N-[2-chloro-4-[[[(3-hydroxyphenyl)methyl]amino]carbonyl]benzoyl]-3-[3-(piperidin-1-yl)propanoyl]amino-L-alanine;
N-[2-chloro-4-[[[(3-hydroxyphenyl)methyl]amino]carbonyl]benzoyl]-3-[(3RS)-3-phenylbutanoyl]-L-alanine;
N-[2-chloro-4-[[[(3-hydroxyphenyl)methyl]amino]carbonyl]benzoyl]-3-[3-cyclohexyl-(2S)-2-(1-pyrrolyl)propanoyl]amino-L-alanine;
N-[2-chloro-4-[[[(3-hydroxyphenyl)methyl]amino]carbonyl]benzoyl]-3-(trimethylacetyl)amino-L-alanine;
N-[2-chloro-4-[[[(3-hydroxyphenyl)methyl]amino]carbonyl]benzoyl]-3-(2-methylpropanoyl)amino-L-alanine; and
N-[2-chloro-4-[[[(3-hydroxyphenyl)methyl]amino]carbonyl]benzoyl]-3-(3-methylbutanoyl)amino-L-alanine.

33. A compound of claim 28 wherein Y is —CH=CH—, —CH=CH—CH$_2$—, or —CH$_2$S—.

34. Compounds of claim 33 which are:
N-[2-chloro-4-[[[(3-hydroxyphenyl)methyl]amino]carbonyl]benzoyl]-3-(4-pyridylthioacetyl)amino-L-alanine;
N-[2-chloro-4-[[[(3-hydroxyphenyl)methyl]amino]carbonyl]benzoyl]-3-(pyrimidin-2-ylthio)acetylamino-L-alanine;
3-(but-2-enoyl)amino-N-[2-chloro-4-[[[(3-hydroxyphenyl)methyl]amino]carbonyl]benzoyl]-L-alanine;
N-[2-chloro-4-[[[(3-hydroxyphenyl)methyl]amino]carbonyl]benzoyl]-3-[3-(4-methoxyphenyl)prop-2-enoyl]amino-L-alanine;
N-[2-chloro-4-[[[(3-hydroxyphenyl)methyl]amino]carbonyl]benzoyl]-3-[3-(pyridin-3-yl)prop-2-enoyl]amino-L-alanine; and
N-[2-chloro-4-[[[(3-hydroxyphenyl)methyl]amino]carbonyl]benzoyl]-3-[3-(2-thienyl)prop-2-enoyl]amino-L-alanine.

35. A compound of claim 28 wherein Y is lower alkylene substituted by amino, lower alkyl, lower alkylamino, or trifluoromethyl.

36. Compounds of claim 35 which are:
N-[2-chloro-4-[[[(3-hydroxyphenyl)methyl]amino]carbonyl]benzoyl]-3-(L-methionyl)amino-L-alanine;
N-[2-chloro-4-[[[(3-hydroxyphenyl)methyl]amino]carbonyl]benzoyl]-3-(L-lysyl)amino-L-alanine;
N-[2-chloro-4-[[[(3-hydroxyphenyl)methyl]amino]carbonyl]benzoyl]-3-(L-phenylalanyl)amino-L-alanine;
N-[2-chloro-4-[[[(3-hydroxyphenyl)methyl]amino]carbonyl]benzoyl]-3-(L-asparaginyl)amino-L-alanine;
N-[2-chloro-4-[[[(3-hydroxyphenyl)methyl]amino]carbonyl]benzoyl]-3-(L-tryptophyl)amino-L-alanine;
N-[2-chloro-4-[[[(3-hydroxyphenyl)methyl]amino]carbonyl]benzoyl]-3-(L-β-glutamyl)amino-L-alanine;
N-[2-chloro-4-[[[(3-hydroxyphenyl)methyl]amino]carbonyl]benzoyl]-3-(N-methyl-L-alanyl)amino-L-alanine;
N-[2-chloro-4-[[[(3-hydroxyphenyl)methyl]amino]carbonyl]benzoyl]-3-(N-methylglycyl)amino-L-alanine;
N-[2-chloro-4-[[[(3-hydroxyphenyl)methyl]amino]carbonyl]benzoyl]-3-(L-leucyl)amino-L-alanine;
3-(2-amino-2-methylpropanoyl)amino-N-[2-chloro-4-[[[(3-hydroxyphenyl)methyl]amino]carbonyl]benzoyl]-L-alanine;
3-(3-amino-4,4,4-trifluorobutanoyl)amino-N-[2-chloro-4-[[[(3-hydroxyphenyl)methyl]amino]carbonyl]benzoyl]-L-alanine;
3-(3-amino-2-methylpropanoyl)amino-N-[2-chloro-4-[[[(3-hydroxyphenyl)methyl]amino]carbonyl]benzoyl]-L-alanine;
N-[2-chloro-4-[[[(3-hydroxyphenyl)methyl]amino]carbonyl]benzoyl]-3-[4-(2,6-dichlorophenyl)methoxy-L-phenylalanyl]amino-L-alanine;
N-[2-chloro-4-[[[(3-hydroxyphenyl)methyl]amino]carbonyl]benzoyl]-3-(L-seryl)amino-L-alanine;
N-[2-chloro-4-[[[(3-hydroxyphenyl)methyl]amino]carbonyl]benzoyl]-3-[O-(phenylmethyl)-L-seryl]amino-L-alanine;
N-[2-chloro-4-[[[(3-hydroxyphenyl)methyl]amino]carbonyl]benzoyl]-3-(L-phenylglycyl)amino-L-alanine;
N-[2-chloro-4-[[[(3-hydroxyphenyl)methyl]amino]carbonyl]benzoyl]-3-(4-nitro-L-phenylalanyl)amino-L-alanine;
N-[2-chloro-4-[[[(3-hydroxyphenyl)methyl]amino]carbonyl]benzoyl]-3-(4-fluoro-D,L-phenylalanyl)amino-L-alanine;
N-[2-chloro-4-[[[(3-hydroxyphenyl)methyl]amino]carbonyl]benzoyl]-3-(D-tyrosyl)amino-L-alanine;
3-(D-aspartyl)amino-N-[2-chloro-4-[[[(3-hydroxyphenyl)methyl]amino]carbonyl]benzoyl]-L-alanine;
N-[2-chloro-4-[[[(3-hydroxyphenyl)methyl]amino]carbonyl]benzoyl]-3-(D-tryptophyl)amino-L-alanine;
N-[2-chloro-4-[[[(3-hydroxyphenyl)methyl]amino]carbonyl]benzoyl]-3-(L-alanyl)amino-L-alanine; and
N-[2-chloro-4-[[[(3-hydroxyphenyl)methyl]amino]carbonyl]benzoyl]-3-(D-alanyl)amino-L-alanine.

37. A compound of claim 28 wherein Y is —CH$_2$CH$_2$CH$_2$—.

38. Compounds of claim 37 which are:
3-(4-aminobutanoyl)amino-N-[2-chloro-4-[[[(3-hydroxyphenyl)methyl]amino]carbonyl]benzoyl]-L-alanine; and
N-[2-chloro-4-[[[(3-hydroxyphenyl)methyl]amino]carbonyl]benzoyl]-3-(4-carboxy-1-oxobutyl)amino-L-alanine.

39. A compound of claim 1 wherein X is carbonyl; k is 0; and Z is thiophene or phenyl, or thiophene or phenyl substituted by one or more of lower alkyl, lower alkoxy, hydroxy, halogen, carboxy, nitro, aminosulfonyl, cyano, or lower alkoxy carbonyl.

40. A compound of claim 39 wherein Z is thiophene or phenyl, or thiophene or phenyl substituted by methyl, methoxy, chlorine, bromine, fluorine, hydroxy, or nitro.

41. Compounds of claim 40 which are:

N-[2-chloro-4-[[[(3-hydroxyphenyl)methyl]amino] carbonyl]benzoyl]-3-(4-methoxythiophene-3-carbonyl)amino-L-alanine; and N-[2-chloro-4-[[[(3-hydroxyphenyl)methyl]amino] carbonyl]benzoyl]-3-(5-chloro-4-methoxythiophene-3-carbonyl)amino-L-alanine.

42. A pharmaceutical composition which comprises a compound of claim 1 and a pharmaceutically acceptable carrier.

43. A pharmaceutical composition which comprises a compound of claim 12 and a pharmaceutically acceptable carrier.

44. N-[2-chloro-4-[[[(3-hydroxyphenyl)methyl]amino] carbonyl]benzoyl]-3-(phenylmethyl)amino-L-alanine.

* * * * *